(12) United States Patent
Johnson et al.

(10) Patent No.: US 8,447,414 B2
(45) Date of Patent: *May 21, 2013

(54) SWITCHED SAFETY PROTECTION CIRCUIT FOR AN AIMD SYSTEM DURING EXPOSURE TO HIGH POWER ELECTROMAGNETIC FIELDS

(75) Inventors: Robert Shawn Johnson, North Tonawanda, NY (US); Warren S. Dabney, Orchard Park, NY (US); Robert A. Stevenson, Canyon Country, CA (US); Christopher Michael Williams, Lancaster, NY (US); Holly Noelle Moschiano, Lancaster, NY (US); Scott Brainard, Columbia Heights, MN (US)

(73) Assignee: Greatbatch Ltd., Clarence, NY (US)

( * ) Notice: Subject to any disclaimer, the term of this patent is extended or adjusted under 35 U.S.C. 154(b) by 391 days.

This patent is subject to a terminal disclaimer.

(21) Appl. No.: 12/731,764

(22) Filed: Mar. 25, 2010

(65) Prior Publication Data

US 2010/0208397 A1 Aug. 19, 2010

Related U.S. Application Data

(63) Continuation-in-part of application No. 12/686,272, filed on Jan. 12, 2010, and a continuation-in-part of application No. 12/686,137, filed on Jan. 12, 2010, and a continuation-in-part of application No. 12/489,921, filed on Jun. 23, 2009, now Pat. No. 7,751,903, and a continuation-in-part of application No. 12/337,376, filed on Dec. 17, 2008, which is a continuation-in-part of application No. 12/337,170, filed on Dec. 17, 2008.

(60) Provisional application No. 61/149,833, filed on Feb. 4, 2009, provisional application No. 61/144,102, filed on Jan. 12, 2009.

(51) Int. Cl.
*A61N 1/08* (2006.01)
*A61N 1/16* (2006.01)
*A61N 1/375* (2006.01)

(52) U.S. Cl.
USPC .................................. 607/63; 607/60; 607/36

(58) Field of Classification Search
USPC .......................................... 607/9, 2, 45, 63, 48
See application file for complete search history.

(56) References Cited

U.S. PATENT DOCUMENTS 3,871,382 A   3/1975 Mann
3,968,802 A   7/1976 Ballis (Continued)

FOREIGN PATENT DOCUMENTS

EP   0243573   11/1987
EP   0145430   5/1991

(Continued)

OTHER PUBLICATIONS

Ariel Roguin et al., Modern Pacemaker and Implantable Cardioverter/Defibrillator Systems Can Be Magnetic Resonance Imaging Safe, Circulation—Journal of the American Heart Association, Aug. 4, 2004 (originally published online Jul. 26, 2004), pp. 475-482, American Heart Association, Dallas, Texas, USA.

(Continued)

*Primary Examiner* — Carl H Layno
*Assistant Examiner* — Jon Eric C Morales
(74) *Attorney, Agent, or Firm* — Michael F. Scalise

(57) ABSTRACT

An energy management system that facilitates the transfer of high frequency energy induced on an implanted lead or a leadwire includes an energy dissipating surface associated with the implanted lead or the leadwire, a diversion or diverter circuit associated with the energy dissipating surface, and at least one switch disposed between the diversion circuit and the AIMD electronics for diverting energy in the implanted lead or the leadwire through the diversion circuit to the energy dissipating surface. The switch may comprise a single or multi-pole double or single throw switch. The diversion circuit may be either a high pass filter or a low pass filter.

75 Claims, 60 Drawing Sheets

U.S. PATENT DOCUMENTS

| | | | |
|---|---|---|---|
| 4,188,598 A | 2/1980 | Hunt | |
| 4,295,467 A | 10/1981 | Mann et al. | |
| 4,320,763 A | 3/1982 | Money | |
| 4,424,551 A | 1/1984 | Stevenson et al. | |
| 4,431,005 A | 2/1984 | McCormick | |
| 4,445,501 A | 5/1984 | Bresler | |
| 4,572,198 A | 2/1986 | Codrington | |
| 4,585,001 A | 4/1986 | Belt | |
| 4,633,181 A | 12/1986 | Muphy-Boesch et al. | |
| 4,643,186 A | 2/1987 | Rosen et al. | |
| 4,654,880 A | 3/1987 | Sontag | |
| 4,672,972 A | 6/1987 | Berke | |
| 4,689,621 A | 8/1987 | Kleinberg | |
| 4,754,752 A | 7/1988 | Ginsburg et al. | |
| 4,757,820 A | 7/1988 | Itoh | |
| 4,766,381 A | 8/1988 | Conturo et al. | |
| 4,799,499 A | 1/1989 | Bisping | |
| 4,813,429 A | 3/1989 | Eshel et al. | |
| 4,823,812 A | 4/1989 | Eshel et al. | |
| 4,832,023 A | 5/1989 | Murphy-Chutorian et al. | |
| 4,858,623 A | 8/1989 | Bradshaw et al. | |
| 4,859,950 A | 8/1989 | Keren | |
| 4,932,411 A | 6/1990 | Fritschy et al. | |
| 4,960,106 A | 10/1990 | Kubokawa | |
| 4,989,608 A | 2/1991 | Ratner | |
| 5,019,075 A | 5/1991 | Spears et al. | |
| 5,095,911 A | 3/1992 | Pomeranz | |
| 5,099,208 A | 3/1992 | Fitzpatrick et al. | |
| 5,167,233 A | 12/1992 | Eberle et al. | |
| 5,178,618 A | 1/1993 | Kandarpa | |
| 5,190,046 A | 3/1993 | Sharman | |
| 5,197,468 A | 3/1993 | Proctor et al. | |
| 5,209,233 A | 5/1993 | Holland et al. | |
| 5,211,165 A | 5/1993 | Dumoulin et al. | |
| 5,217,010 A | 6/1993 | Tsitlik et al. | |
| 5,246,438 A | 9/1993 | Langberg | |
| 5,251,120 A | 10/1993 | Smith | |
| 5,271,400 A | 12/1993 | Dumoulin et al. | |
| 5,300,108 A | 4/1994 | Rebell et al. | |
| 5,307,808 A | 5/1994 | Dumoulin et al. | |
| 5,307,814 A | 5/1994 | Kressel et al. | |
| 5,318,025 A | 6/1994 | Dumoulin et al. | |
| 5,323,776 A | 6/1994 | Blakeley et al. | |
| 5,323,778 A | 6/1994 | Kandarpa et al. | |
| 5,333,095 A | 7/1994 | Stevenson et al. | |
| 5,334,045 A * | 8/1994 | Cappa et al. | 439/506 |
| 5,334,193 A | 8/1994 | Nardelia | |
| 5,348,010 A | 9/1994 | Schnall et al. | |
| 5,352,979 A | 10/1994 | Conturo | |
| 5,358,515 A | 10/1994 | Hurter et al. | |
| 5,363,845 A | 11/1994 | Chowdhury et al. | |
| 5,365,928 A | 11/1994 | Rhinehart et al. | |
| 5,370,644 A | 12/1994 | Langberg | |
| 5,398,683 A | 3/1995 | Edwards et al. | |
| 5,400,787 A | 3/1995 | Marandos | |
| 5,413,104 A | 5/1995 | Buijs et al. | |
| 5,419,325 A | 5/1995 | Dumoulin et al. | |
| 5,433,717 A | 7/1995 | Rubinsky et al. | |
| 5,437,277 A | 8/1995 | Dumoulin et al. | |
| 5,443,066 A | 8/1995 | Dumoulin et al. | |
| 5,443,489 A | 8/1995 | Ben-Haim | |
| 5,447,156 A | 9/1995 | Dumoulin et al. | |
| 5,451,232 A | 9/1995 | Rinehart et al. | |
| 5,462,055 A | 10/1995 | Casey et al. | |
| 5,476,095 A | 12/1995 | Becker et al. | |
| 5,498,261 A | 3/1996 | Strul | |
| 5,507,743 A | 4/1996 | Edwards et al. | |
| 5,512,825 A | 4/1996 | Atalar et al. | |
| 5,514,173 A | 5/1996 | Rebell et al. | |
| 5,540,679 A | 7/1996 | Fram et al. | |
| 5,545,201 A | 8/1996 | Helland et al. | |
| 5,558,093 A | 9/1996 | Pomeranz | |
| 5,578,008 A | 11/1996 | Hara | |
| 5,588,432 A | 12/1996 | Crowley | |
| 5,590,657 A | 1/1997 | Cain et al. | |
| 5,591,218 A | 1/1997 | Jacobson | |
| 5,623,241 A | 4/1997 | Minkoff | |
| 5,629,622 A | 5/1997 | Scampini | |
| 5,662,108 A | 9/1997 | Budd et al. | |
| 5,682,897 A | 11/1997 | Pomeranz | |
| 5,685,878 A | 11/1997 | Falwell et al. | |
| 5,697,958 A | 12/1997 | Paul et al. | |
| 5,699,801 A | 12/1997 | Atalar et al. | |
| 5,706,810 A | 1/1998 | Rubinsky et al. | |
| 5,715,825 A | 2/1998 | Crowley | |
| 5,716,390 A | 2/1998 | Li | |
| 5,722,998 A | 3/1998 | Prutchi et al. | |
| 5,735,887 A * | 4/1998 | Barreras et al. | 607/60 |
| 5,741,321 A | 4/1998 | Brennen | |
| 5,751,539 A | 5/1998 | Stevenson et al. | |
| 5,759,202 A | 6/1998 | Schroeppel | |
| 5,769,800 A | 6/1998 | Gelfand et al. | |
| 5,772,693 A * | 6/1998 | Brownlee | 607/123 |
| 5,775,338 A | 7/1998 | Hastings | |
| 5,779,669 A | 7/1998 | Haissaguerre et al. | |
| 5,792,055 A | 8/1998 | McKinnon | |
| 5,824,029 A | 10/1998 | Weijand et al. | |
| 5,833,608 A | 11/1998 | Acker | |
| 5,840,031 A | 11/1998 | Crowley | |
| 5,864,234 A | 1/1999 | Ludeke | |
| 5,868,674 A | 2/1999 | Glowinski et al. | |
| 5,879,347 A | 3/1999 | Saadat | |
| 5,891,134 A | 4/1999 | Goble et al. | |
| 5,905,627 A | 5/1999 | Brendel et al. | |
| 5,916,162 A | 6/1999 | Snelten et al. | |
| 5,928,145 A | 7/1999 | Ocali et al. | |
| 5,928,159 A | 7/1999 | Eggers et al. | |
| 5,938,609 A | 8/1999 | Pomeranz | |
| 5,938,692 A | 8/1999 | Rudie | |
| 5,959,829 A | 9/1999 | Stevenson et al. | |
| 5,964,705 A | 10/1999 | Truwit et al. | |
| 5,973,906 A | 10/1999 | Stevenson et al. | |
| 5,978,204 A | 11/1999 | Stevenson | |
| 6,004,269 A | 12/1999 | Crowley et al. | |
| 6,008,980 A | 12/1999 | Stevenson et al. | |
| 6,011,995 A | 1/2000 | Guglielmi et al. | |
| 6,026,316 A | 2/2000 | Kucharczyk et al. | |
| 6,027,500 A | 2/2000 | Buckles et al. | |
| 6,031,375 A | 2/2000 | Atalar et al. | |
| 6,045,532 A | 4/2000 | Eggers et al. | |
| 6,055,457 A | 4/2000 | Bonner | |
| 6,066,136 A | 5/2000 | Geistert | |
| 6,099,524 A | 8/2000 | Lipson et al. | |
| 6,101,417 A | 8/2000 | Vogel et al. | |
| 6,128,522 A | 10/2000 | Acker et al. | |
| 6,129,670 A | 10/2000 | Burdette et al. | |
| 6,141,594 A | 10/2000 | Flynn et al. | |
| 6,159,560 A | 12/2000 | Stevenson et al. | |
| 6,171,240 B1 | 1/2001 | Young et al. | |
| 6,171,241 B1 | 1/2001 | McVeigh et al. | |
| 6,188,219 B1 | 2/2001 | Reeder et al. | |
| 6,226,545 B1 | 5/2001 | Gilderdale | |
| 6,236,205 B1 | 5/2001 | Ludeke et al. | |
| 6,238,390 B1 | 5/2001 | Tu et al. | |
| 6,263,229 B1 | 7/2001 | Atalar et al. | |
| 6,272,370 B1 | 8/2001 | Gillies et al. | |
| 6,275,369 B1 | 8/2001 | Stevenson et al. | |
| 6,280,385 B1 | 8/2001 | Melzer et al. | |
| 6,284,971 B1 | 9/2001 | Atalar et al. | |
| 6,332,089 B1 | 12/2001 | Acker et al. | |
| 6,370,427 B1 * | 4/2002 | Alt et al. | 607/4 |
| 6,390,996 B1 | 5/2002 | Halperin et al. | |
| 6,408,202 B1 | 6/2002 | Lima et al. | |
| 6,424,234 B1 | 7/2002 | Stevenson | |
| 6,428,537 B1 | 8/2002 | Swanson et al. | |
| 6,456,481 B1 | 9/2002 | Stevenson | |
| 6,473,291 B1 | 10/2002 | Stevenson | |
| 6,493,591 B1 | 12/2002 | Stokes | |
| 6,529,103 B1 | 3/2003 | Brendel et al. | |
| 6,535,766 B1 | 3/2003 | Thompson et al. | |
| 6,539,253 B2 | 3/2003 | Thompson et al. | |
| 6,539,261 B2 | 3/2003 | Molin | |
| 6,549,800 B1 | 4/2003 | Atalar et al. | |
| 6,556,009 B2 | 4/2003 | Kellman et al. | |
| 6,566,978 B2 | 5/2003 | Stevenson et al. | |
| 6,567,259 B2 | 5/2003 | Stevenson et al. | |
| 6,567,703 B1 | 5/2003 | Thompson et al. | |

| | | |
|---|---|---|
| 6,593,884 B1 | 7/2003 | Gilboae et al. |
| 6,606,513 B2 | 8/2003 | Lardo et al. |
| 6,628,980 B2 | 9/2003 | Atalar et al. |
| 6,633,780 B1 | 10/2003 | Berger et al. |
| 6,643,903 B2 | 11/2003 | Stevenson et al. |
| 6,654,628 B1 | 11/2003 | Silber et al. |
| 6,675,033 B1 | 1/2004 | Lardo et al. |
| 6,675,779 B2 | 1/2004 | King et al. |
| 6,675,780 B1 | 1/2004 | Wendels et al. |
| 6,687,550 B1 | 2/2004 | Doan |
| 6,690,963 B2 | 2/2004 | Ben-Haim et al. |
| 6,701,176 B1 | 3/2004 | Halperin et al. |
| 6,714,809 B2 | 3/2004 | Lee et al. |
| 6,759,388 B1 | 7/2004 | Marchant et al. |
| 6,765,779 B2 | 7/2004 | Stevenson et al. |
| 6,765,780 B2 | 7/2004 | Brendel et al. |
| 6,771,067 B2 | 8/2004 | Kellman et al. |
| 6,829,509 B1 | 12/2004 | MacDonald et al. |
| 6,847,837 B1 | 1/2005 | Melzer et al. |
| 6,868,288 B2 | 3/2005 | Thompson |
| 6,871,091 B2 | 3/2005 | Wilkinson et al. |
| 6,876,885 B2 | 4/2005 | Swoyer et al. |
| 6,882,248 B2 | 4/2005 | Stevenson et al. |
| 6,896,454 B2 | 5/2005 | Atalar et al. |
| 6,898,454 B2 | 5/2005 | Atalar et al. |
| 6,901,292 B2 | 5/2005 | Hrdlicka et al. |
| 6,904,307 B2 | 6/2005 | Karmarkar et al. |
| 6,925,328 B2 | 8/2005 | Foster et al. |
| 6,931,286 B2 | 8/2005 | Sigg et al. |
| 6,944,489 B2 | 9/2005 | Zeijlemaker et al. |
| 6,949,929 B2 | 9/2005 | Gray et al. |
| 6,952,613 B2 | 10/2005 | Swoyer et al. |
| 6,971,391 B1 | 12/2005 | Wang et al. |
| 6,985,347 B2 | 1/2006 | Stevenson et al. |
| 6,985,775 B2 | 1/2006 | Reinke et al. |
| 6,999,818 B2 | 2/2006 | Stevenson et al. |
| 7,013,180 B2 | 3/2006 | Villaseca et al. |
| 7,038,900 B2 | 5/2006 | Stevenson et al. |
| 7,092,766 B1 | 8/2006 | Salys et al. |
| 7,113,387 B2 | 9/2006 | Stevenson et al. |
| 7,149,773 B2 | 12/2006 | Haller et al. |
| 7,155,271 B2 | 12/2006 | Halperin |
| 7,174,219 B2 | 2/2007 | Wahlstrand et al. |
| 7,236,816 B2 | 6/2007 | Kumar et al. |
| 7,276,474 B2 | 10/2007 | Marchant et al. |
| 7,319,905 B1 | 1/2008 | Morgan et al. |
| 7,363,090 B2 | 4/2008 | Halperin |
| 7,422,568 B2 | 9/2008 | Yang et al. |
| 7,751,903 B2 * | 7/2010 | Stevenson et al. ............... 607/63 |
| 2001/0051787 A1 * | 12/2001 | Haller et al. ..................... 604/66 |
| 2002/0055678 A1 | 5/2002 | Scott et al. |
| 2002/0095197 A1 | 7/2002 | Lardo et al. |
| 2002/0177771 A1 | 11/2002 | Guttman et al. |
| 2002/0192688 A1 | 12/2002 | Yang et al. |
| 2003/0028094 A1 | 2/2003 | Kumar et al. |
| 2003/0028095 A1 | 2/2003 | Tulley et al. |
| 2003/0050557 A1 | 3/2003 | Susil et al. |
| 2003/0083726 A1 | 5/2003 | Zeijlemaker et al. |
| 2003/0144720 A1 | 7/2003 | Villaseca et al. |
| 2003/0208252 A1 | 11/2003 | O'Boyle et al. |
| 2003/0212373 A1 | 11/2003 | Hall et al. |
| 2004/0015079 A1 | 1/2004 | Berger et al. |
| 2004/0034338 A1 | 2/2004 | Thierfelder et al. |
| 2004/0167392 A1 | 8/2004 | Halperin et al. |
| 2004/0263173 A1 | 12/2004 | Gray |
| 2004/0263174 A1 | 12/2004 | Gray et al. |
| 2005/0070972 A1 | 3/2005 | Wahlstrand et al. |
| 2005/0197677 A1 | 9/2005 | Stevenson |
| 2005/0222658 A1 | 10/2005 | Hoegh et al. |
| 2006/0009819 A1 | 1/2006 | Przybyszewski |
| 2006/0100506 A1 | 5/2006 | Halperin et al. |
| 2006/0211979 A1 | 9/2006 | Smith et al. |
| 2006/0247684 A1 | 11/2006 | Halperin |
| 2007/0112398 A1 | 5/2007 | Stevenson et al. |
| 2007/0167867 A1 | 7/2007 | Wolf |
| 2007/0168005 A1 | 7/2007 | Gray |
| 2007/0255332 A1 | 11/2007 | Cabelka et al. |
| 2008/0049376 A1 | 2/2008 | Stevenson |
| 2008/0071313 A1 | 3/2008 | Stevenson et al. |
| 2008/0116997 A1 | 5/2008 | Dabney |
| 2008/0132987 A1 | 6/2008 | Westlund |
| 2008/0161886 A1 | 7/2008 | Stevenson et al. |
| 2008/0221638 A1 | 9/2008 | Wedan et al. |
| 2008/0262592 A1 | 10/2008 | Jordan et al. |
| 2009/0163980 A1 | 6/2009 | Stevenson |
| 2009/0243756 A1 | 10/2009 | Stevenson et al. |
| 2010/0160989 A1 | 6/2010 | Legay |
| 2010/0217341 A1 | 8/2010 | John et al. |
| 2010/0234907 A1 | 9/2010 | Dobak, III |

FOREIGN PATENT DOCUMENTS

| | | |
|---|---|---|
| EP | 466424 | 1/1992 |
| EP | 557127 | 8/1993 |
| EP | 0673621 | 9/1995 |
| EP | 0498996 | 3/1997 |
| EP | 0930509 | 12/1998 |
| EP | 1021730 | 4/1999 |
| JP | 60141034 | 7/1985 |
| JP | 61181925 | 8/1985 |
| JP | 62233905 | 10/1987 |
| JP | 4071536 | 3/1992 |
| JP | 6054823 | 3/1994 |
| JP | 6199470902 | 3/1994 |
| JP | 994238 | 4/1997 |
| JP | 11239572 | 9/1999 |
| WO | 87/04080 | 7/1987 |
| WO | 92/10213 | 6/1992 |
| WO | 94/23782 | 10/1994 |
| WO | 97/12645 | 4/1997 |
| WO | 97/40396 | 10/1997 |
| WO | 98/52461 | 11/1998 |
| WO | 99/19739 | 4/1999 |
| WO | 00/10456 | 3/2000 |
| WO | 00/25672 | 5/2000 |
| WO | 02/083016 | 10/2002 |
| WO | 2008077037 | 6/2008 |
| WO | 2010008833 | 1/2010 |

OTHER PUBLICATIONS

Roger Christoph Luchinger, Safety Aspects of Cardiac Pacemakers in Magnetic Resonance Imaging, a dissertation submitted to the Swiss Federal Institute of Technology Zurich, Zurich, Switzerland, 2002.

Constatine A. Balanis, Advanced Engineering Electromagnetics, John Wiley & Sons, Inc., 1989.

Robert C. Susil, Christopher J. Yeung, Henry R. Halperin, Albert CL. Lardo, Ergin Atalar, Multifunctional Interventional Devices for MRI: A Combined Electrophysiology/MRI Catheter, Magnetic Resonance in Medicine, 2002, pp. 594-600, Wiley-Liss, Inc., Departments of Biomedical Engineering, Radiology & Medicine, Johns Hopkins University School of Medicine, Baltimore, Maryland.

Robert C. Susil, Ergin Atalar, Albert Lardo, Multifunctional Interventional Devices for Use in MRI, U.S. Appl. No. 60/283,725, filed Apr. 13, 2001.

European Search Report dated Oct. 10, 2012.

European Search Report dated Sep. 19, 2012.

Mauritis K. Konings, Lambertus W. Bartels, Henk F.M. Smits and Chris J.G. Bakker. "Heating around Intravascular Guidewires by Resonating RF Waves," Journal of Magnetic Resonance Imaging, 12:79-85, 2000.

Michael J. Weiner, Wilson Greatbatch, Patrick R. Connelly, U.S. Appl. No. 60/269,817, filed Feb. 20, 2001, entitled "Electromagnetic Interference Immune Cardiac Assist System."

European search report dated Sep. 19, 2012 from the European Patent Office.

European Search Report dated Oc. 10, 2012.

European Search Report dated Nov. 26, 2012.

Creighton F M et al: Safe Superconducting Current Discharge for the Magnetic Steriotaxis System, IEEE Transactions on Magnetics, IEEE Service Center, New York, NY, US, vol. 35, No. 5, Sep. 1, 1999, pp. 4285-4290, XP011087608.

* cited by examiner

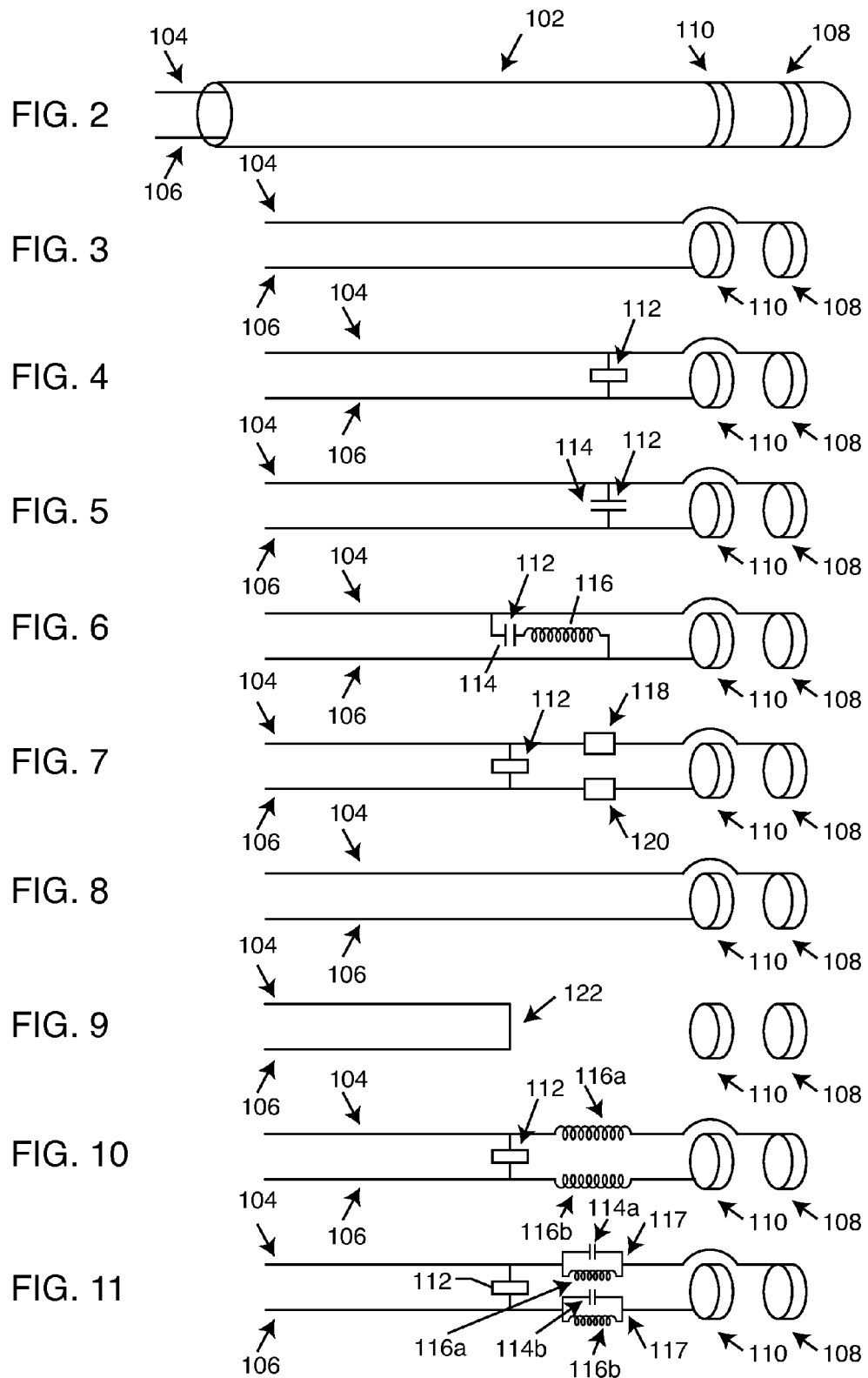

$$f_r = \frac{1}{2\pi\sqrt{LC}}$$

Where:   fr = resonant frequency
         L = inductance in henries
         C = capacitance in farads Solving for C:                    Solving for L:

$$C = \frac{1}{(f_r)^2 (2\pi)^2 L}$$      $$L = \frac{1}{(f_r)^2 (2\pi)^2 C}$$

→ assume a 1.5 Tesla MRI System,
    then the RF pulsed frequency = 64 MHz

→ assume that L = 150 nanohenry (150 x 10$^{-9}$ H)

then; solving for C:

FIG. 20 $$z_{ab} = \frac{(j\omega L)(-j/\omega C)}{(j\omega L - j/\omega C)}$$

FIG. 21 $$X_L = +j(2\pi fL) = +j\omega L$$
$$X_C = -j\left(\frac{1}{2\pi fC}\right) = \frac{-j}{\omega C}$$

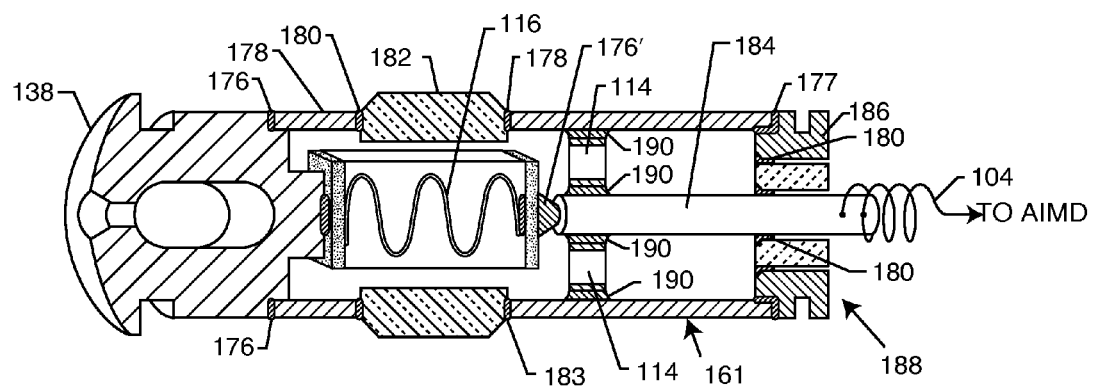
FIG. 34
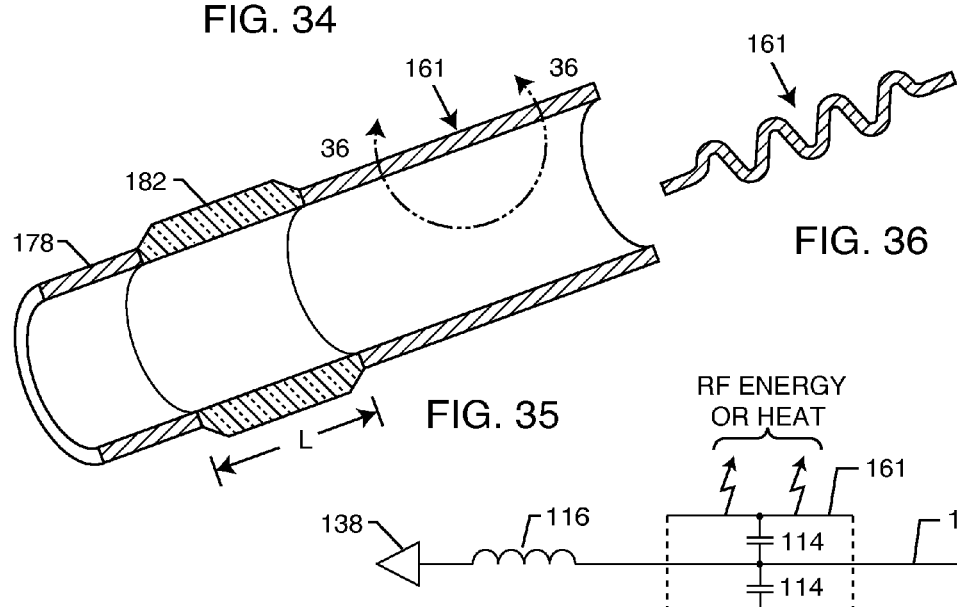
FIG. 36
FIG. 35
FIG. 37
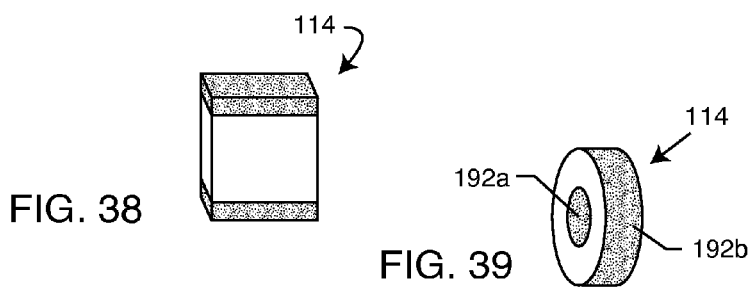
FIG. 38
FIG. 39

WHERE    C = CAPACITANCE IN FARADS
              L = INDUCTANCE IN HENRYS
              R = RESISTANCE (INCLUDES RESISTANCE OF
                     INDUCTOR, HOOK-UP WIRE & CAPACITOR
                     EQUILIVANT SERIES RESISTANCE (ESR)

RESONANT FREQUENCY = $F_r$

WHERE $F_r = \dfrac{1}{2\pi\sqrt{LC}}$

WHERE $F_r$ IS IN HERTZ

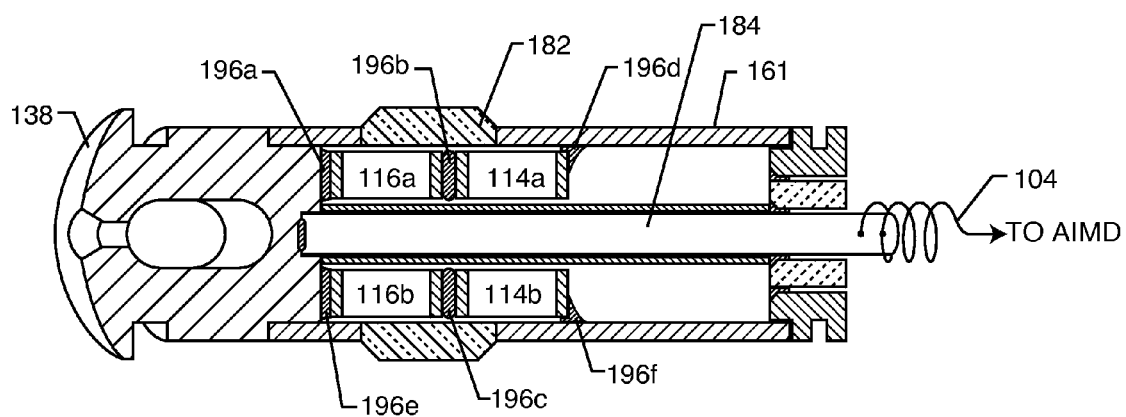
FIG. 48
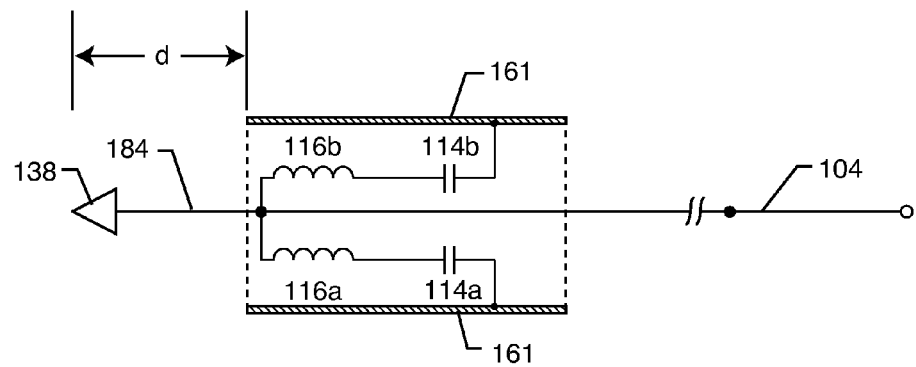
FIG. 49
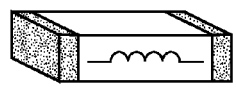 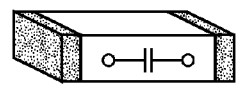
FIG. 50  FIG. 51

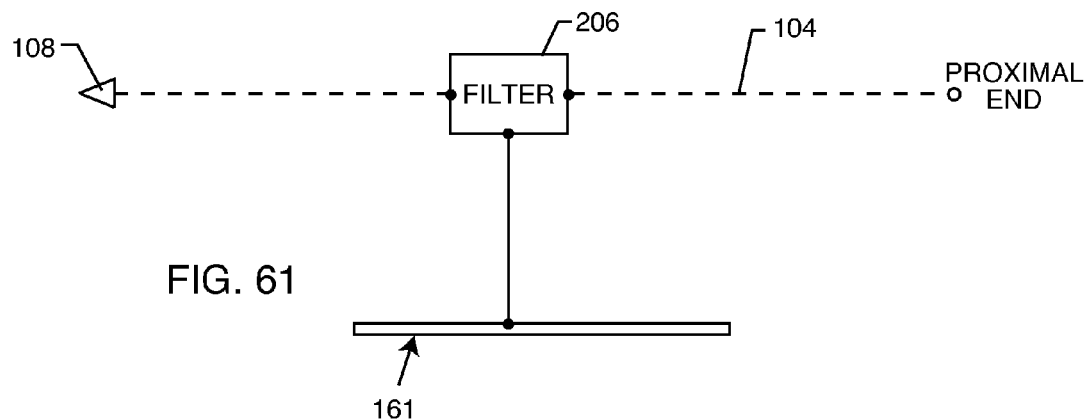
FIG. 61
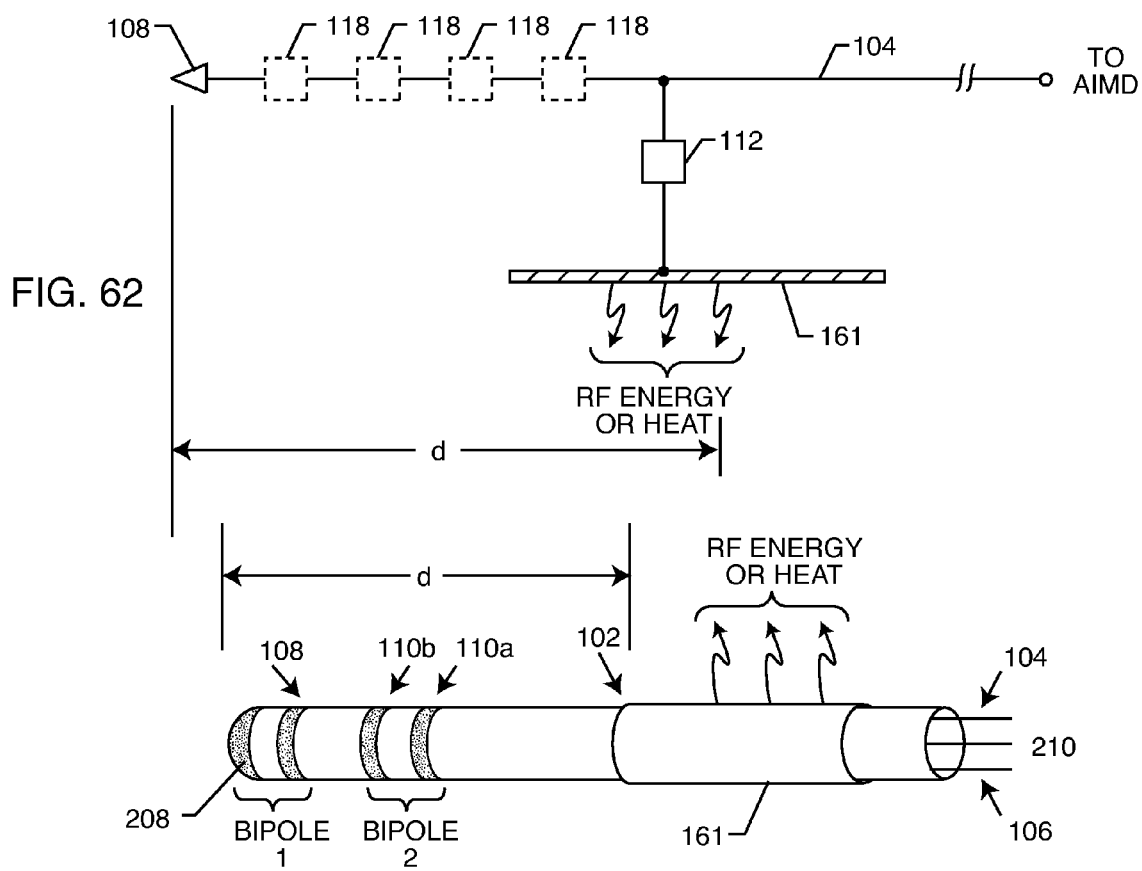
FIG. 62
FIG. 63

NORMAL OPERATING MODE

MRI COMPATIBLE MODE

MRI PULSED RF (HIGH) FREQUENCY MODEL

MRI GRADIENT (LOW) FREQUENCY MODEL

SWITCHED SAFETY PROTECTION CIRCUIT FOR AN AIMD SYSTEM DURING EXPOSURE TO HIGH POWER ELECTROMAGNETIC FIELDS

CROSS-REFERENCE TO RELATED APPLICATIONS

This application claims priority from parent application Ser. Nos. 12/489,921, now U.S. Pat. No. 7,751,903.

FIELD OF INVENTION

This invention generally relates to the problem of energy induced on implanted leads during medical diagnostic procedures such as magnetic resonant imaging (MRI). Specifically, the radio frequency (RF) pulsed field of MRI can couple to an implanted lead in such a way that electromagnetic forces (EMFs) are induced in the lead. The amount of energy that is induced is related to a number of complex factors, but in general, is dependent upon the local electric field that is tangent to lead and the integral of the electric field strength along the lead. In certain situations, these EMFs can cause currents to flow into distal electrodes or in the electrode interface with body tissue. It has been documented that when this current becomes excessive, that overheating of said lead or its associated electrode or overheating of the associated interface with body tissue can occur. There have been cases of damage to such body tissue which has resulted in loss of capture of cardiac pacemaking pulses, tissue damage, severe enough to result in brain damage or multiple amputations, and the like. The present invention relates generally to methods of redirecting said energy to other locations other than a distal tip electrode-to-tissue interface.

BACKGROUND OF THE INVENTION

Compatibility of probes, catheters, cardiac pacemakers, implantable defibrillators and other types of active implantable medical devices with magnetic resonance imaging (MRI) and other types of hospital diagnostic equipment has become a major issue. If one goes to the websites of the major cardiac pacemaker manufacturers in the United States, which include St. Jude Medical, Medtronic and Boston Scientific (formerly Guidant), one will see that the use of MRI is generally contra-indicated with pacemakers and implantable defibrillators. See also:
(1) Safety Aspects of Cardiac Pacemakers in Magnetic Resonance Imaging", a dissertation submitted to the Swiss Federal Institute of Technology Zurich presented by Roger Christoph Luchinger, Zurich 2002;
(2) "1. Dielectric Properties of Biological Tissues: Literature Survey", by C. Gabriel, S. Gabriel and E. Cortout;
(3) "II. Dielectric Properties of Biological Tissues: Measurements and the Frequency Range 0 Hz to 20 GHz", by S. Gabriel, R. W. Lau and C. Gabriel;
(4) "III. Dielectric Properties of Biological Tissues: Parametric Models for the Dielectric Spectrum of Tissues", by S. Gabriel, R. W. Lau and C. Gabriel; and
(5) "Advanced Engineering Electromagnetics, C. A. Balanis, Wiley, 1989;
(6) Systems and Methods for Magnetic-Resonance-Guided Interventional Procedures, U.S. Patent Application Publication No. US 2003/0050557, Susil and Halperin et. al, published Mar. 13, 2003;
(7) Multifunctional Interventional Devices for MRI: A Combined Electrophysiology/MRI Catheter, by, Robert C. Susil, Henry R. Halperin, Christopher J. Yeung, Albert C. Lardo and Ergin Atalar, MRI in Medicine, 2002; and
(8) Multifunctional Interventional Devices for Use in MRI, US 2003/0050557, and its underlying provisional application Ser. No. 60/283,725.

The contents of the foregoing are all incorporated herein by reference.

However, an extensive review of the literature indicates that MRI is indeed often used with pacemaker, neurostimulator and other active implantable medical device (AIMD) patients. The safety and feasibility of MRI in patients with cardiac pacemakers is an issue of gaining significance. The effects of MRI on patients' pacemaker systems have only been analyzed retrospectively in some case reports. There are a number of papers that indicate that MRI on new generation pacemakers can be conducted up to 0.5 Tesla (T). MRI is one of medicine's most valuable diagnostic tools. MRI is, of course, extensively used for imaging, but is also used for interventional medicine (surgery). In addition, MRI is used in real time to guide ablation catheters, neurostimulator tips, deep brain probes and the like. An absolute contra-indication for pacemaker or neurostimulator patients means that these patients are excluded from MRI. This is particularly true of scans of the thorax and abdominal areas. Because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the power of the MRI RF Pulsed field (Specific Absorption Rate—SAR level), programming the pacemaker to fixed or asynchronous pacing mode, and then careful reprogramming and evaluation of the pacemaker and patient after the procedure is complete. There have been reports of latent problems with cardiac pacemakers or other AIMDs after an MRI procedure sometimes occurring many days later. Moreover, there are a number of recent papers that indicate that the SAR level is not entirely predictive of the heating that would be found in implanted leads or devices. For example, for magnetic resonance imaging devices operating at the same magnetic field strength and also at the same SAR level, considerable variations have been found relative to heating of implanted leads. It is speculated that SAR level alone is not a good predictor of whether or not an implanted device or its associated leadwire system will overheat.

There are three types of electromagnetic fields used in an MRI unit. The first type is the main static magnetic field designated $B_0$ which is used to align protons in body tissue. The field strength varies from 0.5 to 3.0 Tesla in most of the currently available MRI units in clinical use. Some of the newer MRI system fields can go as high as 4 to 5 Tesla. At the recent International Society for Magnetic Resonance in Medicine (ISMRM), which was held on 5 and 6 Nov. 2005, it was reported that certain research systems are going up as high as 11.7 Tesla and will be ready sometime in 2010. This is over 100,000 times the magnetic field strength of the earth. A static magnetic field can induce powerful mechanical forces and torque on any magnetic materials implanted within the patient. This would include certain components within the cardiac pacemaker itself and/or leadwire systems. It is not likely (other than sudden system shut down) that the static MRI magnetic field can induce currents into the pacemaker leadwire system and hence into the pacemaker itself. It is a basic principle of physics that a magnetic field must either be time-varying as it cuts across the conductor, or the conductor itself must move within a specifically varying magnetic field for currents to be induced.

The second type of field produced by magnetic resonance imaging is the pulsed RF field which is generated by the body coil or head coil. This is used to change the energy state of the protons and elicit MRI signals from tissue. The RF field is homogeneous in the central region and has two main components: (1) the electric field is circularly polarized in the actual plane; and (2) the H field, sometimes generally referred to as the net magnetic field in matter, is related to the electric field by Maxwell's equations and is relatively uniform. In general, the RF field is switched on and off during measurements and usually has a frequency of 21 MHz to 64 MHz to 128 MHz depending upon the static magnetic field strength. The frequency of the RF pulse for hydrogen scans varies by the Lamor equation with the field strength of the main static field where: RF PULSED FREQUENCY in MHz=(42.56) (STATIC FIELD STRENGTH IN TESLA). There are also phosphorous and other types of scanners wherein the Lamor equation would be different. The present invention applies to all such scanners.

The third type of electromagnetic field is the time-varying magnetic gradient fields designated $B_X$, $B_Y$, $B_Z$, which are used for spatial localization. These change their strength along different orientations and operating frequencies on the order of 1 kHz. The vectors of the magnetic field gradients in the X, Y and Z directions are produced by three sets of orthogonally positioned coils and are switched on only during the measurements. In some cases, the gradient field has been shown to elevate natural heart rhythms (heart beat). This is not completely understood, but it is a repeatable phenomenon. The gradient field is not considered by many researchers to create any other adverse effects.

It is instructive to note how voltages and electro-magnetic interference (EMI) are induced into an implanted lead system. At very low frequency (VLF), voltages are induced at the input to the cardiac pacemaker as currents circulate throughout the patient's body and create voltage drops. Because of the vector displacement between the pacemaker housing and, for example, the tip electrode, voltage drop across the resistance of body tissues may be sensed due to Ohms Law and the circulating current of the RF signal. At higher frequencies, the implanted lead systems actually act as antennas where voltages (EMFs) are induced along their length. These antennas are not very efficient due to the damping effects of body tissue; however, this can often be offset by extremely high power fields (such as MRI pulsed fields) and/or body resonances. At very high frequencies (such as cellular telephone frequencies), EMI signals are induced only into the first area of the lead system (for example, at the header block of a cardiac pacemaker). This has to do with the wavelength of the signals involved and where they couple efficiently into the system.

Magnetic field coupling into an implanted lead system is based on loop areas. For example, in a cardiac pacemaker unipolar lead, there is a loop formed by the lead as it comes from the cardiac pacemaker housing to its distal tip, for example, located in the right ventricle. The return path is through body fluid and tissue generally straight from the tip electrode in the right ventricle back up to the pacemaker case or housing. This forms an enclosed area which can be measured from patient X-rays in square centimeters. Per ANSI/AAMI National Standard PC69, the average loop area is 200 to 225 square centimeters. This is an average and is subject to great statistical variation. For example, in a large adult patient with an abdominal implant, the implanted loop area is much larger (around 400 square centimeters).

Relating now to the specific case of MRI, the magnetic gradient fields would be induced through enclosed loop areas. However, the pulsed RF fields, which are generated by the body coil, would be primarily induced into the leadwire system by antenna action. Subjected to RF frequencies, the lead itself can exhibit complex transmission line behavior.

At the frequencies of interest in MRI, RF energy can be absorbed and converted to heat. The power deposited by RF pulses during MRI is complex and is dependent upon the power (Specific Absorption Rate (SAR) Level) and duration of the RF pulse, the transmitted frequency, the number of RF pulses applied per unit time, and the type of configuration of the RF transmitter coil used. The amount of heating also depends upon the volume of tissue imaged, the electrical resistivity of tissue and the configuration of the anatomical region imaged. There are also a number of other variables that depend on the placement in the human body of the AIMD and its associated leadwire(s). For example, it will make a difference how much EMF is induced into a pacemaker lead system as to whether it is a left or right pectoral implant. In addition, the routing of the lead and the lead length are also very critical as to the amount of induced current and heating that would occur. Also, distal tip design is very important as the distal tip itself can heat up due to MRI RF induced eddy currents. The cause of heating in an MRI environment is twofold: (a) RF field coupling to the lead can occur which induces significant local heating; and (b) currents induced between the distal tip and tissue during MRI RF pulse transmission sequences can cause local Ohms Law heating in tissue next to the distal tip electrode of the implanted lead. The RF field of an MRI scanner can produce enough energy to induce RF voltages in an implanted lead and resulting currents sufficient to damage some of the adjacent myocardial tissue. Tissue ablation (destruction resulting in scars) has also been observed. The effects of this heating are not readily detectable by monitoring during the MRI. Indications that heating has occurred would include an increase in pacing threshold, venous ablation, Larynx or esophageal ablation, myocardial perforation and lead penetration, or even arrhythmias caused by scar tissue. Such long term heating effects of MRI have not been well studied yet for all types of AIMD leadwire geometries. There can also be localized heating problems associated with various types of electrodes in addition to tip electrodes. This includes ring electrodes or pad electrodes. Ring electrodes are commonly used with a wide variety of implanted devices including cardiac pacemakers, and neurostimulators, and the like. Pad electrodes are very common in neurostimulator applications. For example, spinal cord stimulators or deep brain stimulators can include a plurality of pad electrodes to make contact with nerve tissue. A good example of this also occurs in a cochlear implant. In a typical cochlear implant there would be sixteen pad electrodes placed up into the cochlea. Several of these pad electrodes make contact with auditory nerves.

Although there are a number of studies that have shown that MRI patients with active implantable medical devices, such as cardiac pacemakers, can be at risk for potential hazardous effects, there are a number of reports in the literature that MRI can be safe for imaging of pacemaker patients when a number of precautions are taken (only when an MRI is thought to be an absolute diagnostic necessity). While these anecdotal reports are of interest, they are certainly not scientifically convincing that all MRI can be safe. For example, just variations in the pacemaker leadwire length can significantly affect how much heat is generated. A paper entitled, HEATING AROUND INTRAVASCULAR GUIDEWIRES BY RESONATING RF WAVES by Konings, et al., Journal of Magnetic Resonance Imaging, Issue 12:79-85 (2000), does an excellent job of explaining how the RF fields from MRI scanners can couple into implanted leadwires. The paper includes both a theoretical approach and actual temperature measurements. In a worst-case, they measured temperature rises of up to 74 degrees C. after 30 seconds of scanning exposure. The contents of this paper are incorporated herein by reference.

The effect of an MRI system on the function of pacemakers, ICDs, neurostimulators and the like, depends on various factors, including the strength of the static magnetic field, the pulse sequence, the strength of RF field, the anatomic region being imaged, and many other factors. Further complicating this is the fact that each patient's condition and physiology is different and each manufacturer's pacemaker and ICD designs also are designed and behave differently. Most experts still conclude that MRI for the pacemaker patient should not be considered safe.

It is well known that many of the undesirable effects in an implanted lead system from MRI and other medical diagnostic procedures are related to undesirable induced EMFs in the lead system and/or RF currents in its distal tip (or ring) electrodes. This can lead to overheating of body tissue at or adjacent to the distal tip.

Distal tip electrodes can be unipolar, bipolar and the like. It is very important that excessive current not flow at the interface between the lead distal tip electrode and body tissue. In a typical cardiac pacemaker, for example, the distal tip electrode can be passive or of a screw-in helix type as will be more fully described. In any event, it is very important that excessive RF current not flow at this junction between the distal tip electrode and for example, myocardial or nerve tissue. This is because tissue damage in this area can raise the capture threshold or completely cause loss of capture. For pacemaker dependent patients, this would mean that the pacemaker would no longer be able to pace the heart. This would, of course, be life threatening for a pacemaker dependent patient. For neurostimulator patients, such as deep brain stimulator patients, the ability to have an MRI is equally important.

A very important and life-threatening problem is to be able to control overheating of implanted leads during an MRI procedure. A novel and very effective approach to this is to install parallel resonant inductor and capacitor bandstop filters at or near the distal electrode of implanted leads. For cardiac pacemaker, these are typically known as the tip and ring electrodes. One is referred to U.S. Pat. No. 7,363,090; US 2007/0112398 A1; US 2008/0071313 A1; US 2008/0049376 A1; US 2008/0024912 A1; US 2008/0132987 A1; and US 2008/0116997 A1, the contents of all of which are incorporated herein. Referring now to US 2007/0112398 A1, the invention therein relates generally to L-C bandstop filter assemblies, particularly of the type used in active implantable medical devices (AIMDs) such as cardiac pacemakers, cardioverter defibrillators, neurostimulators and the like, which raise the impedance of internal electronic or related wiring components of the medical device at selected frequencies in order to reduce or eliminate currents induced from undesirable electromagnetic interference (EMI) signals.

U.S. Pat. No. 7,363,090 and US 2007/0112398 A1 show resonant L-C bandstop filters to be placed at the distal tip and/or at various locations along the medical device leadwires or circuits. These L-C bandstop filters inhibit or prevent current from circulating at selected frequencies of the medical therapeutic device. For example, for an MRI system operating at 1.5 Tesla, the pulse RF frequency is 64 MHz, as described by the Lamour Equation for hydrogen. The L-C bandstop filter can be designed to resonate at or near 64 MHz and thus create a high impedance (ideally an open circuit) in the lead system at that selected frequency. For example, the L-C bandstop filter, when placed at the distal tip electrode of a pacemaker lead, will significantly reduce RF currents from flowing through the distal tip electrode and into body tissue. The L-C bandstop filter also reduces EMI from flowing in the leadwires of a pacemaker, for example, thereby providing added EMI protection to sensitive electronic circuits.

Electrically engineering a capacitor in parallel with an inductor is known as a bandstop filter or tank circuit. It is also well known that when a near-ideal L-C bandstop filter is at its resonant frequency, it will present a very high impedance. Since MRI equipment produces very large RF pulsed fields operating at discrete frequencies, this is an ideal situation for a specific resonant bandstop filter. Bandstop filters are more efficient for eliminating one single frequency than broadband filters. Because the L-C bandstop filter is targeted at this one frequency, it can be much smaller and volumetrically efficient.

A major challenge for designing an L-C bandstop filter for human implant is that it must be very small in size, biocompatible, and highly reliable. Coaxial geometry is preferred. The reason that coaxial is preferred is that implanted leads are placed at locations in the human body primarily by one of two main methods. These include guide wire lead insertion. For example, in a cardiac pacemaker application, a pectoral pocket is created. Then, the physician makes a small incision between the ribs and accesses the subclavian vein. The pacemaker leadwires are stylus guided/routed down through this venous system through the superior vena cava, through the right atrium, through the tricuspid valve and into, for example, the right ventricle. Another primary method of implanting leads (particularly for neurostimulators) in the human body is by tunneling. In tunneling, a surgeon uses special tools to tunnel under the skin and through the muscle, for example, up through the neck to access the Vagus nerve or the deep brain. In both techniques, it is very important that the leads and their associated electrodes at the distal tips be very small. US 2007/0112398 A1 solves these issues by using miniature coaxial or rectilinear capacitors that have been adapted with an inductance element to provide a parallel L-C bandstop filter circuit.

Prior art capacitors used in design of bandstop filters typically consist of ceramic discoidal feedthrough capacitors and also single layer and multilayer tubular capacitors and multilayer rectangular capacitors, and thick-film deposited capacitors. US 2007/0112398 A1 shows design methodologies to adapt all of these previous tubular, feedthrough or rectangular technologies to incorporate a parallel inductor in novel ways. It will be obvious to those skilled in the art that a number of other capacitor technologies can be adapted. This includes film capacitors, glass capacitors, tantalum capacitors, electrolytic capacitors, stacked film capacitors and the like.

As previously mentioned, the value of the capacitance and the associated parallel inductor can be adjusted to achieve a specific resonant frequency (SRF). The bandstop filters described in US 2007/0112398 A1 can be adapted to a number of locations within the overall implantable medical device system. That is, the L-C bandstop filter can be incorporated at or near any part of the medical device implanted lead system or at or adjacent to the distal tip electrodes. In addition, the L-C bandstop filter can be placed anywhere along the implanted lead system.

The L-C bandstop filters are also designed to work in concert with an EMI filter which is typically used at the point of leadwire ingress and egress of the active implantable medical device. For example, see U.S. Pat. No. 5,333,095; U.S. Pat. No. 5,905,627; U.S. Pat. No. 5,896,627; and U.S. Pat.

No. 6,765,779, the contents of all being incorporated herein by reference. All four of these documents describe low pass EMI filter circuits. Accordingly, the L-C bandstop filters, as described in U.S. Pat. No. 7,393,090, are designed to be used in concert with such low pass filters.

When the value of a hermetic feedthrough filter capacitor is too high, the leading edge of MRI gradient pulse sequences can create an R-C charging circuit. As the feedthrough capacitor charges up this voltage fall can create one of two problems. First, the voltage induced on the leadwire system could directly capture the heart thereby creating a dangerously rapid heart rate which could then result in a dangerous ventricular arrhythmia. For example, ventricular fibrillation can result in sudden death. Another problem associated with too high of a value of a feedthrough capacitor at the input to the AIMD is that this R-C charging circuit can cause pulses to appear at the input sense amplifier (such as a cardiac pacemaker) such that the pacemaker would oversense or falsely interpret this input as a normal heartbeat. In certain cases this can cause a demand pacemaker to inhibit (stop pacing). For a pacemaker dependent patient this can lead to systole and be immediately life threatening. Accordingly, it is desirable for magnetic resonance compatibility to keep the value of the feedthrough capacitor relatively low (in the order of 1000 picofarads). On the other hand, in order to adequately protect AIMD device electronics from the powerful RF pulse field of MRI, we have a trade off in that it would be desirable to have the hermetic feedthrough capacitor be as large as value as possible (in the order of 4,000 to 6,000 picofarads).

When one performs MRI testing on an active implantable medical device (AIMD) with its associated lead system, one first establishes a controlled measurement. That is, with worst-case MRI equipment settings and a worst-case location within the MRI bore, and a worst-case lead configuration, one can measure heating using fiber optic probes at the distal electrodes. Temperature rises of 30 to over 60 degrees C. have been documented. When one takes the same control lead and places miniature bandstop filters in accordance with U.S. Pat. No. 7,363,090 or US 2007/0112398 A1, one finds that the distal electrodes are substantially cooled. In fact, in many measurements made by the inventors, temperature rises of over 30 degrees C. have been reduced to less than 3 degrees C. However, a secondary problem has been discovered. That is, the implanted lead acts very much as like a transmission line. When one creates a very high impedance at the distal electrode to tissue interface by installation of a resonant bandstop filter as described in U.S. Pat. No. 7,038,900 and as further described in US 2007/0112398 A1, there is created an almost open circuit which is the equivalent of an unterminated transmission line. This causes a reflection of MRI induced RF energy back towards the AIMD (for example, toward the pacemaker housing). This energy can be reflected back and forth resulting in temperature rises along the lead. In some cases, the inventors have measured temperature rises immediately proximal to the bandstop filters, which is undesirable.

Accordingly, there is a need for controlling the induced energy in implanted lead system. This may be accomplished by taking a system approach and carefully balance the filtering needs. Moreover, there is a need for novel tuned RF diverting circuits coupled to one or more energy or heat dissipation surfaces, which are frequency selective and are constructed of passive components. Such circuits are needed to prevent MRI induced energy from reaching the distal tip electrode or its interface with body tissue. By redirecting said energy to an energy dissipation surface distant from the distal electrodes, this minimizes or eliminates hazards associated with overheating of said lead and/or its distal electrodes during diagnostic procedures, such as MRI. Frequency selective diverter circuits are needed which decouple and transfer energy which is induced onto implanted leads from the MRI pulsed RF field to an energy dissipating surface. In this regard, a novel system is needed which can utilize the conductive housing (can) of the AIMD itself as the energy dissipation surface. A switched diverter circuit would be beneficial in such a system for minimizing heating of an implanted lead in a high power electromagnetic field environment. The present invention fulfills these needs and provides other related advantages.

SUMMARY OF THE INVENTION

The present invention includes an overall energy management system capable of controlling the energy induced in implanted leads from the RF pulsed field of MRI scanners. The term "implanted lead" as used herein includes permanently implanted leads or long-term implanted leads such as those that might be associated with an active implantable medical device such as a cardiac pacemaker. However, "implanted lead" or "lead" as used herein also includes temporary implants such as those from probes or catheters. For example, it is becoming increasingly important to perform real time mapping and catheter ablation while using MRI for real-time imaging of scar tissue. The term "implanted lead" as used herein can also include temporary implanted leads from loop recorders, probes or catheters or even implanted leads that are attached to an external device such as externally worn spinal cord or pain control stimulator.

More particularly, the present invention relates to a switched safety protection circuit for an AIMD system during exposure to high power electromagnetic fields. The switched safety protection circuit comprises (1) an active implantable medical device (AIMD) including AIMD electronics, (2) an implanted lead or leadwire associated with the AIMD electronics, (3) an energy dissipating surface associated with the implanted lead or the leadwire, (4) a diversion circuit associated with the energy dissipating surface, and (5) at least one switch disposed between the diversion circuit and the AIMD electronics, for diverting energy.

In some embodiments, the diversion circuit is permanently conductively connected between the implanted lead or the leadwire and the energy dissipating surface. In others, a switch is associated with the diversion circuit and disposed between the lead or the leadwire and the energy dissipating surface. In this case, the switch associated with the diversion circuit may be disposed between the implanted lead or the leadwire and the diversion circuit. Alternatively, the switch associated with the diversion circuit may be disposed between the diversion circuit and the energy dissipating surface. The switch associated with the diversion circuit may comprise a single or multi-pole single or multi-throw switch. Said switch may comprise a MEMS switch, a mechanical switch, a reed switch, an electronic switch, a programmable switch, an automatically actuated switch, a Hall Effect switch, or a field effect transistor (FET) switch.

At least one switch may electrically open the implanted lead or the leadwire when diverting energy in the implanted lead or the leadwire through the diversion circuit to the energy dissipating surface, and simultaneously conductively couple the AIMD electronics to the energy dissipating surface. Here again, the switch may comprise a single or a multi-pole double-throw switch.

The AIMD electronics may include non-linear circuit elements, over-voltage circuit elements, transient voltage suppression diodes, Transorbs, AIMD sensing circuits and therapy delivery circuits.

The implanted lead or the leadwire has impedance characteristics at a selected RF frequency or frequency band. The diversion circuit likewise has impedance characteristics at least partially tuned to the implanted lead's or the leadwire's impedance characteristics. The selected RF frequency or frequency band may comprise an MRI frequency or a range of MRI frequencies. The diversion circuit also typically has a reactance and is vectorally opposite to the characteristic reactance of the implanted lead. Moreover, the diversion circuit typically has a capacitive reactance generally equal and opposite to the characteristic inductive reactance of the implanted lead. The capacitive reactance and the inductive reactance each have a resistor component.

The diversion circuit may comprise a low pass filter comprising a capacitor, an inductor, a Pi filter, a T filter, an LL filter, or an "n" element filter. Moreover, the diversion circuit may comprise a unipolar or multipolar feedthrough capacitor, at least one series resonant LC trap filter, or a plurality of L-C trap filters resonant respectively at different MRI frequencies.

The energy dissipating surface may comprise a housing for an active implantable medical device (AIMD). The AIMD may comprise an implantable hearing device, a neurostimulator, a brain stimulator, a cardiac pacemaker, a left ventricular assist device, an artificial heart, a drug pump, a bone growth stimulator, a urinary incontinence device, a spinal cord stimulator, an anti-tremor stimulator, an implantable cardioverter defibrillator, a congestive heart failure device, or a cardio resynchronization therapy device.

The diversion circuit may be disposed within the housing for the AIMD, and further may comprise a short to the housing. Alternatively, the diversion circuit may be disposed within a header block for the AIMD.

An EMI shield may be conductively coupled to the housing and coaxially extend about the lead or the leadwire in non-conductive relation. The diversion circuit may be conductively coupled to the EMI shield.

The diversion circuit may also comprise a high pass filter which prevents low frequency gradient field-induced energy in the implanted lead or the leadwire from passing through the diversion circuit to the energy dissipating surface. The high pass filter may comprise a resistor in series with a capacitor or an L-C trap filter.

The implanted lead typically has a length extending between and to a proximal end and a tissue-stimulating or biological-sensing electrode at or near a distal tip end. The diversion circuit may be disposed at or adjacent to the proximal end of the implanted lead or in a proximal lead connector.

An impedance circuit may be associated with the diversion circuit, for raising the high-frequency impedance of the implanted lead. The impedance circuit may comprise an inductor, a bandstop filter and/or a resistor.

The implanted lead may comprise at least a portion of a probe or a catheter, wherein the energy dissipating surface may comprise at a least a portion of a handle for the probe or the catheter.

The implanted lead may comprise at least a pair of leads each having a length extending between and to a proximal end and a tissue-stimulating or biological-sensing electrode at a distal tip end. The diversion circuit may couple each of the leads to the energy dissipating surface, or the diversion circuit may be coupled between the pair of leads.

The energy dissipating surface may comprise a material capable of being visualized during a magnetic resonance scan, and include a biomimetic coating.

Further, the diversion circuit may include at least one non-linear circuit element such as a transient voltage suppressor or a diode.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 2 is a diagrammatic view of a typical probe or catheter;

FIG. 3 is an electrical diagrammatic view of the interior of the prober or catheter of FIG. 2;

FIG. 4 is an electrical diagrammatic view of the structure shown in FIG. 3, with a general impedance element connected between leadwires;

FIG. 5 is an electrical diagrammatic view similar to FIG. 4, illustrating a capacitor representing a frequency dependent reactive element between the leadwires;

FIG. 6 is a view similar to FIG. 5, wherein the general reactance element has been replaced by a capacitor in series with an inductor;

FIG. 7 is a view similar to FIGS. 4-6, showing the addition of series frequency selective reactances;

FIG. 8 is similar to FIG. 3, showing a low frequency model of the catheter and associated leads described in FIG. 2;

FIG. 9 is a view similar to FIGS. 3-8, illustrating how the distal rings are electrically isolated at a high frequency;

FIG. 10 is a view similar to FIGS. 3-9, showing the addition of series inductor components added to the frequency selective elements 20;

FIG. 11 is similar to FIGS. 3-10, illustrating frequency selective elements which incorporate parallel resonant inductor and capacitor bandstop filters;

FIG. 18 is a chart showing the calculation of the frequency of resonance for a parallel L-C tank circuit of FIG. 15;

FIG. 20 illustrates the equation for the impedance for the inductor in parallel with the capacitor;

FIG. 21 gives the equations for inductive reactance $X_L$ and capacitive reactance $X_C$;

FIG. 34 is a sectional view of an hermetically sealed electrode assembly designed for contact with body fluid;

FIG. 35 is a perspective sectional view of a housing portion of the sealed electrode assembly of FIG. 34;

FIG. 36 is an enlarged sectional view corresponding generally with the encircled region 36-36 of FIG. 35, and illustrating the principle of increasing the surface area of the energy dissipating surface;

FIG. 37 is a schematic circuit diagram corresponding with the sealed electrode assembly of FIG. 34;

FIG. 38 is a perspective view of an exemplary monolithic capacitor for use in the circuit of FIG. 37;

FIG. 39 is a perspective view of an exemplary unipolar feedthrough capacitor for use in the circuit of FIG. 37;

FIG. 48 is a sectional view similar to FIGS. 34, 40 and 41, but shows still another alternative embodiment of the invention for decoupling RF signals from an electrode leadwire;

FIG. 49 is a schematic circuit diagram corresponding with the sealed electrode assembly of FIG. 48;

FIG. 50 illustrates a typical chip inductor for use in the sealed electrode assembly of FIG. 48;

FIG. 51 illustrates a typical chip capacitor for use in the sealed electrode assembly of FIG. 48;

FIG. 61 is a schematic circuit diagram depicting a general filter element constructed in accordance with any one of the embodiments shown and described herein, wherein the filter element is coupled between the distal and proximal ends of a leadwire or the like, for dissipating RF energy or heat to an adjacent energy dissipating surface;

FIG. 62 is a schematic circuit diagram similar to FIG. 61, but showing alternative design considerations;

FIG. 63 depicts in somewhat schematic form a probe or catheter constructed in accordance with the present invention;

FIG. 67 is an enlarged, fragmented sectional view taken along the line 67-67 from FIG. 66, illustrating a roughened surface formed through, for example, plasma or chemical etching, or the like;

DETAILED DESCRIPTION OF THE PREFERRED EMBODIMENTS

Figure 1:
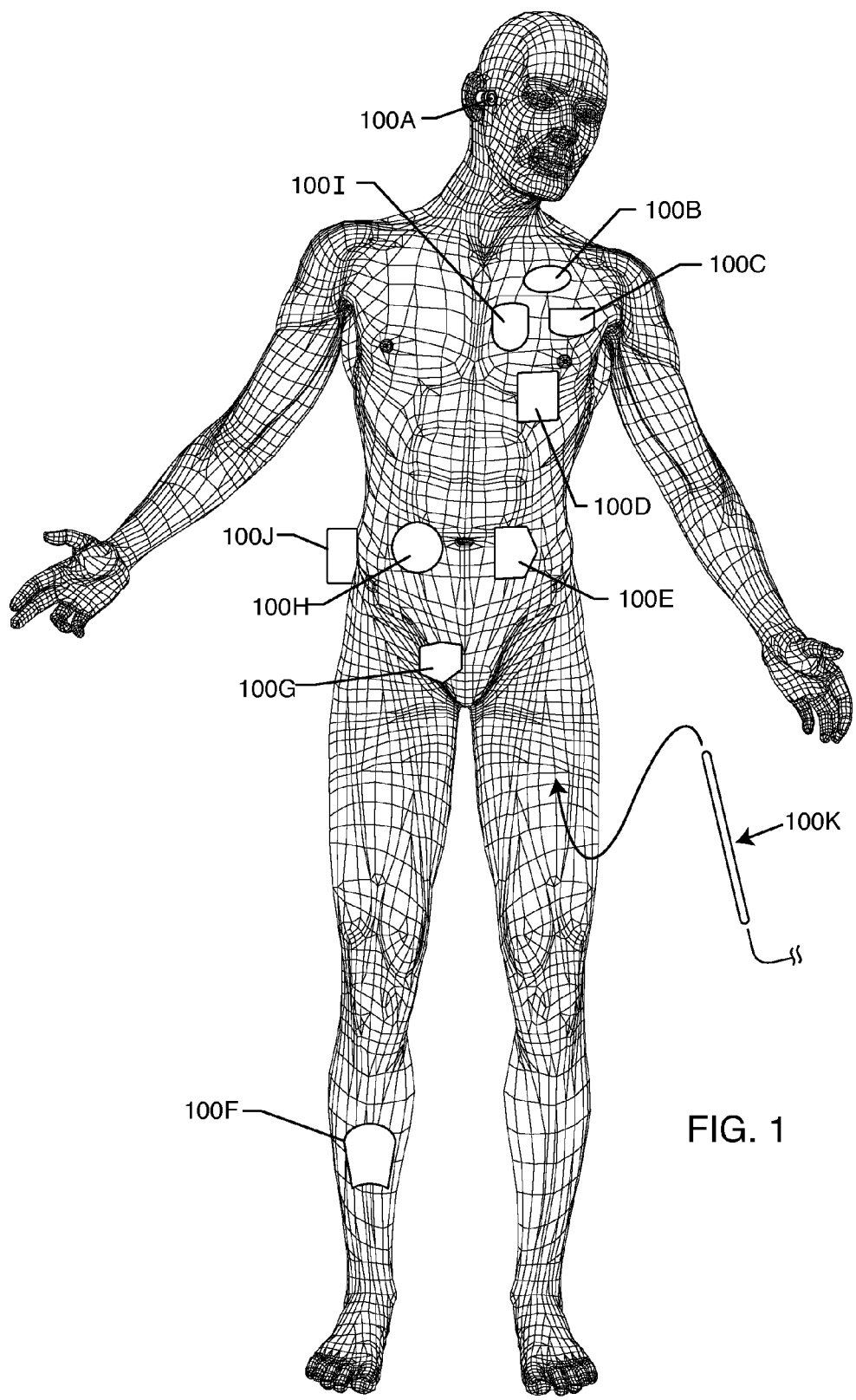
FIG. 1 is a wire-formed diagram of a generic human body showing a number of exemplary implanted medical devices.

As shown in the drawings for purposes of illustration, the present invention resides in a tuned energy balanced system including a switched diverter circuit, for minimizing heating of an implanted lead in a high power electromagnetic field environment. The tuned energy balanced system comprises an implanted lead having impedance characteristics at a selected RF frequency or frequency band, and an energy dissipating surface associated with the implanted lead. An energy diversion circuit conductively couples the implanted lead to the energy dissipating surface. The diversion circuit comprises one or more passive electronic network components whose impedance characteristics are at least partially tuned to the implanted lead's impedance characteristics, to facilitate transfer to the energy dissipating surface of high frequency energy induced on the implanted lead at the selected RF frequency or frequency band.

More particularly, the present invention resides in a switched diverter circuit comprising at least one switch for diverting energy in the implanted lead or a leadwire through the diversion circuit to the energy dissipating surface. In alternate embodiments, the switch is disposed between the implanted lead or the leadwire and the diversion circuit, or it is situated such that it electrically opens the implanted lead or the leadwire when diverting energy in the implanted lead or the leadwire through the diversion circuit to the energy dissipating surface. The switch may comprise a single or a multi-pole double throw or single throw switch.

In one preferred embodiment, the invention resides in a combination of bandstop filters placed at or near the distal electrode-to-tissue interface of implanted leads such bandstop filters are best used in combination with the novel frequency selective diverter circuits of the present invention decouple energy induced on the implanted leads at a frequency or frequency band of an interest to an energy dissipating surface such as the AIMD housing. This can happen to a certain extent, when the AIMD already has a low-pass filter capacitor at its point of leadwire ingress or egress. As previously mentioned, feedthrough filtered capacitors are well known in the art. For example, reference is made to U.S. Pat. Nos. 4,424,551; 5,333,095; 6,765,779 and the like. Feedthrough capacitors, of course, are well known in the prior art and are used as EMI filters. For example, in a cardiac pacemaker application, it is very common that feedthrough-type filter capacitors, at the point of leadwire ingress/egress to the pacemaker housing, would be used to decouple various signals from cell phones and other emitters typically found in the patient environment. As will be described herein, it is very important that the value of a low pass filter capacitor be carefully selected such that the capacitive reactance is approximately equal to the characteristic inductive reactance of the implanted lead system. Certain implanted leads may have a characteristic impedance that includes capacitive reactance. In this case the novel diverter circuits of the present invention would include inductive elements in order to cancel the capacitive reactance of the implanted lead. However, there are many types of AIMDs that do not use feedthrough filters. These AIMDs generally do not have sense circuits and are therefore inherently much less susceptible to electromagnetic interference. Examples include many types of neurostimulators, including pain control stimulators, bladder control stimulators, deep brain stimulators, cochlear implants and the like.

Accordingly, when bandstop filters are installed at or near the distal electrode of an implanted lead, the RF energy induced by the MRI pulse field is prevented from flowing into body tissues and thereby being dissipated. However, when bandstop filters are used, that energy still resides in the lead system. In other words, by preventing this induced energy from flowing to sensitive tissues at distal electrode interfaces, a great deal has been accomplished; however, it is still important to carefully dissipate the remaining energy that's trapped in the lead system. The most efficient way to do this is to use the metallic housing of the AIMD. One type of frequency selective network, is of course, the prior art feedthrough capacitors that were used for EMI filters. However, to provide optimal decoupling, one has to refer to the maximum power transfer theorem. When one has an ideal source, consisting of a voltage source and a series impedance, this is known as a Thevenin Equivalent Circuit. It is well known in electrical engineering that to transfer maximum power to a load that the load impedance must be equal to the source impedance. If the source impedance is completely resistive, for example, 50 ohms, then to transfer maximum power, the load impedance would have to be 50 ohms. When the source impedance is reactive, then to transfer maximum power to another location, the load impedance should have the opposite sign of reactance and the same impedance and resistance. Referring to a typical implanted lead system, the implanted leads typically appear inductive. Accordingly, having a capacitive load at the point of leadwire ingress/egress to the AIMD housing, one has at least some cancellation of these imaginary impedance factors. In electrical engineering, the inductance of the lead would be denoted by $+j\omega L$. The impedance of the capacitor, on the other hand, is a $-j/\omega C$ term. In the present invention, it's important to know the inductance property of the implanted lead system, so that an optimal value of capacitance between the AIMD housing and ground can be selected such that the +J component is nearly or completely canceled by the appropriate −J component of the capacitor.

However, for devices that have sense circuits (such as cardiac pacemakers and implantable cardioverter defibrillators), the typical lead impedance values result in a capacitance at the point of leadwire ingress that is too low for effective AIMD EMI protection. That is, the amount of inductance in the implanted lead system is relatively low which results in a cancellation capacitor which is also relatively low. This result in a capacitance value at the point of leadwire ingress and egress that is too low to effectively attenuate a broad range of EMI frequencies, including cellular telephones all the way down to, for example, 13.56 MHz RFID systems. In other words, one has, for some AIMDs, a trade-off that is simply unacceptable. On the one hand, for maximal MRI energy dissipation from the lead system, one would want the capacitance value to be equal and opposite in value to the inductance of the lead system, which would result in a capacitance value that would be too low (in the order of a few hundred picofarads). However, for optimal EMI filtering, one desires a filtered capacitor in the area of a few thousand picofarads. In other words, there is an order of magnitude problem here. As previously mentioned, this problem does not exist for AIMDs that do not employ feedthrough capacitors (in general, AIMDs that do not have sense circuits).

One does not have to exactly match the impedances of an implanted lead system to the diverter circuits of the present invention. As previously mentioned, implanted leads usually tend to be inductive, although in certain cases they can even be capacitive. What is important is that the diverter circuit has a reactance which is vectorially opposite to the characteristic reactance of the implanted lead. In other words, if the implanted lead is inductive, it will have a $+j\omega L$ inductive reactance in ohms. One would balance this with a $-j/\omega C$ capacitive reactance in the diverter circuit. In an ideal case, the reactance of the diverter circuit would be generally equal and opposite to the characteristic reactance of the implanted lead. In an absolutely ideal situation, the implanted lead would have a characteristic inductive reactance and the diverter circuit would have an equal but opposite vector quantity capacitive reactance which would cancel. In order to obtain optimal energy transfer to an EDS surface in this case, it would further enhance energy transfer if the diverter circuit also had a resistive value that is equal to the characteristic resistance of the implanted lead. Fortunately, when used in combination with a bandstop filter, it is not essential that the impedance or reactance of the diversion circuit be completely equal and opposite to the impedance or reactance of the implanted lead system.

The present invention is ideal for claiming MRI compatibility for a range of implanted leads. Using a cardiac pacemaker as an example, one may either through measurement or modeling characterize the impedance of leads of various lengths, such as 35 to 55 centimeters, and also analyze their characteristic impedance over various implant anatomical geometries. One could then determine an average impedance or reactance of this range of leads in order to design an averaged or optimized diverter circuit. Unlike for bandstop filters, the diverter circuit will generally work over a broad range of circuits, not just a single frequency. Accordingly, by using a properly tuned diverter circuit coupled to an energy dissipation surface of the present invention, one would be able to assure that a range of lead lengths, lead types and implant geometries will all be safe in a high electric magnetic field environment such as MRI.

In a first order approximation, the diverter circuit of the present invention can simply be a resistor which is attached to the characteristic resistance of the average of the implanted leads for which one claims compliance. For example, if the implanted leads generally have a resistance value of around 80 ohms, then one could achieve a very high degree of tuned energy balance with the present invention by having an 80 ohm resistor be coupled between the lead and the energy dissipating surface. This would not cancel the reactance of the lead system but would still go a long way to remove energy from the leads and transfer it to the EDS surface.

A way around this is to use what is known in the industry as an L-C series trap filter in combination with the prior art feedthrough capacitor. When an inductor and a capacitor appear in series, it will always be a single frequency at which the inductive reactance is equal and opposite to the capacitive reactance. At this point, the series L-C trap filter is said to be in resonance. For an ideal series L-C trap filter (one containing zero resistance), at resonance, it would present a short circuit. U.S. Pat. No. 6,424,234 describes L-C trap filters (also known as notch filters). The '234 patent describes notch filters for a completely different purpose and application. FIG. 10 of U.S. Pat. No. 6,424,234 shows notch filter attenuation in the kilohertz frequency range. The reason for this was to provide some degree of attenuation against low frequency emitters, such as 58 kHz electronic article surveillance (store security) gates. These gates detect tags on commercial items (such as clothing) as an anti-theft detection system. However, in the present invention, L-C trap filters can be used in combination with a prior art feedthrough capacitor and optimally tuned to dissipate the RF pulsed energy from an MRI system. For example, from a 1.5 Tesla system, the L-C trap filter would be tuned at the Lamour frequency of 64 MHz. One could also use multiple trap filters within the AIMD or the AIMD header block such that a short circuit or a low impedance was provided to multiple MRI systems such as 1.5 Tesla (64 MHz); 3 Tesla (128 MHz); 4 Tesla (170 MHz) or 5 Tesla (213 MHz). All realizable L-C trap filters have a series resistance. This series resistance comes from the resistance of the inductor windings or from the equivalent series resistance (ESR) of the capacitor, or both. It is a feature of the present invention, that the resistance of an L-C trap filter, when used as an energy tuning element to an EDS surface, approximate the characteristic resistance of the implanted lead. In accordance with Thevenin's maximum power transfer theorem, this will dissipate maximum energy at the selected MRI frequency to the EES surface.

The present invention includes switched frequency selective diversion (decoupling) circuits which transfer RF energy which is induced onto implanted leads from a high power electromagnetic field environment such as an MRI RF field to an energy dissipating surface (EDS). In this way, RF energy can be shunted harmlessly into an EDS surface, the AIMD housing or the bulk thermal mass or handle of a probe or catheter. Thus, the RF or thermal energy can be dissipated in muscle tissue or body tissues distant from the distal electrodes, or even into flowing blood or other body fluids, thereby directing such energy away from an implanted lead and especially its tissue contact electrodes. The diversion (decoupling) circuits of the present invention may also be combined with impeding circuits which can raise and further control the overall impedance of the system to achieve maximal energy transfer and minimum thermal rise in the implanted lead system.

In other words, an energy dissipating surface is provided with means for decoupling RF signals from implantable leadwires selectively to said energy dissipating surface. In previous studies, concerns have been raised about the safety of using metallic structures in MR scanners. Radio frequency energy (MHz), transmitted from the scanner in order to generate the MR signal, can be deposited on the interventional device. This results in high electrical fields around the instrument and local tissue heating. This heating tends to be most concentrated at the ends of the electrical structure. This is certainly true of the implanted leadwires associated with AIMDs. We can address this safety issue using the tuned energy balance methods and switched diverter circuits of the invention. The concern is that the lead electrodes, which directly contact the tissue, could cause local tissue changes including burns. The present invention is extended beyond the leadwires of probes and catheters to include the distal tip electrodes associated with the implanted leads of devices such as pacemakers, cardioverter defibrillators, neurostimulators and the like. All of these devices have a distal electrode which contacts body tissue in order to deliver pacing pulses or sense biologic activity. It is extremely important that that interface junction not overheat and cause localized tissue damage or burning.

U.S. 2003/0050557 explains the need to cut/remove the electrodes from the circuit in the MHz frequency range. This is accomplished with the inductor circuit elements. In the MHz frequency range, the surface ring electrodes are not connected to the rest of the electrical leads. Therefore, the ends of the leads are now buried inside of the catheter. The coupled high electric fields will now be located inside of the catheter instead of in the tissue. This results in significant reduction and unwanted tissue heating.

In U.S. 2003/0050557, the inside of the catheter, of course, includes a body with a specific thermal mass and specific thermal properties. Over time, it will rise in temperature and therefore heat surrounding body tissue. However, this temperature rise is minimal due to the large area and thermal mass of the catheter which acts as an energy dissipating area or surface. Also, any such minimal heating that does occur is in body tissue in an area that is distant from the therapy electrode(s). Therefore, the ability for the pacing or stimulus electrode to delivery energy in the proper location will not be compromised. By spreading the RF energy over a larger energy dissipating surface area (i.e. inside the catheter or to an AIMD housing) the temperature rise is therefore reduced and the resulting small amount of heat is generally dissipated into bulk body tissues instead of at a specific point.

This is accomplished through switched energy diverting circuits such as broad band filtering such as capacitive low pass filters, or by resonant filtering such as creating resonant diverter (trap) circuits consisting of a series inductor and capacitor (L-C trap). Diverting circuits work best with electrode protecting bandstop filters as described in U.S. Pat. No. 7,363,090; US 2007/0112398 A1; US 2008/0071313 A1; US 2008/0049376 A1; US 2008/0132987 A1; and US 2008/0116997 A1, the contents of which are incorporated herein by reference.

There are three types of electromagnetic fields used in an MRI unit. The first type is the main static magnetic field designated $B_0$ which is used to align protons in body tissue. The field strength varies from 0.5 to 3 Tesla in most of the currently available MRI units in present clinical use. The second electromagnetic field is the pulsed RF field which is given by the Lamor Frequency. The Lamor Frequency formula for hydrogen is 42.56 (static field strength in Tesla)=RF frequency. For example, for a 1.5 Tesla common hydrogen (proton) scanner, the frequency of the pulsed RF field is approximately 64 MHz. The third type of field is the gradient field which is used to control where the slice is that generates the image that is located within body tissue.

The present invention is primarily directed to the pulsed RF field although it also has applicability to the gradient field as well. Because of the presence of the powerful static field, non-ferromagnetic components are used throughout the present invention. The use of ferromagnetic components is contraindicative because they have a tendency to saturate or change properties in the presence of the main static field.

FIG. 1 illustrates various types of active implantable medical devices referred to generally by the reference numeral 100 that are currently in use. FIG. 1 is a wire formed diagram of a generic human body showing a number of exemplary implanted medical devices. 100A is a family of implantable hearing devices which can include the group of cochlear implants, piezoelectric sound bridge transducers and the like. 100B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for sensing the onset of the seizure and also providing electrical stimulation to brain tissue to prevent the seizure from actually happening. 100C shows a cardiac pacemaker which is well-known in the art. 100D includes the family of left ventricular assist devices (LVAD's), and artificial hearts, including the recently introduced artificial heart known as the Abiocor. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted leadwires. 100F includes a variety of implantable bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillator (ICD) devices and also includes the family of congestive heart failure devices (CHF). This is also known in the art as cardio resynchronization therapy devices, otherwise known as CRT devices. 100J illustrates an externally worn pack. This pack could be an external insulin pump, an external drug pump, an external neurostimulator or even a ventricular assist device. 100K illustrates an entire family of probes, catheters, venous insert devices such as femoral ICDs, ablation catheters, loop recorders, and the like.

Referring to US 2003/0050557, Paragraphs 79 through 82, the contents of which are incorporated herein, metallic structures, particularly leadwires, are described that when placed in MRI scanners, can pick up high electrical fields which results in local tissue heating. This heating tends to be most concentrated at the ends of the electrical structure (either at the proximal or distal lead ends). This safety issue can be addressed using the disclosed systems and methods of the present invention. The concern is that the distal electrodes, which directly contact body tissue, can cause local tissue burns. FIGS. 1A through 1G in U.S. 2003/0050557 have been redrawn herein as FIGS. 2 through 11 and are described as follows in light of the present invention.

As used herein, the lead means an implanted lead, including its electrodes that are in contact with body tissue. In general, for an AIMD, the term lead means the lead that is outside of the AIMD housing and is implanted or directed into body tissues. The term leadwire as used herein, refers to the wiring that is generally inside of an AIMD generally between its hermetic terminal and circuit board substrates or internal circuitry. The term leadwire can also be inclusive of leadwires inside of a probe or catheter body or handle.

FIG. 2 is a diagrammatic view of a typical prior art device 102 such as a probe, catheter or AIMD lead distal electrode. There are two leadwires 104 and 106 which thread through the center of the illustrative probe, catheter or AIMD lead and terminate respectively in a corresponding pair of distal conductive electrode rings 108 and 110. Leadwires 104 and 106 are electrically insulated from each other and also electrically insulated from any metallic structures located within the catheter or lead body. The overall catheter or implanted lead body is generally flexible and is made of biocompatible materials, which also have specific thermal properties. In addition to flexibility, probes and catheters are typically steerable. AIMD implanted leads are generally more flexible and are implanted by first placing guide wires. It is well known that a push-pull wire (not shown in FIG. 2) can be run down the center of the catheter or probe in a lumen and then be attached to a catheter handle or pistol grip or other device so that the physician can carefully steer or thread the probe or catheter through the torturous path of the venous system, even into the ventricles of the heart. Such probes and catheters, for example, can be used for electrical mapping inside of a heart chamber, or for application of RF energy for ablation, which is used to treat certain cardiac arrhythmias. Probes and catheters have wide application to a variety of other medical applications. There are also combined catheters that can do electrical mapping and can also perform RF ablation. When the physician finds the area of arrhythmic electrical activity and wishes to ablate, he activates a switch which applies RF energy to the tip of the catheter (see, e.g., FIG. 55, which will be discussed herein in more detail). This would involve a third electrode right at the catheter tip of FIG. 2 (not shown). It would be extremely valuable if the catheter could be guided during real-time MRI imaging. This is important because of MRI's incredible ability to image soft tissue. In addition, when one is doing deliberate ablation, for example, around a pulmonary vein, it is important that a full circle of scar tissue be formed, for example, to stop atrial fibrillation. MRI has the ability to image the scar as it is being formed (for example, see U.S. Pat. No. 7,155,271). However, it would be highly undesirable if the MRI RF energy that is coupled to the leadwires caused the distal ablation tip or the electrode rings to overheat at an improper time, which could burn or ablate healthy tissues.

FIG. 3 shows the interior taken from FIG. 2 showing leadwires 104 and 106 which are routed to the two distal electrodes 108 and 110 as previously described in FIG. 2.

FIG. 4 shows the electrical circuit of FIG. 3 with a general frequency selective diverting impedance element 112 connected between leadwires 104 and 106. In the present invention, the impedance element 112 can consist of a number of frequency selective elements as will be further described. In general, the first conductive leadwire 104 is electrically coupled to the first electrode 108, the second conductive leadwire 106 is electrically coupled to the second electrode 110, and the frequency dependent diverting reactive element 112 electrically couples the first and second leadwires 104 and 106 such that high frequency energy is conducted between the first leadwire 104 and the second leadwire 106.

Referring once again to FIG. 4, the frequency selective reactive diverting element 112 tends to be electrically invisible (i.e., a very high impedance) at selected frequencies. The reactive element is desirably selective such that it would not attenuate, for example, low frequency biological signals or RF ablation pulses. However, for high frequency MRI RF pulsed frequencies (such as 64 MHz), this frequency reactive element 112 would look more like a short circuit. This would have the effect of sending the energy induced into the leadwires 104 and 106 by the MRI RF field back into the catheter body energy dissipating surface into which the leadwires are embedded. In other words, there are desirably both RF energy and thermal conductivity to the probe or catheter body or sheath or shield which becomes an energy dissipating surface all along the lengths of leadwires 104 and 106 such that MRI induced energy that is present in these leadwires is diverted and converted to heat into the interior and along the catheter body itself. This prevents the heat build up at the extremely sensitive locations right at the ring electrodes 108 and 110 which are in intimate and direct contact with body tissue. In addition, the amount of temperature rise is very small (just a few degrees) because of the energy being dissipated over such a relatively high surface area. As previously mentioned, the high frequency RF pulsed energy from an MRI system can couple to implanted leads. This creates electromagnetic forces (EMFs) which can result in current flowing through the interface between electrodes that are in contact with body tissue. If this current reaches sufficient amplitude, body tissue could be damaged by excessive RF current flow or heat buildup. This can create scar tissue formation, tissue damage or even tissue necrosis such to the point where the AIMD can no longer deliver appropriate therapy. In certain situations, this can be life threatening for the patient.

FIG. 5 shows a capacitor 114 which represents one form of the frequency selective diverting reactive element 112 previously described in FIG. 4. In this case, the reactive element 112 comprises a simple capacitor 114 connected between the first conductor or leadwire 104 and the second conductor or leadwire 106 and will have a variable impedance vs. frequency. The following formula is well known in the art: $X_C=1/(2\pi fc)$. Referring to the foregoing equation, one can see that since frequency (f) is in the denominator, as the frequency increases, the capacitive reactance in ohms decreases. With a large number in the denominator, such as the RF pulsed frequency of a 1.5 Tesla MRI system, which is 64 MHz, the capacitive reactance drops to a very low number (essentially a short circuit). By shorting the leadwires together at this one frequency, this diverts and prevents the RF energy from reaching the distal ring electrodes 108 and 110 and being undesirably dissipated as heat into body tissue. Referring once again to FIG. 4, one can see that the frequency selective diverting element 112 thereby diverts the high frequency RF energy back into the leadwires 104 and 106. By spreading this energy along the length of leadwires 104 and 106, it is converted to heat, which is dissipated into the main body of the probe, catheter or energy dissipating sheath. In this way, the relatively large thermal mass of the probe or catheter becomes an energy dissipating surface and any temperature rise is just a few degrees C. In general, a few degrees of temperature rise is not harmful to body tissue. In order to cause permanent damage to body tissue, such as an ablation scar, it generally requires temperatures above 20° C. In summary, the frequency selective reactive element 112, which may comprise a capacitor 114 as shown in FIG. 5, forms a diversion circuit such that high frequency energy is diverted away from the distal electrodes 108 and 110 along the leadwires 104 and 106 to a surface that is distant from the electrodes 108 and 110, at which point the energy is converted to heat.

FIG. 6 describes a different way of diverting high frequency energy away from the electrodes 108, 110 and accomplishing the same objective. The general diverting reactance element 112 described in FIG. 4 is shown in FIG. 6 to comprise a capacitor 114 in series with an inductor 116 to form an L-C trap circuit. For the L-C trap, there is a particular frequency ($f_r$) at which the capacitive reactance $X_C$ and the inductive reactance $X_L$ are vectorally equal and opposite and tend to cancel each other out. If there are no losses in such a system, this results in a perfect short circuit between leadwires 104 and 106 at the resonant frequency. The frequency of resonance of the trap filter is given by the equation $$f_r = \frac{1}{2\pi\sqrt{LC}},$$

wherein $f_r$ is the frequency of resonance in Hertz, L is the inductance in henries, and C is the capacitance in farads.

FIG. 7 illustrates any of the aforementioned frequency dependent diverting impedance elements 112 with the addition of series frequency selective impeding reactances 118 and 120. The addition of series impedance further impedes or blocks the flow of high frequency MRI induced currents to the ring electrodes 108 and 110 as will be more fully described in the following drawings.

FIG. 8 is the low frequency model of FIG. 4, 5 or 6. In this regard, FIG. 8 is identical to FIG. 3, in that, once again it shows the electrical leadwires 104 and 106 connected to the distal ring electrodes 108 and 110 of the probe or catheter 102. In the low frequency model, the frequency reactive diverting impedance elements 112 disappear because at low frequency their impedances approach infinity. Of course, elongated leads in a probe or catheter are electrically and even functionally equivalent to leads used for cardiac pacemakers, implantable cardioverter defibrillators, neurostimulators and the like. For example, reference is made to U.S. Pat. No. 7,363,090, the contents of which are incorporated herein. Accordingly, any discussion herein related to probes or catheters apply equally to leadwires for all active implantable medical devices as described in FIG. 1, and vice versa. Referring once again to FIG. 8, this is also the low frequency model of the circuits shown in FIG. 7. At low frequency, the frequency selective or reactive diverting component 112 tends to look like a very high or infinite impedance. At low frequency, the series reactive or frequency variable impeding elements 118 and 120 tend to look like a very low impedance or short circuit. Accordingly, they all tend to disappear as shown in FIG. 8.

FIG. 9 is a high frequency model that illustrates how the distal electrodes or rings 108 and 110 are electrically isolated at high frequency by shorting leadwires 104 and 106 at location 122. As previously mentioned, such shorting or current diverting could be accomplished by a capacitor, a capacitive low pass filter or a series resonant L-C trap circuit. FIG. 9 also shows the electrodes 108 and 110 as cut or disconnected and electrically isolated from the rest of the circuit. This is because, at very high frequency, series impeding elements 118 and 120 tend to look like a very high impedance or an open circuit. In summary, by reactive elements 112, 118 and 120 acting cooperatively, reactive element 112 diverts the high frequency energy back into energy dissipating surfaces in the probe or catheter while at the same time reactive elements 118 and 120 impede the high frequency RF energy. Accordingly, in the ideal case, at high frequencies, the equivalent circuit of FIG. 9 is achieved. Accordingly, excessive high frequency MRI RF energy cannot reach the distal ring electrodes 108, 110 and cause undesirable heating at that critical tissue interface location.

FIG. 10 shows any of the previously described diverting frequency selective impedance elements 112 in combination with series reactance components shown in the form of a pair of inductors 116a, 116b. It is well known to electrical engineers that the inductive reactance in ohms is given by the equation $X_L = 2\pi f L$. In this case the frequency term (f) is in the numerator. Accordingly, as the frequency increases, the reactance (ohms) of the inductors also increases. When the frequency is very high (such as 64 MHz) then the reactance in ohms becomes extremely high (ideally approaches infinity and cuts off the electrodes). By having a short circuit or very low impedance between the leadwires and the probe/catheter body 104 and 106 and then, at the same time, having a very high impedance in series with the electrodes from inductors 116, this provides a very high degree of attenuation to MRI RF pulsed frequencies thereby preventing such energy from reaching the distal ring electrodes 108 and 110. In FIG. 10, the line-to-line selective impedance element 112 diverts high frequency energy back into leadwires 104 and 106 while at the same time the series inductors 116 impede (or cut-off) high frequency energy. When the line-to-line element 112 is a capacitor 114 as shown in FIG. 5, then this forms what is known in the prior art as an L section low pass filter, wherein the capacitor 114 electrically cooperates with the inductors 116 (FIG. 10) to form a 2-element low pass filter. By definition, a low pass filter allows low frequencies such as biological signals to pass to (stimulation pulses) and from (biologic sensing) the distal electrodes freely without attenuation while at the same time providing a high degree of attenuation to undesirable high frequency energy. It will be obvious to those skilled in the art that FIG. 5 describes a single element (capacitor) low pass filter, and that FIG. 10 describes a 2-element or L-section low pass filter. Moreover, any number of inductor and capacitor combinations can be used for low pass filters, including 3-element Pi or T circuits, LL, 5-element or even "n" element filters.

FIG. 11 offers an even greater performance improvement over that previously described in FIG. 10. In FIG. 11, modified frequency selective impeding elements each incorporate a parallel resonant inductor 116 and capacitor 114 which is also known in the industry as a bandstop filter 117. The L-C components for each of the reactive elements are carefully chosen such that each of the bandstop filters 117 are resonant, for example, at the pulsed resonant frequency of an MRI scanner. For common hydrogen scanners, the pulsed resonant frequency of an MR scanner is given by the Lamor equation wherein the RF pulsed frequency in megahertz is equal to 42.56 times the static field strength. For example, for a popular 1.5 Tesla scanner, the RF pulsed frequency is 64 MHz. Common MR scanners that are either in use or in development today along with their RF pulsed frequencies include: 0.5 Tesla-21 MHz; 1.5 Tesla-64 MHz; 3 Tesla-128 MHz; 4 Tesla-170 MHz; 5 Tesla-213 MHz; 7 Tesla-300 MHz; 8 Tesla-340 MHz; and 9.4 Tesla-400 MHz. When the bandstop filters 117 are resonant at any one of these RF pulsed frequencies, then these elements tend to look like an open circuit which impedes the flow of RF current to distal electrodes. When compatibility with different types of MR scanners is required, for example, 1.5, 3 and 5 Tesla, then three separate bandstop filter elements in series may comprise the reactive element 118 (FIG. 7), and three separate bandstop filter elements in series may comprise the reactive element 120 (FIG. 7). Each of these would have their L and C components carefully selected so that they would be resonant at different frequencies. For example, in the case of MR scanners operating at 1.5, 3 and 5 Tesla, the three bandstop filters comprising the reactive element 118 as well as the three bandstop filters comprising the reactive element 120 would be resonant respectively at 64 MHz, at 128 MHz, and at 170 MHz. The resonant frequencies of the bandstop filter elements could also be selected such that they are resonant at the operating frequency of other emitters that the patient may encounter such as diathermy and the like. The use of bandstop filters 117 is more thoroughly described in U.S. Pat. No. 7,363,090; US 2007/0112398 A1; US 2007/0288058; US 2008/0071313 A1; US 2008/0049376 A1; US 2008/0161886 A1; US 2008/0132987 A1 and US 2008/0116997 A1, the contents of which are incorporated herein.

Figure 12:
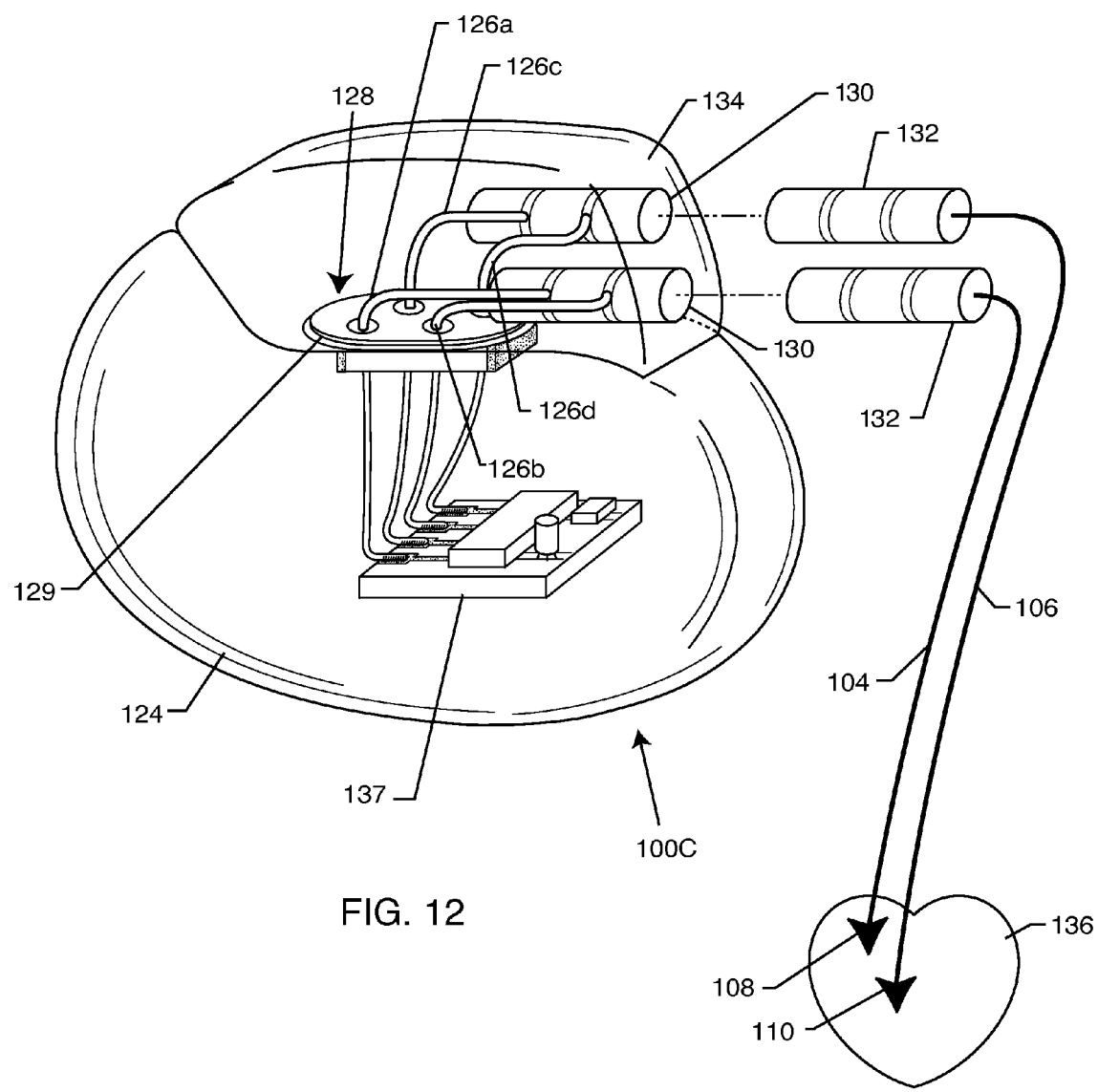
FIG. 12 is a perspective and somewhat schematic view of a prior art active implantable medical device (AIMD) including a leadwire directed to the heart of a patient.

Referring now to FIG. 12, a prior art active implantable medical device (AIMD) 100C is illustrated. In general, the AIMD 100C could, for example, be a cardiac pacemaker which is enclosed by a titanium or stainless steel housing 124 as indicated. The titanium housing 124 is hermetically sealed and contains circuit board 137, however, there is a point where conductors such as the illustrative conductors 126a, 126b, 126c and 126d must ingress and egress in non-conductive relationship relative to the housing 124. This is accomplished by providing a hermetic terminal assembly 128. Hermetic terminal assemblies 128 are well known and generally consist of a ferrule 129 which is laser welded to the titanium housing 124 of the AIMD 100C. In FIG. 12, four conductors 126a-126d are shown for connection to a corresponding number of leadwires, such as the illustrative bipolar leads 104 and 106 shown for coupling to the connector receptacles 130. In this configuration, the four leadwires coupled respectively to the conductors 126a-126d comprise a typical dual chamber bipolar cardiac pacemaker. It should be noted that each of the bipolar leads 104 and 106 have a pair of leadwires associated with them. These are known as bipolar electrodes wherein one wire is routed to the tip electrode and the other is routed to the ring electrode in locations 108 and 110.

Connectors 132 are commonly known as IS-1 connectors and are designed to plug into mating receptacles 130 on a header block 134 mounted on the pacemaker housing 124. These are low voltage (pacemaker) leadwire connectors covered by an International Standards Organization (ISO) standard IS-1. Higher voltage devices, such as implantable cardioverter defibrillators, are covered by a standard known as the ISO DF-1. A new standard was recently published that will integrate both high voltage and low voltage connectors into a new miniature quadpolar connector series known as the ISO IS-4 standard. Leads plugged into these connectors are typically routed in a pacemaker or ICD application down into the right ventricle and right atrium of the heart 136. There are also new generation devices that have been introduced to the market that couple leads to the outside of the left ventricle. These are known as biventricular devices and are very effective in cardiac resynchronization therapy (CRT) and treating congestive heart failure (CHF).

It should be obvious to those skilled in the art that all of the descriptions herein are equally applicable to other types of AIMDs. These include implantable cardioverter defibrillators (ICDs), neurostimulators, including deep brain stimulators, spinal cord stimulators, cochlear implants, incontinence stimulators and the like, and drug pumps. The present invention is also applicable to a wide variety of minimally invasive AIMDs. For example, in certain hospital cath lab procedures, one can insert an AIMD for temporary use such as a probe, catheter or femoral artery ICD. Ventricular assist devices also can fall into this type of category. This list is not meant to be limiting, but is only example of the applications of the novel technology currently described herein. In the following description, functionally equivalent elements shown in various embodiments will often be referred to utilizing the same reference number.

Figure 13:
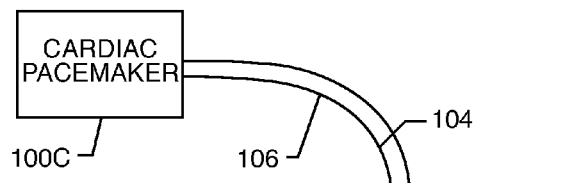
FIG. 13 is a schematic illustration of a bipolar leadwire system with a distal tip and ring typically as used with a cardiac pacemaker.

FIG. 13 illustrates a prior art single chamber bipolar AIMD 100C and leadwires 104 and 106 with a distal tip electrode 138 and a ring electrode 108 typically as used with a cardiac pacemaker 100C. Should the patient be exposed to the fields of an MRI scanner or other powerful emitter used during a medical diagnostic procedure, currents that are directly induced in the leadwires 104, 106 can cause heating by $I^2R$ losses in the leadwires or by heating caused by RF current flowing from the tip and ring electrodes 138, 108 into body tissue. If these induced RF currents become excessive, the associated heating can cause damage or even destructive ablation to body tissue 136.

Figure 14:
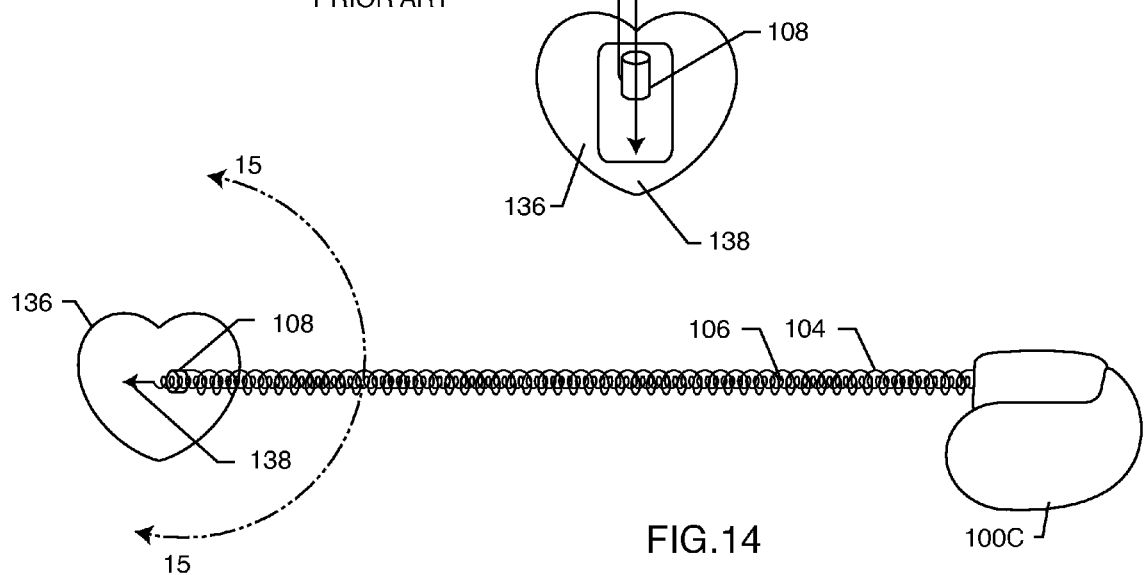
FIG. 14 is a schematic illustration of a prior art single chamber bipolar cardiac pacemaker lead showing the distal tip and the distal ring electrodes.

FIG. 14 illustrates a single chamber bipolar cardiac pacemaker 100C, and leadwires 104 and 106 having distal tip 138 and distal ring electrode 108. This is a spiral wound (coaxial) lead system where the tip electrode leadwire 104 is wrapped around the ring electrode leadwire 106. The characteristic impedance of this lead type usually has an inductive component. There are other types of pacemaker lead systems in which these two leadwires that lay parallel to one another (known as a bifilar lead system), which are not shown.

Figure 15:
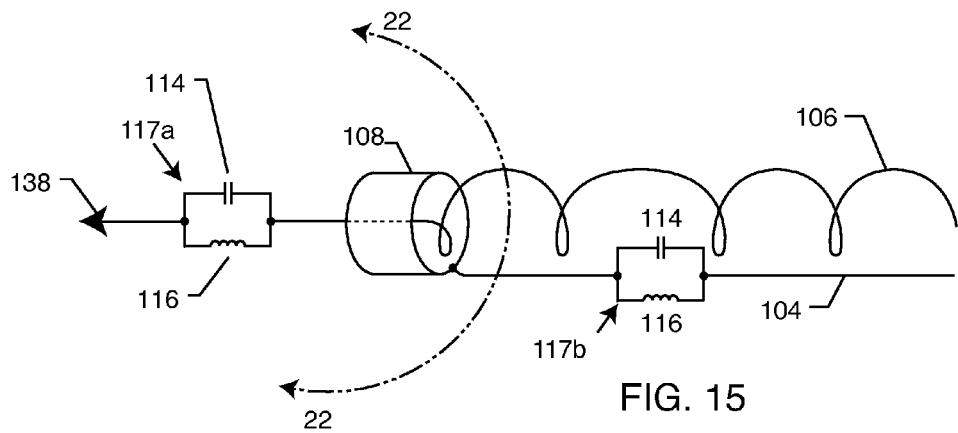
FIG. 15 is an enlarged, fragmented schematic view taken generally along the line 15-15 of FIG. 14, illustrating placement of bandstop filters adjacent to the distal tip and ring electrodes.

FIG. 15 is an enlarged schematic illustration of the area "15-15" in FIG. 14. In the area of the distal tip 138 and ring electrode 108, bandstop filters 117a, 117b have been placed in series with each of the respective ring and tip circuits. The ring circuit leadwire 104 has been drawn straight instead of coiled for simplicity. The bandstop filters 117 are tuned such that, at an MRI pulsed RF frequency, a high impedance will be presented thereby reducing or stopping the flow of undesirable MRI induced RF current from the electrodes 138 and 108 into body tissues.

The tip electrode 138 is designed to be inserted into intimate contact with myocardial tissue. Over time it can become encapsulated and fully embedded or buried within such tissue. However, the ring electrode 108 is designed to float within the blood pool, for example, in a cardiac chamber such as a ventricle or atrium. With the constant blood perfusion, the ring electrode 108 can be somewhat cooled during medical diagnostic procedures, such as MRI. However, the tip electrode 138, which is embedded in the myocardial tissue, is thermally insulated in comparison. Moreover, it can't always be assumed that a ring electrode 108 that is floating in the blood pool will be adequately cooled by the flow of blood. There are certain types of patients that have cardiovascular diseases that lead to very low ejection fractions and low blood flow rates and even perfusion issues. The ring electrode 108 can also become encapsulated by body tissues. Accordingly, both the distal tip electrode 138 and the ring electrode 108 are preferably both associated with bandstop filters 117a, 117b. However, since the operation of the bandstop filter 117 is more important with the tip electrode 138 than it is with the ring electrode 108, in order to prevent distal tip heating and associated tissue damage, in many AIMD applications only a tip bandstop filter 117a may be required for MRI compatibility.

Figure 16:
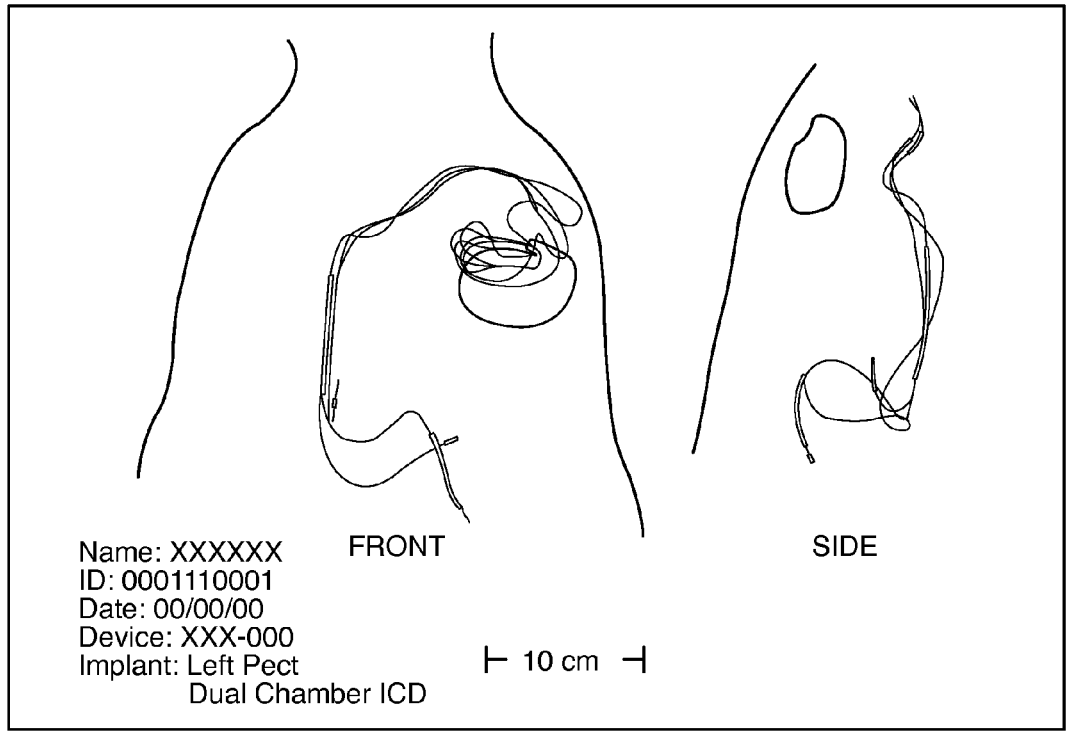
FIG. 16 is a tracing of an exemplary patient X-ray showing an implanted pacemaker and cardioverter defibrillator and corresponding leadwire system.

FIG. 16 is a front and side view tracing of an actual patient X-ray. This particular patient required a cardiac pacemaker. The corresponding implantable leadwire system, as one can see, makes for a very complicated antenna and loop coupling situation. The reader is referred to the article entitled, "Estimation of Effective Lead Loop Area for Implantable Pulse Generator and Implantable Cardioverter Defibrillators" provided by the AAMI Pacemaker EMC Task Force. In FIG. 16, one can see from the X-ray tracing that there are electrodes in both the right atrium and in the right ventricle. Both these involve a separate tip and ring electrode (not shown in FIG. 16). In the industry, this is known as a dual chamber bipolar leadwire system. It will be obvious to those skilled in the art that any of the passive frequency selective networks, as previously described in FIGS. 2 through 11, can be incorporated into the leadwires as illustrated in the X-ray tracing of FIG. 16. Frequency selective diverter and/or impeding filters of FIGS. 2-11 of the present invention are needed so that MRI exposure cannot induce excessive currents into the associated leads or electrodes. There are also newer combined pacemaker/ICD systems which include biventricular pacemaking (pacing of the left ventricle). These systems can have as many as 12 implanted leads, 140.

Figure 17:
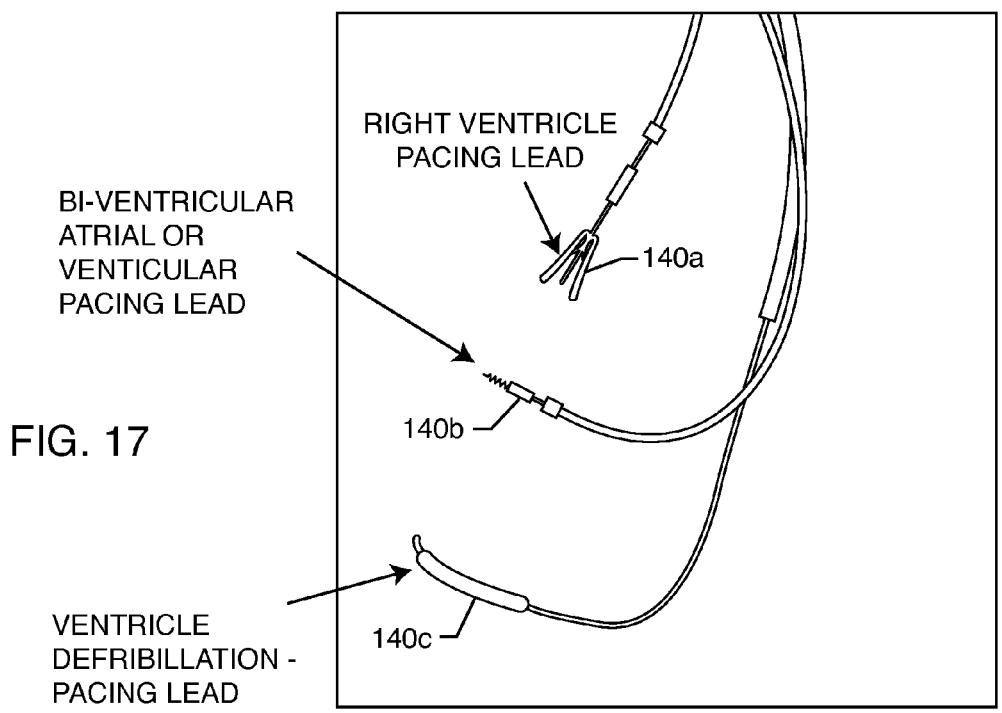
FIG. 17 is a line drawing of an exemplary patient cardiac X-ray of a bi-ventricular leadwire system.

FIG. 17 is a line drawing of an actual patient cardiac X-ray of one of the newer bi-ventricular leadwire systems with various types of electrode tips 140 shown. For instance, electrode tip 140a is a passive fixation right atrium pacing lead, electrode tip 140b is an active fixation bi-ventricular pacing lead, and electrode tip 140c is a ventricle defibrillation lead. The new bi-ventricular systems are being used to treat congestive heart failure, and make it possible to implant leads outside of the left ventricle. This makes for a very efficient pacing system; however, the implantable leadwire system is quite complex. When a leadwire system, such as those described in FIGS. 12-17, are exposed to a time varying electromagnetic field, electric currents can be induced into the electrodes of such leadwire systems. For the bi-ventricular system, a passive component frequency diverting network of FIGS. 2-11 would need to be placed in conjunction with each of the three distal tips and ring electrodes to corresponding energy dissipating surfaces.

The word passive is very important in this context. Active electronic circuits, which are defined as those that require power, do not operate very well under very high amplitude electromagnetic field conditions. Active electronic filters, which generally are made from microelectronic chips, have very low dynamic range. Extremely high fields inside an MRI chamber would tend to saturate such filters and make them become nonlinear and ineffective. Accordingly, frequency selective networks are preferably realized using non-ferromagnetic passive component elements. In general, this means that the frequency selective components for both diverters and impeders preferably consist of capacitors, inductors, and resistors in various combinations. Passive component elements are capable of handling very high power levels without changing their characteristics or saturating. Moreover, the inductor elements are preferably made from materials that are not ferromagnetic. The reason for this is that MRI machines have a very powerful main static magnetic field ($B_0$). This powerful static magnetic field tends to saturate ferrite elements and would thereby change dramatically the value of the inductance component. Accordingly, in the present invention, the inductor elements are preferably fabricated without the use of ferrites, nickel, iron, cobalt or other similar ferromagnetic materials that are commonly used in general electronic circuit applications.

FIG. 18 gives the frequency of resonance $f_r$ for the parallel L-C bandstop filter circuit 117 of FIG. 15: where $f_r$ is the frequency of resonance in Hertz, L is the inductance in Henries and C is the capacitance in Farads. The same equation given in FIG. 18 also applies to a series L-C trap filter illustrated as a frequency diverter element 112 in FIG. 6. The inductor L is designated by 116 and the capacitor C is designated by 114 in FIG. 6. Clinical MRI systems vary in static field strength from 0.5 Tesla all the way up to 3 Tesla with newer research machines going as high as 11.4 T. The frequency of the pulsed RF field associated with the static field is given by the Lamour Equation, $f=\gamma T$, where T is the field strength in Teslas, and $\gamma$ is gyromagnetic ratio for hydrogen, which is 42.58 MHz/T. Accordingly, a 3 Tesla MRI system has a pulsed RF field of approximately 128 MHz.

By referring to FIG. 18, one can see that the resonant frequency fr of an ideal tank filter can be predicted by using the equation:

$$f_r = \frac{1}{2\pi\sqrt{LC}},$$

Where $f_r$ is the resonant frequency, L is the inductance, in Henries, of the inductor component, and C is the capacitance, in Farads, of the capacitor component. In this equation, there are three variables: $f_r$, L, and C. The resonant frequency, $f_r$, is a function of the MRI system of interest. As previously discussed, a 1.5 T MRI system utilizes an RF system operating at approximately 64 MHz, a 3.0 T system utilizes a 128 MHz RF, and so on. By determining the MRI system of interest, only L and C remain. By artificially setting one of these parameters, a filter designer needs only to solve for the remaining variable.

Figure 19:
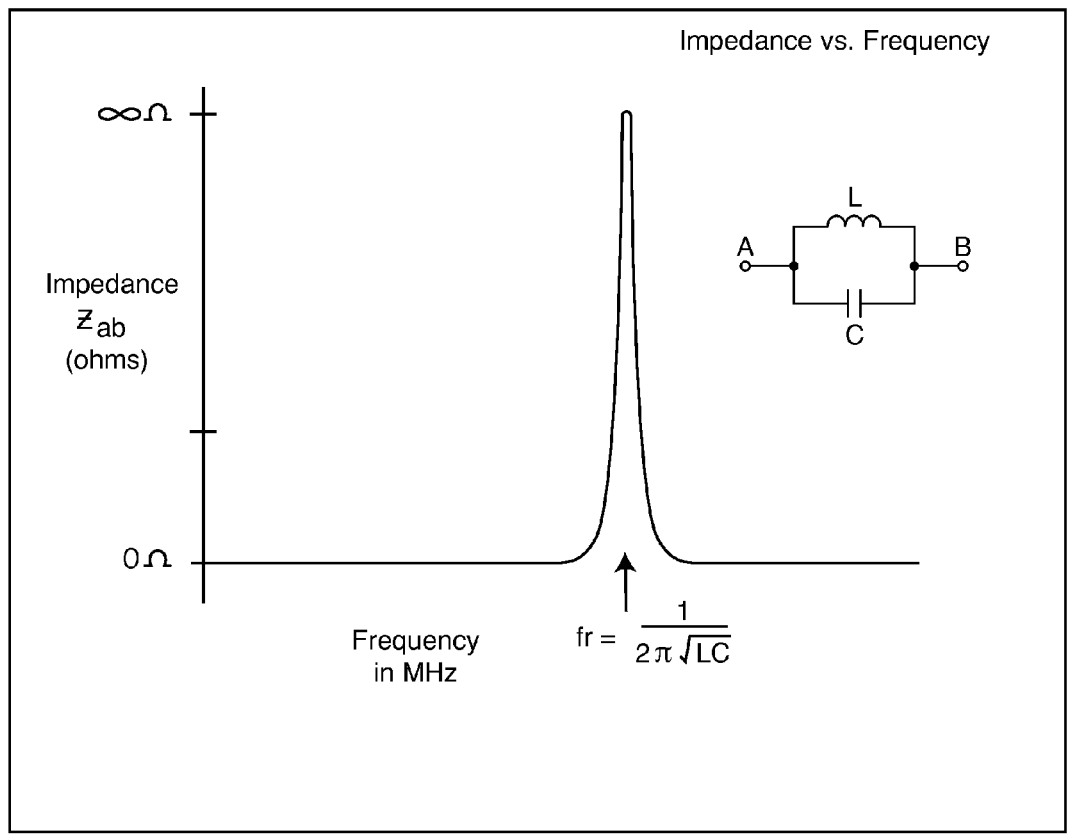
FIG. 19 is a graph showing impedance versus frequency for the ideal parallel tank circuit of FIG. 15.

FIG. 19 is a graph showing the impedance versus frequency for a bandstop filter as previously described in U.S. Pat. No. 7,363,090 and US 2007/0112398 A1. One can see that at frequencies outside of the resonant frequency, impedance is nearly zero ohms. When the capacitor and parallel inductor is in resonance, the impedance is very high (ideally infinity).

FIG. 20 is the impedance equation for the capacitor in parallel with an inductor of a bandstop filter.

FIG. 21 gives the equations for inductive reactance $X_L$ and capacitive reactance $X_C$. In all of these equations (f) is frequency in hertz, L is inductance in henries, and C is capacitance in farads.

It should also be noted that the L-C parallel bandstop filter also captures the RF energy. That is, for example, for a 1.5 Tesla system, the energy will swap back and forth between the capacitor and the inductor at 64 MHz The energy is stored first in the capacitor's static field and then discharged into the magnetic field of the inductor and back and forth. Accordingly, relatively high currents can circulate back and forth between these two circuit elements during an MRI procedure. Accordingly, it is important that these two components be robust enough to handle these currents. It is also important that their resistive elements be relatively low such that the bandstop filter itself does not become a heating element within the lead system. One way to increase the current handling capabilities and reduce the resistance of the capacitor elements is the use of dual electrode plates as described in U.S. Pat. No. 5,978,204, the contents of which are incorporated herein. It should also be noted that RF power handling is a special concern for all of the frequency diverter circuits 112 as illustrated in FIGS. 4, 5, 7, 10, and 11. The diverter elements have to be designed in a very robust manner since they are carrying high levels of RF current to the energy dissipating surface EDS. The impeding elements tend to reduce current and therefore usually are not required to carry extremely high levels of RF current. For example, referring once again to FIG. 5, once can see that in this case, the diverter element is a capacitor 114. The capacitive reactance is a very low impedance at high frequency, such as 64 megahertz wherein relatively high amplitude RF currents flow in and out of the capacitor's internal electrodes. If a capacitor has high equivalent series resistance, or high ohmic loss, the capacitor itself could get very hot. One of the ways to reduce the internal resistance and/or RF current handling capability of the passive diverter elements of the present invention will be described in detail further on.

FIG. 19 is a graph showing impedance versus frequency for the ideal parallel tank circuit 117 of FIG. 15. As one can see, using ideal (zero resistance) circuit components, the impedance measured between points A and B for the parallel tank circuit 117 shown in FIG. 15 is zero until one approaches the resonant frequency $f_r$. At the frequency of resonance, these ideal components combine together to approach an infinite impedance. This comes from the equation $Z_{ab}$ for the impedance for the inductor in parallel with the capacitor shown as FIG. 20. When the inductive reactance is equal to the capacitive reactance, the two imaginary vectors cancel each other and sum to zero causing the equation to become discontinuous at this point. Referring to the equations in FIGS. 20 and 21, one can see in the impedance equation for $Z_{ab}$, that a zero will appear in the denominator when $X_L = X_C (j\omega L = -j/\omega C)$. This has the effect of making the impedance approach infinity as the denominator approaches zero. This means that at one unique frequency, the impedance between points A and B in FIG. 19 will appear very high (analogous to opening a switch). Accordingly, it would be possible, for example, in the case of a cardiac pacemaker, to design the cardiac pacemaker for compatibility with one single popular MRI system. For example, in the patient literature, the device manual and perhaps contained in the digitally stored information on an implanted RFID chip, it could be noted that the pacemaker leadwire system has been designed to be compatible with 3 Tesla MRI systems. Accordingly, with this particular device, a distal tip bandstop filter 117 would be incorporated where the L and the C values have been carefully selected to be resonant at 128 MHz, presenting a high or almost infinite impedance at the MRI pulse frequency.

Figure 22:
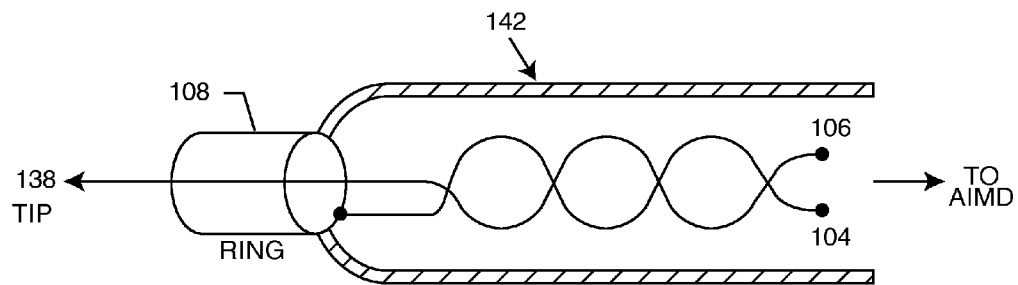
FIG. 22 is an enlarged schematic illustration of the area indicated by Line 22-22 in FIG. 15, showing details of the bipolar pacemaker leadwire system.
Figure 23:
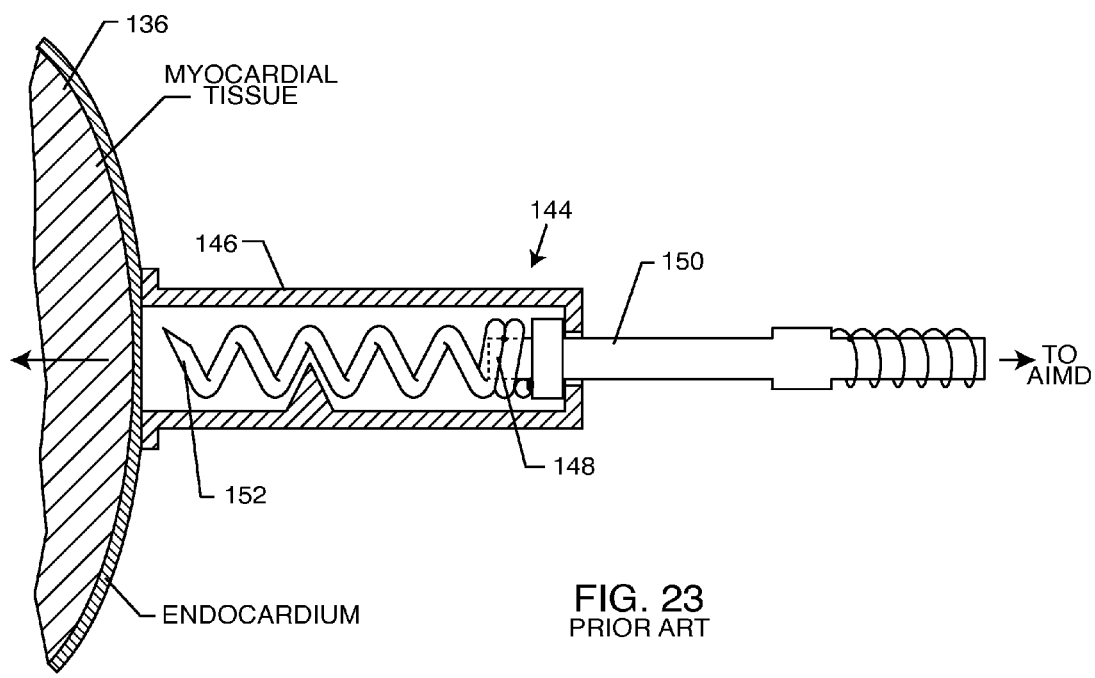
FIG. 23 is similar to FIG. 22, but depicts an active fixation tip for a bipolar pacemaker leadwire system.

FIG. 22 is generally taken from FIG. 15 showing a typical prior art bipolar pacemaker leadwire system. Shown is the distal tip electrode 138 and ring electrode 108. An insulation or insulative lead body 142 is also illustrated. The distal tip electrode 138 can be passive (meaning that it can be bent back in a "J" or shoved against myocardial tissue so that it just rests against the tissue). A more commonly used electrode today is known as the active fixation tip. This is an electrode where by turning the entire center of the lead, the physicians can screw a helix into myocardial tissue thereby firmly affixing it. A prior art active fixation electrode tip 144 is shown in FIG. 23. This is typically used in conjunction with a cardiac pacemaker, an implantable defibrillator or the like. One can see that an active fixation tip housing 146 is pressed up against the tissue to be stimulated, e.g., the myocardial tissue 46 of the patient's heart. For example, this could be the septal wall between the right ventricle and the left ventricle. A helix electrode assembly 148 is shown in a retracted position relative to the adjacent heart tissue 46. At the lead proximal end in the pectoral pocket, the physician uses a tool to axially twist the assembly shaft 150, which drives the pointed tip helix screw 152 into the myocardial tissue, firmly affixing it. As can be seen, it would be highly undesirable for the active fixation helix screw 152 to heat up during an MRI scan. Because the helix screw 152 is deeply embedded into myocardial tissue, if excessive heating and temperature rise did occur, not only could scarring or ablation of cardiac tissue occur, but an actual cardiac wall perforation or lesion could result in sudden death. It will also be obvious to those skilled in the art that any of the frequency impeding or diverting circuits, as shown in FIG. 4, 5, 6, 7, 10 or 11, would be highly undesirable if they were located within the overall housing 146 of the active fixation tip 144. This is because the heat would indeed be removed from the helix screw 152, but it would be transferred into the active fixation housing 146 which also rests in intimate contact with the endocardium heart tissue. What this means is that redirecting the MRI induced electromagnetic energy from the helix tip 152 to the housing 146 simply moves the heat from one bad location to another bad location. Because the housing 146 is also in intimate contact with heart tissue, one would experience excessive temperature rise and resulting tissue burning, scarring or necrosis at that location as well.

Referring once again to FIG. 22, one can see that there is a ring electrode 108 which is placed back (spaced proximally) a suitable distance from the distal tip electrode 138. In a bipolar pacing system, the cardiac pacing pulse is produced between the tip electrode 138 and the ring electrode 108. This electrical pulse induced into myocardial tissue produces a heartbeat. Sensing can also be accomplished between these two electrodes 138, 108 wherein the pacemaker can constantly monitor the electrical activity of the heart. There are similar analogies for neurostimulators, cochlear implants and the like. There is usually a point at which the distal electrodes, for example electrode 138, contact body tissue or fluid for delivery of therapy involving electrical energy. In a neurostimulator application, such as a spinal cord stimulator, small electrical currents or pulses are used to block pain in the spinal nerve roots (create paresthesia). In a urinary incontinence stimulator, a distal electrode is used to cause a muscle contraction and thereby prevent undesirable leakage of urine. In all of these examples, it would be highly undesirable for excess heating defined as temperature rise above a few degrees C., to occur particularly at the implanted lead electrode(s).

In previous studies, concerns have been raised about the safety of using metallic structures, such as leadwires and MR scanners. Radio frequency energy (MHz) transmitted from the MRI scanner in order to generate the MR signal can be coupled onto the interventional device or its associated leads. This results in high electrical fields around the instrument and local tissue heating. This heating tends to be most concentrated at the ends of the electrical structure or leads.

We can address this safety issue using the methods of the present invention. The concern is that distal electrodes or distal surface ring electrodes, which directly contact body tissue, will cause local tissue burns. We need to re-direct the RF induced energy from the leads to an EDS surface. In the current embodiment, this is accomplished primarily with tuned frequency selective diverter circuit elements to an EDS surface or housing.

A very effective way to "cut" or impede RF energy current flow to implanted lead distal electrodes is to use a parallel resonant bandstop filter circuit in place of the inductors in FIG. 10. This resonant circuit could consist of an inductor in parallel with a capacitor (an L-C bandstop filter as shown in FIG. 11). If this parallel L-C circuit is tuned to the MR frequency, it will present a very high impedance at this frequency. This will effectively cut or disconnect the electrodes from the elongated leads at the MRI frequency and prevent unwanted heating. For maximal effectiveness, the L-C circuit should be shielded. For a probe or a catheter application, with these design concepts, the electrical end of the leads (in the MHz range) are buried inside of the catheter body and as a result, the concentrated electric fields are also located inside of the capacitor, instead of in the tissue. This results in a significant reduction in unwanted tissue heating. As previously mentioned, a resonant circuit is an effective way to "cut" the surface electrodes from the rest of the electrical circuit. This resonant circuit could be an inductor in parallel with the capacitor (a bandstop filter also known as an L-C "tank" circuit). Probes and catheters often incorporate metallic sheaths which also assist in dissipating the unwanted energy over large surface areas. This is equivalent to the energy dissipating surface (EDS) structures as described herein. One of the advantages of bandstop filters is that they will allow low frequency pacing pulses and biologic sensing signals to freely pass through. This is very important for a lifesaving AIMD such as a cardiac pacemaker. However, there are many neurostimulator applications, for example, spinal cord stimulators that might have eight, sixteen or even 24 electrodes. These electrodes may have to be placed in the spinal cord nerve root, which is a very small space adjacent to the spine. Accordingly, it becomes very impractical to place that many bandstop filters into such a small and torturous location. Similar analogies exist for multiple deep brain stimulation electrodes which must be physically very small in size to penetrate through deep brain tissue without collateral damage. Accordingly, there is a need for a supplement or an alternative to bandstop filters. An ideal solution is the tuned energy balance system and energy dissipating surfaces of the present invention. While optimally or even sub-optimally tuning the frequency selective diverter elements to an EDS surface, one can draw the RF-induced energy out of the implanted lead system and thereby dissipate it at an EDS surface at a location away from sensitive body tissues. A perfect example is a spinal cord stimulator. As mentioned, the electrodes are placed along the spine in the spinal cord nerve root/canal. The leads routed from these electrodes are generally routed to an AIMD which is typically implanted either in the buttocks or the lower back. This is an ideal situation for the tuned energy balance system and EDS of the present invention. For one thing, in an MRI scanner, the human spine is generally located fairly close to the MRI bore iso-center. At iso-center, the RF electric fields in a scanner tend to be quite low in amplitude (nearly zero). Therefore, the induced energy on the electrodes is relatively small compared to the RF-induced energy along the rest of the lead path. In fact, in this scenario, the highest electric fields will be furthest from iso-center, which means the leads routed into the buttocks or lower back that are adjacent to the AIMD itself. It will be obvious to those skilled in the art, that it is far preferable to have a slight temperature rise over the relatively large surface area (housing) of the AIMD in the buttocks area. This is far less dangerous to the patient than a temperature rise at the electrodes that are placed immediately adjacent the spinal cord nerve. Thermal injury to the spinal nerve can cause very serious and lasting neurologic deficits.

All of the circuit elements as described in connection with FIGS. 4 through 11 are for purposes of redirecting high frequency RF energy away from lead electrodes into a location that has larger thermal mass and larger area such that the energy is not being dissipated at the concentrated point of electrode to tissue contact. Concentrating the MRI RF energy at an electrode causes excessive temperature rise which can result in damage to adjacent body tissues. Referring back to FIG. 3, one can see that the leadwires 104 and 106 are embedded in the insulating sheath of a probe, a catheter, a cardiac pacemaker lead or the like. Accordingly, if excess heat is dissipated along these leadwires, it is then dissipated into these surrounding structures. As previously mentioned, there is also a parasitic capacitance that's formed along these leadwires and the surrounding structures or insulating sheaths. It is a feature of the present invention that any of the passive component frequency selective circuits can also be directly connected to energy dissipating elements that are proximal from the electrodes themselves.

Referring to FIG. 22 (and also FIGS. 24-26), the insulation sheath 142 typically encapsulates the leadwires 104 and 106 in silicone or polyurethane to provide strength and resistance to body fluids. The insulation sheath 142 has thermal conduction properties and also provides important electrical isolation between the leadwires 104 and 106 themselves and also surrounding body fluids and tissues.

Figure 24:
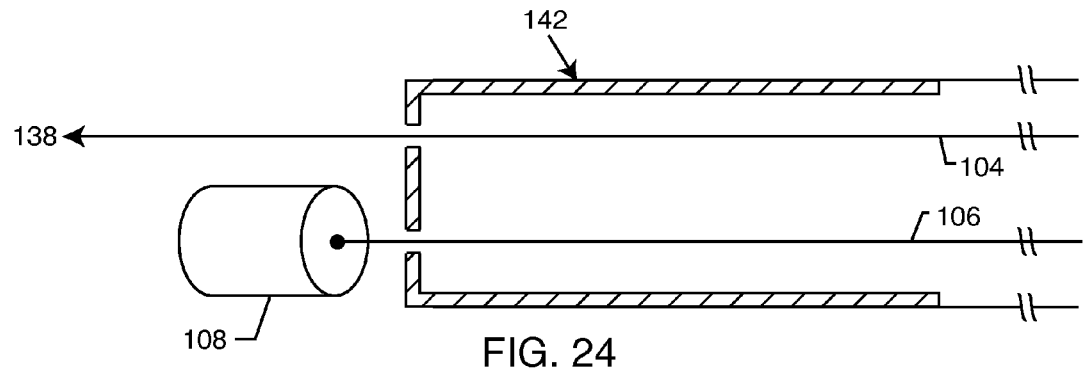
FIG. 24 is similar to FIG. 22, except that the twisted or coaxial electrode wires have been straightened out.

FIG. 24 is generally taken from FIG. 22 except that the twisted or coaxial lead wires 104 and 106 have been straightened out for better illustration of the examples of the present invention. This is also analogous to FIG. 2 for the wires of probes and catheters previously described herein. The straightened and elongated leadwires 104, 106 of FIG. 24 are also illustrative of certain bifilar leadwire systems, which can also be used for pacemakers, neurostimulators and the like. In other words, the leadwires are not always twisted as shown in FIG. 22 as there are certain applications where it is desirable to have the leadwires 104, 106 running parallel to each other in a straight fashion. For illustrative purposes, we will focus on the straight leadwires 104, 106 of FIG. 24, but realize that all of these same principles to follow are equally applicable to twisted or coaxial leadwires. In FIG. 22, one can see that the insulation sheath 142 generally runs up to and fixates the ring electrode 108, but does not cover or encapsulate it. This is also true for the distal tip electrode 138. This is important such that the electrodes are not insulated, so that they can contact body tissue and deliver therapy and/or sense biologic signals. If they were insulated, they would not be able to function and conduct electrical current into body tissue. In practice, the parasitic capacitance value is quite low. For differential mode induced EMFs, by electrically shorting leadwires 104 and 106 together, the energy induced from an MRI system is contained into a loop whereby it will create relatively high RF currents in leadwires 104 and 106. Importantly, this loop disconnects this current flow from the distal electrodes 138 and 108. Accordingly, this energy will be converted to heat within leadwires 104 and 106 where it will be thermally conducted into the insulation sheath 142 and dissipated over a much larger surface area. In the case where the induced EMFs are common mode, frequency selective networks diverting of the present invention are used to couple the high frequency energy to a metallic surface of the probe or catheter, such as a shield, or to an equivalent energy dissipating surface (EDS). This has the effect of preventing a large temperature rise at the electrode to tissue interface which could be damaging to body tissue. More importantly, said RF energy or heat is diverted away from the distal electrodes, which make direct contact with sensitive body tissues. It is in this location where excessive heat dissipation can cause temperature rises that can cause damage to body tissue and therefore, undesirable loss of therapy or even life-threatening tissue damage. In a preferred embodiment, the parasitic capacitances or heat conductive interface would be replaced by passive component capacitances that are connected directly to a conductive energy dissipating surface. This is a more efficient way of diverting the energy to a point distant from the distal electrodes and converting it to heat. By re-directing the RF and/or thermal energy to a point or an area distant from the distal electrodes, one thereby provides a high degree of protection to the sensitive junction between the electrodes and body tissue. For example, that junction may be the point where a distal electrode contacts myocardial tissue and provides critically important pacing pulses. Energy concentration at distal electrode can cause dangerous temperature rises.

Figure 25:
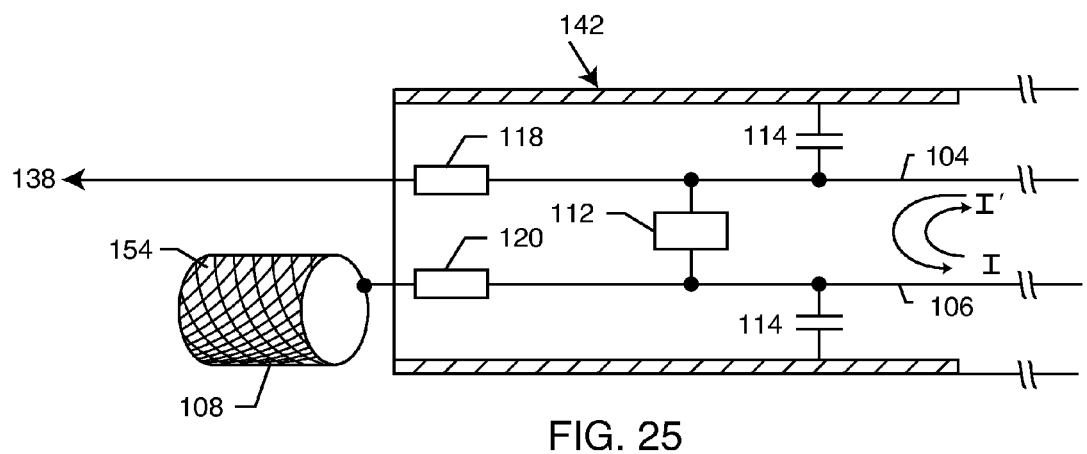
FIG. 25 is similar to FIG. 24 and incorporates electrical features discussed in FIGS. 2-11.

FIG. 25 is generally equivalent and incorporates and embodies the concepts previously described in FIGS. 2 through 11 herein. In FIG. 25, one can see the lead insulation 142. There are parasitic capacitances 114 which are formed between leadwires 104 and 106 and the insulation layer 142. At high frequency, this has the desired effect of diverting or shunting high frequency MRI RF energy away from the leadwires 104 and 106 thereby redirecting energy into the insulation sheath 142 where it can be dissipated over a much larger surface area with minimal temperature rise. Series reactive impeding elements 118 and 120, as previously described and shown in connection with FIG. 7, block, cut or impede the flow of MRI induced RF energy to the distal tip electrode 138 and/or the distal ring electrode 108, wherein these electrodes 138, 108 correspond respectively with the ring electrodes 108, 110 shown in FIGS. 2-11. These series frequency selective reactances 118 and 120 are optional, but do increase the efficacy of the present system.

Reactance 112 can be a simple capacitor as shown in FIG. 5, a low-pass filter or it can be an L-C series trap filter as shown in FIG. 6. This tends to short leadwires 104 and 106 together at high frequency thereby diverting undesirable high frequency energy and thereby preventing it from reaching distal tip electrode 138 or ring electrode 108. Referring once again to FIG. 25, we can see high frequency RF currents I and I'. These, for example, are the RF pulsed currents induced in an elongated implanted lead from a 1.5 Tesla MRI system, and they would oscillate back and forth at 64 MHz thereby reversing directions, as shown, at that frequency. This is better understood by referring to FIG. 9. The currents are cut off (as indicated at 122 in FIG. 9) and are effectively contained within leadwires 104 and 106. This redirects the energy that is induced by the high frequency MR fields back into the EDS sheath 142 at a point distant from the distal electrodes 138 and 108. This EDS desirably prevents the distal electrodes from overheating at their point of contact with body tissue.

Figure 26:
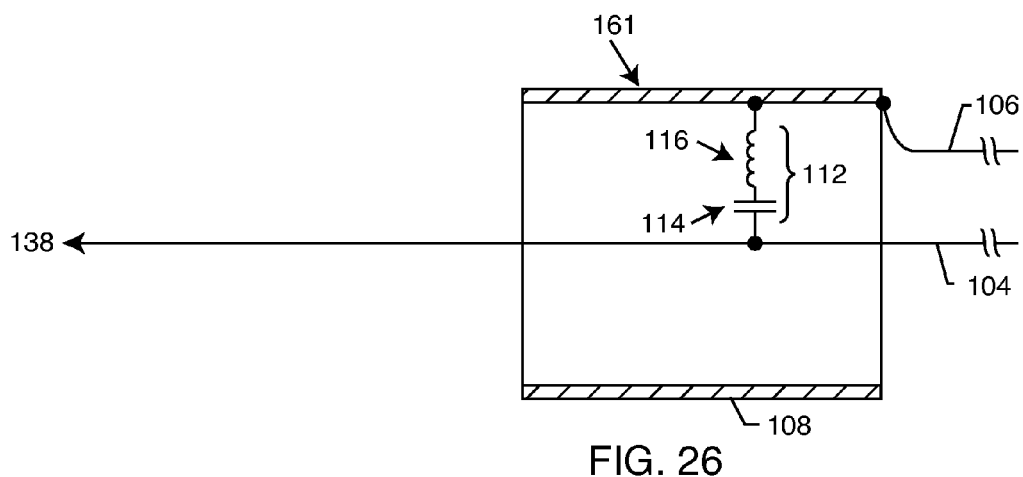
FIG. 26 is similar to a portion of FIGS. 24 and 25, and depicts an L-C trap filter coupled between a distal tip electrode wire and a cylindrical ring electrode.

FIG. 26 is very similar to the structures shown in FIGS. 22 and 24 for active implantable medical devices (AIMDs) such as cardiac pacemakers and the like. Shown is a frequency selective diverter element 112 in accordance with FIG. 6, which in this case consists of an inductor 116 in series with a capacitor 114 (L-C trap filter). The component values of the inductor 116 and the capacitor 114 can be selected such that they are resonant at a particular frequency. In this case, for illustrative purposes, they shall be resonant at 64 MHz thereby providing a low impedance short circuit for 1.5 Tesla MRI signals. This has the effect of diverting or shunting the energy off of leadwire 104 to the relatively large surface area of the ring electrode 108. The ring electrode 108 is typically a metallic structure consisting of a cylindrical ring and very high thermal conductivity. It also has, by necessity, very high electrical conductivity. Accordingly, referring once again to FIG. 26, the ring electrode 108, by its inherent nature, becomes an energy dissipating surface 161 wherein the high frequency RF energy is diverted to it, wherein said RF energy will either be converted to heat, which will be directed into the surrounding blood flow, or said RF energy will be harmlessly dissipated into surrounding body tissues. More specifically, for example, in the right ventricle, the distal tip electrode 138, 152 is designed to be screwed into myocardial tissue in accordance with FIG. 23. The ring electrode 108, on the other hand, is designed to be placed back away from distal tip electrode 138, 152 such that it actually floats in the pool of blood that is flowing in the particular cardiac chamber. In an ideal situation, the wash of blood over it tends to provide a constant cooling action through heat transfer over the ring electrode 108 thereby dissipating undesirable heat from high frequency RF energy harmlessly into the flowing blood (or other body fluids such as lymph in other applications). A disadvantage of this approach is that in a certain percentage of patients both the tip and the ring tend to be overgrown by tissue. Accordingly, the use of a separate energy dissipating surface 161, which is located further back from both the distal tip and ring electrode, is desirable such that it is guaranteed to remain in the blood pool. For the energy dissipating surface 161, which can either be the ring electrode itself or a separate energy dissipating structure 161, it is a desirable feature that it includes some type of biomimetic coating such that tissue overgrowth is inhibited. Referring back to FIG. 25, for example, a biomimetic coating 154 could be deposited all over the ring electrode 108 to thereby inhibit tissue overgrowth.

Figure 27:
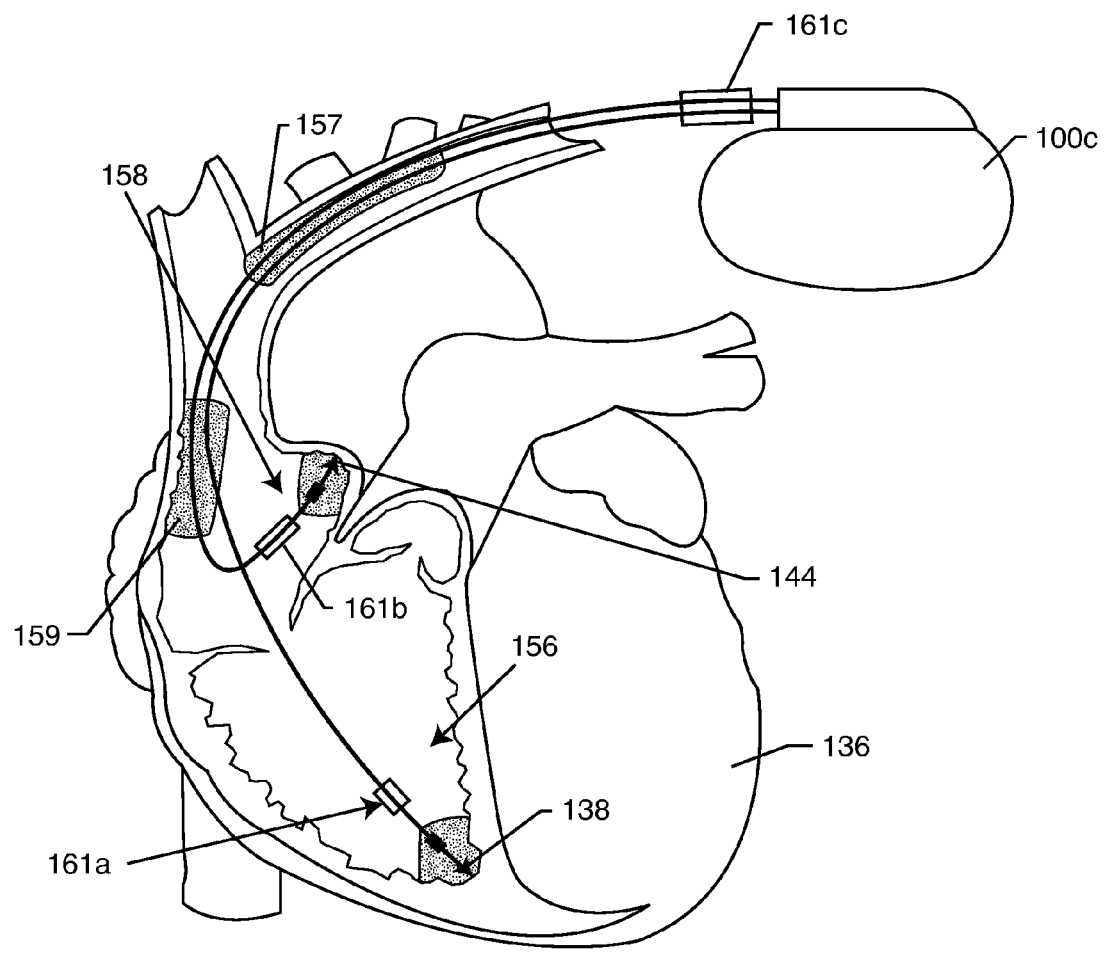
FIG. 27 is a line drawing of a human heart with cardiac pacemaker dual chamber bipolar leads shown in the right ventricle and the right atrium.

FIG. 27 is a line drawing of a human heart with cardiac pacemaker dual chamber bipolar leads shown in the right ventricle 156 and the right atrium 158 of a human heart 136. FIG. 27 is taken from slide number 3 from a PowerPoint presentation given at The 28$^{th}$ Annual Scientific Sessions of the Heart Rhythm Society by Dr. Bruce L. Wilkoff, M. D. of the Cleveland Clinic Foundation. This article was given in Session 113 on Friday, May 11, 2007 and was entitled, ICD LEAD EXTRACTION OF INFECTED AND/OR REDUNDANT LEADS. These slides are incorporated herein by reference and will be referred to again simply as the Wilkoff reference. In FIG. 27, one can see multiple leadwires extending from an active implantable medical device 100C (such as a cardiac pacemaker or the like) coupled to associated electrodes, one of which comprises the distal tip ventricular electrode 138 located in the right ventricular 156 apex. The dark shaded areas in FIG. 25 show the experience of the Cleveland Clinic and Dr. Wilkoff (who is a specialist in lead extraction), where extreme tissue overgrowth and vegetation tends to occur. There are numerous cases of extracted leads where both the tip and ring electrodes have been overgrown and encapsulated by tissue. Referring once again to FIG. 27, one can see tip electrode 138, which is located in the right ventricular apex. The shaded area encasing this electrode 138 shows that this area tends to become encapsulated by body tissue. A distal tip electrode 144 in the right atrium 158 may similarly be overgrown and encapsulated by tissue, as shown by the encasing shaded area. There are other areas in the superior vena cava and venous system where leads tend to be encapsulated by body tissue a great percentage of the time. These are shown as areas 157 and 159. This is particularly important to know for the present invention since these would be highly undesirable areas to place an energy dissipating surface 161 in accordance with the present invention. Ideal locations for energy dissipating surfaces are shown where there tends to be little to no tissue overgrowth as 161a, 161b, or 161c.

Referring once again to FIG. 27, as previously mentioned, it is very important that this leadwire system does not overheat during MRI procedures particularly at or near the distal tip electrodes and rings. If both the distal tip and ring electrode become overgrown by body tissue, excessive overheating can cause scarring, burning or necrosis of said tissues. This can result in loss of capture (loss pacing pulses) which can be life-threatening for a pacemaker dependent patient. It is also the case where implanted leads are often abandoned (where the lead has been permanently disconnected from the AIMD). Often times when the device such as a pacemaker 102 shown in FIG. 27 is changed out, for example, due to low battery life and a new pacemaker is installed, the physician may decide to install new leadwires at the same time. Leadwires are also abandoned for other reasons, such as a dislodged or a high impedance threshold. Sometimes over the course of a patient life-time, the distal tip electrode to tissue interface increases in impedance. This means that the new pacemaker would have to pulse at a very high voltage output level which would quickly deplete its battery life. This is yet another example of why a physician would choose to insert new leads. Sometimes the old leads are simply extracted. However, this is a very complicated surgical procedure which does involve risks to the patient. Fortunately, there is plenty of room in the venous system and in the tricuspid valve to place additional leads through the same pathway. The physician may also choose to implant the pacemaker on the other side. For example, if the original pacemaker was in the right pectoral region, the physician may remove that pacemaker and choose to install the new pacemaker in the left pectoral region using a different part of the venous system to gain lead access. In either case, the abandoned leads can be very problematic during an MRI procedure. In general, abandoned leads are capped at their proximal connector points so that body fluids will not enter into the lead system, cause infections and the like. However, it has been shown in the literature that the distal electrodes of abandoned leads can still heat up during MRI procedures. Accordingly, a passive frequency selective circuit of the present invention is very useful when placed at or near the proximal electrical contact after a pacemaker is removed and its leads are disconnected (abandoned). For example, for an abandoned (left in the body) lead, an energy dissipating surface 161c at or near the proximal lead end is an ideal place to eliminate excess energy induced by MRI in the leadwire system. As it will be shown in subsequent embodiments, the energy dissipating surface 161 can actually be a conductive housing of the AIMD 102. Referring back to the article by Dr. Bruce Wilkoff, attention is drawn to slide number 2, which is an example of a lead extraction showing both a distal tip electrode and a distal ring which have been heavily overgrown and encapsulated by body tissue. Special cutting tools were used to free the lead so it could be extracted, so the tissue shown here is only a small remaining portion of the mass that was originally present. Slide 13 is a dramatic illustration of what a larger mass of encapsulated tissue would look like. In this case, the entire tip was completely surrounded, but if one looks carefully to the right, one can see that some of the ring was still exposed. The situation is highly variable in that the ring is not always fully encapsulated. Slide 16 is an example of tissue removal after a pacemaker bipolar lead was extracted. One can see at the end of the lead, the helix screw that was affixed to myocardial tissue. The surgeon in this photo was removing the tissue encapsulation, which completely surrounded the tip and is still surrounding the ring area. A blow-up of this is shown in slide 17. Again, the tissue that is still affixed to the lead has completely encapsulated the ring, which cannot be seen. Accordingly, there is a need for either a way to prevent the overgrowth of body tissue onto the ring or to ensure that an energy dissipating surface 161 is located far enough away from myocardial tissue to guarantee that it will remain floating in the blood pool.

Figure 28:
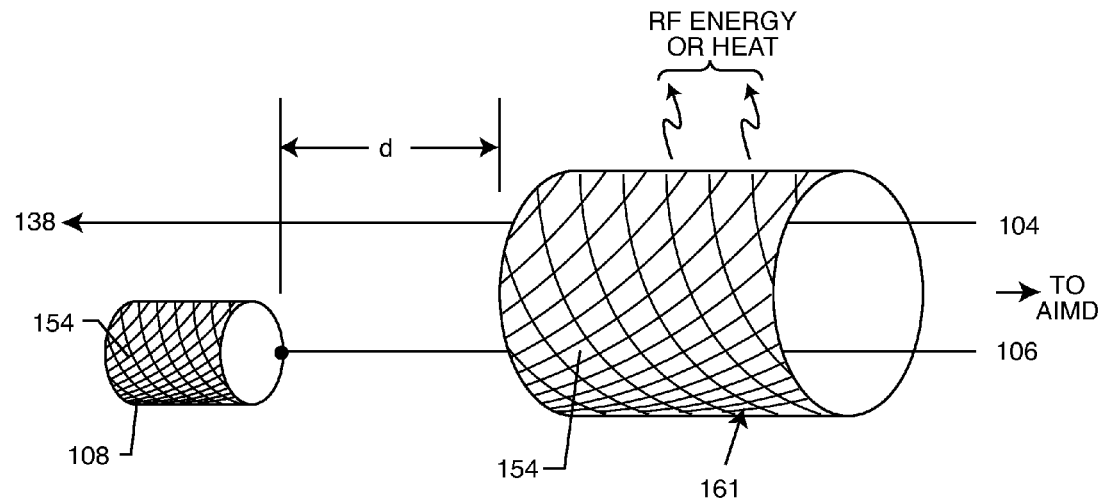
FIG. 28 is a schematic diagram illustration of an energy dissipating surface in spaced relation with tip and ring electrodes.

FIG. 28 illustrates an energy dissipating ring 161 which is located at some distance "d" from both a pacemaker tip electrode 138 and a ring electrode 108 mounted respectively at the distal ends of leadwires 104 and 106. The distance "d" should be sufficient so that the energy dissipating surface 161 is far enough away from both the distal tip and ring electrodes 138, 108 such that there is no heating or temperature rise associated with the tissues that contact the tip and ring electrodes. Another advantage of moving the energy dissipating surface 161 away from the distal electrodes, particularly for a cardiac pacemaker application, is that there would be less tendency for the energy dissipating surface 161 to become encapsulated or overgrown with body tissue. If the energy dissipating surface 161, when it is disassociated at some distance from the electrodes 138, 108, does become overgrown with body tissue, this is not of great concern. Obviously, it would be superior to have the 161 surface floating in freely flowing blood so that there would be constant cooling. However, for example, if the 161 surface did touch off to the right ventricular septum and became overgrown, the only effect would be a slight heating of tissue in an area that is far away from where the actual electrical stimulation and sensing is being done by the electrodes. The ideal distance for the energy dissipating surface does depend on the particular application and ranges from approximately 0.1 cm to 10 cm distance from the distal electrodes.

Referring once again to FIG. 28, the energy dissipating surface 161 is shown as a cylindrical ring. It can be semi-circular, rectangular, octagonal, hexagonal or even involve semi-circles on the lead or any other metallic or similar structure that is also thermally conductive. Literally any shape or geometry can be used as an energy dissipation surface 161. It is a desirable feature of the present invention that the surface area be relatively large so that it can efficiently dissipate heat into the surrounding blood pool and surrounding tissues that are distanced from the electrodes. In FIG. 28, within the ring 161, there are electrical connections (not shown) between leadwire 104 and 106 and to the energy dissipating surface 161 that embody the passive frequency selective circuits previously discussed in connection with FIGS. 2 through 11. The purpose of these frequency selective circuits is to remove RF induced energy caused by the RF pulsed field of MRI from leadwires 104 and 106 and redirect it to the surface 161 where it is dissipated as heat. By having a large surface area, the heat can be dissipated without significant temperature rise such that surrounding tissues would be burned.

In cardiac rhythm management applications, the surface 161 is ideally located in areas where there is freely flowing blood, lymph or equivalent body fluids which adds to the cooling. A biomimetic coating 154 can be applied to the energy dissipating surface area 161 and/or to the ring electrode 108 if it is used as an energy dissipating surface 161. This special biomimetic coating 154 provides a non-thrombogenic and anti-adhesion benefits. This coating can be comprised of a surfactant polymer having a flexible polymeric backbone, which is linked to a plurality of hydrophobic side chains and a plurality of hydrophilic side chains. This coating prevents the adhesion of certain plasma proteins and platelets on the surface and hence initiation of the clotting cascade or colonization of bacteria. Biomimetic coatings also tend to prevent overgrowth or adhesion of body tissues as illustrated in the Wilkoff paper. This polymer compound is described in U.S. Pat. No. 6,759,388 and U.S. Pat. No. 7,276,474, the contents of both patents being incorporated by reference herein. Additional benefits of biomimetic coatings include the prevention of bacterial colonization and resulting infections. It will be obvious to those skilled in the art that other types of coatings could be used on the 161 ring to inhibit or prevent overgrowth of body tissue. As used herein, the term biomimetics includes all such type coatings.

Figure 29:
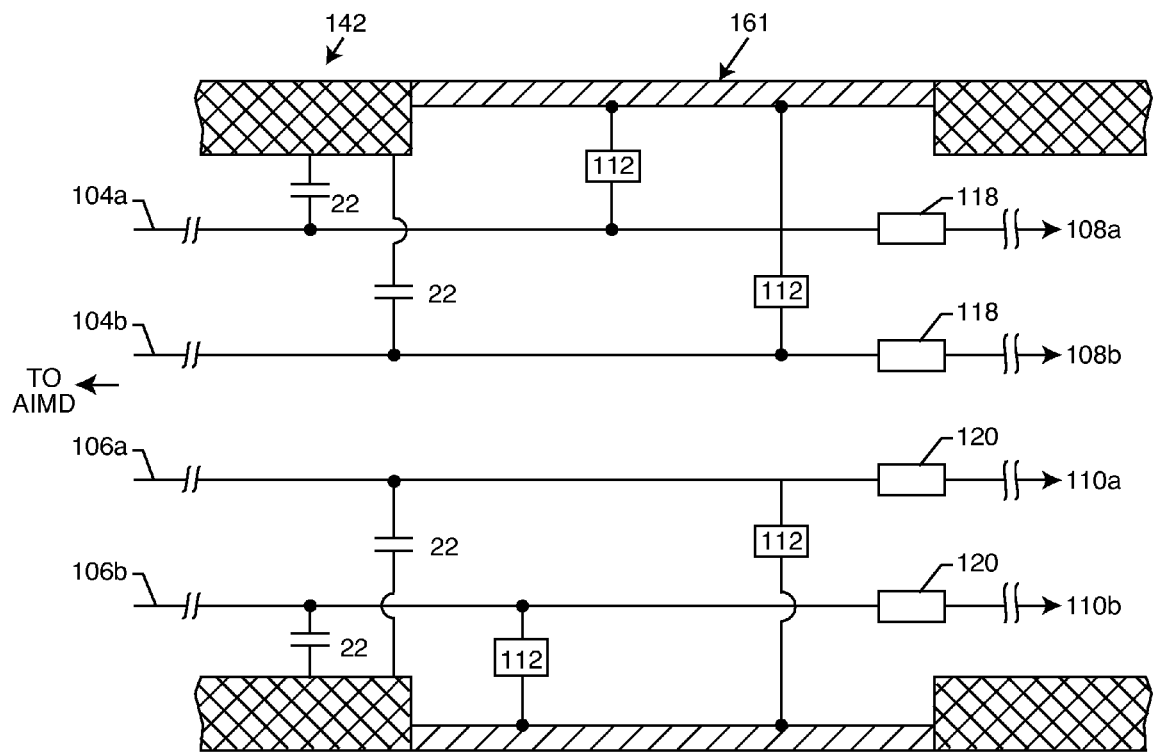
FIG. 29 is a schematic diagram depicting a typical quad polar neurostimulation lead system.

FIG. 29 is a typical quad polar neurostimulation lead system. It will be appreciated that the following discussion also applies to bipolar, hex polar, and even sixteen to twenty-four electrode lead systems (the present invention is applicable to any number of implanted leads or leadwires or electrodes). In FIG. 29, four leadwires 104a, 104b, 106a and 106b are shown which are each directed respectively toward an associated distal electrode 108a, 108b, 110a and 110b. In this case, the electrical stimulation pulses are applied in various combinations between the various electrodes. Unlike a cardiac pacemaker application, there is no particular ring electrode in this case. However, the insulation sheath 142 that surrounds the leadwires, which as mentioned could be of silicone or the like, forms a surrounding surface, which encapsulates the leadwires.

Parasitic capacitances 22 are formed respectively between each of the leadwires 104a, 104b, 106a and 106b and the insulating sheath 142. As previously mentioned, these parasitic capacitances are desirable as they divert high frequency pulsed RF energy from an MRI system to the insulation sheath 142 thereby redirecting the energy so that heat will be dissipated over a larger surface area and away from the interface between the distal tip electrodes 108a, 108b, 110a, and 110b and body tissue. There is also heat that is directly dissipated off of the leadwires, which is conductively coupled into the insulation sheath 142. Again, it is desirable that this occur at a location that is spaced from or distant from the therapy delivery electrodes 108a, 108b, 110a, and 110b. This can be greatly improved by providing a passive component frequency selective diverter circuit 112 which provided a very low impedance at a selected high frequency or frequencies between each of the associated leadwires and the energy dissipating surface 161. The energy dissipating surface 161 would typically either be a metallic ring or a metallic plate or even a separated metallic surface which has both the property of conducting the high frequency energy and also having a relatively large surface area for dissipating said energy into surrounding body tissues. In a preferred embodiment, the energy dissipating surface 161 would be placed sufficiently far back from the distal electrodes 108a, 108b, 110a, and 110b so that in the associated heating of surrounding body tissue would not have any effect on the delicate electrode-to-tissue interface. In addition, by having an energy dissipating surface 161 with a sufficiently large surface area, this will prevent a dangerously large temperature rise as it dissipates energy into the surrounding tissues. By controlling the temperature rise to a small amount, damage to tissue or tissue changes are therefore avoided. The frequency selective reactances 112 are designed to present a very low impedance at selected high frequencies thereby redirecting undesirable high frequency RF energy (in the MHz range) away from the electrodes to the insulating sheath and/or energy dissipating surface 161. In addition, further protection is offered by the optional series frequency selective components 118 and 120. Typically, these can be series inductors or they can be parallel inductor-capacitor bandstop filters in accordance with the present invention (see FIGS. 10-11). Accordingly, substantial protection is provided such that during MRI procedures, the distal electrodes 108a, 108b, 110a, 110$_n$ do not overheat.

Figure 30:
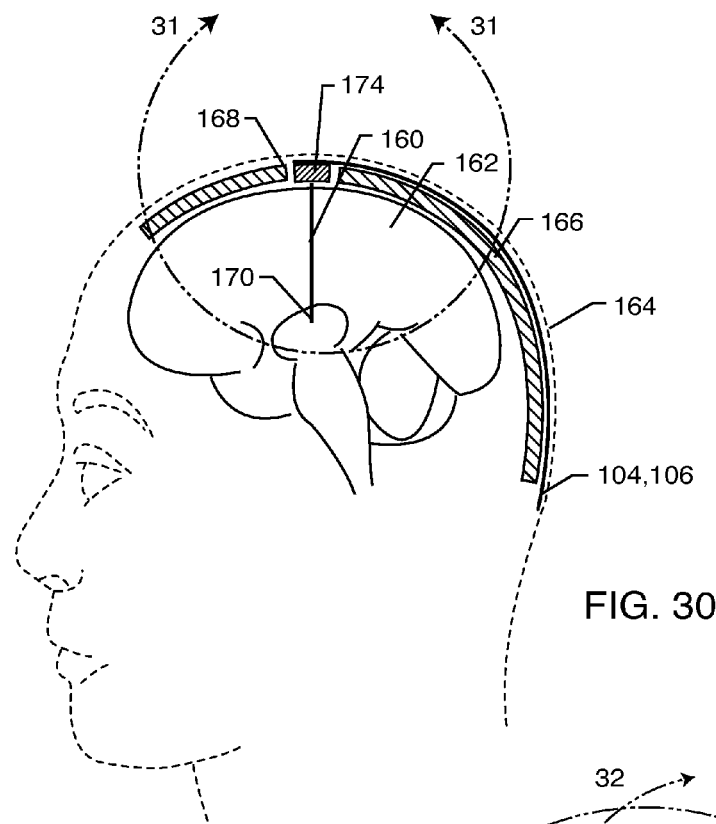
FIG. 30 is a somewhat schematic side view of the human head with a deep brain stimulation electrode shaft assembly implanted therein.

FIG. 30 is taken from FIG. 13 of U.S. 2008/0132987 A1, the contents of which are incorporated herein by reference. Illustrated is a side view of the human head with a deep brain stimulation electrode shaft assembly 160. At the distal end of the electrode shaft 160 are two distal electrodes 108 and 110 (see FIG. 31) implanted into the patient's brain matter 162 at a selected implantation site (there can be any number of electrodes). One or more leadwires 104, 106 (see FIG. 27A) are routed between the skin 164 and the skull 166 down to a pectorally implanted AIMD (pulse generator) which is not shown. Referring back to FIG. 30, one can see that a burr opening 168 in the skull 166 has been made so that the electrode shaft assembly 160 can be inserted.

Figure 31:
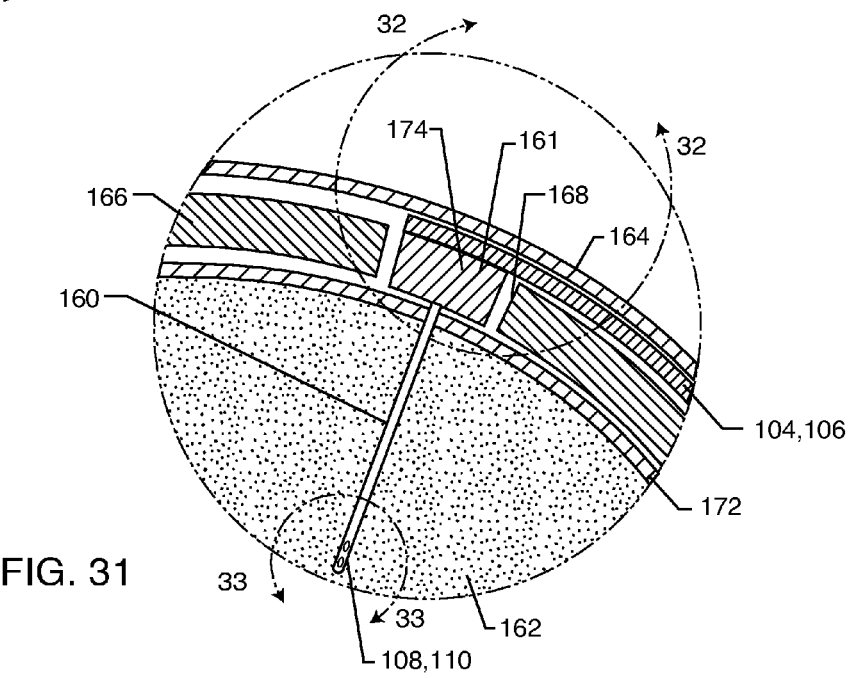
FIG. 31 is an enlarged sectional view corresponding generally with the encircled region 31-31 of FIG. 30.

FIG. 31 is taken generally from section 31-31 in FIG. 30. Shown are bipolar distal electrodes 108 and 110 at or near the end or tip 170 of the electrode shaft 160. The skull is shown at 166 and the dura is shown as 172. Housing 174 acts as an energy dissipating surface 161 and can be hermetically sealed to protect the passive frequency selective diverter and/or impeder components of the present invention from direct exposure to body fluids.

Figure 32:
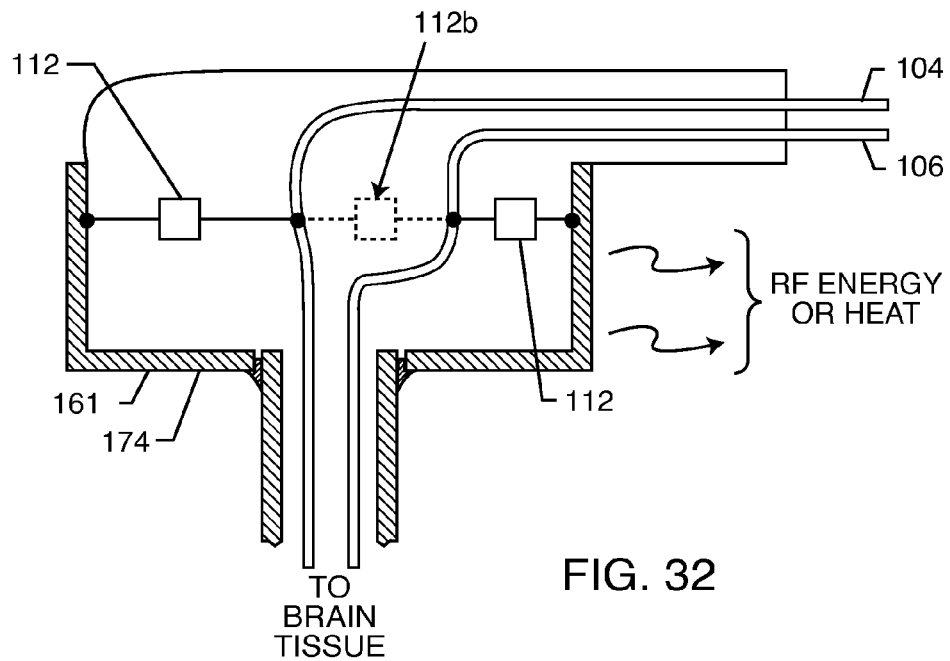
FIG. 32 is a further enlarged and somewhat schematic view corresponding generally with the encircled region 32-32 of FIG. 31.

FIG. 32 is taken from section 32-32 of FIG. 31. Shown are frequency selective passive component diverter circuit elements 112 which are generally taken from FIG. 5 or 6. As previously described, these diverter circuit elements 112 could be combined with series impeder reactance elements 118 and 120 as previously illustrated in FIGS. 7, 10 and 11. These have been omitted for clarity, but would generally be placed in series with the leadwires 104 and 106 and placed between frequency selective circuit elements 112 and the distal electrodes 108, 110. Referring back to FIG. 32, circuit elements 112 would divert high frequency RF energy induced from an MR scanner to the energy dissipating surface 161 where it would be dissipated as RF or thermal energy into the area of the skull 166 and/or dura 172. Frequency selective circuit element 112b is also shown connected between the leadwires 104 and 106. This is optional and would be effective for any differential mode signals that are present in the leadwires 104 and 106. In accordance with FIG. 4 of the present invention, the diverter 112 would redirect or divert MRI induced RF energy back into leadwires 104 and 106 and away from the distal electrodes 108, 110. This is an example of redirecting RF or thermal energy away from a critical tissue interface point. The skull is considered to be a relatively non-critical or less susceptible type of body tissue to thermal injury. This is in comparison with the very thermally sensitive brain matter into which the distal tip electrodes 108, 110 are implanted. It has been shown that even a temperature rise as small as a few degrees C. can cause damage to sensitive brain matter.

Figure 33:
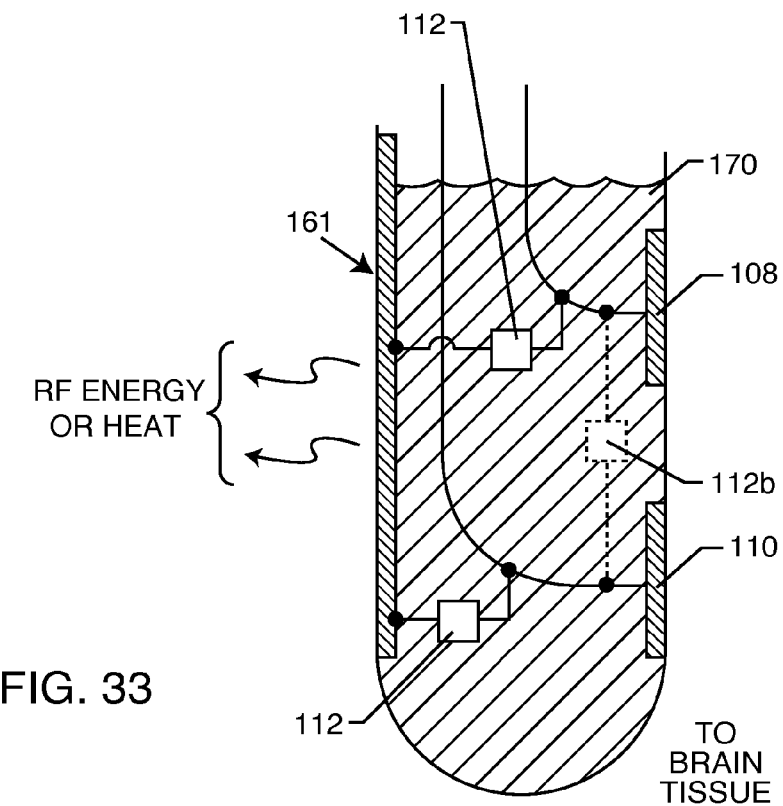
FIG. 33 is an enlarged and somewhat schematic view corresponding generally with the encircled region 33-33 of FIG. 31.

FIG. 33 is generally taken from area 33-33 of FIG. 31. Shown are the two bipolar electrodes 108 and 110. The frequency selective elements 112 and 112b have been moved relative to the location shown in FIG. 32 to illustrate one wrong way to approach this particular problem. Specifically, an energy dissipating surface 161 is shown mounted generally at or near the end portion of the probe shaft 170 in proximity to and/or direct contact with sensitive brain tissue. The frequency selective reactance components 112 and 112b are coupled for redirecting the RF energy from MRI to the energy dissipating surface 161, whereby heat will be dissipated by the energy dissipating surface 161. In the case where it was chosen not to use an energy dissipating surface 161, but simply to rely on the line-to-line frequency selective element 112b, heat would still build-up in the entire distal electrode area and thence be conducted into thermally sensitive brain tissue 162. Accordingly, the placement of the circuit elements as shown in FIG. 33 illustrates a disastrous way to place the frequency selective elements of the present invention. Severe overheating of this distal tip would occur with resulting brain damage. Reference is made to a paper given at the 8$^{th}$ World Congress of the National Neuromodulation Society which was held in conjunction with the 11$^{th}$ Annual Meeting of the North American Neuromodulation Society, Dec. 8-13, 2007, Acapulco, Mexico. This paper illustrates severe tissue damage surrounding a distal tip electrode. This paper was given by Dr. Frank Shellock, Ph. D. and was entitled, MRI ISSUES FOR NEUROMODULATION DEVICES.

Shellock slide 31 shows X-ray views of the placement of deep brain stimulator electrodes into the skull and brain of a human patient. There is also an X-ray view showing the placement of the AIMDs and tunneled leadwires that are associated with the deep brain stimulation electrodes. Slide number 35 shows an extensive thermally induced lesion shown in white with a red arrow to it. This was representative of two patients that inadvertently received MRI wherein their deep brain stimulators overheated and caused extensive thermal injury to the brain. Both patients had neurologic deficits and were severely disabled.

In summary, the configuration illustrated in FIGS. 30, 31 and 32, wherein the thermal energy as dissipated into the skull or dura, is highly desirable as compared to the configuration as illustrated in FIG. 33, which could cause thermal damage to sensitive brain tissue.

Referring once again to the Shellock paper, one can see that the deep brain stimulator involved multiple electrodes. In FIG. 31 one can see that in this example, there are only two electrodes 108 and 110. This is a way of illustrating that with real time MRI guidance, the physician can much more accurately place the electrodes into the exact area of the brain, which needs to be electrically stimulated (for example, to control Parkinson's tremor, Turret's Syndrome or the like). What is typically done is that precise MR imaging is performed prior to electrode implantation which is referenced to fiducial marks that's placed on the skin in several locations outside of the patient's skull. The patient's head is first shaved, then these marks are placed and then the MRI is performed. Then when the patient enters the operating room, a fixture is literally screwed to the patient's head at these fiducial marks. This fixture contains a bore into which the various drilling and electrode implanting tools are located. Because of the need for all of this mechanical fixturing, tolerances are involved. This means that by the time the electrodes are implanted in the brain, they may be not in the precise locations as desired. Accordingly, extra electrodes are inserted which involves more leads than are really necessary. The patient is usually awake during parts of this procedure wherein the physician will use trial and error to stimulate various electrode pairs until the desired result is achieved. In contrast, the present invention minimizes the need for all these extra electrodes and extra wiring. This is because by eliminating the potential for the distal electrodes to overheat and damage brain tissue, this entire procedure can be done under real time MRI imaging. In other words, the physician can be watching the MRI images in real time as he precisely guides the electrodes to the exact anatomy of the brain that he wishes to stimulate.

FIG. 34 is a hermetically sealed package consisting of a passive distal tip electrode 138 which is designed to be in intimate contact with body tissue, such as inside the right atrium of the heart. A hermetic seal is formed at laser weld 176 as shown between the tip electrode 138 and a metallic ring 178. Gold brazes 180 are used to separate the metallic ring 178 from the energy dissipating surface 161 by use of an intervening insulator 182. This insulator 182 could typically be of alumina ceramic, other types of ceramic, glass, sapphire or the like. The energy dissipating surface 161 is typically gold brazed 183 to the other side of the insulator 182 as shown. An inductor 116, such as an inductor chip in accordance with FIG. 10, is shown connected between the distal tip electrode 138 and a conductive leadwire or pin 184 which is attached by laser welds 176 to the end of the leadwire 104 extending to the AIMD. As shown, the lead 184 protrudes through a hermetic seal assembly 188 formed by a metallic flange 186 which is typically of titanium or platinum or the like. The flange 186 is hermetically attached to the lead 184 by gold brazes 180, and is typically laser welded as shown at 177 to a proximal end of the energy dissipating surface 161.

FIG. 35 is a cut-away view taken generally from the housing of FIG. 34. It is important that the electrical insulating material 182 either be of very low thermal conductivity or have a relatively long length "L" as shown. The reason for this is that the thermal energy that is developed in the energy dissipating surface 161 must not be allowed to reach the distal tip electrode 138 as shown in FIG. 34 where heat could cause damage to the adjacent tissue.

The energy dissipating surface 161 is typically of biocompatible metals, such as titanium, platinum or the like. It is important that the energy dissipating surface be both electrically conductive and thermally conductive so that it can transfer RF and thermal energy into body fluid or tissue. The energy dissipating surface 161 can be roughened or even corrugated or bellowed as shown in FIG. 36 to increase its surface area and therefore its energy dissipating properties into surrounding body fluids or body tissue.

In accordance with FIG. 5, capacitive elements 114 are shown in FIG. 34 are designed to act as a low impedance at higher frequencies. Electrical connections 190 (FIG. 34) couple the capacitors 114 from the leadwire 184 to the energy dissipating surface 161. This forms a broadband low pass filter wherein the inductor 116 acts in cooperation with the capacitive elements 114. The presence of the inductor element 116 is not required; however, it does enhance the performance of the capacitor elements 114. Capacitor elements 114 are typical off-the-shelf commercial monolithic ceramic capacitors (MLCCs). These are better illustrated in FIG. 38.

There is an advantage in the present invention in using a capacitor for the selective frequency element 112 as shown in FIG. 5. The capacitor tends to act as a broadband filter which will attenuate a range of MRI frequencies. For example, placement of an effective capacitor 114 could attenuate 64 megahertz, 128 megahertz and higher MRI frequencies. However, if one were to use an L-C series trap filter as shown in FIG. 6 for the variable frequency element 112, then this would only be effective at one MRI frequency, for example, 64 megahertz only. Of course, as already been disclosed herein, one could use multiple L-C trap filters. However, in a preferred embodiment the use of a capacitor as illustrated in FIG. 5 is desirable because with a single component, one can attenuate a broad range of MRI frequencies.

The schematic diagram for the circuitry of FIG. 34 is shown in FIG. 37. Capacitors 114 are actually in parallel and act as a single capacitive diverter element to the EDS surface. The reason for multiple capacitors is to obtain a high enough total capacitance value so that the capacitive reactance is very low at the frequency of interest (for example, 64 MHz for a 1.5 T MR system).

An alternative capacitor 114 for use in the circuit of FIG. 37 is known as a unipolar feedthrough capacitor is shown in FIG. 39. It has inside diameter and outside diameter termination surfaces 192 for electrical contact. Feedthrough capacitors can be unipolar or multipolar. These are completely described in the prior art; for example, refer to U.S. Pat. No. 7,363,090, particularly FIGS. 3, 5, 29 through 31, and 39. See also U.S. Pat. Nos. 4,424,551; 5,333,095; and 6,765,779.

Figure 40:
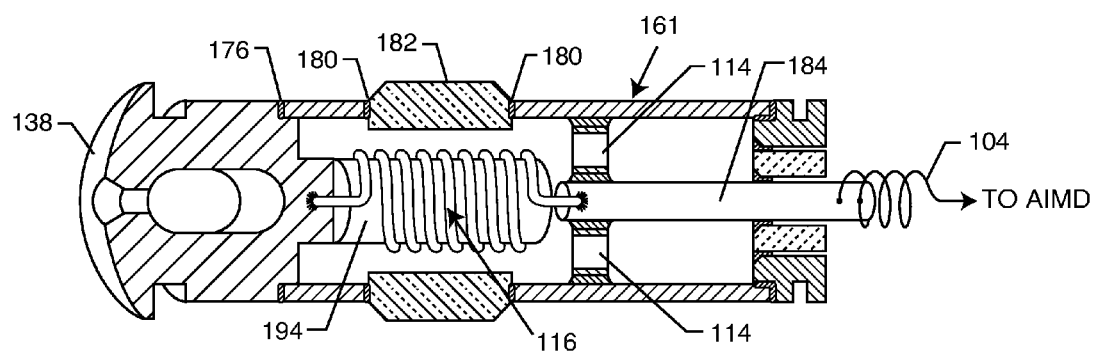
FIG. 40 is a sectional view similar to FIG. 34 and depicts an alternative embodiment wherein an inductor element is wound or printed about a central mandrel.

FIG. 40 is similar to FIG. 34 (using common reference symbols) except that the inductor element 116 is wire wound around a non-ferromagnetic mandrel 194 (formed from a material such as a ceramic or plastic). This type of wound inductor 116 has much higher current handling capability as compared to the inductor chip of FIG. 34. The inductor chip of FIG. 34 can be fabricated from a variety of shapes including Wheeler's spirals and the like. Refer to U.S. 2007/0112398 A1, FIG. 83 and FIGS. 70 and 71 of U.S. 2009/0243756. These inductors can be manufactured by a number of printing techniques including lithographic or copper clouting and etching. However, this results in relatively thin and high resistivity inductor traces.

It is important that the inductor element 116 of the present invention be able to handle substantially high currents when it is in series with the lead 184. The reason for this has to do with either ICD applications for shock electrodes or automatic external defibrillation (AED) events. AEDs have become very popular in government buildings, hospitals, hotels, and many other public places. When the external defibrillator paddles are placed over the chest of a cardiac pacemaker patient, the high voltage that propagates through body tissue can induce powerful currents in implanted leads. Accordingly, the inductor 116 of the present invention has to be designed to handle fairly high current (as high as the 4 to 8 amp range in short bursts). The wire wound inductor 116 of FIG. 40 has wire of a larger cross-sectional area and is therefore a higher current handling inductor and is therefore a preferred embodiment.

Figure 41:
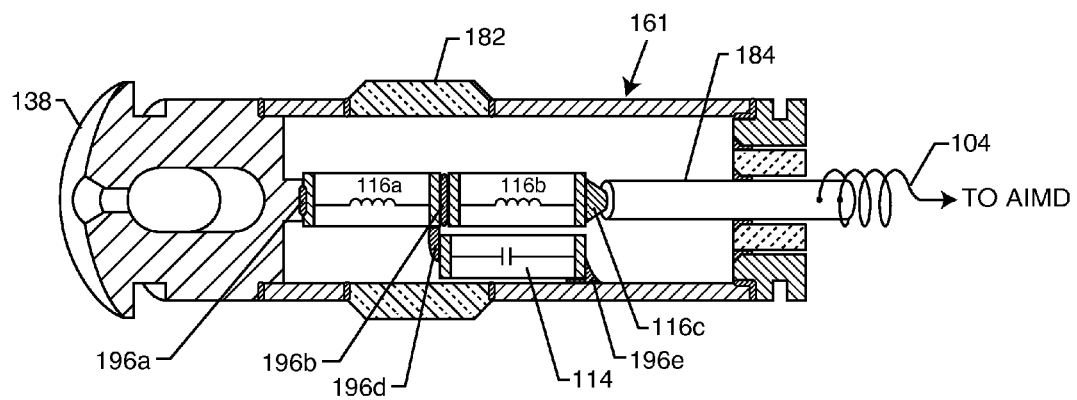
FIG. 41 is a sectional view similar to FIGS. 34 and 40, but illustrates a further alternative embodiment of the invention with alternative means for decoupling signals from a leadwire to an energy dissipating surface.

FIG. 41 illustrates an entirely different approach for the diverting of RF energy away from the electrode 138 to the energy dissipation surface 161. Shown are electrical connections 196a, 196b between a first inductor 116a and the distal tip electrode assembly 138. The other end of the first inductor 116a is connected to a second inductor 116b which is in turn electrically connected at 116c to the leadwire 184, 104. The capacitor 114 is connected between the junction of the two inductors 116a and 116b at electrical connection 196d. The other end of the capacitor is electrically connected at 196e to the energy dissipating surface 161. An insulating sleeve (not shown) can be used to ensure that the capacitor termination and electrical connection 196d does not inadvertently make contact (short out) with the energy dissipating surface 161. As shown, this connection is made adjacent to the insulator 182 so there is no chance for such shorting out.

Figure 42:
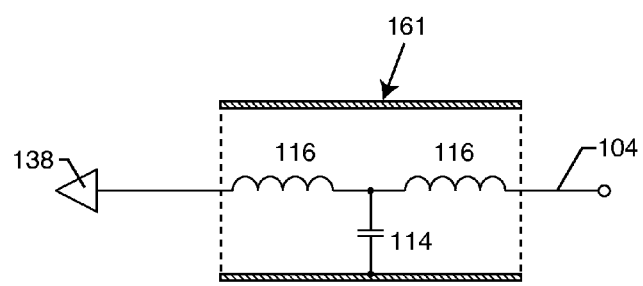
FIG. 42 is a schematic circuit diagram corresponding with the sealed electrode assembly of FIG. 41.

The electrical schematic for FIG. 41 is shown in FIG. 42. In accordance with FIG. 7, this forms what is known in the art as a low pass filter (in this example, a T filter), which tends to enhance the filtering performance by directing more of the RF energy to the energy dissipating surface 161. As previously mentioned, a single or multi-element low pass filter would attenuate a broad range of MRI frequencies and would be an advantage in the present invention for that reason.

Figure 43:
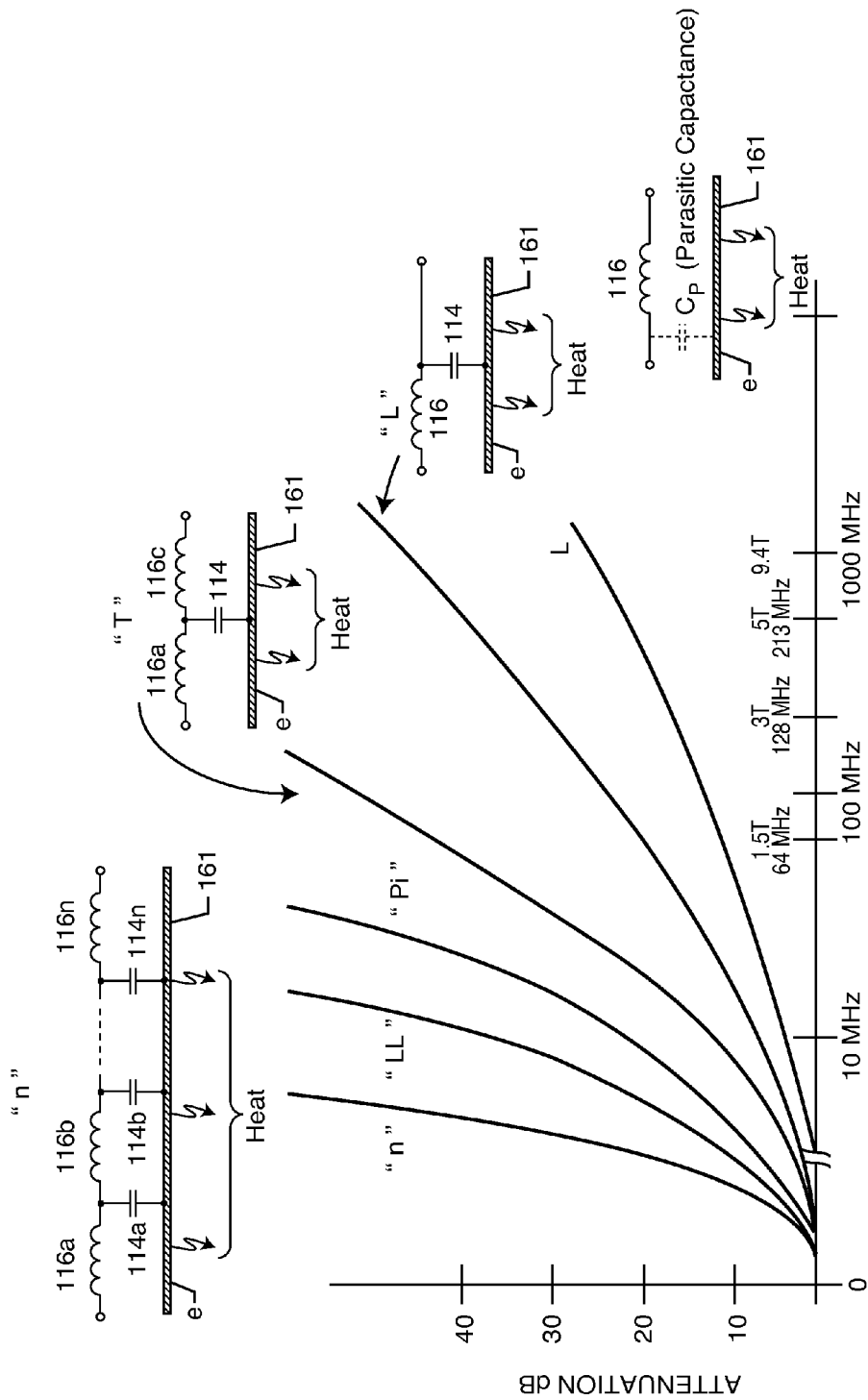
FIG. 43 is an attenuation versus frequency chart for various types of low pass filters.
Figure 44:
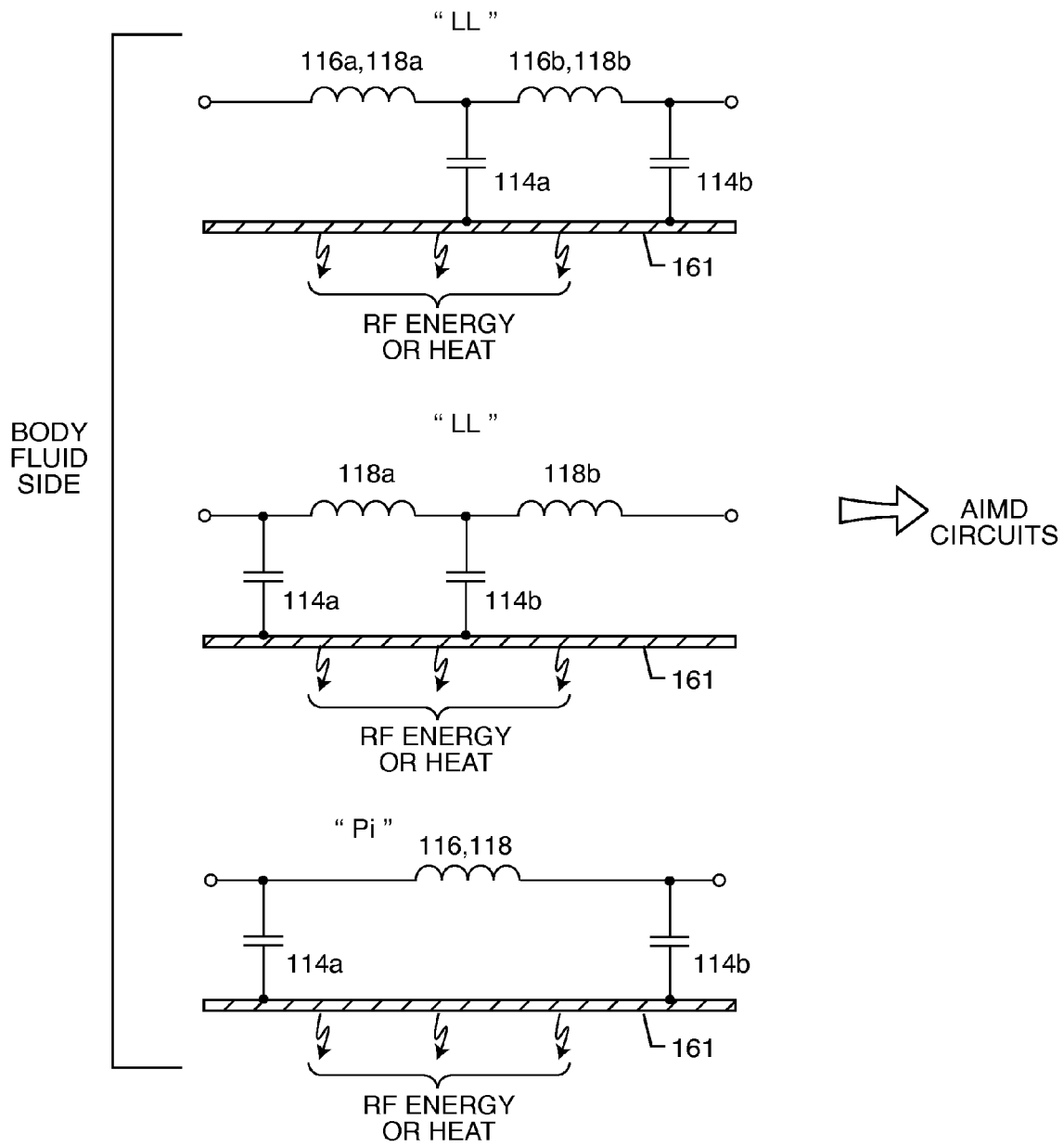
FIG. 44 shows schematic circuit diagrams for different types of low pass filters charted in FIG. 43.

The various types of low pass filters are more thoroughly shown in FIGS. 43 and 44 which compares the filtering efficiency measured as attenuation in dB with increasing numbers of filter elements. The low pass filters illustrated in FIG. 43 perform two very important functions. First, they are very effective EMI filters in order to protect AIMD electronics from the powerful electromagnetic fields during MRI scans and the like. Secondly, they all have capacitor diverter elements that are associated with their inductor impeder elements. Accordingly, the capacitors act as energy diverters in the present invention thereby redirecting induced RF energy on the leads to the energy dissipating surfaces (161). Shown are single element low pass filters consisting of either the capacitor 114 or an inductor 116, an L filter which consists of an inductor 116 and a capacitor 114, a T filter, a Pi filter (FIG. 44), an LL filter (FIG. 44) or an "n" element filter (FIG. 43). FIG. 43 shows the general response curves of these types of filters as attenuation versus frequency. Selected schematics for these various filters, which are correlated to the curves in FIG. 43, are shown in FIG. 44. As one increases the number of filter elements, the ability to attenuate or block high frequency signals from reaching sensitive AIMD electronics is improved. Referring once again to FIG. 43, for example, one can see that for a particular value of a single element capacitive filter, the attenuation for a 1.5 Tesla MRI system operating at 64 MHz is only about 12 dB. This means that a certain amount of the RF energy would still reach the distal tip electrode. Now compare this to the T filter of FIG. 43, where one can see that there is in excess of 45 dB of attenuation. In this case, an insignificant amount of RF energy from the RF pulsed frequency of the MRI, would reach the distal electrode. Accordingly, one preferred embodiment of the present invention is that a capacitor combined with one or more inductors would be an optimal configuration. As the number of elements increases, the filtering efficiency improves. When the filtering efficiency improves, this means that less and less RF energy will reach the distal tip.

Figures 45, 46:
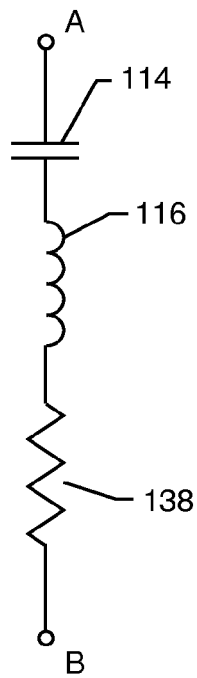
FIG. 45 is a schematic circuit diagram illustrating an L-C trap filter.
FIG. 46 depicts a resonant frequency equation for the L-C trap filter of FIG. 45.

FIG. 45 illustrates a schematic diagram of a series inductor 116-capacitor 114 filter which is commonly known in the industry as an L-C trap filter. The L-C trap filter was previously described in connection with FIG. 6. Referring once again to FIG. 45, there is a particular frequency for a trap filter when the capacitive reactance becomes equal and opposite to the inductive reactance. At this single frequency, the capacitive reactance and the inductive reactance cancel each other out to zero. At this point, all one has left is the residual resistance 198. If one selects high quality factor (Q) components, meaning that they are very low in resistance, then the trap filter of FIG. 46 ideally tends to look like a short circuit at its resonant frequency $f_r$ between points A and B which may comprises connections respectively to a pair of leadwires 104 and 106. FIG. 46 gives the resonant frequency equation where $f_r$, in this case, was measured in hertz. FIG. 9 shows the effect of a short circuit 122 between leadwires 104 and 106. Referring once again to FIG. 45, it is important that the amount of resistance 138 be controlled. This is better understood by referring to FIG. 47.

Figure 47:
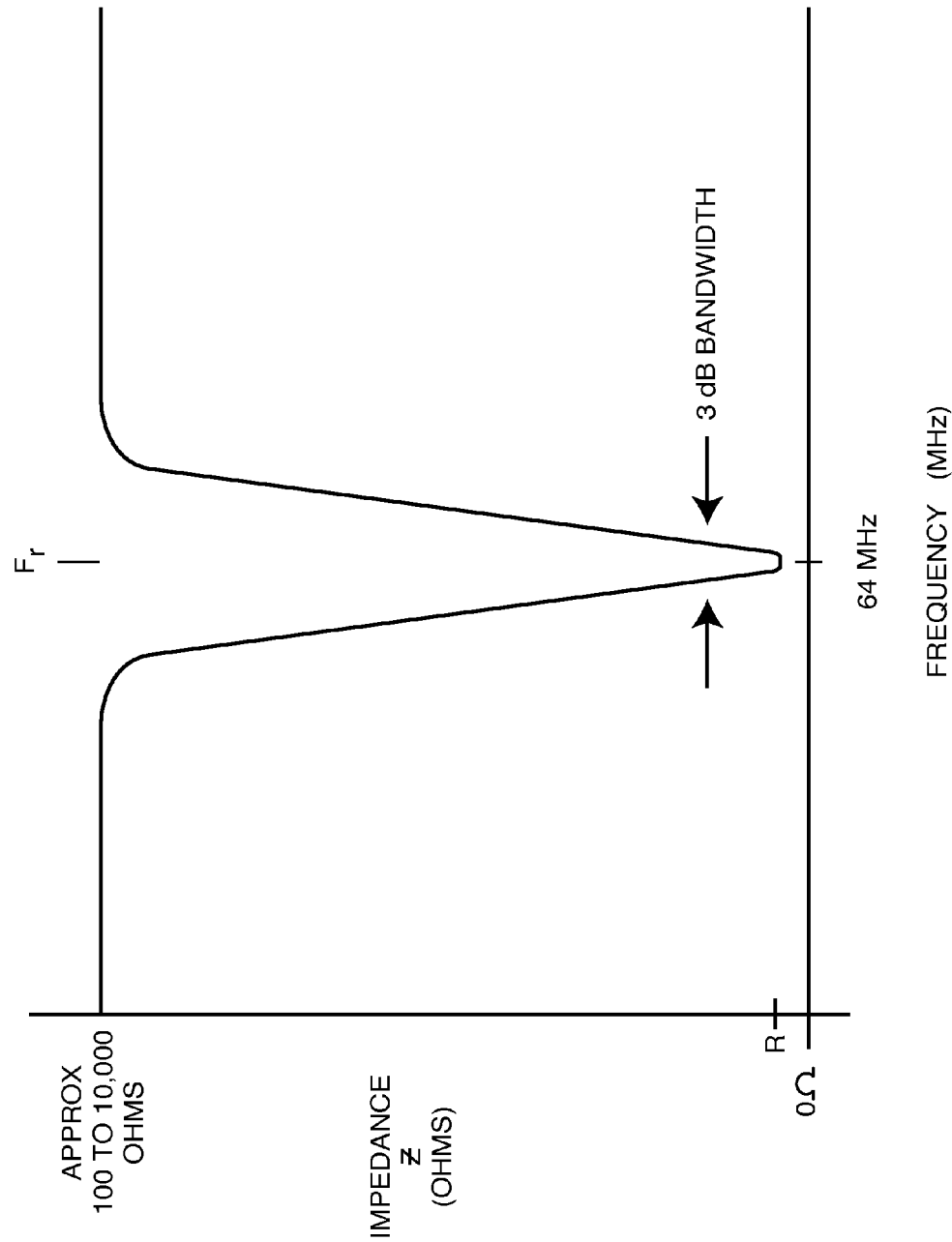
FIG. 47 is an impedance versus frequency chart for the L-C trap filter of FIG. 35.

FIG. 47 illustrates the impedance Z in ohms versus frequency of the series resonant L-C trap filter of FIG. 45. As one can see, the impedance is quite high until one reaches the frequency of resonance $f_r$. At this point, the impedance of the series L-C trap goes very low (nearly zero ohms). For frequencies above or below resonance $f_r$, depending on the selection of component values and their quality factor (Q), the impedance can be as high as 100 to 1000 or even 10,000 ohms or greater. At resonance, the impedance tries to go to zero and is limited only be the amount of resistance 138 (FIG. 45) that is generally composed of resistance from the inductor 116 and also the equivalent series resistance from the electrode plates of the capacitor 114. The resistance 138 could also be a discrete resistor that is added in series with the capacitor 114 and the inductor 116. In a preferred embodiment, this would be a chip resistor. There is a trade off in proper selection of the components that controls what is known as the 3 dB bandwidth. If the resistance is extremely small, then the 3 dB bandwidth will be narrower. However, this makes the trap filter more difficult to manufacture. Accordingly, the 3 dB bandwidth and the resistive element R are preferably selected so that it is convenient to manufacture the filter and tune it to, for example, 64 MHz while at the same time providing a very low impedance R at the resonant frequency. For an ideal L-C series resonant trap filter, wherein ideal would mean that the resistance R would be zero, then the impedance at resonance would be zero ohms. However, in this case, the 3 dB bandwidth would be so narrow that it would be nearly impossible to manufacture. Accordingly, some amount of resistance R is in fact desirable. In a preferred embodiment, the resistance R in an L-C trap filter is equal to the characteristic resistance of an implanted lead so that maximum energy transfer will occur to the energy dissipating surface. The resistance in the L-C series resonant trap filter can be controlled by the amount of resistance in the inductor itself and/or the equivalent series resistance of the capacitor. For example, one can control or even increase the resistance of an inductor by adding more turns of wire or making the wire or circuit traces smaller in cross-section. One could also use higher resistivity materials in the construction of the inductor. One could also add a discrete resistor in series with the inductor and capacitor of the L-C trap. In a preferred embodiment, this could be a discrete chip resistor. In summary, controlling the resistance of the L-C trap filter is a novel feature in its application herein as a frequency selected diverter to a surface 161.

As previously mentioned, there is a disadvantage to use the L-C trap filter as shown in FIG. 6. That is, it is really only effective for attenuating the one MRI frequency (for example, 64 megahertz for a 1.5 megahertz scanner). Accordingly, when the AIMD manufacturer would apply for their FDA conditional labeling, they could only claim compliance with 1.5 Tesla MRI scanners. However, the L-C trap filter of FIG. 6 also offers a very important advantage in that it offers a very high degree of attenuation at this one selected frequency and is also highly volumetrically efficient. Accordingly, there is a trade-off here. When one uses a broadband low pass filter, a broad range of frequencies is attenuated at the cost of increased size and complexity (an additional number of components). An L-C trap filter such as shown in FIG. 6 is more of a "rifle-shot" approach wherein only one selected frequency is attenuated. In physics, this is more efficient and tends to make the components smaller. By controlling the value of the resistance 138 in FIG. 45, energy transfer is maximized from the implanted leads to the 161 surface or housing of the AIMD. In accordance with Thevenin's Maximum Power Transfer Theorem, assuming a resistive system, maximum energy transfer to a load occurs when the characteristic source impedance (the lead system impedance) is equal to the load resistance. For example, if the implanted lead had an implanted characteristic resistance of 2 ohms, it would be desirable to have the resistance of the L-C trap filter illustrated in FIG. 45 also be 2 ohms. A potential disadvantage of a high Q (low resistance) L-C trap filter is that at resonance, its inductive and capacitive reactive components cancel each other out. In other words, at resonance the L-C trap becomes purely resistive. In accordance with the present invention, it is a relatively simple matter though to add resistance in series with the L-C trap filter. This can be done through using a discrete resistor such as a chip resistor or by deliberately building addition resistance into the design of the inductor and/or the capacitor's equivalent series resistance.

FIG. 48 illustrates yet another method of decoupling RF signals from leadwire 104. Referring back to FIGS. 34 through 43, all of the aforementioned decoupling techniques involve broad band low pass filtering. The advantage with these is that they would be applicable to a wide range of MRI machines including 0.5, 1.5, 3.0, 5.4 Tesla and so on. In other words, these broad band EMI filters would attenuate a broad range of RF frequencies. In FIG. 48, one can see that there are two discrete L-C trap filters. The first trap filter consists of inductor 116a and capacitor 114a acting in series, and the second trap filter consists of inductor 116b and capacitor 114b operating in series. This is best understood by referring to the schematic of FIG. 49 which shows the series connection of 116a, 114b from the lead 184 to the energy dissipating surface 161. Inductor 116b and capacitor 114b are also connected in series from the lead 184 to the energy dissipating surface 161.

In FIG. 48, one can see that an electrical connection 196a is made between the distal tip electrode 138 and inductor chip 116. Inductor chip 116a is then electrically connected via electrical connection material 196b to monolithic chip capacitor (MLCC) capacitor 114a. The other end of the chip capacitor 114a is electrically connected at 196d to the energy dissipating surface 161. Inductor 116b is also connected to the distal tip electrode 138 by material 116e. The other end of inductor 116a is connected in series at 116c with capacitor 114b. The other end of capacitor 114b is electrically connected at 116f to the energy dissipating surface 161. In this way, the two trap filters are connected in parallel between the lead 184 and the energy dissipating surface 161 as shown in the schematic diagram of FIG. 49.

FIG. 50 illustrates a typical chip inductor 116a, 116b which can be used in FIG. 50.

FIG. 51 is a typical prior art MLCC chip capacitor 114a, 114b which can also be used in conjunction with the package shown in FIG. 48.

Figure 52:
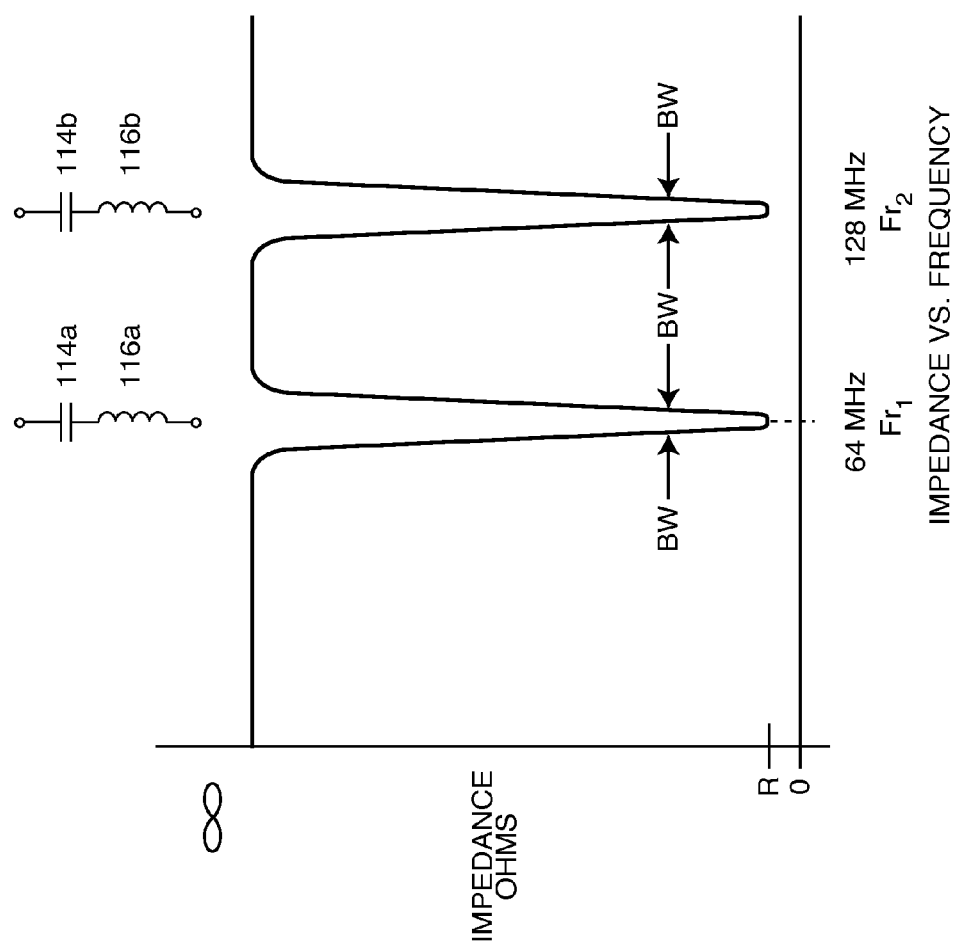
FIG. 52 is an impedance versus frequency chart for the dual L-C trap filter embodiment of FIG. 48.

FIG. 52 is a graph of impedance versus frequency showing the impedance in ohms for the two L-C trap filter elements that were previously described in FIGS. 48 and 49. By carefully selecting the component values 114a and 116a and also 114b and 116b, one can select the frequencies at which the two (or more) L-C trap filters will self-resonate. In the present example, the first trap filter including components 114a and 116b has been selected to resonate at 64 MHz, and the second trap filter including element 114b and 116b has been selected to resonate at 128 MHz.

Referring once again to FIG. 52, one can see that we now effectively have dual trap filters which tend to act as very low impedance between the leadwire 184, 104 and the energy dissipating surface EDS at two different frequencies. In this case, by example, the first trap filter resonates at 64 MHz, which is the RF pulsed frequency of a 1.5 Tesla MRI system. The second trap filter, which has resonant frequency 128 MHz, is designed to divert RF energy to the EDS surface from a 3 Tesla MRI frequency. It will be appreciated that a multiplicity of trap filters can be used depending on how many different types of MRI systems that one wants to claim compatibility with for an implanted lead and electrode. The method of selecting the resonant frequency was already described in FIG. 46 and is applicable to FIG. 52. Referring once again to FIG. 52, one will note that except at the resonant frequency $f_{r1}$ and $f_{r2}$, the impedance of the trap filter is very high. This is very important so that low frequencies are not attenuated. Accordingly, using a cardiac pacemaker application as an example, pacing pulses would be free to pass and also low frequency biologic signals, such as those that are produced by the heart. It is very important that pacemaker sensing and pacemaker pacing can occur while at the same time, high frequency energy, for example, that from the RF pulsed frequency of an MR system can be diverted to an appropriate energy dissipating surface 161. The parallel trap filters, as described in FIGS. 48, 49 and 52, have to be carefully designed so that they will not resonate or interact with each other. This is best accomplished if one were to place a bandstop filter between them which would tend to electrically isolate them. This is not shown, but would be understood by those skilled in the art.

Figure 53:
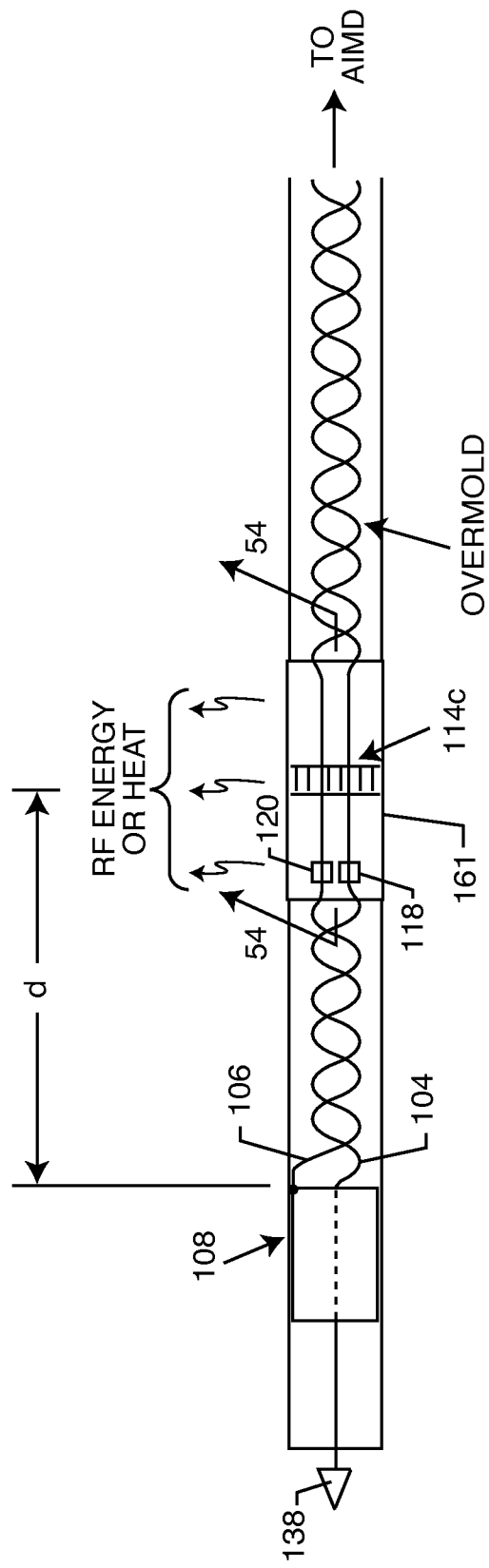
FIG. 53 is a schematic representation of an implantable medical device bipolar leadwire system.

FIG. 53 illustrates a typical active implantable medical device bipolar leadwire system. On the left is shown a distal tip electrode 138 and a distal ring electrode 108. The energy dissipating surface 161 of the present invention is shown along with coaxial leadwires 104 and 106 which would be connected to the AIMD. These could be endocardial or epicardial in accordance with the prior art.

Figure 54:
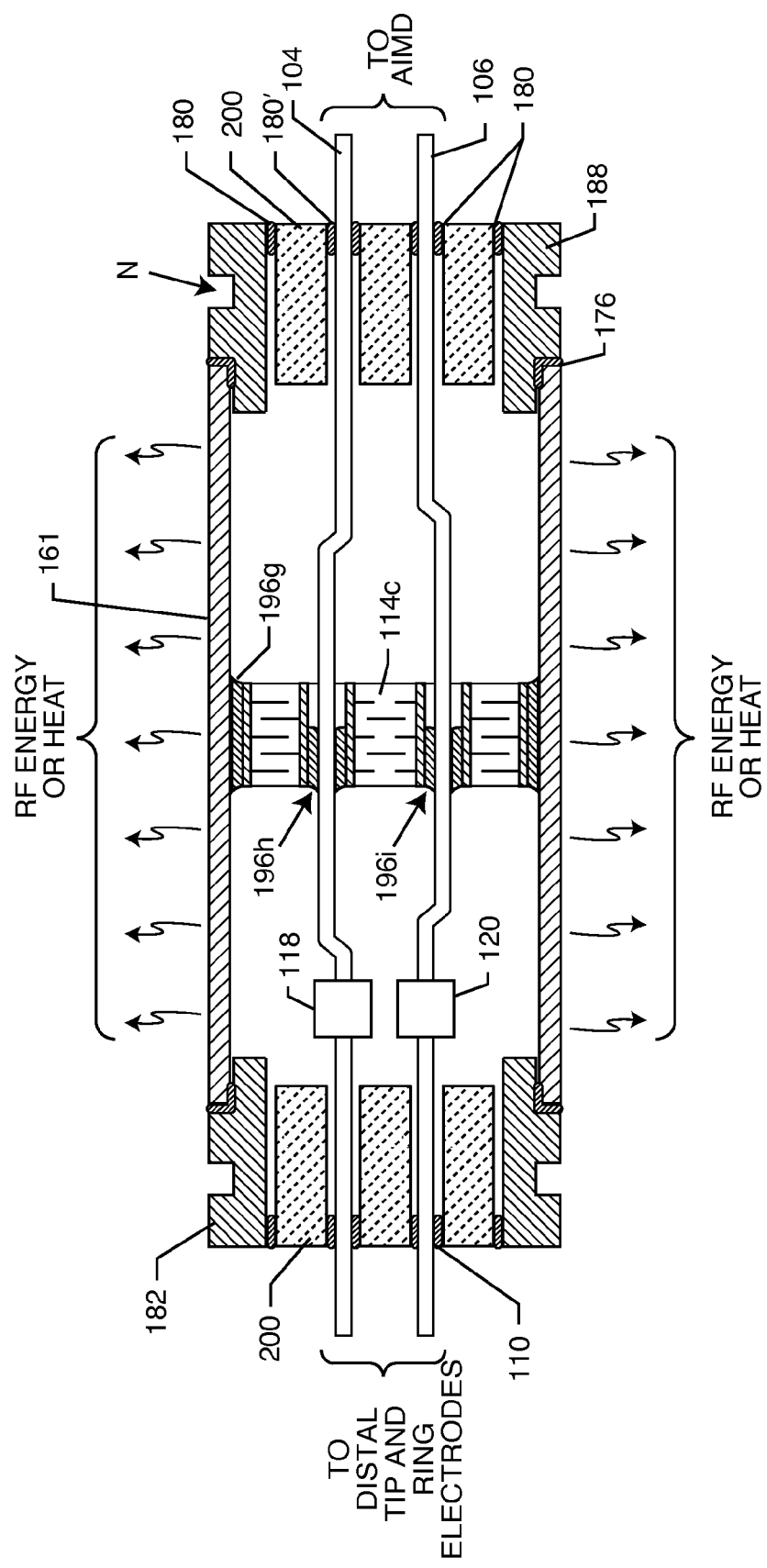
FIG. 54 is an enlarged and somewhat schematic sectional view taken generally on the line 54-54 of FIG. 53.

FIG. 54 is a blown up sectional view generally taken from section 54-54 from FIG. 53. In FIG. 54, one can see that there is an energy dissipating surface 161 which is enclosed at both ends by two hermetic seal flanges or flange assemblies each consisting of a flange 188, an insulator 200 and gold brazes 180, 180'. The flange 188 is designed to be laser welded 176 into the metallic energy dissipating surface 161 as shown. A bipolar feedthrough capacitor 114c is shown in cross-section in FIG. 54 where the two leadwires 104 and 106 pass through it. The feedthrough capacitor 114c is a very efficient broadband filter which would tend to decouple or divert high frequency signals such as 64 MHz (1.5 Tesla) and 128 MHz (3 Tesla) from the leadwires 104, 106 to the energy dissipating surface 161 in accordance with the present invention. Each leadwire 104 and 106 may additionally include the frequency selective impeding reactances 118 and 120 (as previously shown and described in FIGS. 7, 10 and 11).

Figure 55:
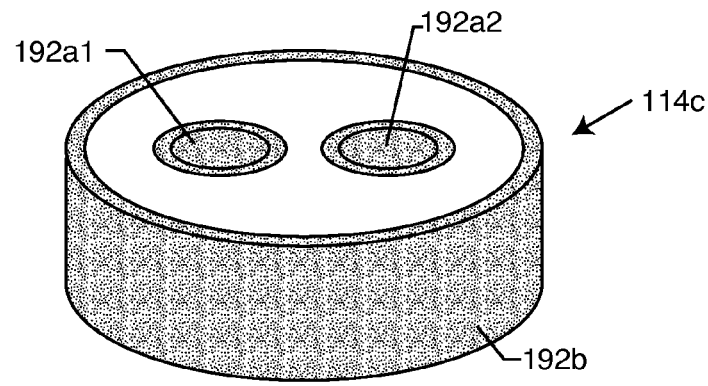
FIG. 55 is an isometric view of a bipolar feedthrough capacitor for use in the device of FIGS. 53-54.

The bipolar feedthrough capacitor 114c is illustrated in isometric view in FIG. 55. Shown is an outside diameter termination surface 192b which is electrically and thermally connected to the inside diameter of the energy dissipating surface 161 of FIG. 54, as by electrical connection 196g. Also shown, are termination surfaces 192a1 and 192a2 located on the inside diameter of two feedthrough capacitor ID holes for electrical connection at 196h and 196i (FIGS. 54, 55) between leadwires 104 and 106, respectively to the feedthrough capacitor termination surfaces 192a1 and 192a2, respectively. The use of a feedthrough capacitor in this case makes for a truly broadband performance. As MR systems continue to evolve in their static magnetic field strength, the RF pulse frequencies go higher and higher. For example, for a 10 Tesla scanner, the RF pulse frequency is 426.5 megahertz. Prior art MLCC chip capacitors have internal inductance and tend to self-resonate at frequencies around 400 megahertz or above. Accordingly, the use of a feedthrough capacitor accommodates much higher frequency MRI systems.

Referring once again to FIG. 28 and FIG. 31, one can understand why the energy dissipating surface 161 of FIG. 53 has been moved back a suitable distance "d" from the distal tip electrode 138 and the distal ring electrode 108. This is because of the tendency for distal tip 138 and ring electrodes 108 to become completely embedded or encapsulated with body tissue. In other words, one cannot guarantee that the distal ring electrode 108 will always be freely floating in the blood pool, for example, of the right ventricle or the right atrium. Referring once again to FIG. 27, one can see shaded areas where tissue encapsulation tends to be the greatest. An ideal location for the energy dissipating surface 161, as described in FIG. 53, is shown as 161' in FIG. 27. This guarantees that the energy dissipating surface 161 is placed generally into the area of the right ventricle that is free of trabecula tissue and where there is always freely flowing blood. Of course, this is particularly important for cardiac rhythm management applications wherein pacemakers and implantable defibrillators are commonly used. For implantable neurostimulators, generally, these are not placed in areas where there is freely flowing blood. However, it is still important in these cases that the energy dissipating surface 161 be a sufficiently large enough distance from the associated electrode(s) so that if there is adjacent tissue heating, it does not affect the delicate interface between the electrodes and surrounding body tissue. This would be particularly important, for example, in a deep brain stimulator. As shown in FIG. 31, for example, an ideal location for the energy dissipating surface 161 would be either at the skull or subdural (slightly below the skull). In this case, the deep brain stimulation electrode would protrude down into the brain tissue below the energy dissipating surface 161. In this case, the RF energy and/or heat would be dissipated over a relatively large surface area well away from the very heat sensitive and delicate brain tissues 162. For a spinal cord stimulator, there is generally freely flowing spinal fluid which can act as a cooling agent as well. In this case, it is desirable to have the surface 161, again, spaced at some distance from the therapy delivery electrode such that cooling effectively takes place within the cerebral spinal fluid. See U.S. Publication Nos. US 2008/0132987 A1 and US 2007/0112398 A1, which are incorporated by reference herein. In some cases, the separation distance can be quite small, for example on the opposite surface of a paddle electrode as shown herein in FIGS. 72, 73 and 74.

Figure 56:
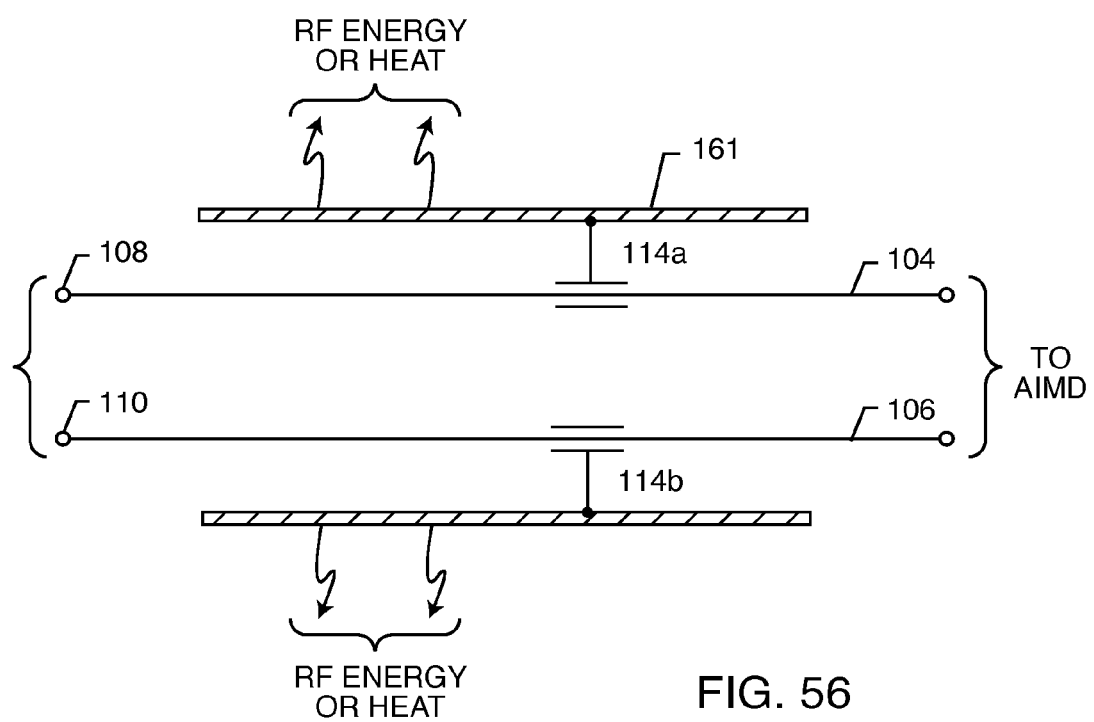
FIG. 56 is a schematic circuit diagram corresponding with the embodiment shown in FIGS. 53-54.

FIG. 56 is a schematic diagram of the energy dissipating surface 161 assembly previously described in FIGS. 53 and 54. In FIG. 56, one can see that the passive frequency selective diverter elements 114a and 114b could be replaced by any of the circuits previously described in FIGS. 4 through 11 as element 20.

Figure 57:
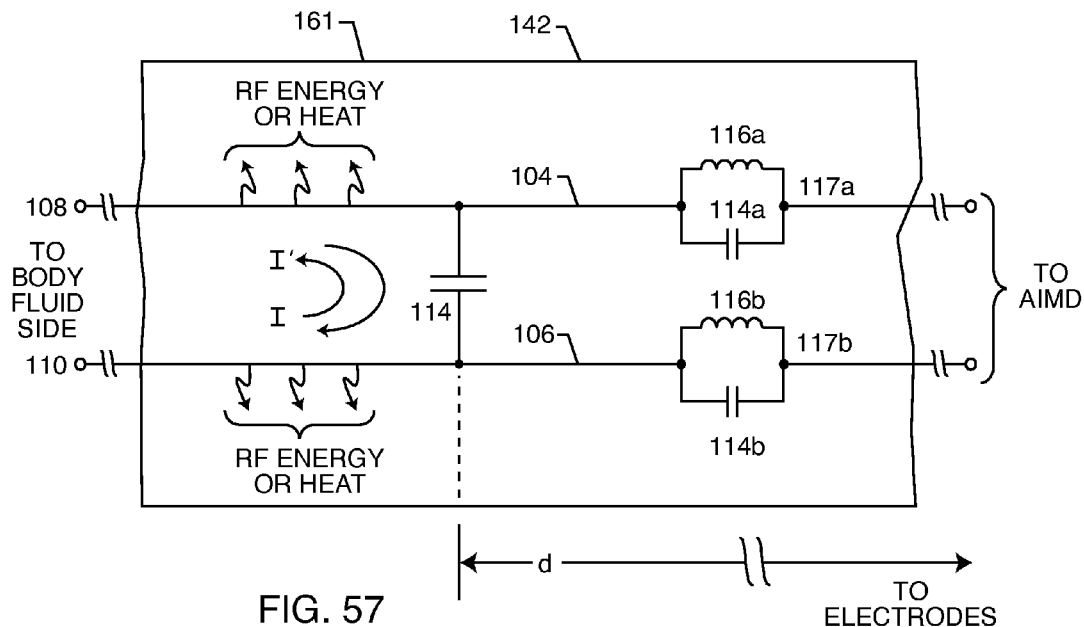
FIG. 57 is a schematic circuit diagram illustrating a bipolar lead assembly with distal tip and ring electrodes shown at a suitable distance from an energy dissipation surface.

FIG. 57 illustrates a bipolar lead of the present invention with distal tip and ring electrodes 108, 110 (not shown) at a suitable distance d from an energy dissipation surface 161 such that energy dissipation in the surface 161 would not cause a temperature rise at the distal electrodes. Shown is a capacitor 114 connected between the leadwires 104 and 106. Also shown are a pair of bandstop filters 117a and 117b as previously illustrated in FIG. 11. Referring once again to FIG. 57, one can see that the capacitor element 114 acts as a high frequency energy diverter. This works in cooperation with the two bandstop filter elements 117a and 117b which act as energy impeders at a selected MRI frequency. Accordingly, high frequency energy that is induced on the leadwires 104 and 106 is converted to RF circulation currents $I_1$ and $I_2$. $I_1$ and $I_2$ are shown in opposite directions to illustrate, for example, for a 1.5 Tesla MRI system, that these oscillate back at 64 million times per second. This creates a great deal of current in the associated leadwires to the right (as viewed in FIG. 47) of the diverting element 114. This causes heat to be dissipated in the leadwires 104 and 106 into the energy dissipating surface 161 such as the overall insulation sheath or shield of the probe, catheter or implanted device as shown.

Figure 58:
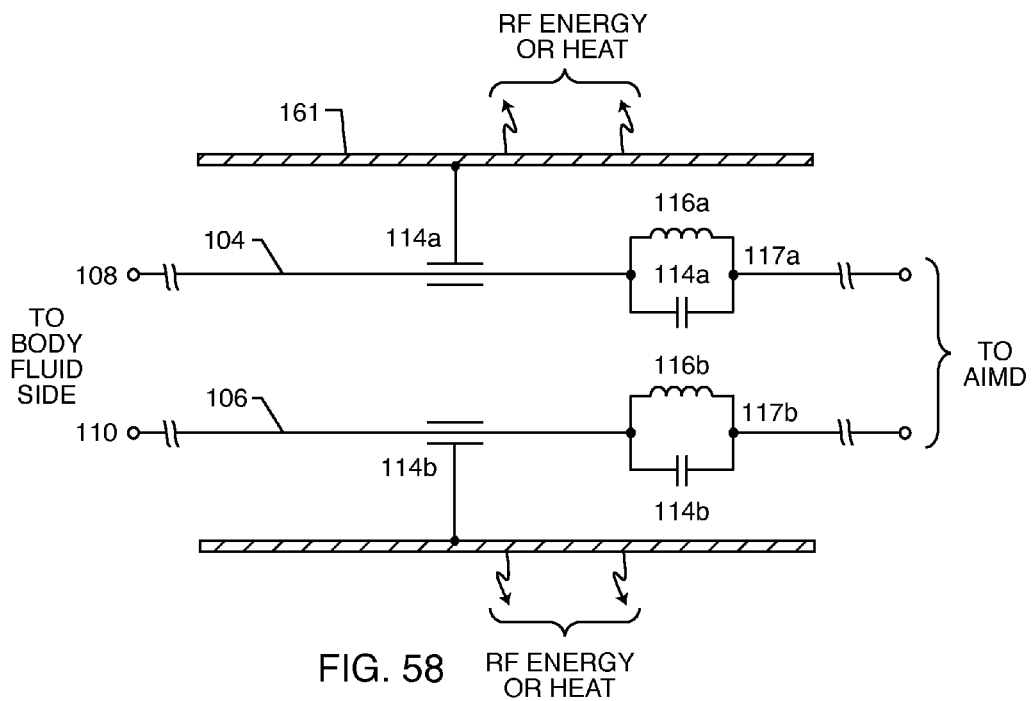
FIG. 58 is a schematic circuit diagram similar to FIG. 57, except that a pair of capacitors are used.

FIG. 58 is very similar to FIG. 57 except that diverting element 112 had been replaced by a pair of capacitor elements 114a and 114b which connect from leadwires 104 and 106 respectively to an electromagnetic shield or an energy dissipating surface 161. It is a desirable property of the present invention that the surface 161 be highly thermally conductive, have relatively high surface area for efficient transfer of RF or heat energy into surrounding fluids and body tissue and also be electrically conductive at RF frequencies. Referring once again to FIG. 58, the diverter elements 114 work best when they are on the body fluid side (towards the distal electrode) related to the bandstop filters 117a and 117b. When the impeders or bandstop filters are placed between the distal electrodes and the impeder capacitors 114, the distal electrodes will heat up significantly. This is because the energy is now trapped in the lead system and reflects back and forth along the implanted lead which causes distal tip overheating. The bandstop filters 117a and 117b, if placed incorrectly between the impeder capacitors and the distal electrodes, represent a very high impedance. This makes it very hard or even impossible for the RF energy entrapped in the lead system to reach the surface 161 or housing of the AIMD where it can be dissipated over a large surface area. Instead, the energy bounces back off and reflects back down to the distal electrodes where it concentrates as an RF current which causes significant overheating.

The bandstop filters 117a and 117b of FIG. 58 look like a very high impedance (ideally an infinite impedance) at the resonant frequency. In practice, the impedance of the bandstop filters at resonance will be around 2000 ohms. This has the effect of disconnecting or impeding RF current to the distal electrodes at these high frequencies from the leadwires 104 and 106. These work in conjunction with the low pass filter elements 114a and 114b which act as a way to divert the high frequency energy to the energy dissipating surface 161 which in a preferred embodiment is the AIMD housing. As previously mentioned, the low pass filter elements 114a and 114b can consist of any of the low pass filters as previously described in FIGS. 43 and 44 or the L-C trap filter as previously described in FIGS. 45, 46, 47, 48, 49 and 52. A high frequency model of FIG. 50 is illustrated in FIG. 9 wherein the leadwires are effectively shorted together to an energy dissipating surface 161 and the distal electrodes 108 and 110 have been effectively cut or disconnected (in this case, by the bandstop filter elements) from the electrodes. For a more complete description of bandstop filter elements and their design and operation, refer to U.S. Pat. No. 7,363,090.

Figure 59:
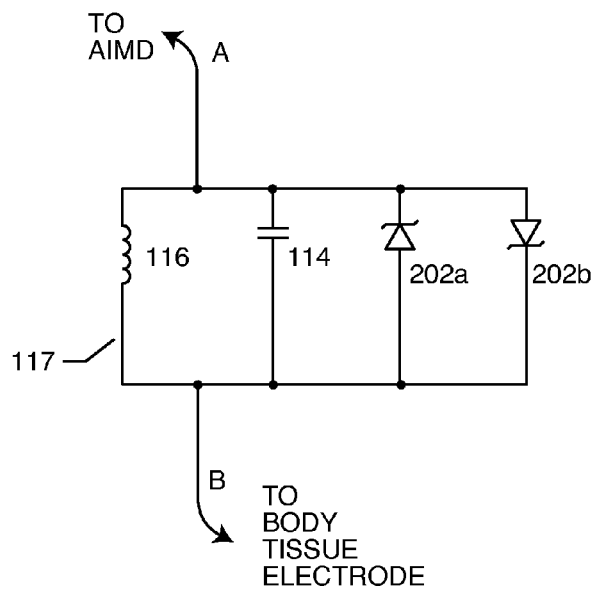
FIG. 59 is a schematic circuit diagram illustrating a bandstop filter modified to include a pair of diodes in a parallel or back-to-back configuration.

FIG. 59 illustrates an exemplary bandstop filter 117a or 117b consisting of a parallel inductor 116 and capacitor 114 (as previously shown and described herein) with nonlinear circuit elements such as diodes 202a and 202b placed in parallel therewith. These diodes 202a, 202b are oriented in what is known in the prior art as a back-to-back configuration. The diode elements 202a, 202b, as illustrated in FIG. 49, can be placed in parallel with each other, and with any of the frequency selective circuit elements as previously described in FIGS. 4 through 11. For example, referring to FIG. 5, the diode elements 202a and 202b could be placed in parallel with the capacitive element 114. Referring to FIG. 10, two diode elements 202a, 202b could also be placed in parallel with each of the inductor elements 116a and 116b. Back-to-back diodes are one form of a transient voltage suppressor. Transient voltage suppressors (TVS) are well known in the prior art for providing over voltage circuit protection. They are sold under various trade names including the name Transorb. The diodes 202a, 202b can also be pin diodes. As previously discussed, automatic external defibrillators (AEDs) have become very popular in the patient environment. Accordingly, implanted leads must be able to withstand very high pulsed currents. These pulse currents can range anywhere from 1 to 8 amps. It is also a feature of the present invention that the passive frequency selective components be very small in size. In order for an inductor element L to be able to handle 1 to 8 amps, it would have to be exceedingly large. However, by using physically small diode elements 202a and 202b, one can have the circuits switched to a different state. That is, when a high voltage, such as that from an AED appears, the diodes would forward bias thereby temporarily shorting out the bandstop filter 117a or 117b consisting of the parallel combination of inductor L and capacitor C (FIG. 59). Thereby the correspondingly high AED induced currents would be diverted away from the relatively sensitive (small) passive elements L and C in such a way that they not be harmed.

Figure 60:
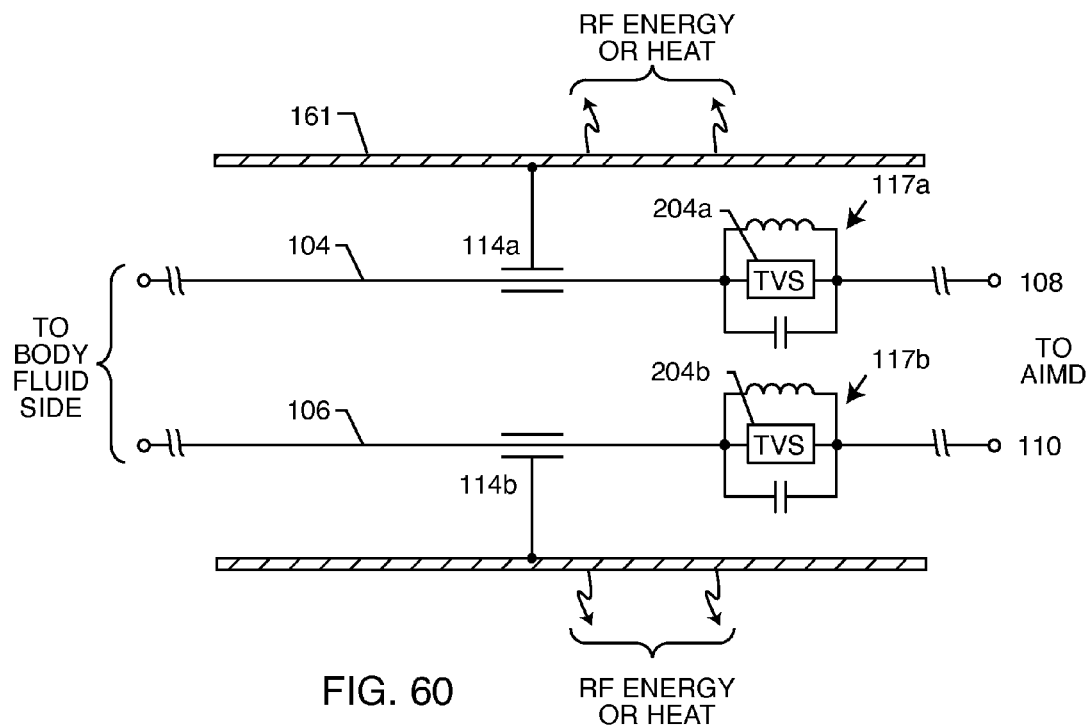
FIG. 60 is a schematic circuit diagram similar to FIG. 58, except that transient voltage suppressors are installed in parallel relation with each of the bandstop filter elements.

FIG. 60 is nearly identical to FIG. 58 except that transient voltage suppressors 204a and 204b have been added respectively in parallel with the bandstop filter elements 117a and 117b. Transient voltage suppressors are nonlinear circuit elements which operate in much the same fashion as previously described for the back-to-back diodes 202a and 202b of FIG. 51. This family includes diodes, zener diodes, Transorbs™, Transguard®, metal oxide varistors, $Z_n0$ varisters, and other similar nonlinear circuit elements. The purpose of the transient voltage suppressors 204a and 204b in FIG. 60 is to bypass any high voltage induced currents such that these currents not flow through the relatively sensitive bandstop passive component inductor and capacitor elements.

FIG. 61 illustrates a general diverter and/or impeder filter element 206 which can be representative of any of the filters previously described. The filter element 206 of FIG. 61 is shown disposed between an electrical connection to an energy dissipating surface 161 which can be an AIMD housing as illustrated. The filter is shown connected to a proximal end of a leadwire 104 or the like with dashed lines, and connected to a distal end electrode 108 shown coupled to the leadwire 104 or the like with dashed lines. The reason for the dashed lines is an indication that the filter 206 can be placed anywhere between the distal end and the proximal end of the leadwire 104 or even inside the AIMD housing. The filter 206 and energy dissipating surface 161 could be located near the distal end, at the distal end, at a distal ring electrode 108 or near a distal ring electrode 108 such that it would float in the blood pool. The filter 206 can also be placed at or near the proximal end, or at any point between the distal and proximal ends.

In particular, the filter and associated energy dissipating surface 161 could be located all the way at the proximal end of an abandoned lead. Leads are often abandoned and left in patients for various reasons. Sometimes the lead becomes slightly dislodged, for example, from cardiac tissue such that the pacing threshold increases or is lost. Sometimes lead insulation becomes abraded and/or the leadwire itself is broken. Removing leads once they've been in the body for a long time can be very difficult as portions of the lead tend to become overgrown by body tissue. One is again referred to the article entitled, ICD EXTRACTION INFECTED/REDUNDANT LEADS EVERYDAY CLINICAL PRACTICE by Dr. Bruce Wilkoff. When one looks at the photographs of the extracted leads, one can see that they are very often substantially overgrown with tissue. Therefore, it is common practice to simply abandon leads.

In the prior art, the abandoned lead is simply capped such that body fluid will not enter it. This cap is nothing more than an insulative cap. However, it is also well known in the literature that abandoned leads can be quite dangerous in an MR scanning situation. High energy electromagnetic fields from the RF pulsed energy of a scanner intensifies at the ends of implanted leads. Because they are abandoned or capped at one end, this creates a reflection situation whereby all of the intense energy has no way to escape the lead except at the distal electrode end. This is the worst case situation because the distal electrode makes intimate contact with body tissue. For example, if the tissue was myocardial tissue, one runs a severe risk of creating burning or lesions in the heart. In the case of a deep brain stimulator, one runs the risk of causing deep lesions within the brain. In an abandoned lead, therefore, it is much more desirable that energy be dissipated at or near the proximal end as opposed to the distal end where there are sensitive body tissues involved. In general, active implantable medical devices are implanted in muscle or in fat tissues, for example, in the pectoral areas which are not so heat sensitive, but more importantly, are not implanted in an organ, whose function could be compromised. Accordingly, it is a feature of the present invention that any of the filter networks, as previously described herein, including those as shown in FIGS. 4 through 11, could be incorporated in a cap structure to be attached to the proximal end of the leadwire wherein such said cap structure includes an energy dissipating surface 161. For a further description of the problem and the need to provide a cap for abandoned leads, one is referred to U.S. Pat. No. 6,985,775.

FIG. 62 shows an energy dissipating surface 161 in a relatively fixed location along the length of a leadwire 104. In accordance with the present invention, the energy dissipating surface 161 is placed a suitable distance d from a distal electrode 108 such that energy dissipation in the area of the 161 surface will not cause tissue overheating at or near the distal electrode 108. Also shown is a frequency impeding element 118 which can be moved to various locations along the length of the leadwire 104 as indicated by the multiple dashed-line boxes 118. For example, impeding element 118 could be placed near the energy dissipating surface 161, or it could be moved toward the distal electrode 108 at any one of several successive locations. The impeding element 118 such as a bandstop filter 117 or a series inductor will still work in conjunction with the diverting element 112 at any of these various locations. In fact, this can be an advantage in the present invention in order to make the distal tip electrode 108 and its associated leadwire 104 within the distance "d" smaller in diameter. In general, most leads for cardiovascular applications are restricted to the six French (0.079 inches in diameter) region. This can be problematic for a biventricular implant where the endocardial electrode must be threaded through the venous system and then into the coronary sinus and through the great cardiac vein to one of many branch vessels which are outside of the left ventricle. These branch vessels tend to be very small in diameter and very difficult to navigate, particularly for a large lead (size four French or smaller would be ideal). There is also a similar need for certain spinal cord and deep brain stimulators which must embody electrodes that are very small in diameter. Referring back to FIG. 62, one can see that by having a relatively large valve capacitive diverter element 112 associated with a energy dissipating surface 161 that is located at a distance d from the distal electrode, one can then downsize the diameter of the wiring along the length of distance d. By putting the frequency impeding element such as any one of the elements 118a, 118b and/or 118c, one can make this single component smaller than multiple components. Accordingly, frequency impeding elements do not have to be in direct physical proximity to diverting frequency selective elements 112. As taught in FIGS. 4, 5, 6, 42 and 43, the diverting element 112 can consist not only in a capacitor or an L-C resonant trap filter, but also could include a variety of low pass filters. Referring to FIG. 43, for example, one could see that an L section low pass filter is identical to the filter described in FIG. 62, wherein element 118 represents the inductor element and element 112 represents the capacitor element. Referring once again to FIG. 62, one can incorporate a T-type filter which embodies two inductor elements. In this embodiment, the left hand inductor element 118 would be to the left of the frequency diverting element 112 and a second inductor (not shown) would be located to the right of the diverter element 112. This right hand inductor could be located in close physical proximity to the diverter element 112, or it could also be moved away as was described for the left hand inductor element at various locations as shown in FIG. 52.

Referring back to FIG. 62, it should be noted that the variable impedance element 112 can be monolithic ceramic (MLCC) capacitors, ceramic feedthrough capacitors, or other types of capacitive circuit components. In addition, the frequency selective element 112 can be a parasitic or distributive capacitor wherein the capacitance is formed through relatively high-dielectric materials between leadwires or electrodes in an energy dissipating surface 161.

FIG. 63 illustrates a type of probe or catheter 102 which is typically used to both map and ablate the inside of cardiac chambers to eliminate or control certain types of arrhythmias. For example, in a patient with uncontrollable atrial fibrillation, this type of probe or catheter 102 would be inserted so that electrical mapping, between bipolar distal electrodes 108 and 208 or between electrodes 110a and 110b, could be performed to isolate and locate those areas from which the sporadic electrical activity is occurring. For example, this might be around a pulmonary vein. Reference is made to U.S. Pat. No. 7,155,271 for a more complete description of this type of need and procedure. After the areas that need to be ablated are located, the surgeon can apply RF ablation energy at a distal ablation electrode 208. This has the effect of burning the inside of cardiac tissue creating a scar which will isolate this area of erratic electrical activity. The goal here is to complete a scar structure such that the atrial fibrillation is terminated. Unfortunately, in the prior art, this procedure is done using real-time X-ray, fluoroscopy, landmarks based on C-T scans, or other types of guidance, which does not adequately visualize soft tissue. Accordingly, the surgeon is working pretty much blind as the scars forming cannot be seen in real time. As explained in U.S. Pat. No. 7,155,271, it would be a great advantage if such procedures could be performed during real time MRI guidance. The problem is the MRI RF energy induced into the ablation catheter could cause overheating and sporadic formation of scar tissue at the wrong time and/or in the wrong location. In FIG. 63, one can see that there is a novel energy dissipating surface 161 of the present invention. This surface 161 is located at a distance "d" back from the distal tip such that the energy dissipating surface 161 will redirect energy away from both the electrical sensing electrodes 108, 110 and the RF ablation electrode 208 where they cannot overheat at inappropriate times. Frequency selective passive components (not shown), in accordance with the present invention, are connected in series with the leadwires, or from the inside of the energy dissipating surface 161 to the various leadwires 104, 106 and 210. These are the circuits that have generally been described in FIGS. 4 through 11 herein. For simplicity, they have not been shown in FIG. 63, but should be obvious to one skilled in the art from the previous drawings. In other words, the RF ablation electrode tip 208 will only overheat when the surgeon decides to activate the RF circuitry to deliberately form the scar tissue.

The energy dissipating surface 161 may include some materials or antenna structures that are readily visualized during active MRI guidance. This may be important so that a physician can ensure that if the probe or catheter is manipulated that the surface 161 not rest against the inside of, for example, the atrial septum. This is the area that is dissipating RF energy and heat during the active MRI. If the surface area of this surface 161 is sufficiently large so that very little temperature rise would occur, it would not matter if the surface 161 touched off against, for example, the inside wall of the cardiac septal wall. However, if the surface 161 was relatively small, then substantial temperature rise could occur if it was not kept within the freely flowing blood stream. In this case, it would be important that the physician be able to visualize the surface 161 and the MRI images so that it not be allowed to rest inappropriately against sensitive tissues on the inside of the atrium and cause inadvertent scar tissue or ablation to occur. Referring once again to FIG. 63, one can see that the ablation electrode 208 is connected to an RF ablation leadwire 210 which comes from RF ablation equipment (not shown) which is external to the patient. The sensing ring electrodes 108 and 110 are coupled to leadwires 104 and 106 which run through the center of the probe or catheter and also are connected to external equipment which is used to monitor electrical cardiac activity. These would typically be connected to an ECG or EKG recorder.

Figure 64:
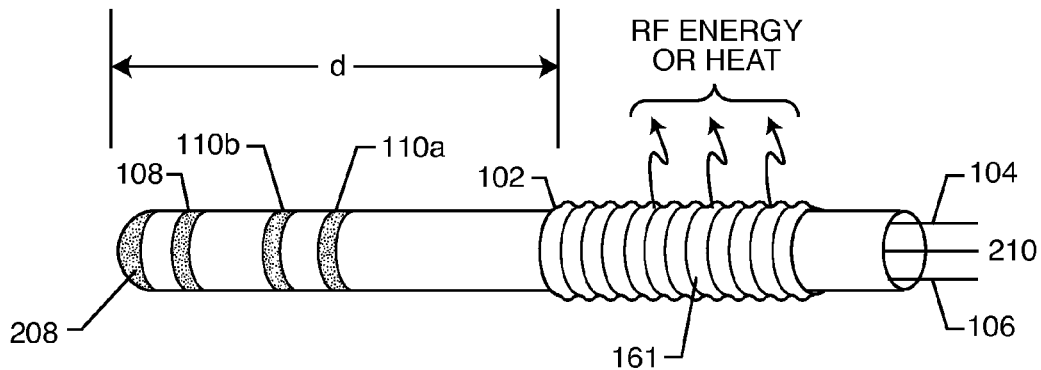
FIG. 64 is an illustration similar to FIG. 63, illustrating an alternative embodiment wherein the energy dissipating surface has been convoluted so that its surface area has been increased.

FIG. 64 shows a probe or catheter similar to that illustrated in FIG. 63 except that the energy dissipating surface 161 has been convoluted so that its surface area has been increased. Such increasing of the surface area, which is in contact with fluids, such as body fluids, will increase the amount of MRI induced RF energy that is dissipated.

Figure 65:
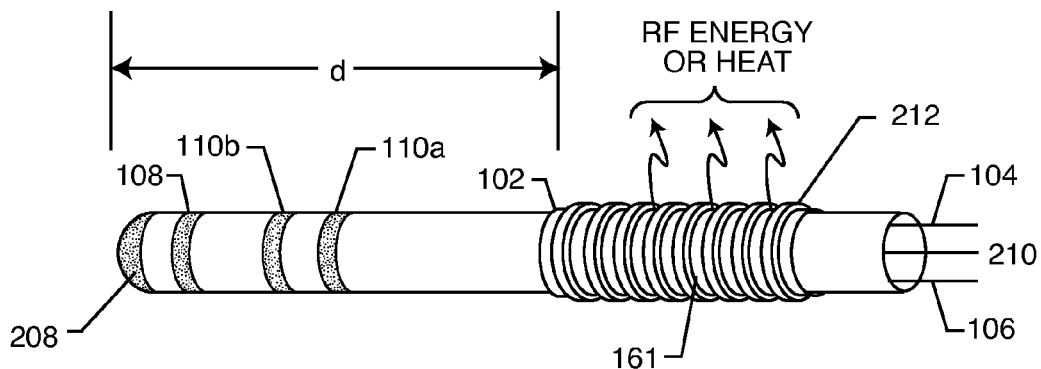
FIG. 65 is similar to FIG. 64, except that instead of convolutions, fins have been added to the energy dissipating surface.

FIG. 65 is very similar to FIG. 64 except that instead of convolutions, fins 212 have been added. These fins 212 also increase the surface area and increase the amount of energy or heat which is dissipated into surrounding fluids and tissues.

Figure 66:
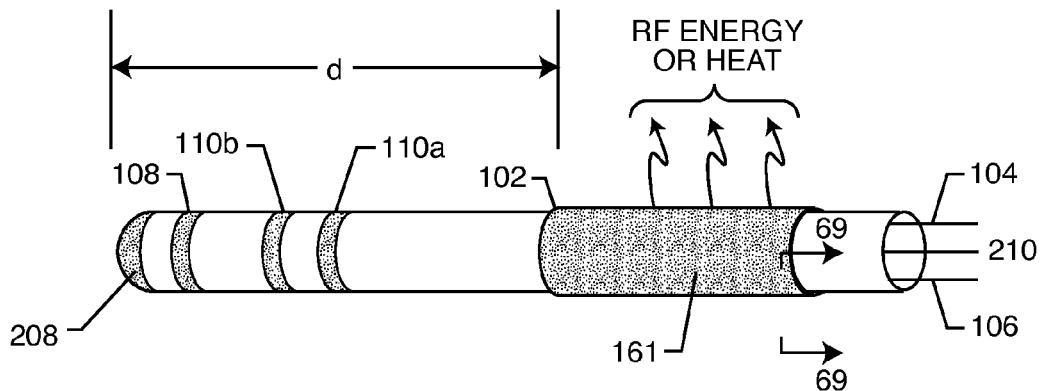
FIG. 66 is similar to FIGS. 64 and 65, except that the energy dissipating surface has its surface area increased through various surface roughening processes.
Figure 67:
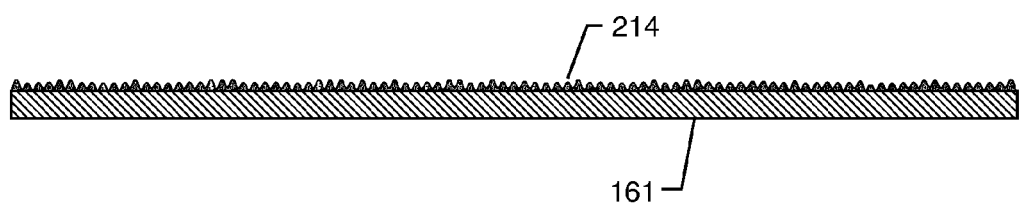
Figure 68:
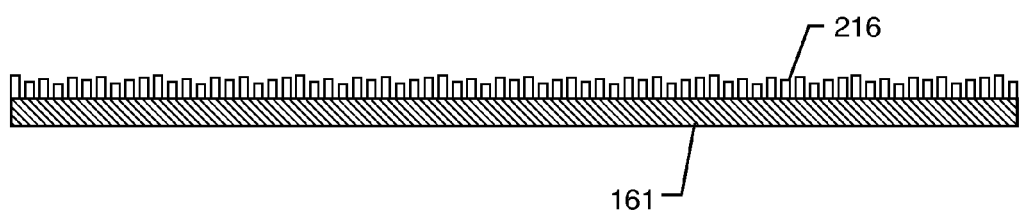
FIG. 68 is a view similar to FIG. 67, and illustrates the use of carbon nanotubes or fractal coatings to increase the surface area of the energy dissipating surface.

FIG. 66 is similar to FIGS. 64 and 65 except that the energy dissipating surface 161 has its surface area increased through various processes which are more thoroughly described in connection with FIGS. 67 and 68. FIG. 67 is an enlarged, fragmented sectional view of the surface 161 taken from FIG. 66. The energy dissipating surface 161 area has been roughened to create a high surface area, through, for example, plasma etching 214, chemical etching, or the like. A high surface area can also be accomplished by porous coating deposits utilizing physical vapor deposition, chemical vapor deposition or electron beam deposition processes. Such porous coating deposits can include fractal coatings, metal nitrides, titanium nitrides, metal oxides, metal carbides, or virtually anything that would provide a high surface or porous substrate. In addition, electrochemical deposition of porous coating, such as iridium-oxide, can also be utilized, as well as nucleate high surface area morphologically structured coatings, such as whiskers, sub-micron filaments, tubes, nanotubes, or other morphological structures such as columnar, titanium-nitride or iridium-oxide. Any of these types of surface conditionings can greatly increase the energy dissipating surface area 161. FIG. 68, which is similar to FIG. 67, illustrates the use of carbon nanotubes or fractal coatings 216 to increase the surface area and therefore the energy dissipation.

Figure 69:
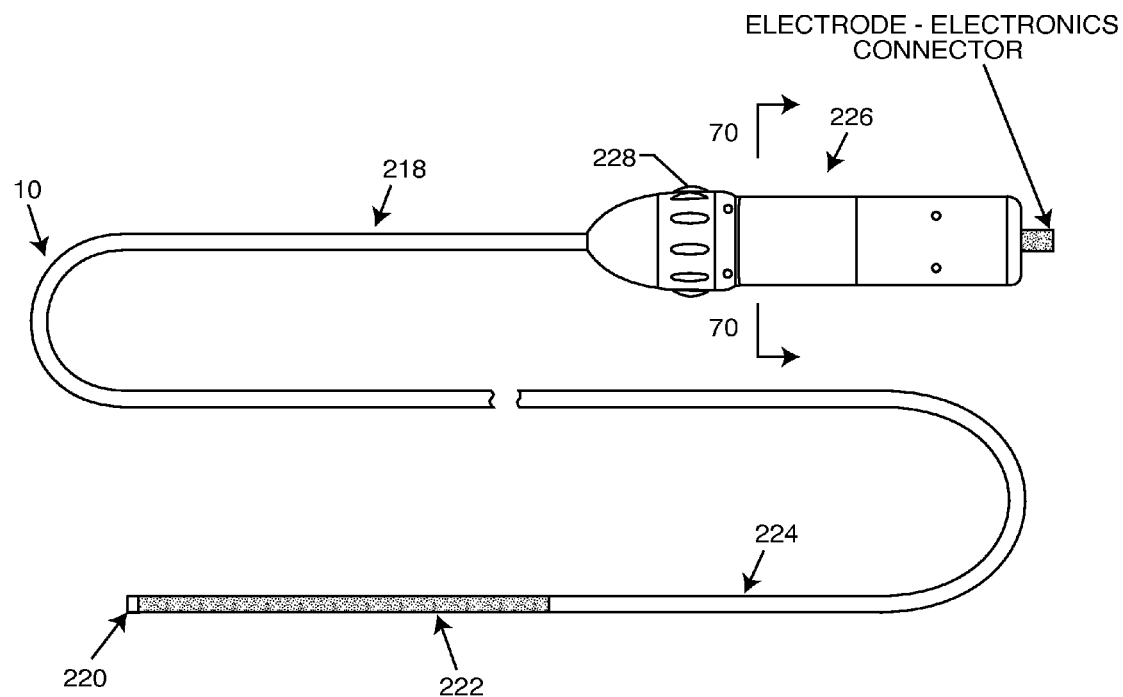
FIG. 69 is an illustration of a steerable catheter.

FIG. 69 shows a steerable catheter 218, which is typically used for a variety of applications including RF or cryo-ablation, cardiac mapping and many other purposes. Examples of RF ablation include treatment for nephrotic conditions, liver, brain, cancers and the like. For example, this would enable stereotactic ablation of certain lesions within the lung. An emerging field is the entire field of using ablation to treat various ventricular arrhythmias, including ventricular tachycardia. The illustrated catheter 218 in FIG. 69 is meant to be representative of all types of catheters or probes which can be inserted into the venous system or other areas of the human body. The catheter 218 has a tip 220 and an adjacent electrode surface 222, and a main catheter body 224, which can be steered around torturous paths. The steerable catheter 218 has a handle 226 which can have various shapes, sizes and configurations in the prior art. By twisting the illustrated cap 228 of the handle 226, one is able to steer the catheter 218 causing its tip 220 or other segments to bend as one guides it.

Figure 70:
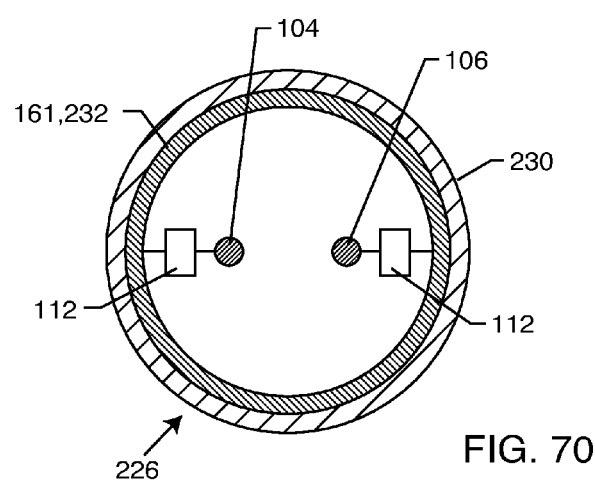
FIG. 70 is an enlarged section view taken generally along the line 70-70 from FIG. 69.

FIG. 70 is an enlarged section taken along line 70-70 in FIG. 69. FIG. 70 illustrates that the handle 226 includes an optional but preferred outer insulation sheath 230 which would typically be of plastic or similar material that would preferably not be highly thermally conductive. Inside of the handle (or even the catheter body itself—not shown) 226 are shown in cross-section leadwires 104 and 106. The illustration of two leadwires is not meant to be limiting since any number of wires could be inside the handle 226 and/or catheter 218 to sense electrical activity or deliver ablation energy.

In accordance with the present invention, there are frequency selective diverter impedance elements 112 shown between the leadwires 104, 106 and an energy dissipating surface 161, such as a metallic sheath 232. The energy dissipating surface 161 does not necessarily have to be metallic, but it has to be capable of collecting RF energy and conducting thermal energy. This heat energy is therefore dissipated over the large surface area and thermal mass of the catheter body or the handle 226 itself. This results in very little temperature rise, but at the same time, accomplishes the goal of the present invention in redirecting RF energy out of the leadwires 104 and 106 that may be picked up by MRI RF pulsed fields and directing said energy into the relatively large surface area 232 inside the handle 226. Of course, one could eliminate the outer insulation sheath 230. However, in a preferred embodiment, the insulation sheath 230 would be relatively poor in thermal conductivity so that one did really not feel any temperature increase in his or her hand. Referring once again to FIG. 70, the diverter elements 112 can, of course, be combined with any of the previously mentioned impeder elements such as inductors or bandstop filters.

Figure 71:
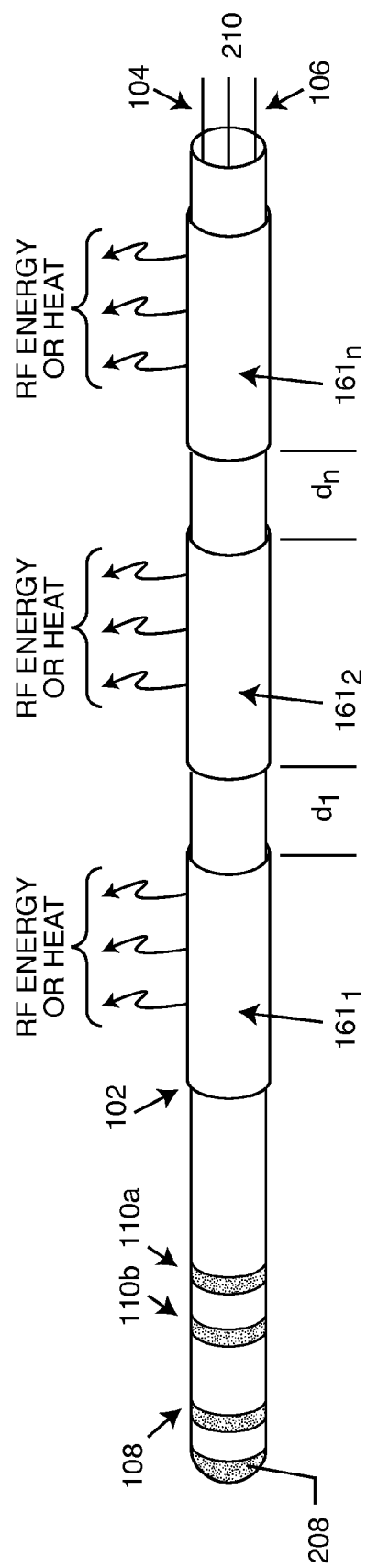
FIG. 71 is a schematic view of a probe or catheter similar to FIG. 63, except that the number of individual energy dissipating surfaces have been provided in distinct and spaced-apart segments.
Figure 73:
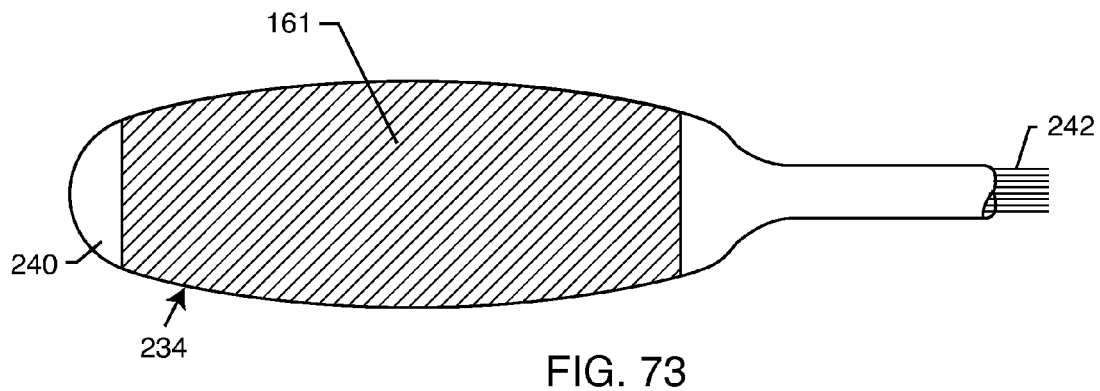
FIG. 73 is a bottom plan view of the paddle electrode shown in FIG. 72.

FIG. 71 is very similar to FIG. 63 except that a number of individual RF energy or heat dissipating segments $161_1$, $161_2$ and $161_n$ are shown. These are shown spaced apart by separation gaps $d_1$ and $d_n$, which in reality can be quite small. The reason that these energy dissipating surfaces are segmented is so that they do not become physically and electrically long enough to become a significant fraction or multiple of a wavelength of the MRI pulsed frequency. Such short conductive sections do not pick up significant energy from MRI whereas elongated leadwires or conductors can, for example, resonate and pick up very significant amounts of MRI RF energy. It would be highly undesirable if the energy dissipating surfaces, as illustrated in FIG. 73, were formed to be continuous along the entire length of the catheter 102 as previously described in connection with FIG. 71. In this case, the energy dissipating surface would actually become an energy collecting surface because it would become a very effective antenna for the MRI pulsed RF signals. Accordingly, breaking this up into discrete segments prevents the surface 161 from actually becoming a receiver or antenna for the MRI induced energy.

Figure 72:
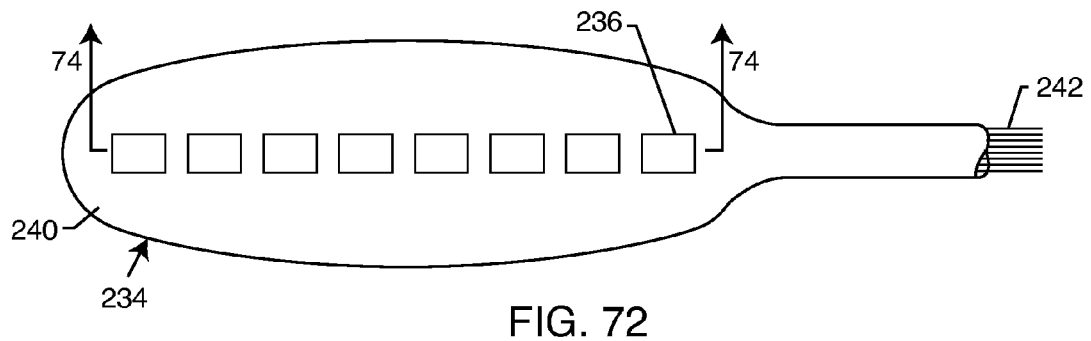
FIG. 72 is a fragmented top plan view of an exemplary paddle electrode embodying the present invention.

FIG. 72 illustrates a paddle electrode 234 which could be used, for example, in spinal cord simulator applications. It has eight electrodes 236 housed in a biocompatible insulative and flexible body 240. Eight leadwires 242 (there can be any number) are connected respectively to each of the eight electrodes 236. As previously discussed, the elongated leadwires 242 can pick up significant amounts of RF energy during MRI scanning. It is very important that the electrodes 236 do not overheat since they are in direct contact with the body, for example, with the spinal cord.

Figure 74:
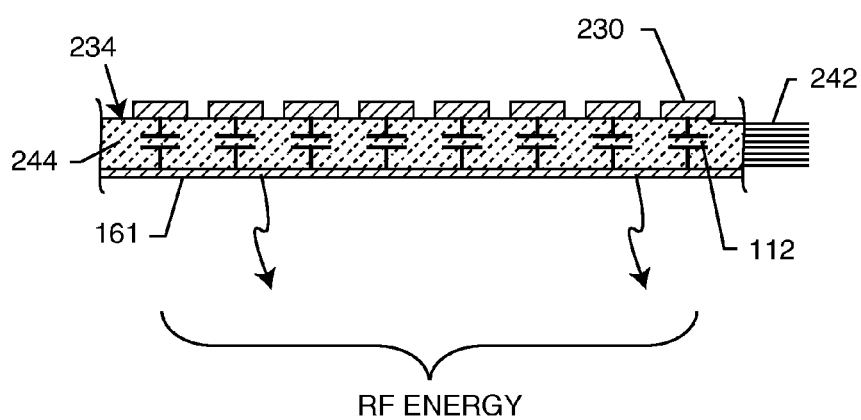
FIG. 74 is an enlarged sectional view taken generally along the line 74-74 in FIG. 72.

FIG. 73 illustrates the reverse side of the paddle electrode 234, where an energy dissipating surface 161 is located. As shown in FIG. 74, one can see that the electrodes 236 are conductive pads that contact the spinal nerve route or at least are closely associated with it. The leadwires 242 are each electrically connected to respective electrodes 236. There is a frequency variable impedance for diverter) element 112 in accordance with the present invention shown between each electrode 236 and the energy dissipating surface 161. These can be individual discrete capacitors or individual discrete L-C traps as shown in FIGS. 5 and 6. These can also be one continuous parasitic capacitance element that formed between the overlap of each of the electrodes and the area of the 161 surface itself. In this case, the insulative dielectric material 244 shown in FIG. 74 would be of relatively high dielectric constant. A high dielectric constant material is desirable so that the amount of parasitic capacitance would be relatively large. By using parasitic capacitance and appropriate dielectric materials, one eliminates the need to use individually installed passive circuit elements. Referring to FIGS. 72-74, one can see that the undesirable RF energy is dissipated on the opposite face of the paddle electrode 234 relative to the electrodes that are in contact with the spinal nerve route. In other words, the RF or thermal energy is dissipated over a relatively large surface area and is directed away from the sensitive juncture between the electrode body tissue contact area. This is important for two reasons, if the RF energy was allowed to concentrate on any one of the electrodes due to resonance phenomenon, then a very high temperature rise could occur which could cause thermal injury to the spinal nerve itself. By redirecting the energy in the opposite direction towards the muscle tissue and over a much larger surface area, much less temperature rise occurs, and even if it does, it is directed into less sensitive tissue.

Figure 75:
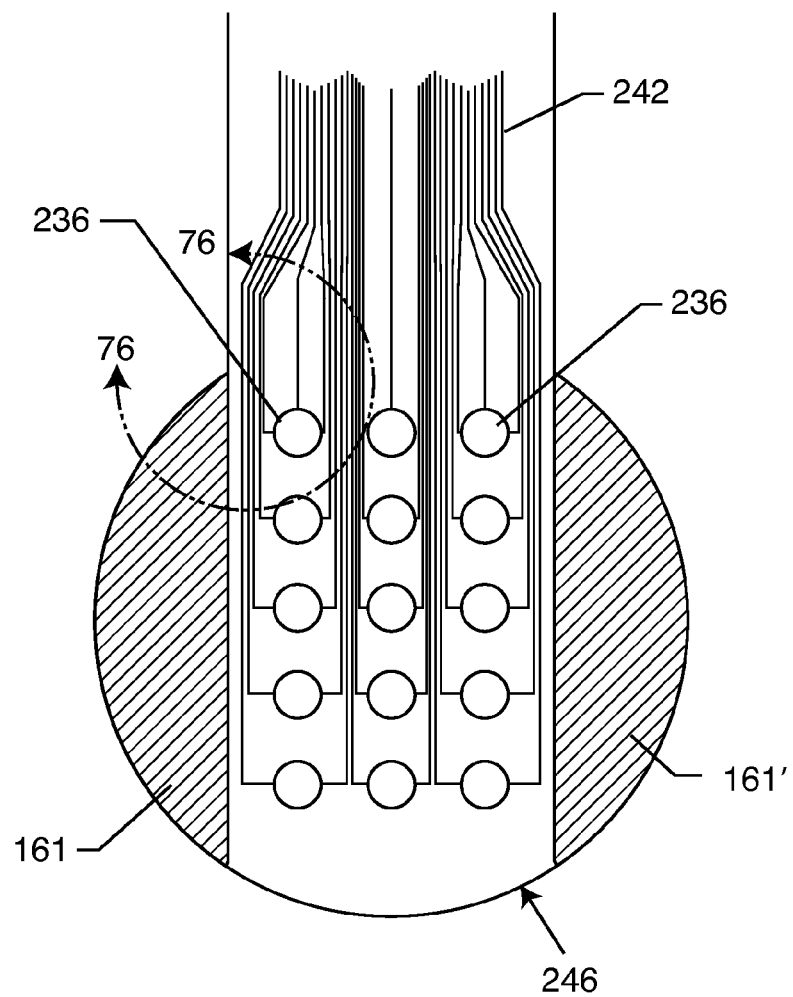
FIG. 75 is a top plan view of a different type of paddle lead structure in comparison with that shown in FIGS. 72-74.
Figure 76:
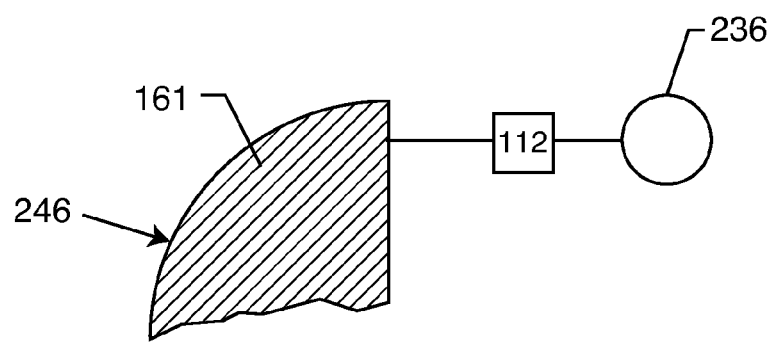
FIG. 76 is an enlarged electrical schematic view taken generally of the area indicated by the line 76-76 in FIG. 75.

FIG. 75 illustrates a different type of paddle lead structure 246 showing a total of fifteen electrodes 236. In this case there are two energy dissipating surfaces 161 and 161'. For maximum surface area, the energy dissipating surfaces could be on the top surface of the paddle lead structure 246, as well as on the backside or back surface (not shown). In accordance with the present invention, FIG. 76 illustrates a frequency selective variable impedance element 112 which is used to divert RF energy from the electrodes 236 to the 161 surfaces.

Figure 77:
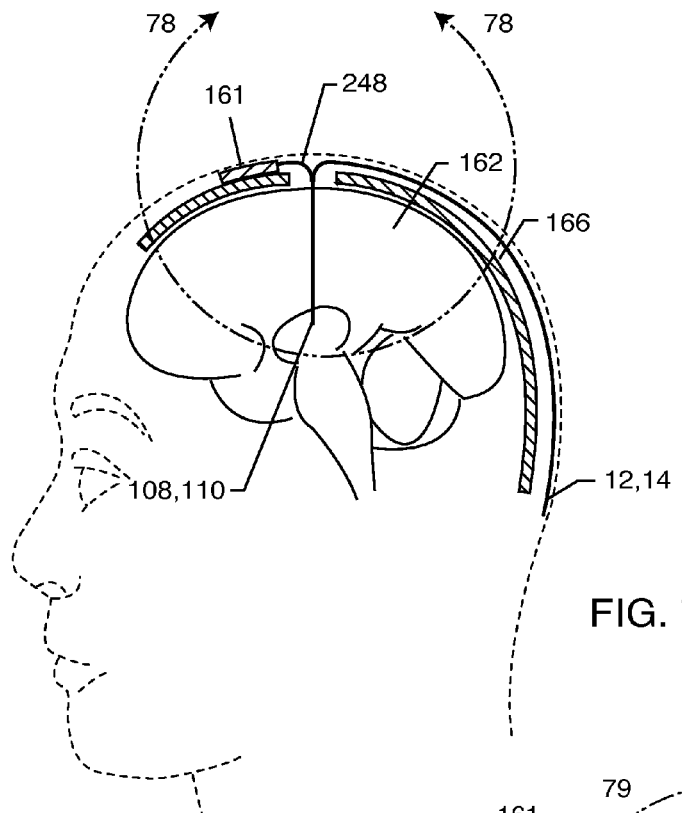
FIG. 77 is a schematic illustration similar to FIG. 30, showing use of a tethered energy dissipating surface in accordance with the present invention.
Figure 78:
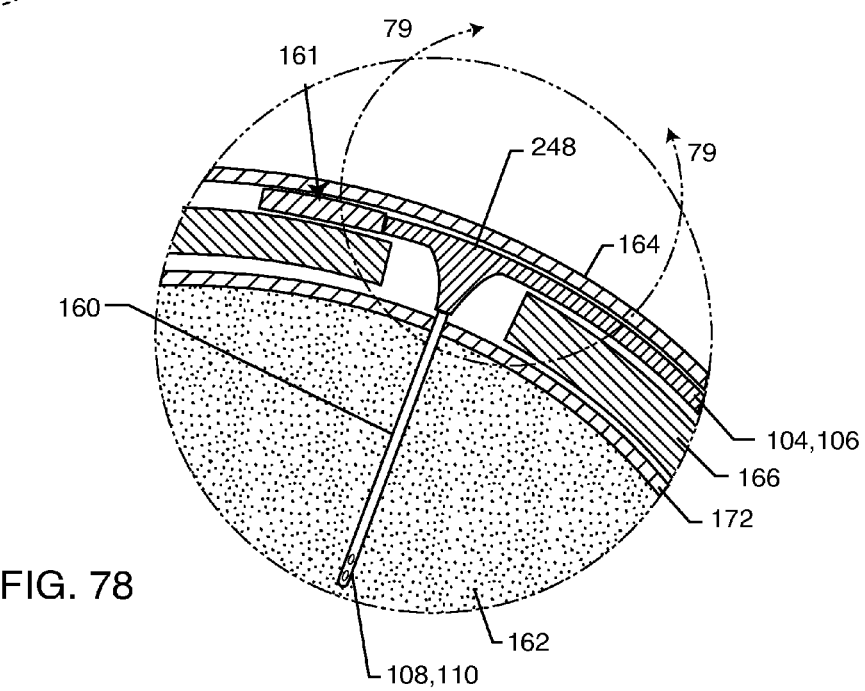
FIG. 78 is an enlarged sectional view of the area indicated by the line 78-78 in FIG. 77.
Figure 79:
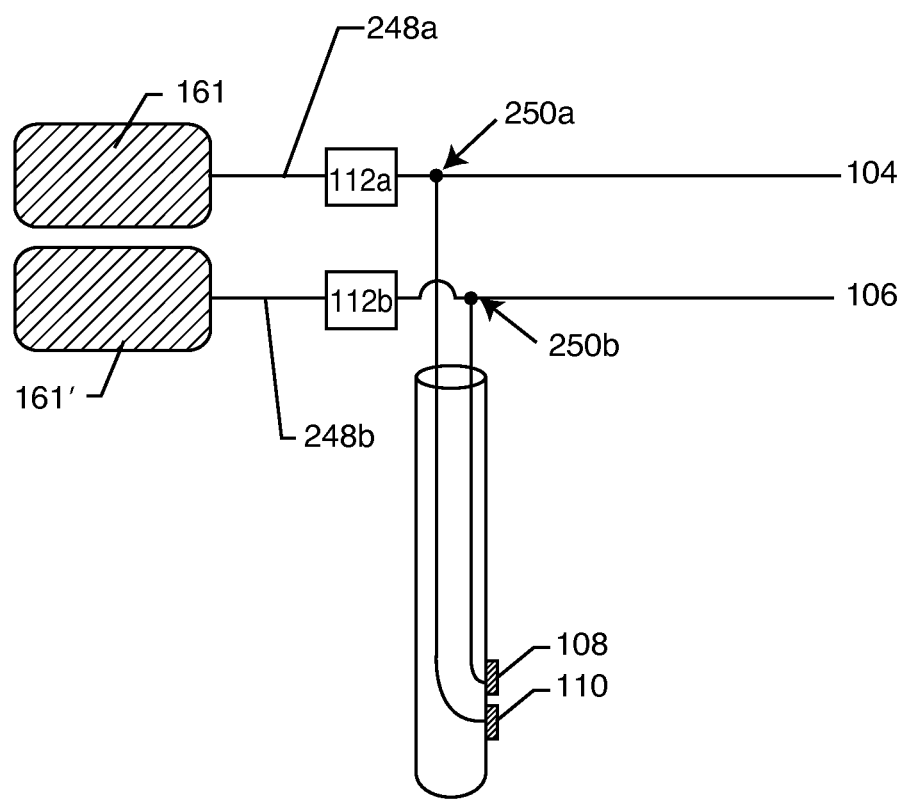
FIG. 79 is an enlarged, somewhat schematic illustration of the components found within the area designated by the line 79-79 in FIG. 78.

FIG. 77 is very similar to FIGS. 31, 32 and 33 in that it shows a section of human head with a deep brain stimulator disposed therein. There are a plurality of leadwires 104 and 106 which are connected to an AIMD or pulse generator (not shown). The pulse generator would typically be placed in the pectoral region and leadwires 104 and 106 would be routed up along the patient's neck to the deep brain electrodes 108 and 110. Referring to FIGS. 77-79, one can see that there is a novel tether 248 or wire arrangement where the leadwires 104, 106 are not only connected to the distal electrodes 108, 110, but they are also connected to a pair of energy dissipating surfaces 161 and 161'. In FIG. 78, one can see the tether area 248 wherein the leadwires 104, 106 connect individually to the electrodes. As shown in FIG. 79, the leadwires 104, 106 have a connection inside the tether area 248 such that the wires are routed both to the distal electrodes 108 and 110 and also through respective junctions 250a and 250b to two individual energy dissipating surfaces (161 and 161'). The leadwire 104 has a direct electrical connection at junction 250a to distal electrode 110. In turn, leadwire 106 has a direct connection at junction 250b to distal electrode 108. However, at the junctions 250a and 250b, also connected are frequency selective elements 112 which in turn are connected to respective energy dissipating pad or surfaces 161 and 161'. Of course the separate energy dissipating pads could be one large energy dissipating pad. However, in order to maximize surface area and facilitate surgical implantation, two pads are shown. These are originally implanted by the physician underneath a skin flap which is then sewn back down in place. In this way, any heat that is generated during MRI procedures is generated on the top side of the skull well away from any brain matter.

It will be obvious to those skilled in the art that the present invention can be extended to a number of other types of implantable medical devices, including deep brain stimulators, spinal cord stimulators, urinary incontinence stimulators and many other types of devices.

Figure 80:
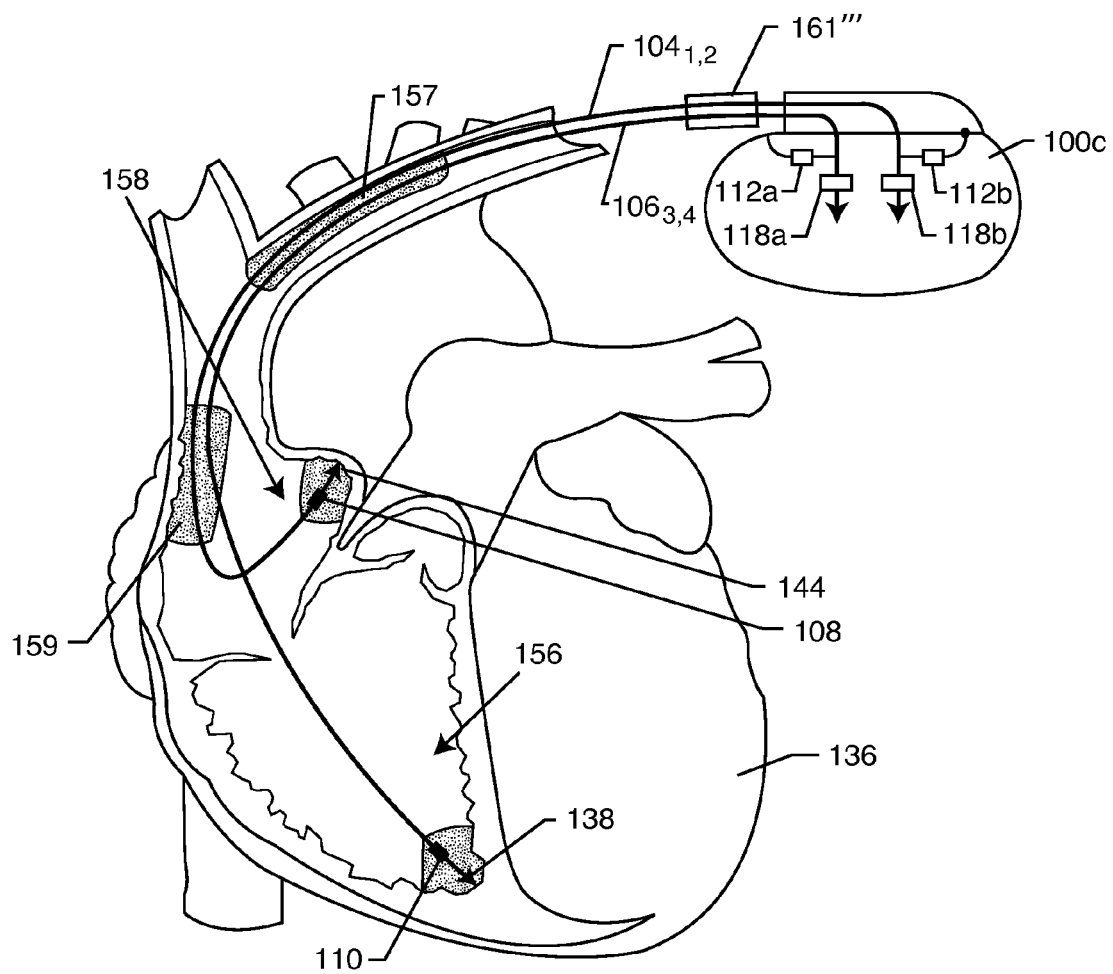
FIG. 80 is an overall outline drawing showing a cardiac pacemaker with endocardial leadwires implanted into a human heart.

FIG. 80 is an overall outline drawing showing a cardiac pacemaker 102 with endocardial leads $LW_{1,2}$ and $LW_{3,4}$ implanted into a human heart 136 as shown. Each lead is bipolar meaning that it contains two leadwires $104_1$, $104_2$ and $106_3$, $106_4$. One can see that lead $104_1$, $104_2$ is routed into the right atrium and that leadwire $106_3$, $106_4$ is routed into the right ventricular apex (RV). The distal electrodes for the atrial lead are shown at tip 144 and ring electrode 108. In the right ventricle, the distal electrode tip 138 is shown in close proximity to distal ring electrode 110. As previously mentioned, bandstop filters in accordance with U.S. Pat. No. 7,363,090 could be placed at or near the distal electrodes 138, 110, 144, 108 as needed. Referring to the AIMD housing, one can see that there are variable impedance elements 112 and 118 associated with each one of the leadwires $104_1$, $104_2$ and $106_3$, $106_4$.

Figure 81:
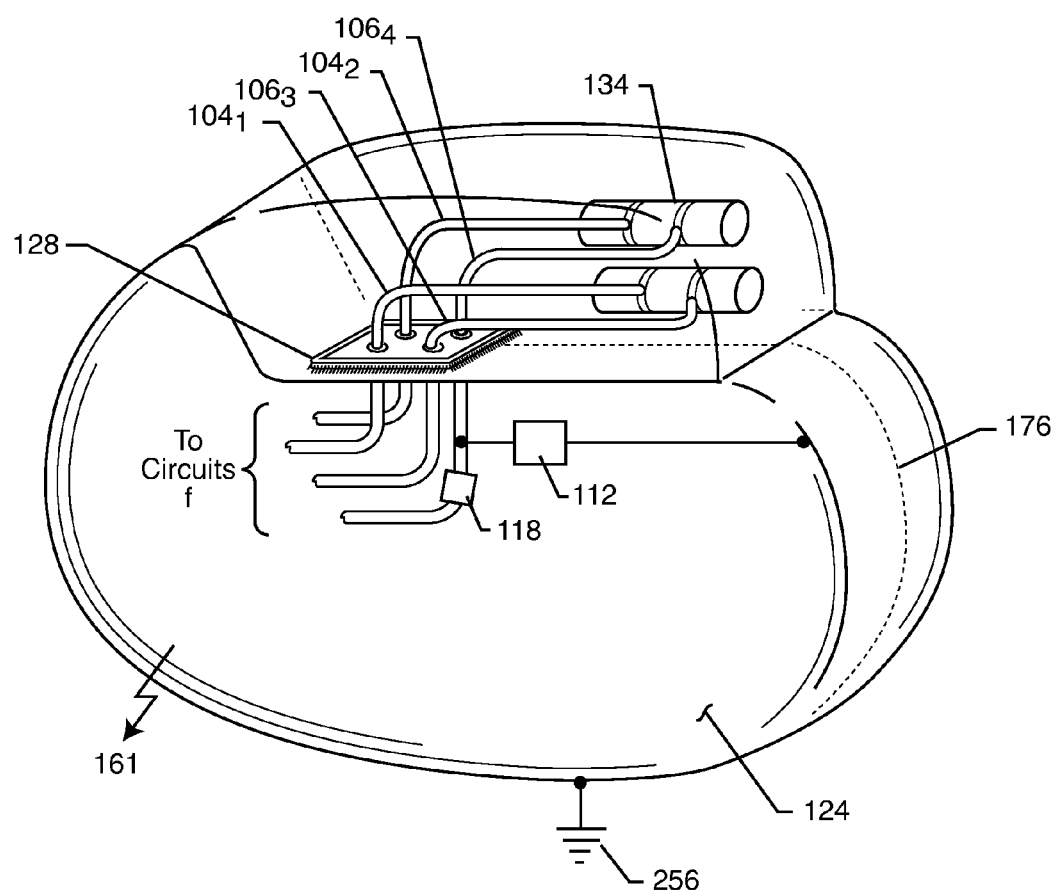
FIG. 81 is an illustration of an AIMD similar to FIG. 12, illustrating the use of variable impedance elements in connection with a leadwire within the housing of the AIMD.

FIG. 81 is an outline drawing of an AIMD such as a cardiac pacemaker. Shown is a metallic, typically titanium, housing 124. Its housing 124 hermetically sealed with a laser weld 176 as shown. It has a hermetic seal 128, which is also laser welded into the titanium housing 124. The hermetic seal has an insulator, which is well known in the prior art, through which leadwires $104_1$, $104_2$, $106_3$ and $106_4$ pass through in non-conductive relationship with conductive housing 124. A typical pacemaker connector block 134 is shown. This can be in accordance with various international standards organization (ISO) such as IS-1, DF-1, IS-4 and the like. Connector ports 130 allow for convenient connection of a lead, which can be routed to the appropriate body tissue to be sensed or stimulated. Referring once again to FIG. 83, one can see that the leadwires $104_1$ through $106_4$ are generally routed to circuit boards (f), integrated circuits or substrates within the active implantable medical device housing 124. These can include cardiac sense circuits, pace circuits and the like. Referring once again to FIG. 81, one can see that there are variable frequency impedance elements 112 and 118 as illustrated on leadwire 106₄. It should be noted that these variable frequency impedance circuit elements would appear on all or some of the leadwires $104_1$ through $106_4$. They are only shown on $106_4$ to simplify the drawing. In this example, the metallic housing (titanium) 124 of the AIMD as an energy dissipating surface 161. Typically the AIMD is installed in a pectoral pocket, an abdominal pocket or in some other location that is not in intimate contact with a body organ. Accordingly, if the housing 124 were to overheat, it would be surrounded by fat and muscular tissue which is not nearly as sensitive to thermal damage as, for example, cardiac tissue or brain tissue. Also referring back to FIG. 81, one can see that for AIMDs, the relative surface area of the housing 124 is quite large in comparison to the electrode at or near the end of an implanted lead. In other words, it embodies a great deal of surface area over which to dissipate the MRI RF energy. Accordingly, the thermal rise will be very low (just a few degrees) as opposed to if the energy were concentrated over a small area in electrode tip where the thermal rise can exceed 30 or even 60 degrees centigrade. Accordingly, it is a primary feature of the present invention that the housing of the AIMD be used as an energy dissipating surface 161 working in combination with or without bandstop filters installed at or near the distal electrode to tissue interface. In FIG. 81, this energy dissipation is represented by the arrow marked 161. In fact, the energy is being dissipated at all points all around the metallic housing 124 to the surrounding tissues.

Referring once again to FIG. 81, the diverter element 112 can be any of the diverter elements 112 described in FIGS. 4-11 herein. Impeded element 118 can be any of the impeded elements 118 that are also illustrated in FIGS. 4-11 herein. The impeder and diverter elements 112 and 118 can also be placed within a molded header block 134 of a cardiac pacemaker or the like. These are shown as diverter element 112A and impeder element 118A. The impeder elements 112 and 118, as illustrated in FIG. 81, are desirably but not necessarily used in combination. In other words, only the diverter element 112A could be used. An advantage to locating the diverter element 112A and/or impeder element 118A in the header block 134 (outside of the AIMD housing 124) is that the component values of these impeder and diverter elements could be optimized to match a particular lead. Typically, cardiac pacemakers are manufactured in high volume (there are over 600,000 pacemakers manufactured every year). It is really not practical to build a custom pacemaker for every type of lead. Leads vary in length from about 20 centimeters to over 60 centimeters, depending on whether it's a pediatric or a large adult application. Accordingly, the characteristic impedance of the lead will vary widely with its length and also its implanted lead trajectory in human tissues. By having the diverter and/or impeder elements 112A and 118A located in the header block, then they can be easily customized to match a particular lead. In a particularly preferred embodiment, the diverter element 112 and/or the impeder element could also be placed in the proximal end of the lead or even in the male proximal lead connector. In this way, each lead could be optimally tuned with a diverter such that maximal energy transfer would occur between the implanted lead and the medical device housing 124. Referring once again to FIG. 81, diverter element 112B and impeder element 118B are shown disposed within a proximal lead connector. In accordance with the present invention, in order to maximize energy transfer, the diverter element 112B would be tuned and opposite to the characteristic impedance of the lead. These principles are more fully described in FIGS. 90-94.

Figure 82:
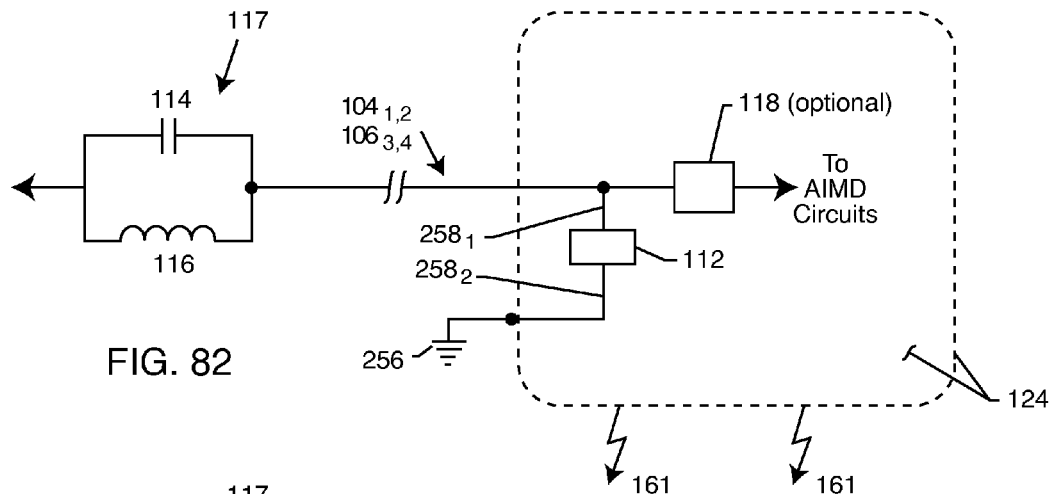
FIG. 82 is a schematic illustration of the structure shown in FIG. 81, showing use of variable impedance elements on leads that ingress and egress the AIMD.
Figure 83:
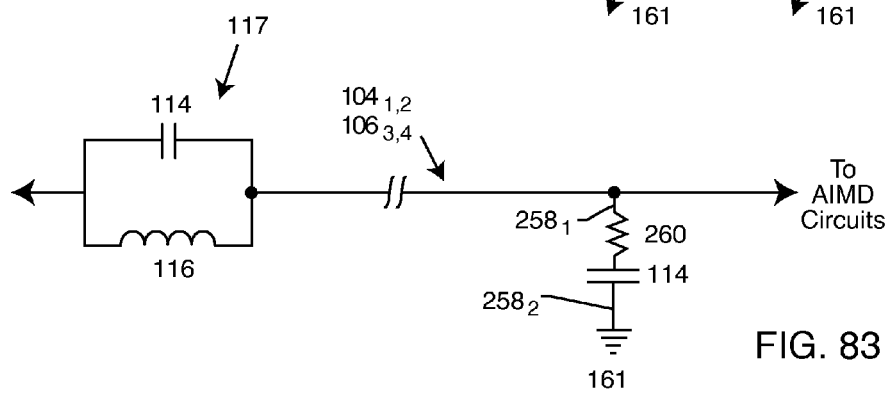
FIG. 83 is a schematic illustration showing that a variable impedance element can be a capacitor element.
Figure 84:
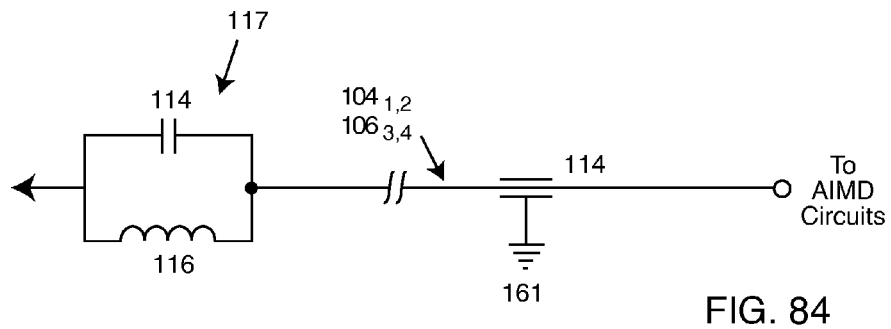
FIG. 84 is a schematic illustration similar to FIG. 83, showing that the variable impedance element can be a feedthrough capacitor element.

FIG. 82 illustrates that variable frequency impedance diverter element 112 can be any type of capacitor element, including MLCC chip capacitors and the like. FIG. 84 illustrates that the variable frequency impedance element 112 can also be a feedthrough capacitor as has been noted is in the prior art. Referring once again to FIG. 83, one can see there is a resistor 260 in series with the capacitor element 114. This resistor can simply be the equivalent series resistance (ESR) of the capacitor 114 itself, or it can be a separate discrete resistor mounted as a separate component. Ideally, the value of the resistance 260 would be equal to the characteristic impedance of the implanted lead at the same time the capacitor's, 114 capacitive reactance would tend to cancel out the inductive reactance of the implanted lead. This would facilitate transfer of a substantial amount of RF energy out of the leads to the surface 161. It will be obvious to those skilled in the art that a discrete resistor 260 could be added to any of the diverting elements of the present invention including diverting elements such as illustrated in FIG. 83. Resistors can also be associated with any of the low pass filters as previously described in FIG. 43. For a feedthrough capacitor as illustrated in FIG. 84, it is difficult to control the amount of series resistance (ESR) to achieve optimal energy transfer to the 161 surface. One is referred to U.S. Pat. No. 7,623,336, the contents of which are incorporated herein. FIGS. 3 through 6 illustrate novel ways to deliberately increase the feedthrough capacitors' equivalent series resistance (ESR). These are methods to increase the resistivity of the electrode plates at high frequency. The capacitor ESR can also be deliberately increased by using fewer electrodes (this necessitates thinner dielectric) and also deposition of thinner electrode plates. There is a tradeoff here between the power handling ability of the feedthrough capacitor. Accordingly, the preferred embodiment that a discrete chip resistor and capacitor would be used as illustrated in FIG. 83.

FIG. 84 is a close-up view of the variable impedance elements 112 and 118 from FIG. 81 located within the housing of an AIMD can 124. As previously mentioned, the variable impedance elements 112 and 118 would be installed on all of the leads that ingress and egress the AIMD. The ground symbol 256 is shown to indicate that variable impedance element 112 is connected to the housing 124 of the AIMD. The leadwire lengths should be very short to minimize inductance. These sections of leadwire $258_1$ and $258_2$ are kept very short so that high frequency energy from MRI will not be reradiated to sensitive AIMD circuits. Ideally, circuit element 112 would be a chip which would be bonded right at the point of leadwire ingress and egress.

Figure 85:
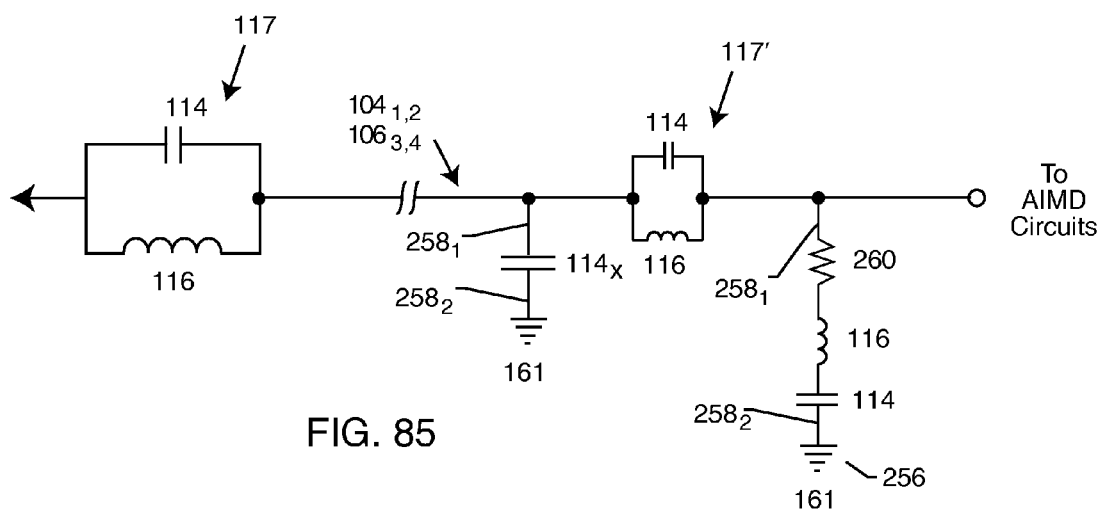
FIG. 85 is a schematic illustration similar to FIG. 84, showing use of a capacitor element in parallel with the L-C trap filter.

FIG. 85 illustrates that the trap filter of FIG. 45 can be used in combination with a second diverter such as a capacitor $114_x$ as previously illustrated in FIG. 83 or a feedthrough capacitor as illustrated in FIG. 84. For a pacemaker or an ICD, this would be the most common embodiment. Typical capacitance value for the series resonant trap would be 270 nanohenries of inductance and 22 picofarads of capacitance. This would make the series trap filter series resonant at 64 MHz. It's also important that the designer realize that at a certain frequency, the combination of the trap filter 206 and the EMI filter $C_X$ will at some point become a parallel resonant bandstop filter. This happens at frequencies at which the trap filter becomes inductive. In other words, at resonance, the inductive reactance cancels out the capacitive reactance and the impedance of the series trap is essentially zero except for its real or resistive losses. As previously mentioned, ideally the value of resistor 260 is selected such as to be equal to the equivalent or characteristic series resistance of the implanted lead system for maximal energy transfer. However, at frequencies above resonance, the inductive reactance term tends to increase and dominate the capacitive reactance term. In other words, at frequencies above resonance the series LC trap will tend to look like an inductor which could then cause a secondary resonance in parallel with the capacitor 114x. This means that there would be a minor degradation in the overall attenuation to electromagnetic interference. This resonant point should not appear at the frequency of a new and powerful emitter. Resonance at these emitter frequencies therefore should be avoided. Bandstop filter BSF' is optional, but does separate the diverter capacitor CX from the L-C trap filter.

Figure 86:
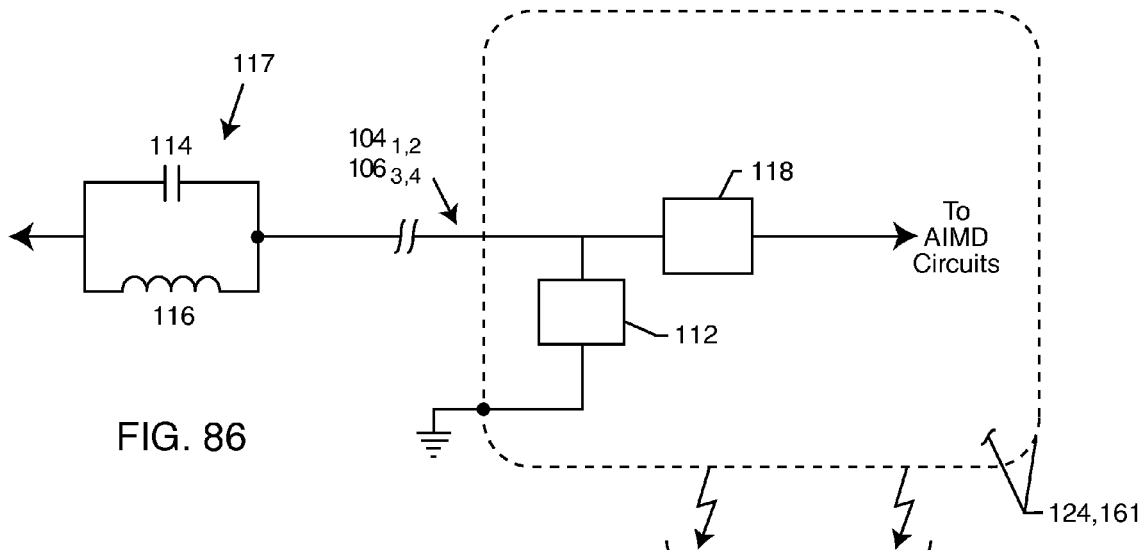
FIG. 86 is similar to FIG. 81 with emphasis on the series variable impedance element 118.

FIG. 86 is essentially the same as FIG. 82 except the focus is on the series variable impedance impeder element 118. The use of a series impedance element 118 is optional, but highly desirable for AIMDs that have sense circuits.

Figure 87:
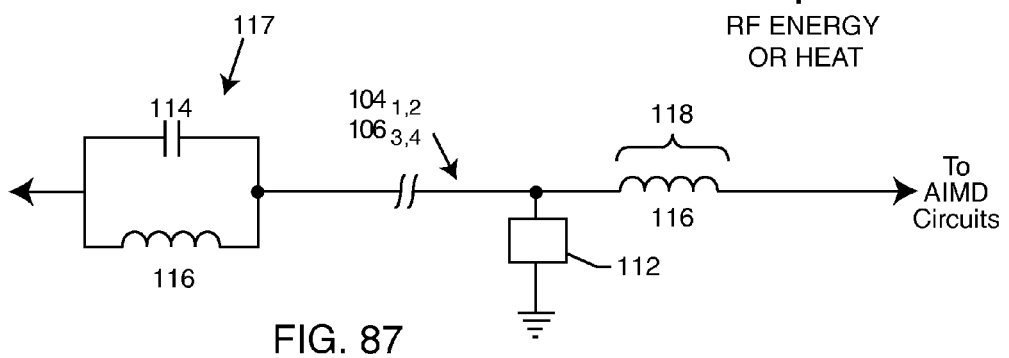
FIG. 87 illustrates that the variable impedance element 118 can be an inductor.

FIG. 87 indicates that the variable impedance impeder element 118 can be an inductor 116 as shown. This forms what is known in the art as a single element low pass filter. The inductor element 116 would freely pass low frequencies such as biologic frequencies that would offer a higher impedance at high frequencies such as those of MRI pulse frequencies, cellular telephones and the like.

Figure 88:
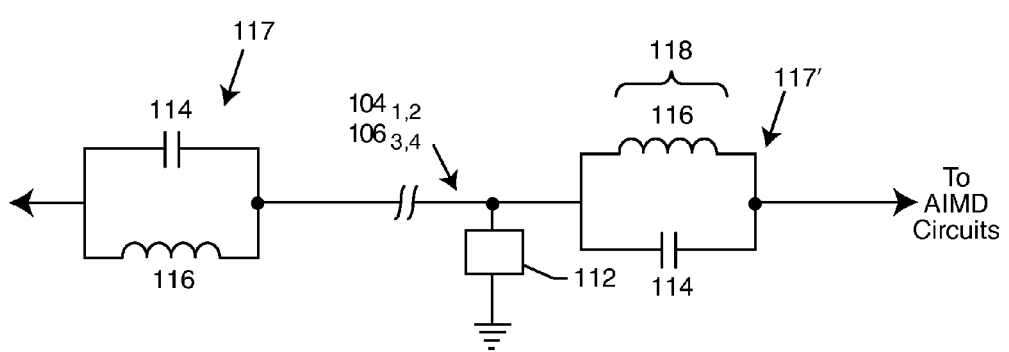
FIG. 88 illustrates that the variable impedance element 118 can be an L-C bandstop filter.

FIG. 88 illustrates that the variable impedance element 118 can be a parallel resonant L-C bandstop filter BSF' as shown. The operation of the bandstop filter has been clearly described in U.S. Pat. No. 7,363,090 and US 2007/0112398 A1.

Figure 89:
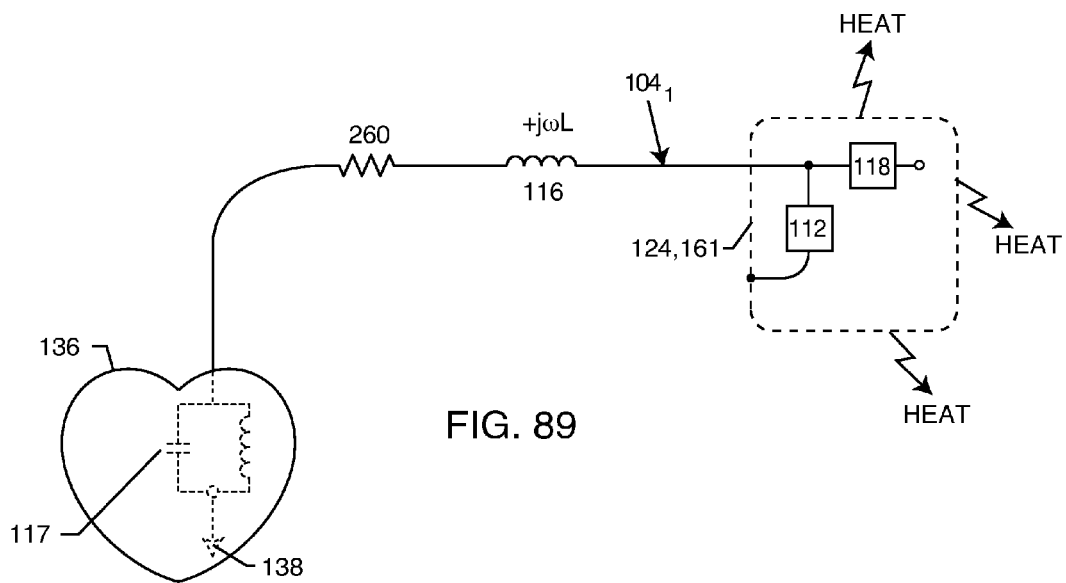
FIG. 89 is a schematic illustration of a unipolar lead system for an AIMD.
Figure 90:
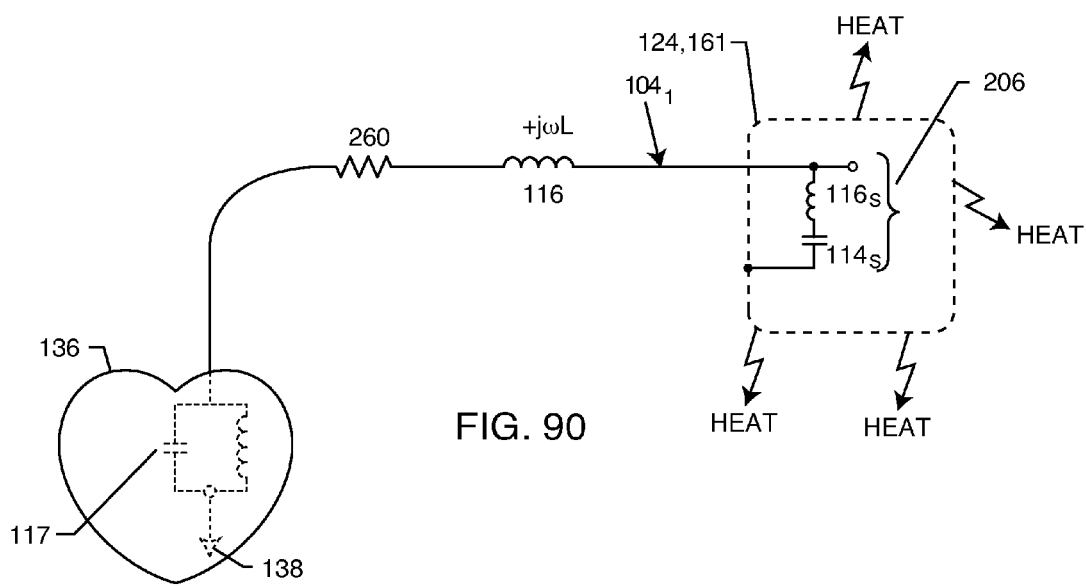
FIG. 90 is an illustration similar to FIG. 89, wherein an L-C trap filter has been placed inside an abandoned lead cap assembly.

FIG. 89 shows a unipolar lead system $104_1$ for an active implantable medical device. A unipolar lead system is shown for simplicity. It will be obvious to those skilled in the art that any number of lead wires $104_1$ could be used. In FIG. 90, one will see that this system involves an AIMD and its associated housing 124 attached to unipolar lead wire $104_1$ to a human heart 136. At the distal tip or distal end of lead wire $104_1$ is an optional bandstop filter 117. The optional bandstop filter 117, which is located at or near the distal electrode 138, is more thoroughly described in U.S. Pat. No. 7,363,090 the contents of which are incorporated herein. As shown, the implanted lead has inductive 116 and resistive 260 properties along its length (it may also have capacitive properties as well). The total or equivalent inductive reactance of the lead in ohms is given by the formula +jωL as shown in FIG. 89. As mentioned, the distal electrode bandstop filter 117 may or may not be present. The equivalent inductance 116 and resistance 260 of the lead system also includes the impedance of any tissue return path. It should be noted that the present invention applies to any type of AIMD including those AIMDs whose housing may actually be an active electrode or part of an electrode return path. For example, there are certain neurostimulator applications involving a number of distal electrodes that all have return paths through body tissue from a digital electrode 138 all the way to a common electrode which is also the device housing. One of the best ways to actually determine the characteristic lead impedance, including its inductive, capacitive, and resistive properties, is through human body modeling using software such as SAMCAD. Using SAMCAD, one can calculate the electric field vectors all along the lead trajectory. One can then calculate the induced energy into the implanted leads and their characteristic impedances. Referring once again to FIG. 89 one can see that on the interior of the generally metallic housing of the AIMD 124 there are frequency selective components 112 and 118. These frequency selective elements can consist of various arrangements of capacitors, inductors and resistors or even short circuits as will be more fully described in FIGS. 90 though 93.

FIG. 90 illustrates the lead system of FIG. 89 wherein an L-C trap filter 206 has been placed at the point of leadwire ingress into of the housing 124 of the AIMD. In this case, $L_s$ and $C_s$ have been designed to be resonant at the pulsed RF frequency of the MRI equipment. Therefore, this forms an RF short to the AIMD housing 124 which becomes an energy dissipating surface 161 of the present invention. As previously described, a series resistance could be added in series with $116_s$ and $114_s$ in order to further optimize energy transfer from the leadwire $104_1$. It is desirable that this surface area be relatively high so that very little temperature rise occurs on surface 124 as the MRI RF energy is being dissipated.

Figure 91:
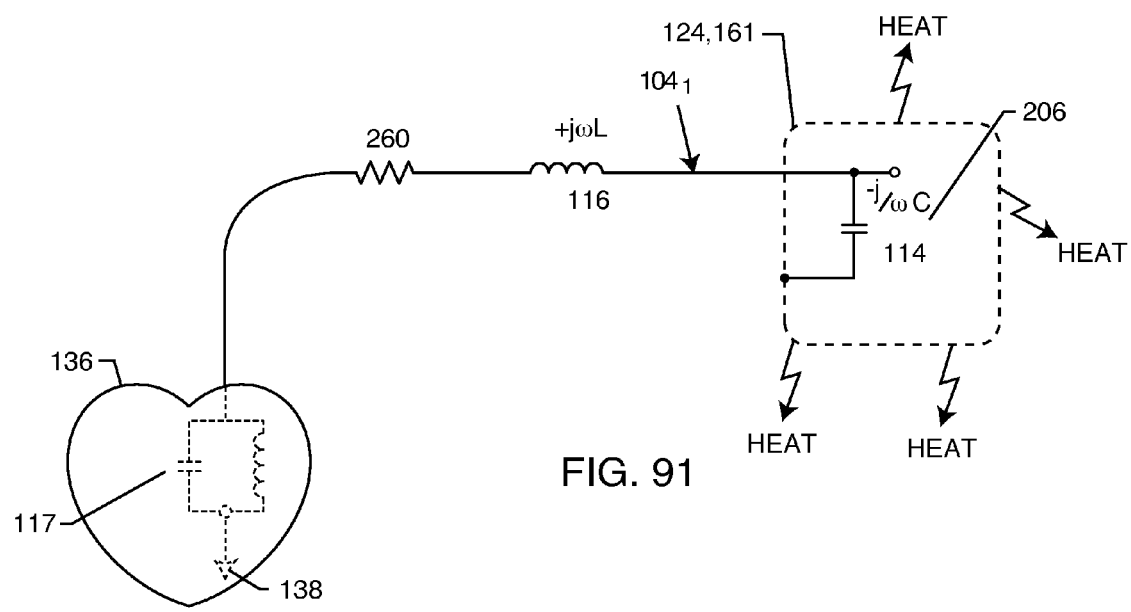
FIG. 91 is another illustration similar to FIG. 89, wherein the frequency selective components comprise capacitive elements.

FIG. 91 is another illustration of the unipolar lead system of FIG. 89. In this case, diverter element 112 features a capacitive element 114 whose capacitive reactance is given by the equation –j/ωC. In a preferred embodiment, the inductance of the implanted lead would first be modeled, calculated or measured. Therefore, the value of capacitance could be tuned or selected such that –j/ωC is equal and opposite to +jωL. In this case, the reactances cancel each other so that one gets maximal energy transfer to the energy dissipating surface 124, 161. As previously described, the capacitor's equivalent series resistance (ESR) could be controlled or a discrete resistance approximately equal to the characteristic resistance of the implanted lead could be added in series in order to further maximize energy transfer from the implanted lead system $104_1$ to the 161 surface 124.

Figure 92:
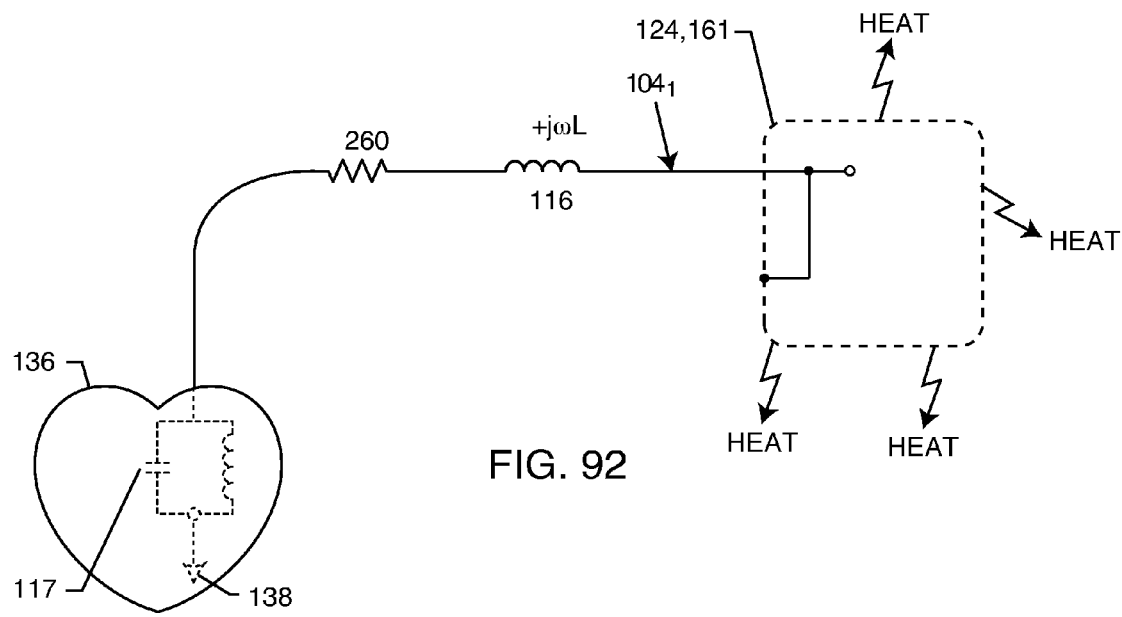
FIG. 92 is another illustration similar to FIG. 89, illustrating the simplest arrangement where the leadwire is shorted to the housing of the AIMD.

FIG. 92 embodies the simplest arrangement wherein lead wire $104_1$ is simply shorted to the housing 124 of the AIMD which makes said housing an efficient energy dissipating surface 161. Of course, creating a short to housing as illustrated in FIG. 92 would also short out the proper operation of the AIMD. This generally would not be acceptable for a lifesaving device such as cardiac pacemaker. However, for a neurostimulator such as a spinal cord pain control stimulator, this could be a programmable function wherein the AIMD leads were shorted out only for the MRI scan.

Figure 93:
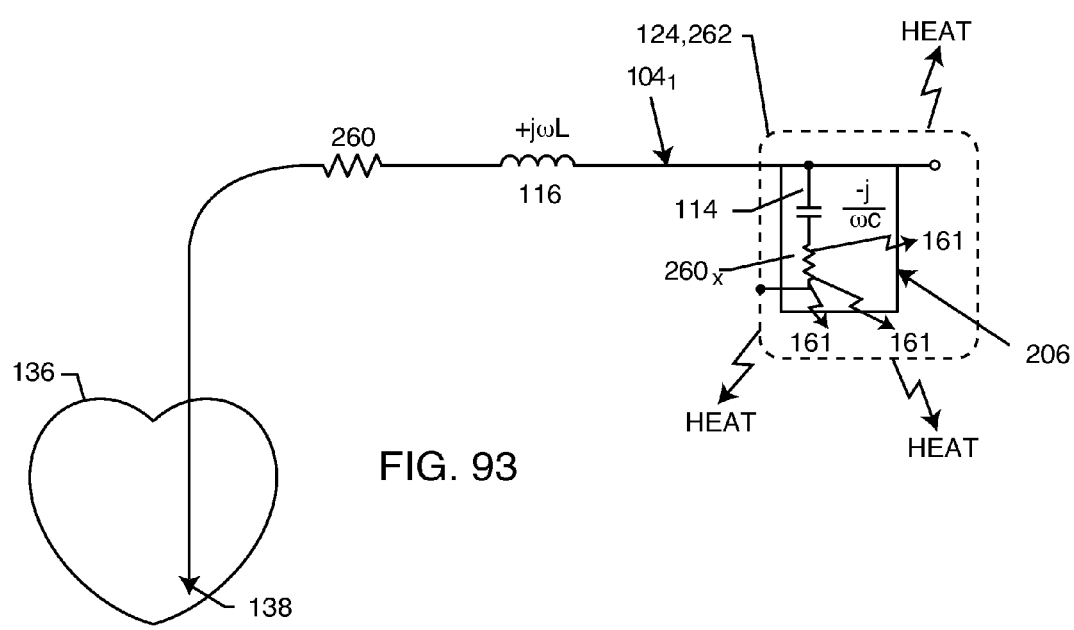
FIG. 93 is another illustration similar to FIGS. 89 and 91, wherein the capacitance value C has been selected such that the capacitive reactance will be equal and opposite to the inductive reactance of the implanted lead.

FIG. 93 is similar to the unipolar lead system previously described in FIGS. 89 and 91. In this case, as for FIG. 91, the capacitance value 114 has been selected such that the capacitive reactance will be ideally equal and opposite to the inductive reactance of the implanted lead. However, in this case, the resistances are also balanced. In other words, the resistance of the implanted lead 260 is equal in value to a discrete resistor $260_X$ placed inside or outside of the housing 124 of the AIMD. In this case, maximum power transfer or energy will be dissipated by this internal resistance $260_X$ as heat. In a preferred embodiment, a thermally conductive but electrically insulative filler material (not shown) will be placed between the resistor $260_X$ and the AIMD housing 124 such that maximum energy transfer from resistor $260_X$ will occur. In fact, in a preferred embodiment, resistor $260_X$ shall have a finned high surface area housing for maximal energy transfer to the surrounding encapsulant. Referring once again to FIG. 93, one can see that energy is radiated and conducted from a discrete resistance element $260_X$ shown as 161. This energy being dissipated turns to thermal (heat) energy. It is desirable to have a relatively large thermal mass located within housing 124. The AIMD housing 124 then becomes a heat dissipating surface 262. This thermal energy will be dissipated over the relatively large surface area 124 into body fluids and tissues that surround the AIMD. For example, in a cardiac pacemaker application, housing 124 would be in a pectoral muscle pocket.

Referring back to FIGS. 91 and 93, it is not necessary that the reactances completely cancel, or in the case of FIG. 93, it's not particularly important that the resistances are exactly equal. In fact, there is a tradeoff between EMI filtering of the input capacitance and exact cancellation of the +jωL component lead system. As it turns out, through actual testing, it is really only important that the impedance generally be cancelled in the lead system so that at least the bulk of the excess energy from the MRI RF pulse field will be dissipated to the housing of the AIMD 124. For example, if one calculates that a 75 picofarad capacitor would exactly cancel the inductive reactance of the lead system, one may instead choose to use a 1000 picofarad capacitor. The 1000 picofarad capacitor would still draw a large amount of energy from the lead system to the housing 124. The reason one would do this, is that a 1000 picofarad capacitor would offer much more effective EMI filtering to not only the RF pulse frequency (64 MHz or 1.4 Telsa MR system), but also for cell phones and other emitters commonly found in the pace environment. The energy balance systems and circuits of the present invention can also be combined with knowledge of the implanted lead design. By varying the coil pitch on the outer coil to create enough impedance so that a pacemaker ring electrode does not heat up is possible when combined with a bandstop filter and the distal tip electrode circuit. This becomes a balancing act so that one can be sure that not too much energy is transferred from the ring electrode to the inner electrode lead coils.

Figure 94:
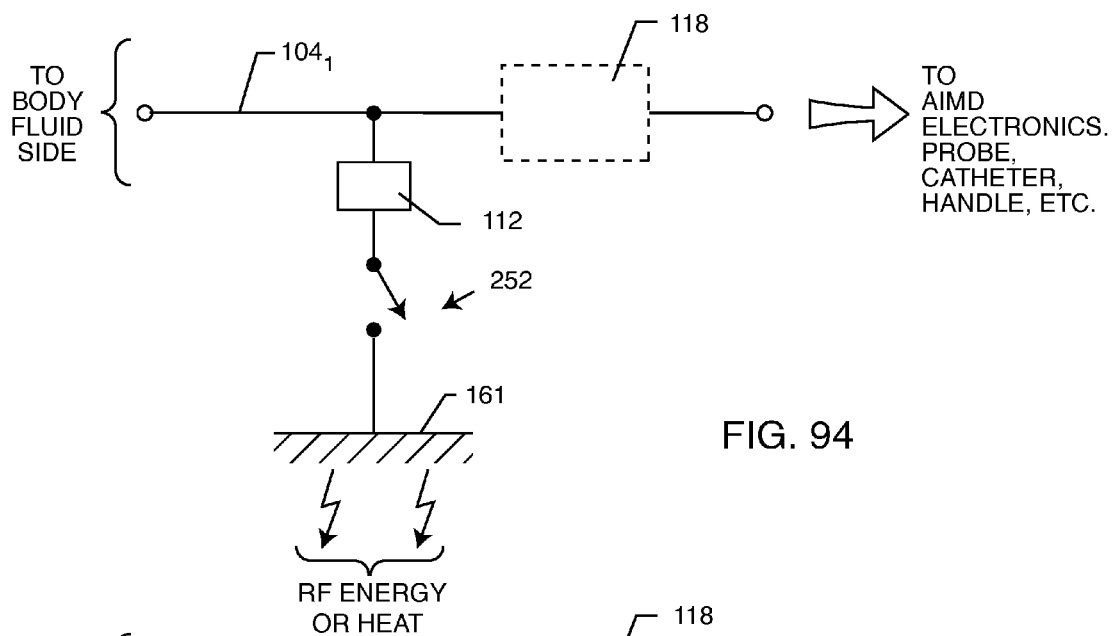
FIG. 94 is a schematic illustration similar to FIG. 89, illustrating a novel switch.
Figure 98:
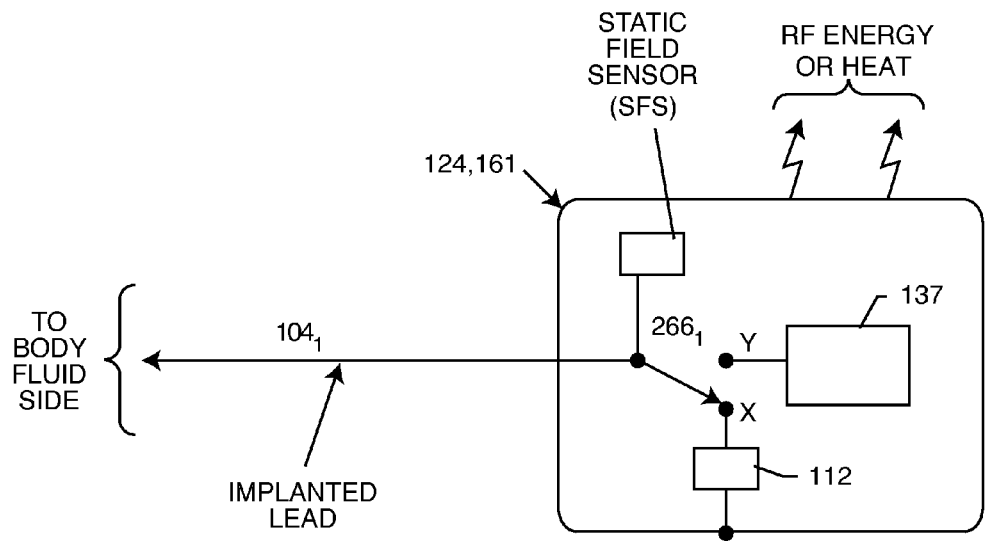
FIG. 98 is similar to FIGS. 96-97 except that switches have been replaced by a single switch which can be either a single or multipole double pole switch.

FIG. 94 is a schematic diagram of an implanted lead system very similar to that which was previously described in FIG. 89. Shown is an implanted lead $104_1$ which is directed into body fluids and to at least one distal electrode. Shown is a diverter element 112 in accordance with the present invention and an optional impeder element 118 also in accordance with the present invention. The novel switch 252 shown in the open position. The switch 252 is inclusive of all types of mechanical or electronic or microelectronic switches. This includes mechanical switches, DIP switches, MEMS switches, microelectronic switches, microelectronic switch arrays, any type of electronic switches including field effect transistor (FET) switches, varistor type switches and the like. In a preferred embodiment, switch 252 is programmable through AIMD telemetry. In a probe or catheter application, a signal can be sent into the probe or catheter to cause the switch 252 to switch positions. In another preferred embodiment, switch 252 could be automatically activated by a static field sensor. As previously described, there are three main fields associated with magnetic resonance imaging. This is the main static $B_0$ field, which for most modern scanners is either 1.5 or 3.0 Tesla. There is also an RF field and a gradient field. The switch 252 as illustrated in FIG. 94 can be associated with a static field $B_0$ sensor. As shown in FIG. 98, this could be a Hall effect device, a reed switch, a ferrite chip or any other type of magnetic field sensor. In this way, no device reprogramming would be necessary. In other words, when the patient is introduced to the MRI bore, the $B_0$ field sensor SFS located in the AIMD and/or the probe, catheter or the like in association with switch 252 would automatically sense the presence of the MRI main static field, thereby switching the switch 252 into the closed position (the switch shown in FIG. 94 is shown in the open position). The reason for the configuration as illustrated in FIG. 94 is that in order to provide for optimal energy transfer, the frequency diverting element 112 may place a burden (electrical load) on the AIMD during normal operations. In other words, it may degrade pacing pulses or rob energy during normal operation. Using the novel circuit as illustrated in FIG. 94, the frequency diverting element 112 could be conductively coupled to the energy dissipating surface only when needed during MRI scans. The switch diverter of FIG. 94 is for minimizing heating of an implanted lead and/or its distal electrodes when in the presence of a high power electromagnetic field environment such as that created by the RF pulse field of an MRI scanner. The diversion circuit, as illustrated in FIG. 94, can even embody a short circuit as will be further described. The frequency diverting element 112 can also be a bandstop filter as previously described as element 117 in FIG. 11. Since the novel switch 252 is only closed during exposure to high electromagnetic field environments, this enables a wider variety of impeder elements 112. It is also important to note that this also opens up a wider variety of passive component values for element 112. For example, when diverter element 112 is a capacitor as described in FIG. 5, it can now be of a very high capacitance value. This may rob some energy from the AIMD and even cause some miniscule battery depletion; however, this is unimportant during the relatively short time period required to complete an MRI scan compared to the overall lifetime of the AIMD.

Figure 95:
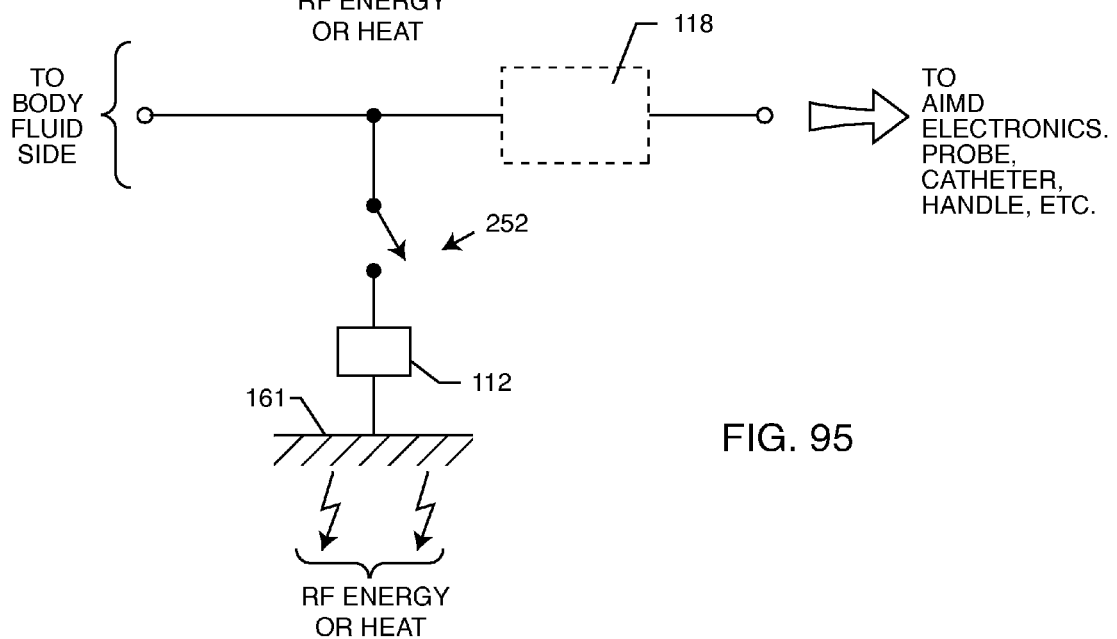
FIG. 95 is similar to FIG. 94, wherein the novel switch is shown disposed between the leadwires.

FIG. 95 is very similar to FIG. 94 except that the novel switch 252 is shown disposed between the implanted lead or leadwires or wiring inside of the AIMD in diverter circuit 112. Since the diverter is in series, it really does not matter where the switch 252 appears. Referring once again to FIG. 95, one can see that the circuits described can also be associated with an optional impeder element 118 that has been previously described in FIGS. 7, 10 and 11.

Figure 96:
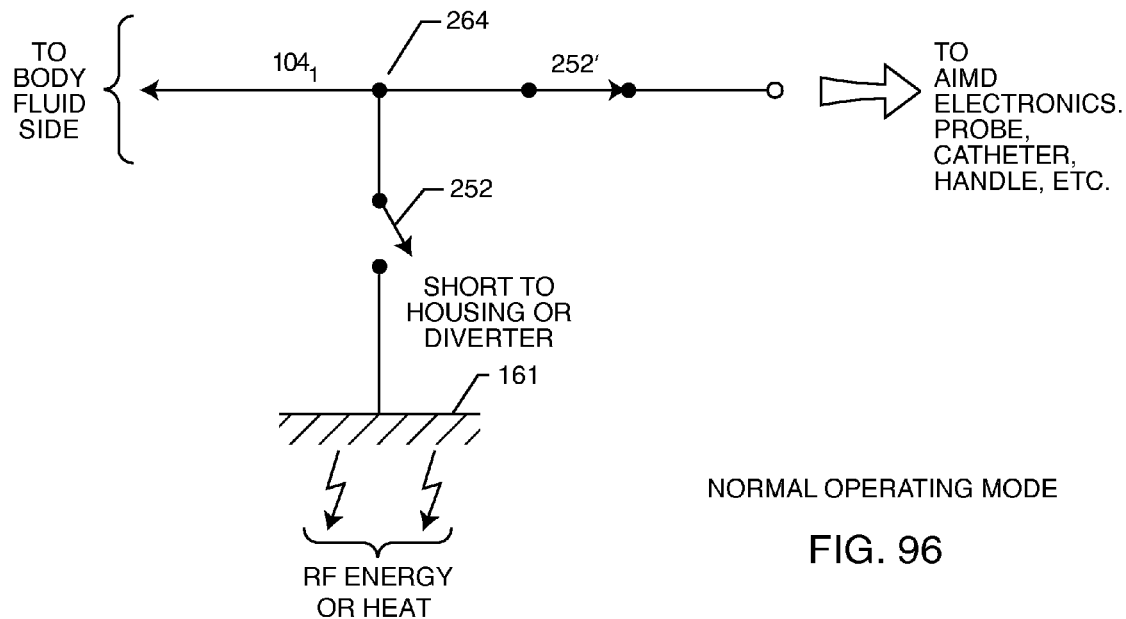
FIG. 96 is similar to FIG. 94, wherein two switches are employed.
Figure 97:
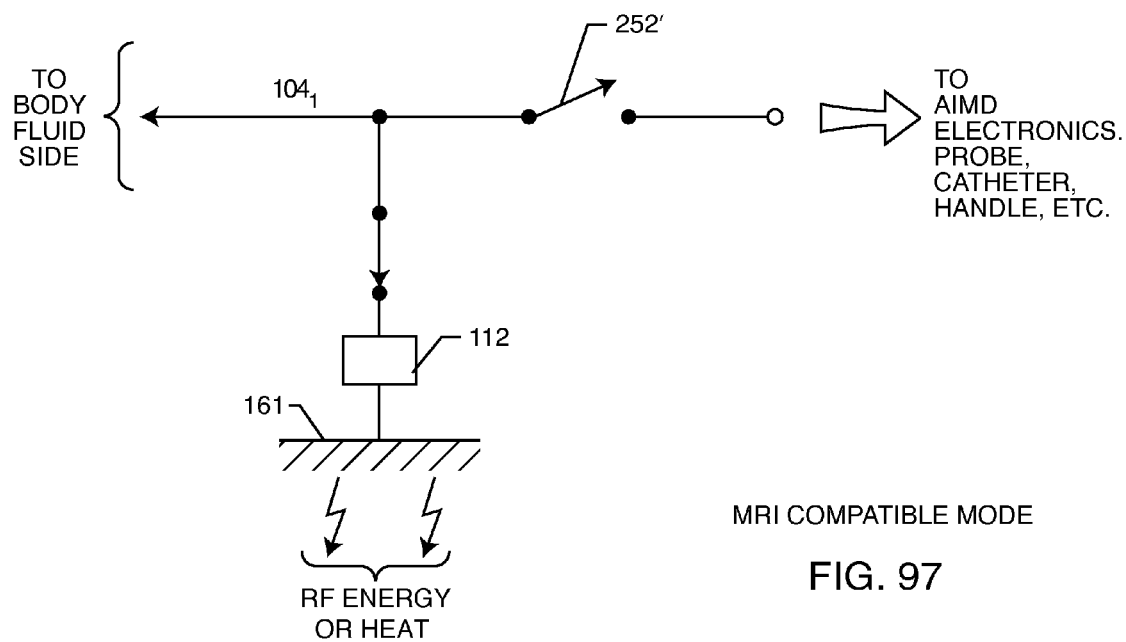
FIG. 97 is similar to FIG. 96, wherein the position of the two switches are changed.

FIG. 96 illustrates that two switches 252 and 252' may be employed. Switch 252 is shown in the open position and works in a very similar fashion to switch 252 that was previously described in FIGS. 94 and 95. In this case, the diverter element 112 is shown as a short circuit to the housing. This would not be desirable for a cardiac pacemaker patient who was pacemaker dependent. In this case, the patient depends on the beat pulse or the pacemaker to provide each and every heartbeat. It would be disastrous for each and every patient to short out their device to the energy dissipating surface 161. Referring to FIG. 96, the switch 252 is shown open which would be the normal operating mode. In preparation for and during an MRI scan, switch 252 would be switched to the closed position which would short an associated leadwire $104_1$ or implanted lead to the energy dissipating surface 161. This would work for many types of AIMDs including neurostimulators and the like, where the therapy they provide is convenient, but not life-sustaining. Accordingly, for the MRI compatible mode as shown in FIG. 97, switch 252 would be closed, thereby shorting or diverting energy from leadwire $104_1$ directly to the energy dissipation surface 161. As previously described, the short could be replaced by any of the diverter circuits 112 as previously described. Referring once again to FIG. 96, one can see that there is a second switch 252'. This switch would normally be closed, as shown, during normal AIMD, probe or catheter operations. However, this switch 252' would be opened as shown in FIG. 97 during MRI scanning. This has a desired effect of disconnecting the AIMD's electronic circuits from the implanted lead system during MR scans. This is very important to provide a very high level of EMI protection to AIMD circuits and also to prevent an effect known as RF rectification. MRI RF pulses consist of high frequencies that are determined by the Lamour frequency. For a 1.5 Tesla scanner, this means that there would be 64 MHz bursts of RF energy. These packets of energy, if detected by a non-linear element (like a diode) in the AIMD, could turn into the equivalent of digital pulse trains. This has the potential to directly capture the heart, for example, at 200 beats per minute or higher, thereby introducing a very dangerous tachyarrhythmia. Ventricular defibrillation, for example, can be immediately life-threatening. By disconnecting AIMD electronics during MRI scans, one eliminates any possibility of RF rectification. A discussion of where non-linear elements come from in an AIMD is important. Almost all modern AIMDs have over-voltage circuit protection. There typically are in the form of diodes, Transorbs, or the like. These diodes act as detection circuits and can strip off the pulse modulation from MRI RF frequencies. Therefore, it's important that switch 252' be opened up prior to encountering any protection diodes or non-linear elements inside of the AIMD. Pacemaker or neurologerlator sense circuit can also become very non-linear in the presence of high amplitude signals. This has to do with limitations of the dynamic range of their electronic (active) bandpass of other filters or amplifiers. There is also another problem that can be associated with MRI scans and that is induced currents on the implanted leads to the MRI gradient fields. In general, MRI gradient fields are low frequency and are generally in the 1-2 kHz (maximum 10 kHz) frequency range. At low frequencies, such as MRI gradient frequencies, currents are induced in implanted leads primarily by Faraday's Law of Induction. This is further explained herein in FIG. 101. Since there is a loop current involved that flows from the leads through the AIMD and then from the AIMD case back through body tissues, it is very useful if the AIMD has a very high impedance. The high impedance at the AIMD limits the amount of current flowing in this loop. There is also a problem associated with what is known in the industry as gradient induced rectification. This is very similar to RF rectification in that low frequency gradient currents consist of pulses. If these pulses encounter an AIMD or catheter non-linear circuit element, such as a diode, they can become demodulated, wherein they end up showing up on the leads or in the implanted medical device as a series of low frequency pulses. This can have an EMI effect, for example, inhibit a pulse generator which might falsely interpret these gradient pulses as a normal heart beat. Worse yet, these gradient pulses can appear on the implanted lead as a dangerously high biologic frequency (for example, 50 Hz) where the pulses would directly capture the heart and induce fibrillation. For a neurostimulator, they can also directly induce pain, for example, in the spinal cord. By having switch 252' open, as illustrated in FIG. 97, one disconnects AIMD internal electronic circuitry. In a preferred embodiment, the switch 252' would disconnect all non-linear circuit elements including AIMD high voltage protection diodes, bandstop filters, non-linear active filters and the like. It is also very important that the switch 252' itself not become non-linear. This would definitely be a possibility for certain types of electronic switches that were not robust enough. Accordingly, it is a principle of the present invention that switch 252' be of a type that will not become non-linear in the presence of MRI gradient or RF current/voltages. Referring once again to FIG. 94, a short circuit to the energy dissipating surface housing would not be the preferred embodiment for elongated lead exposure to gradient fields. A preferred embodiment would use a frequency selective diverter 112 as is shown in FIG. 95 and as described in FIGS. 2-11. The frequency selective diverter 112 acts as a high pass filter, meaning that it will allow 64 MHz or other MRI RF frequencies to flow freely to the EDS housing. However, the diverter element 112 will look like a very high impedance or open circuit at extremely low frequencies, such as MRI gradient frequencies. This tends to open the loop thereby preventing excessive currents from flowing in the implanted lead and through body tissues, such as cardiac tissue. In a particularly preferred embodiment, the diverter 112 would be a capacitor as shown in FIG. 91 or an L-C trap filter as shown in FIG. 90 or a resistor in series with a capacitor as illustrated in FIG. 93.

Referring once again to FIGS. 94, 95, 96, and 97, it is not necessary or even required that the switches 252 or 252' be installed in each and every AIMD implanted lead circuit. For example, for an implantable cardioverter defibrillator (ICD), there are typically sense circuits, high voltage shock circuits and pacing circuits. One can install the novel switches 252 and 252' only as required to achieve optimal performance. For example, referring once again to the ICD, one may choose to leave a pacing circuit in its normal operating mode while switching all other AIMD implanted leads to an MRI compatible mode. Referring once again to FIG. 96, switch 252' can appear on the right hand side of Node 264 as shown or it could be placed on the left hand side of Node 264 (not shown).

Figure 99:
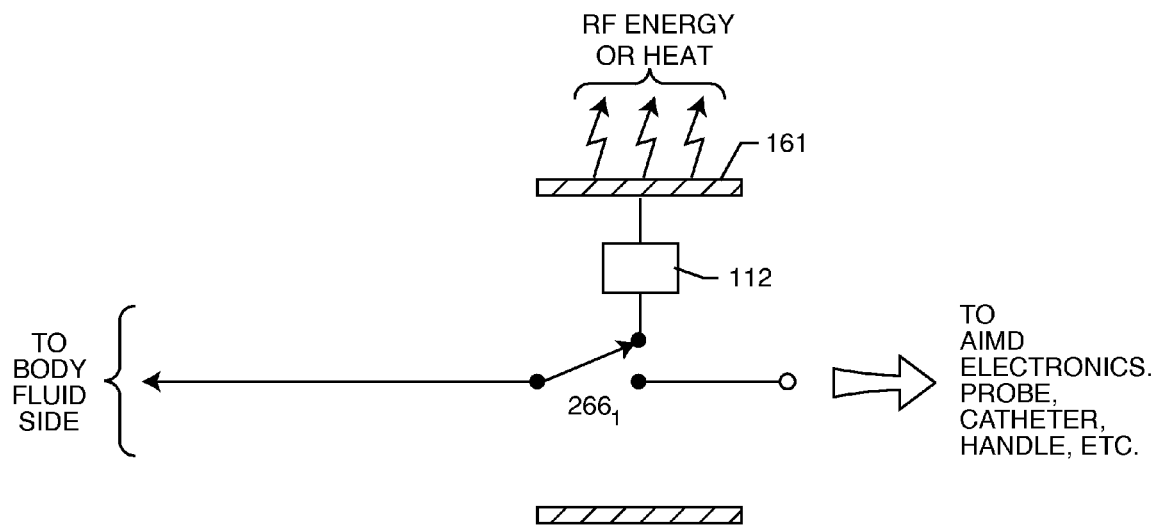
FIG. 99 illustrates the switch in FIG. 98 can be disposed within an energy dissipating surface located anywhere along an implanted lead.

FIG. 98 is very similar to FIGS. 96 and 97 except that switches 252 and 252' have been replaced by a single switch $266_1$ which can be either a single or multipole double throw switch as illustrated. In other words, the switches as previously illustrated in FIGS. 96 and 97 have been combined into a single switch. FIG. 99 is shown for just one circuit of an AIMD or a probe or a catheter. It will be obvious to those skilled in the art that any number of switches $266_1$ can be installed in any or all of the implanted leads as required. The switch $266_1$ as shown in FIG. 98 can be disposed anywhere along the implanted lead or inside of an energy dissipating surface 161 or inside of an AIMD housing 124 as shown, or even anywhere along the handle or wiring or body of a probe or catheter. Switch $266_1$ could also be installed in an external electronics box, for example, that connected to the handle of a probe or catheter, a loop recorder or the like.

Referring once again to FIG. 98, one can see that the switch is shown in position X which connects the leadwire to the diverter circuit 112. As previously mentioned, diverter circuit 112 can be any of the frequency selective diverter circuits, a short circuit or even a bandstop filter. When switch $266_1$ is thrown to position X as shown, it is in the MRI mode. During normal operations, it would be switched to position Y so that the AIMD, probe or catheter could normally operate. Any of the switch technologies previously described in FIG. 94 apply to any and all of the switches described herein.

FIG. 99 illustrates that the switch $266_1$, as previously described in FIG. 98, can also be disposed within an energy dissipating surface 161 located anywhere along an implanted lead. The use of switches, as illustrated in FIGS. 94 through 99, are applicable to any of the designs illustrated herein.

Figure 100:
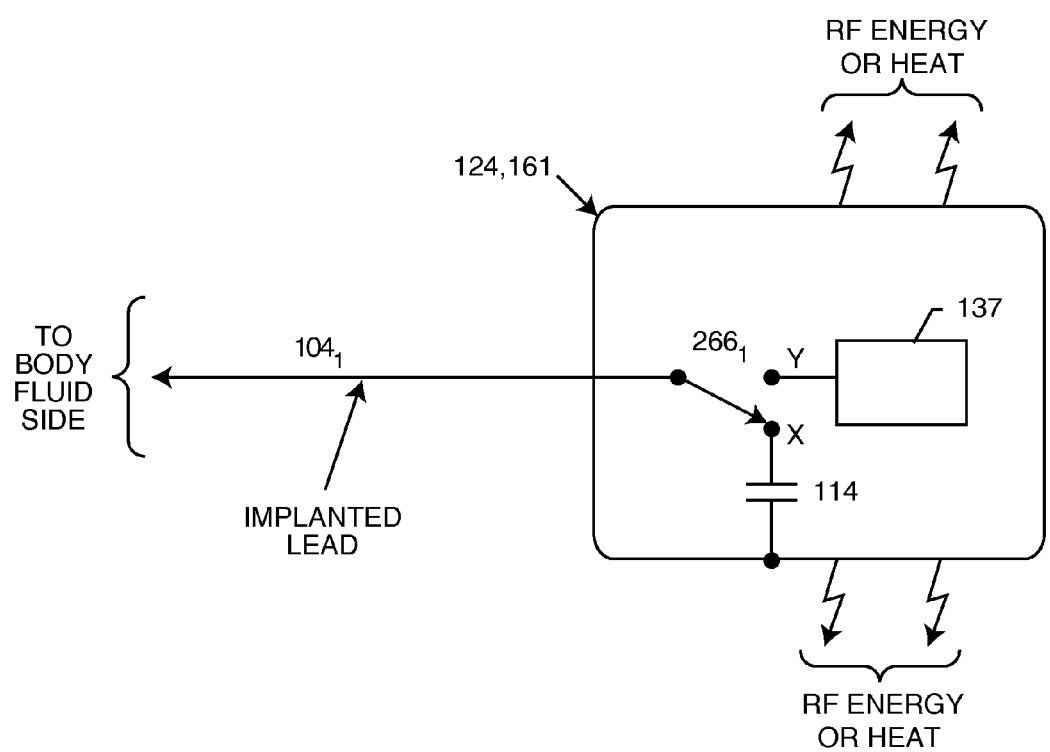
FIG. 100 is similar to FIG. 98, wherein a capacitor is connected between the switch point and the energy dissipating surface.

FIG. 100 shows a preferred embodiment of the switch $266_1$ and diverter 112 that was previously described in FIG. 98. Shown is a capacitor 114 that is connected between switch point X and the energy dissipating surface 161, such as the housing of an AIMD, or body of a probe or catheter. Capacitor 114 as shown or a resistor in series with a capacitor or an L-C trap filter (not shown) are preferred because they tend to look like high pass filters in an MRI environment. MRI equipment produces three main fields consisting of the main static field $B_0$, the RF pulsed field, and the gradient field. We can ignore the static field for these purposes since it does not induce currents on implanted leadwires. It is a basic principle of physics that either the field has to be moving or a conductor has to be moving in relation to the magnetic field for there to be an induced electromotive force. Both the RF pulsed field and the gradient field are time varying and can induce undesirable currents on implanted leads. Capacitor 114, as shown in FIG. 100, is a frequency variable impedance diverter element in accordance with the present invention. Accordingly, it has a very high impedance at low frequency and a very low impedance at high frequency (hence, when wired in a circuit like this, it is known as a high pass filter). It, therefore, shunts or diverts undesirable high frequency RF energy to the energy dissipating surface housing while at the same time blocking the flow of low frequency energy such as that induced by MRI gradient fields. Preventing the flow of gradient currents into AIMD circuitry is very important so that gradient rectification does not occur. In addition, opening up the loop at gradient frequencies, as shown in FIG. 100 (effectively open by the high impedance of the capacitor 114), also prevents flow of current through distal tissues at the electrode-to-tissue interface.

Figure 101:
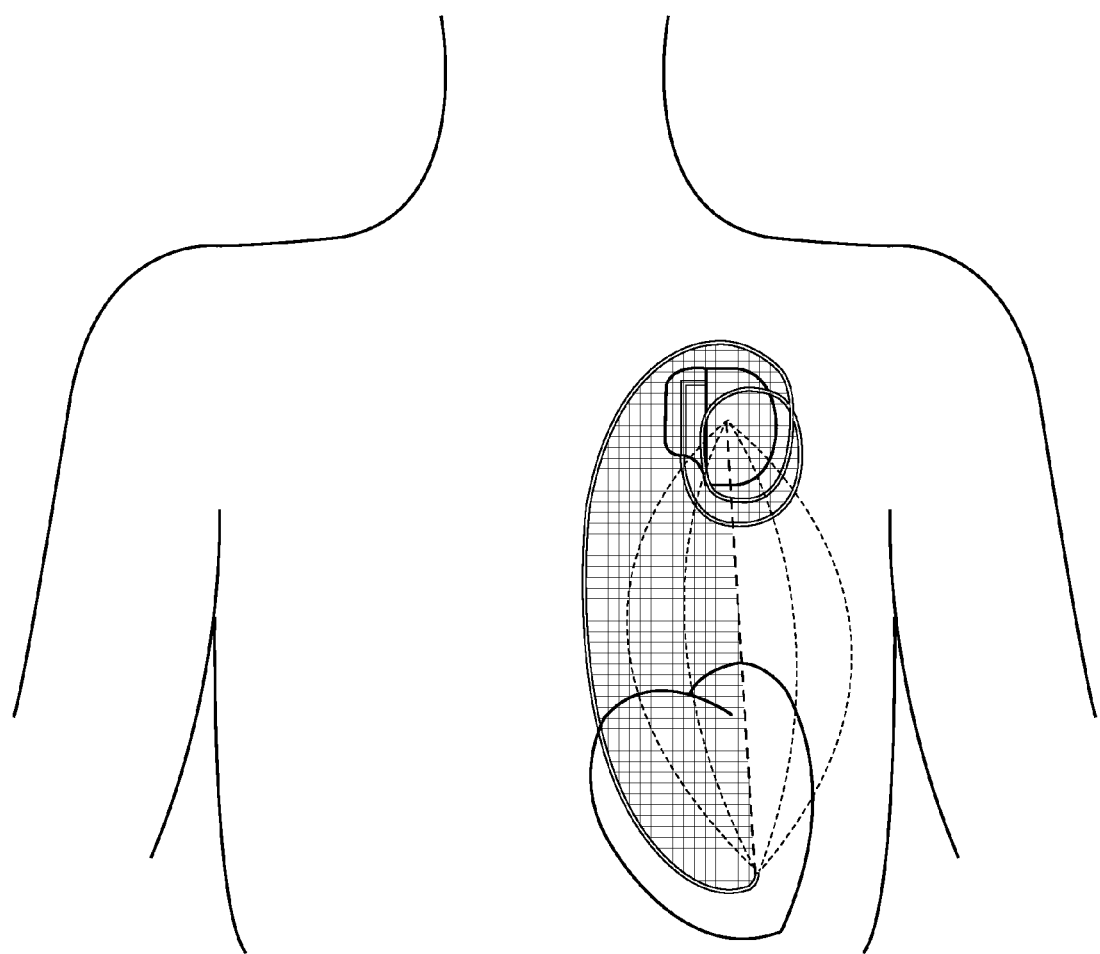
FIG. 101 is an illustration of an X-ray tracing of an implanted cardiac pacemaker in a patient.

FIG. 101 is a patient front view representative of an X-ray tracing of an implanted cardiac pacemaker. The pacemaker is shown installed in a pectoral pocket, which can either be left pectoral (as shown) or right pectoral (not shown). There can be one or more turns of excess leadwire that's coiled up in the pectoral pocket and then the lead is routed endocardially down through the superior vena cava into cardiac chambers as shown. A loop area shown by the checker pattern is formed between the distal tip electrode all along the lead to the AIMD housing and then through a multi-path tissue return path shown as a dashed line from the AIMD housing to the distal tip electrode in the heart. MRI low frequency gradient fields couple into this loop by Faraday's Law of Induction. In general, Faraday's Law states that a voltage induced in this loop is directly proportionate to the area of the loop times the rate of change of the magnetic field in Teslas per second. A worse case coupling situation occurs when the field is orthogonal to the loop area. Current will flow in the lead unless the lead is opened up (switched open). It is highly undesirable that this low frequency MRI gradient induced current flow into cardiac tissues as this could directly induce cardiac arrhythmias. It is also undesirable if this current should flow into the AIMD electronics as it could either interfere with AIMD electronics (EMI) or it could lead to gradient rectification. In the art, direct cardiac or tissue stimulation is known as Gradient STIM.

Figure 102:
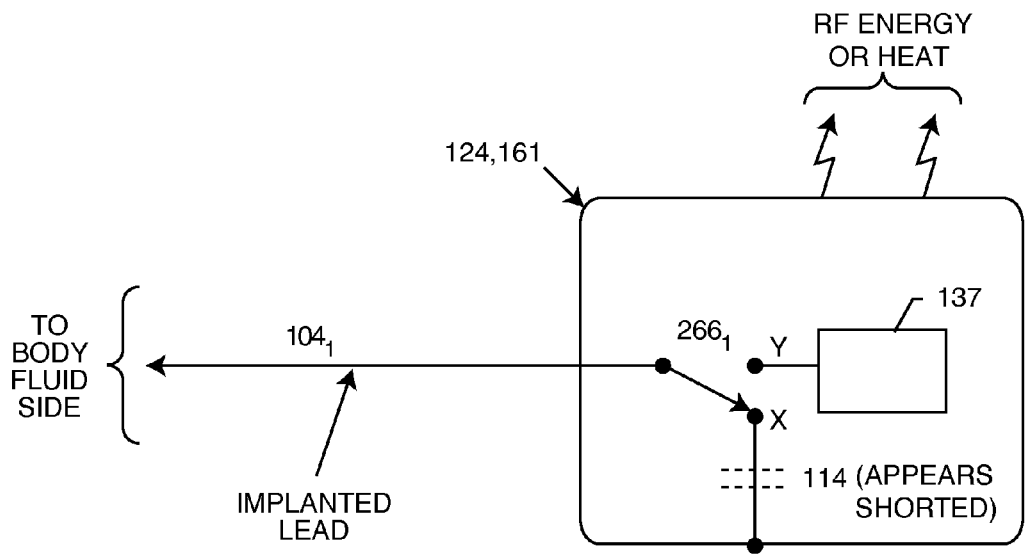
FIG. 102 is similar to FIG. 100, where the circuit is a high frequency model.

FIG. 102 is the high frequency model of the circuit illustrated in FIG. 100. In this case, at high frequencies, such as MRI RF pulsed frequencies, the capacitor 114 is a very low impedance which effectively appears as a short circuit. This has the desirable effect of pulling or diverting high frequency energy on the lead $104_1$ through the low impedance of the capacitor 114 to the energy dissipating surface 161, which in this case, is the AIMD housing. As previously stated, when wired between point X and 161, the capacitor 114 acts as a high pass filter. The capacitive reactance of capacitor 114 as previously described is a $-j$ vector which tends to cancel the $+j$ vector that is associated with the inductance of an implanted lead. As previously described, this aids in maximal (tuned) energy transfer to the energy dissipating surface 161.

Figure 103:
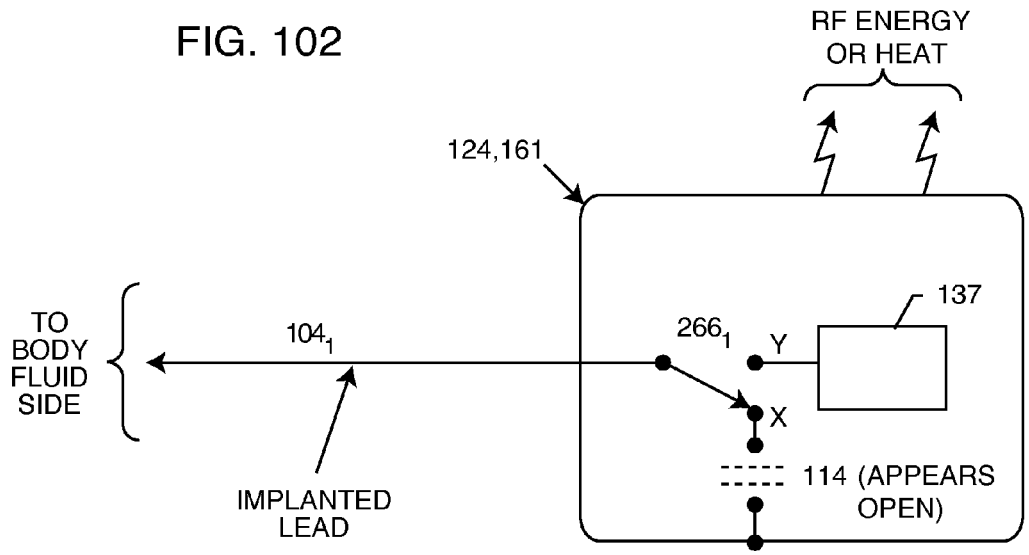
FIG. 103 is similar to FIG. 100, where the circuit is a low frequency model.

FIG. 103 is the low frequency model of the circuit previously illustrated in FIG. 100. In this case, at low frequencies, the capacitor 114 appears as a very high impedance which effectively appears electrically as an open circuit. As previously mentioned, this has the desirable effect of preventing gradient currents from flowing in the implanted lead and the associated loop through body tissue and AIMD electronics.

Figure 104:
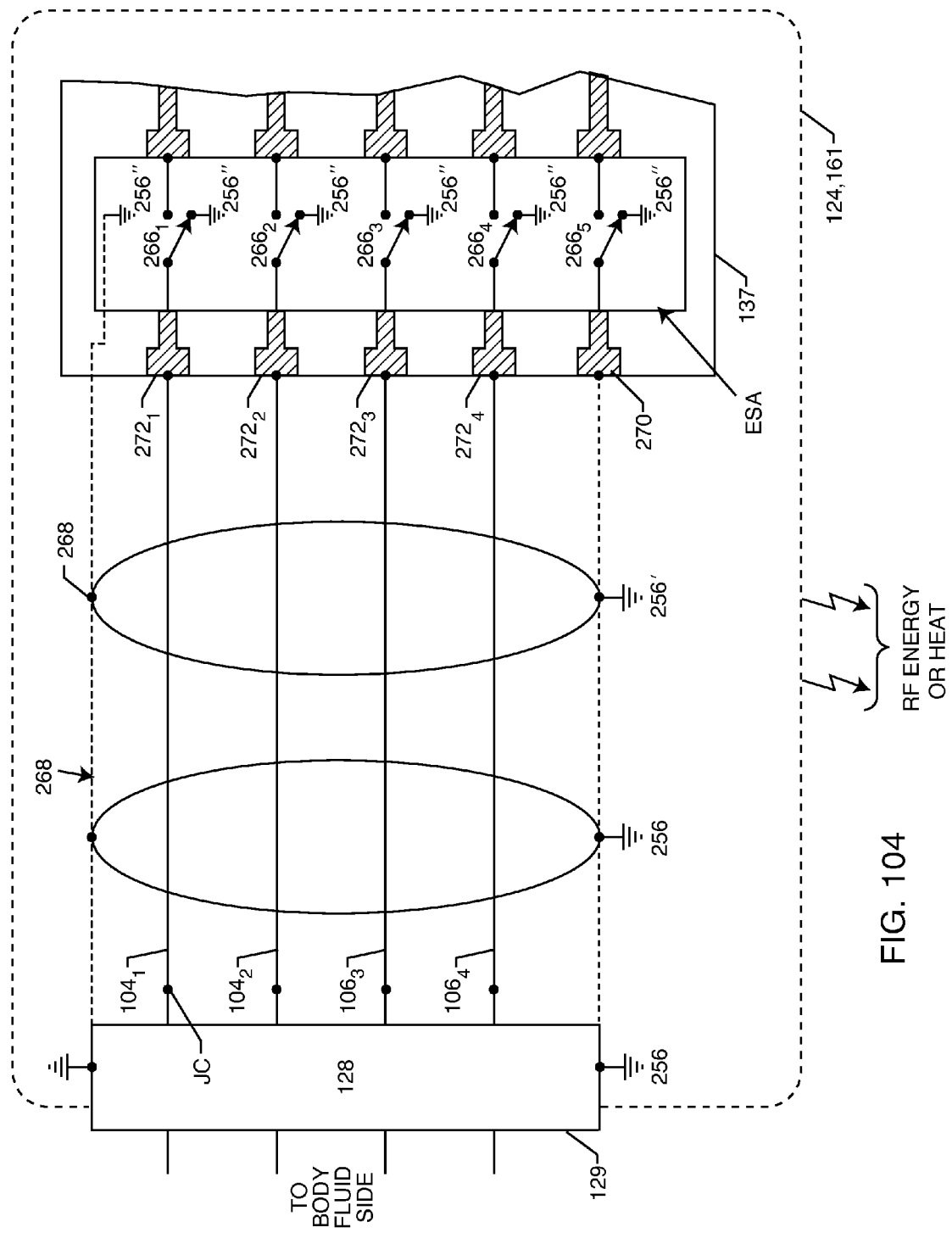
FIG. 104 shows the application of the switch of FIG. 98 to a circuit board or housing of an AIMD.

FIG. 104 shows the application of the switch $266_1$ of FIG. 98 to a circuit board 137 or housing located inside of the housing 124 of an AIMD. Shown is a hermetic terminal 128 that was previously described for a cardiac pacemaker in FIG. 12. The overall AIMD housing 124 is shown connected to the ferrule 129 of the hermetic terminal 128. Leadwires $104_{1,2}$ through $106_{3,4}$ pass through the hermetic terminal in non-conductive relation as previously described in FIG. 12 (only $104_1$ is shown). Internal leadwires are routed from the hermetic terminal 128 through circuit terminals 272 to the circuit board or substrate 137. Shown is an optional shielded conduit 268 of the grounded 256 and 256' to a ground trace located within the wiring or flex cable. The switches $266_1$ through $266_5$ could, of course, all be incorporated into a single microelectronic chip. In the art, the switch $266_1$ would be known as a multipolar double throw switch. Switching the ground circuit 270 would, of course, be optional. As previously described, one could switch any or all of the implanted lead circuits $104_{1,2}$ through $106_{3,4}$ as shown. In this case, the implanted leads (not shown) and associated leadwiring $104_{1,2}$ through $106_{3,4}$ are all shown shorted to circuit ground 256".

Figure 105:
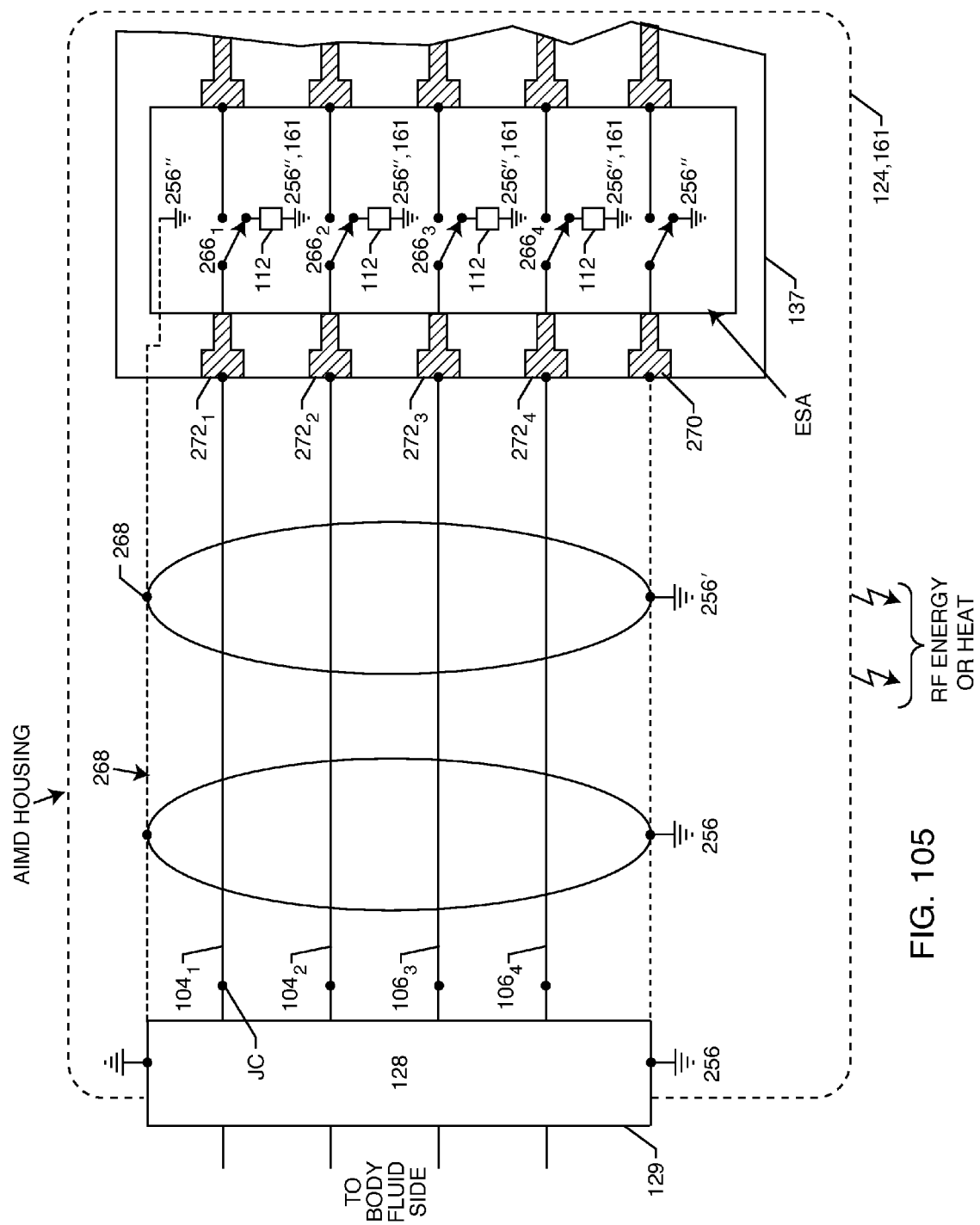
FIG. 105 similar to FIG. 104, except that the short has been replaced by a frequency variable impedance element.

FIG. 105 is very similar to FIG. 104 except that the short has been replaced by a frequency variable impedance element 112 in accordance with the present invention. As previously described in FIG. 2, variable frequency element 112 could be a capacitor 114, could be an L-C trap filter consisting of a capacitor 114 in series with an inductor element 116, or even a short or a bandstop filter as previously described.

Figure 106:
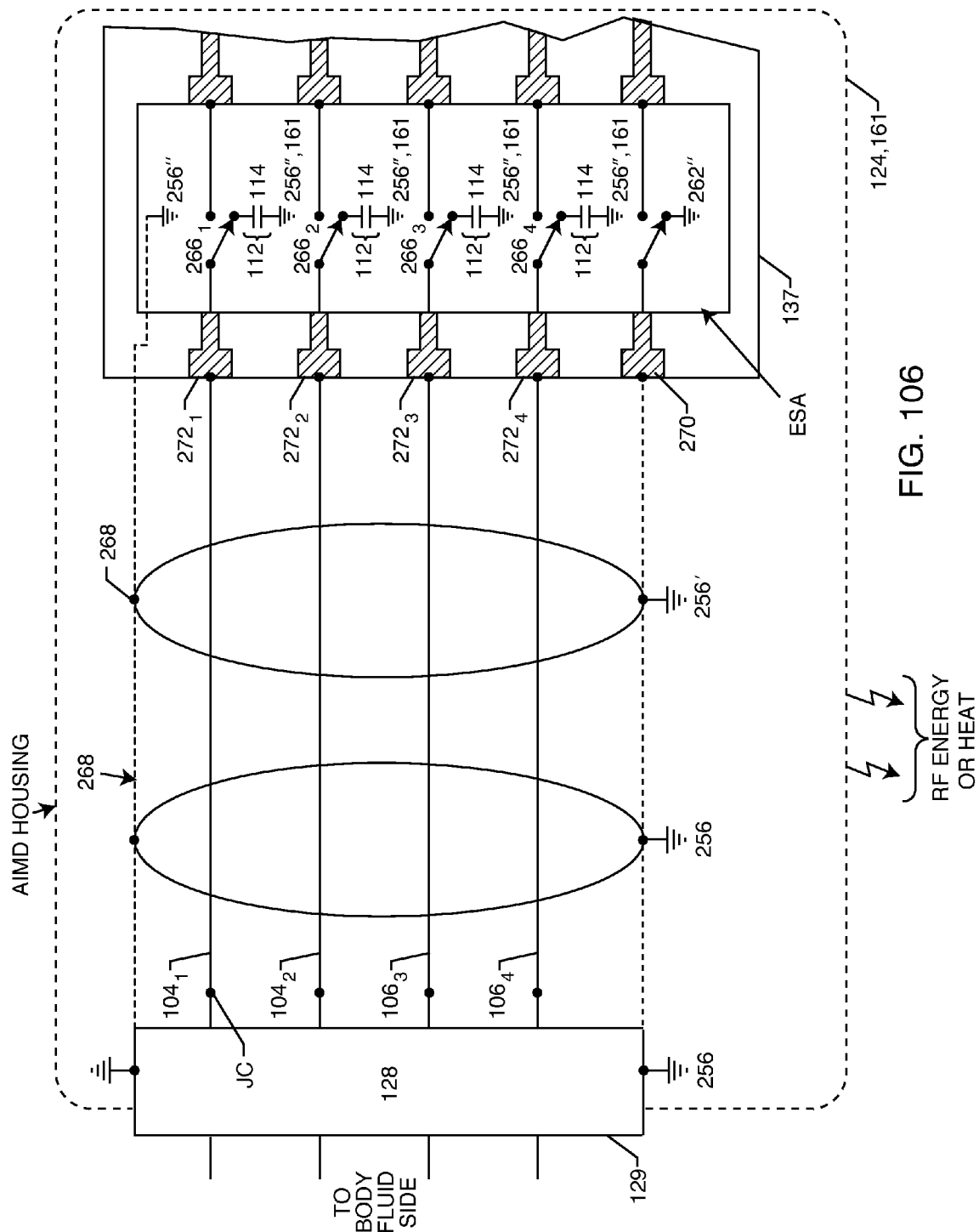
FIG. 106 is similar to FIGS. 104-105, except that the diverter element is shown as a capacitor.

FIG. 106 is very similar to FIGS. 104 and 105 except that the diverter element 112 is shown as a capacitor 114.

Figure 107:
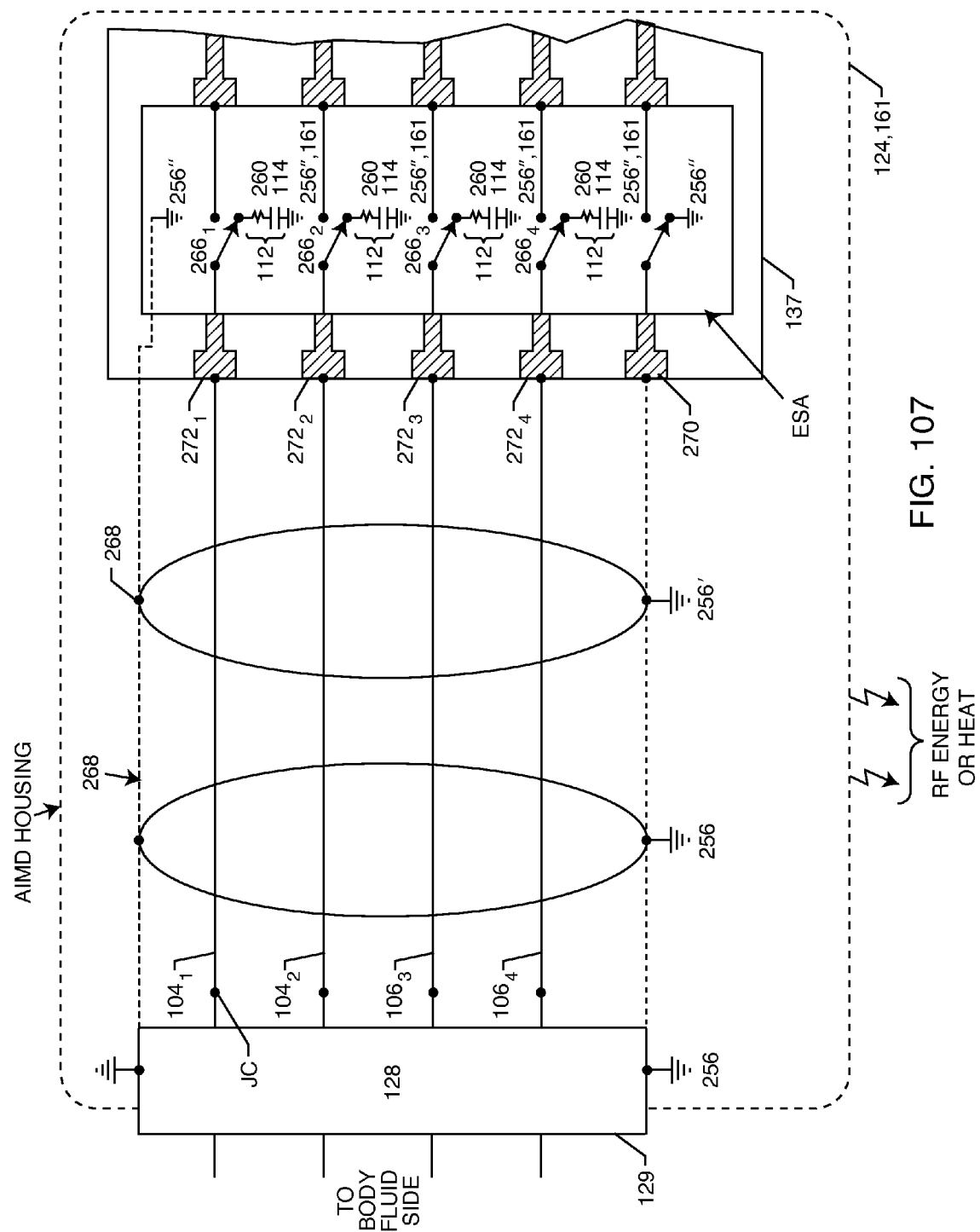
FIG. 107 is similar to FIG. 106, except that a resistor has been added in series with the diverter capacitor.

FIG. 107 is very similar to FIG. 106 except that a resistor has been added in series with the diverter capacitor 114 as shown. One is referred to the drawing description for FIG. 93 to see why adding a resistance in series with a capacitor can lead to tuned energy balance in order to draw the maximum amount of induced energy out of the leads into the energy dissipating surface 161.

Figure 108:
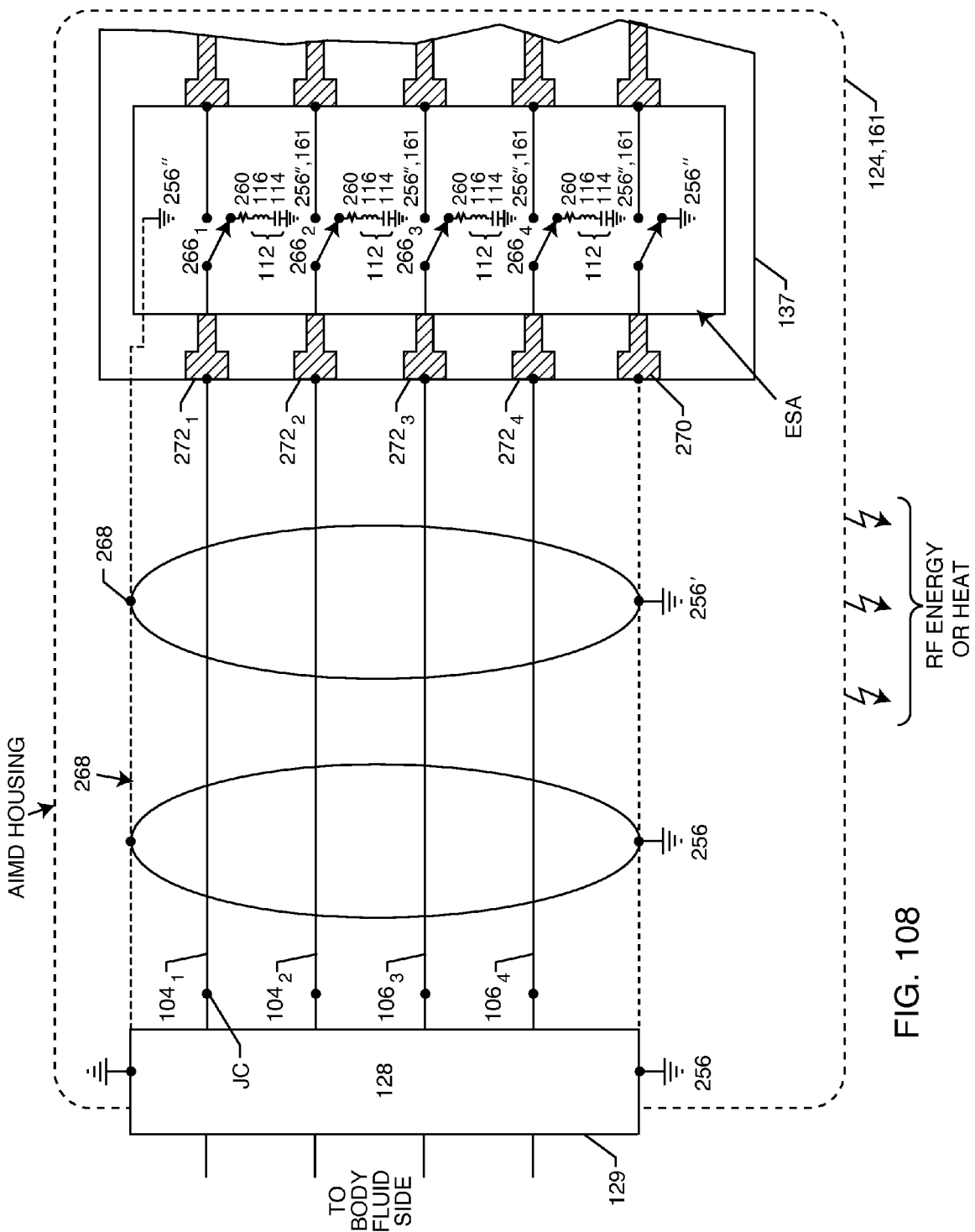
FIG. 108 is similar to FIGS. 104-107, except that the diverter element is an RLC trap filter.

FIG. 108 is very similar to FIGS. 104-107 except that the diverter element 112 is an R-L-C trap filter. Resistance has been added to control the Q and also tuned for maximum energy transfer in accordance with FIGS. 45 and 46.

Figure 109:
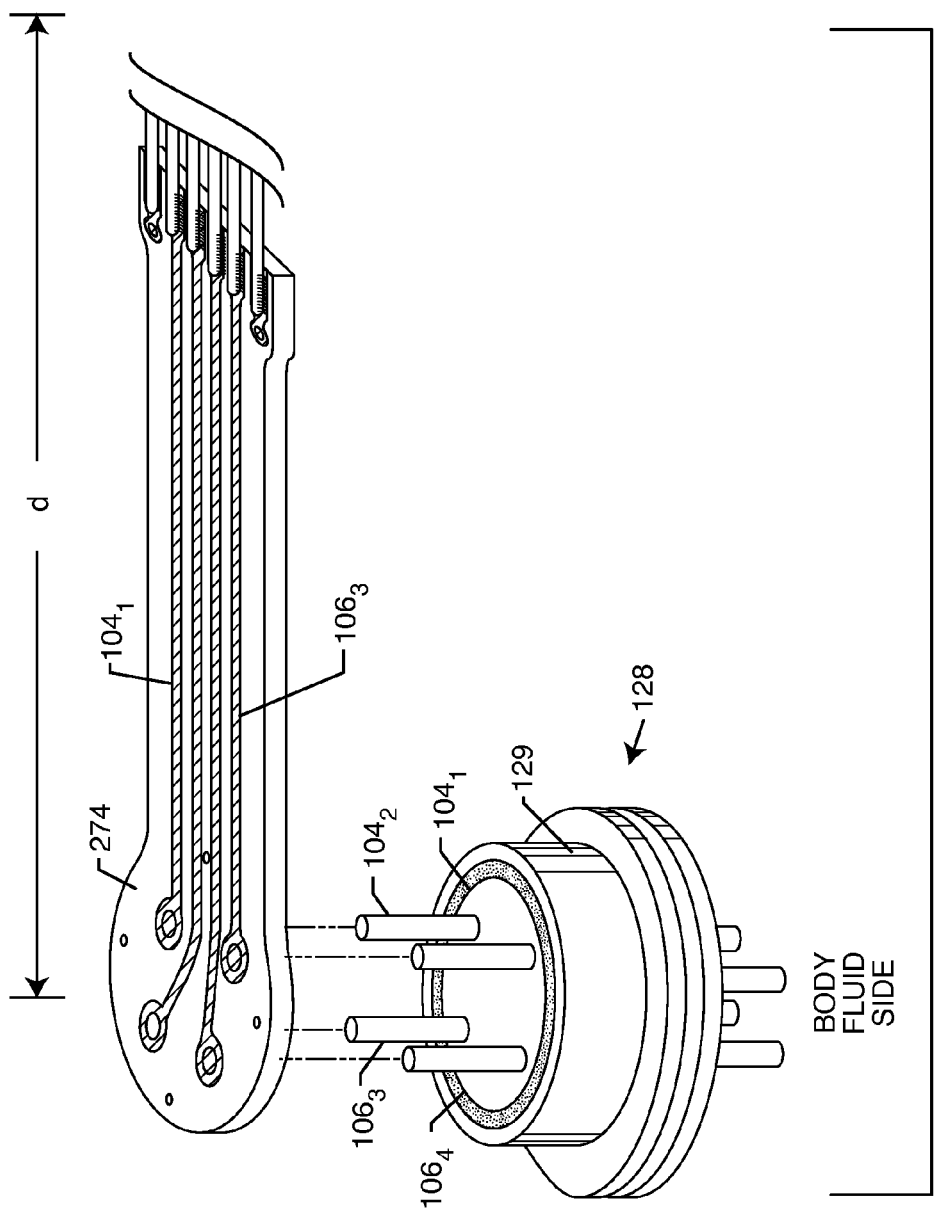
FIG. 109 is an illustration of connecting a flex cable to leadwires that pass through the hermetic terminal in non-conductive relationship.

FIG. 109 illustrates one method of connecting a flex cable 274 to leads $104_{1,2}$ through $106_{3,4}$ that pass through the hermetic terminal 128 in non-conductive relationship. The conductive ferrule 129 as shown, which would be laser welded into the conductive housing 124 of the AIMD. Leadwires $104_{1,2}$ through $106_{3,4}$ are routed through the flex cable for convenient attachment to a circuit board or substrate located within the AIMD.

Figure 110:
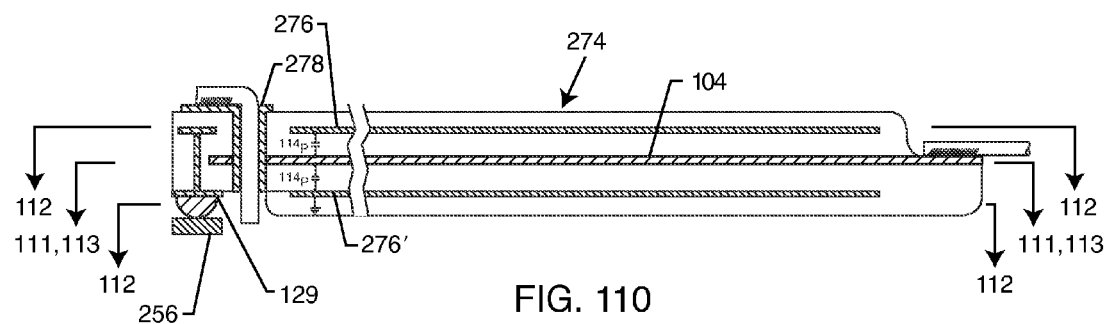
FIG. 110 is a cross-sectional view taken generally from the attachment of the flex cable to the hermetic terminal previously described in FIG. 109

FIG. 110 is a cross-sectional view taken generally from the attachment of the flex cable 274 to the hermetic terminal 128 previously described in FIG. 109. Shown are optional ground shield traces 276 and 276' which serve two purposes. The first is to prevent re-radiation of EMI inside of the AIMD housing. The second is to provide a very long impedance ground connection from the AIMD housing to the circuit board or substrate where the novel switches of the present invention are preferably located. Referring once again to FIG. 110, one can see circuit trace 104 which representative of circuit traces $104_{1,2}$ through $106_{3,4}$. On the left side, there is a ground connection 256 to the ferrule 129 of the hermetic terminal 128. Ground shield traces 276 and 276' sandwich or surround the flex cable or substrate circuit traces 104. Desirably, parasitic capacitances $114_P$ are formed between the circuit traces 104 and the surrounding ground planes 276, 276'. The parasitic capacitance $114_P$ acts as additional low pass filtering.

Figure 111:
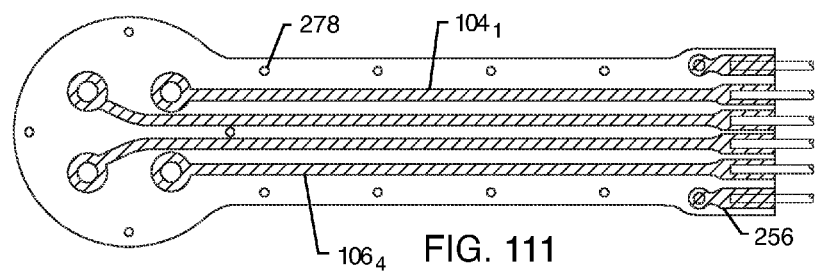
FIG. 111 is taken from section 111-111 of FIG. 110 and illustrates the internal circuit traces.

FIG. 111 is taken generally from section 111-111 from FIG. 110. This illustrates the internal circuit traces $104_{1,2}$ through $106_{3,4}$. Also shown are a number of via holes 278 which are used to stitch together and electrically reduce the impedance of the internal ground shield plates 276 and 276'.

Figure 112:
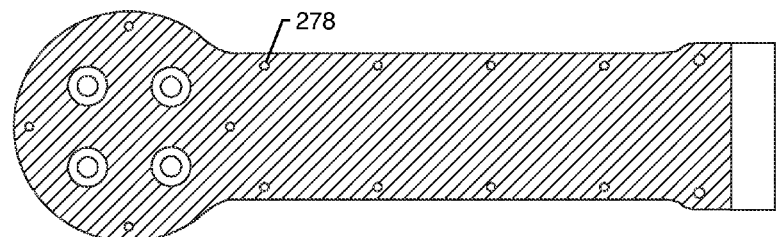
FIG. 112 is taken from section 112-112 of FIG. 110 and illustrates one of a pair of coaxially surrounding shields disposed about the circuit traces.

FIG. 112 is one of a pair of coaxially surrounding shields disposed about the circuit traces 104 in non-conductive relation and is taken generally from section 112-112 from FIG. 110 and shows a preferred form of an upper and lower ground plane 276, 276'. As mentioned, this effectively shields circuit traces $104_{1,2}$ through $106_{3,4}$ and also at the same time provides a very low impedance RF ground connection to a switch or switch network located on a remote AIMD circuit board or substrate 137. It will be obvious to those skilled in the art that the pair of coaxial shields that are shown in FIG. 112 could also be a tubular shield or shielded conduit that extends from the hermetic terminal to the circuit board and provides the same function. This forms a shielded conduit which prevents EMI re-radiation from the leadwires inside of an AIMD and at the same time, extends a low impedance RF ground to the circuit board or substrate. This is useful, not just for the novel switches and impeder and diverter elements of the present invention, but is also very useful to facilitate on board EMI filtering, high voltage suppression arrays, and the like. All of these depend on a low impedance RF ground to the AIMD housing.

Figure 113:
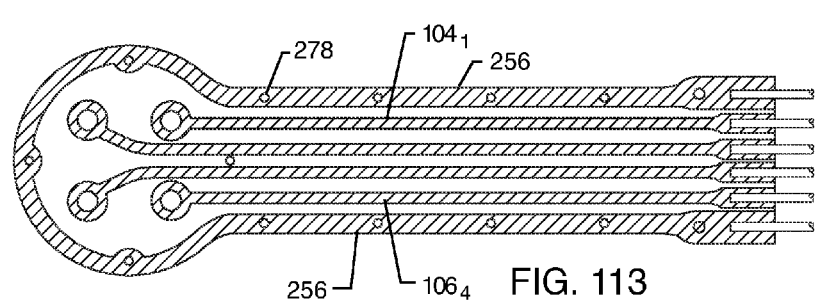
FIG. 113 is taken from section 113-113 of FIG. 110 and illustrates an alternative to the layer previously described in FIG. 111.

FIG. 113 is taken generally from section 113-113 of FIG. 110 and shows an alternative to the layer previously described in FIG. 111 in that the circuit traces $104_{1,2}$ through $104_{3,4}$ are shown further surrounded by grounds 256 as shown.

Figure 114:
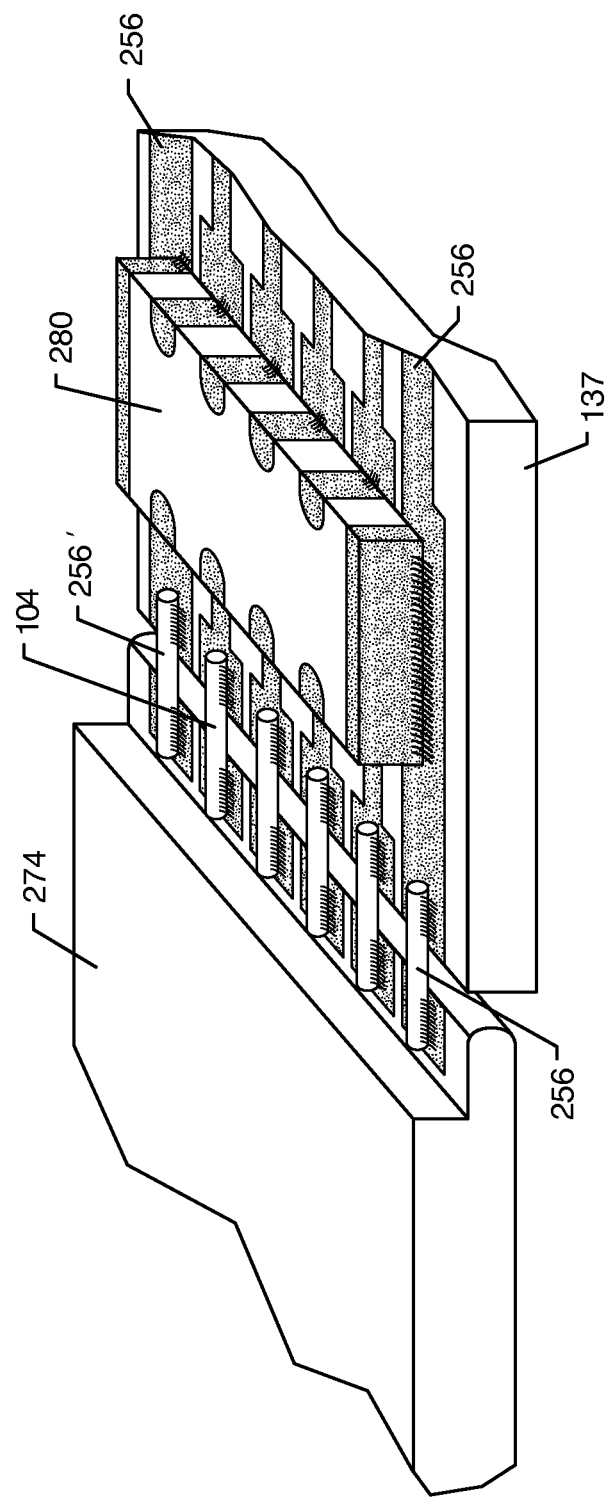
FIG. 114 illustrates the flex cable arrangement of FIGS. 109-113 now connected to a circuit board or substrate.

FIG. 114 illustrates the flex cable arrangement 274 previously described in FIGS. 109 through 113 connected to a circuit board or substrate 137 which is generally located inside an AIMD housing, inside a probe or catheter body, or inside of an energy dissipating surface 161. A flex cable 274 is shown connected to circuit traces on the circuit board or substrate. Also shown is an electronic switch module 280 in accordance with the present invention. This electronic switch module could be a discrete module as shown in FIG. 114, or it could be integrated within an overall microelectronic chip on the AIMD. Preferred schematic diagrams for the arrangements illustrated in FIG. 114 have been previously described in FIGS. 104 through 108.

Figure 115:
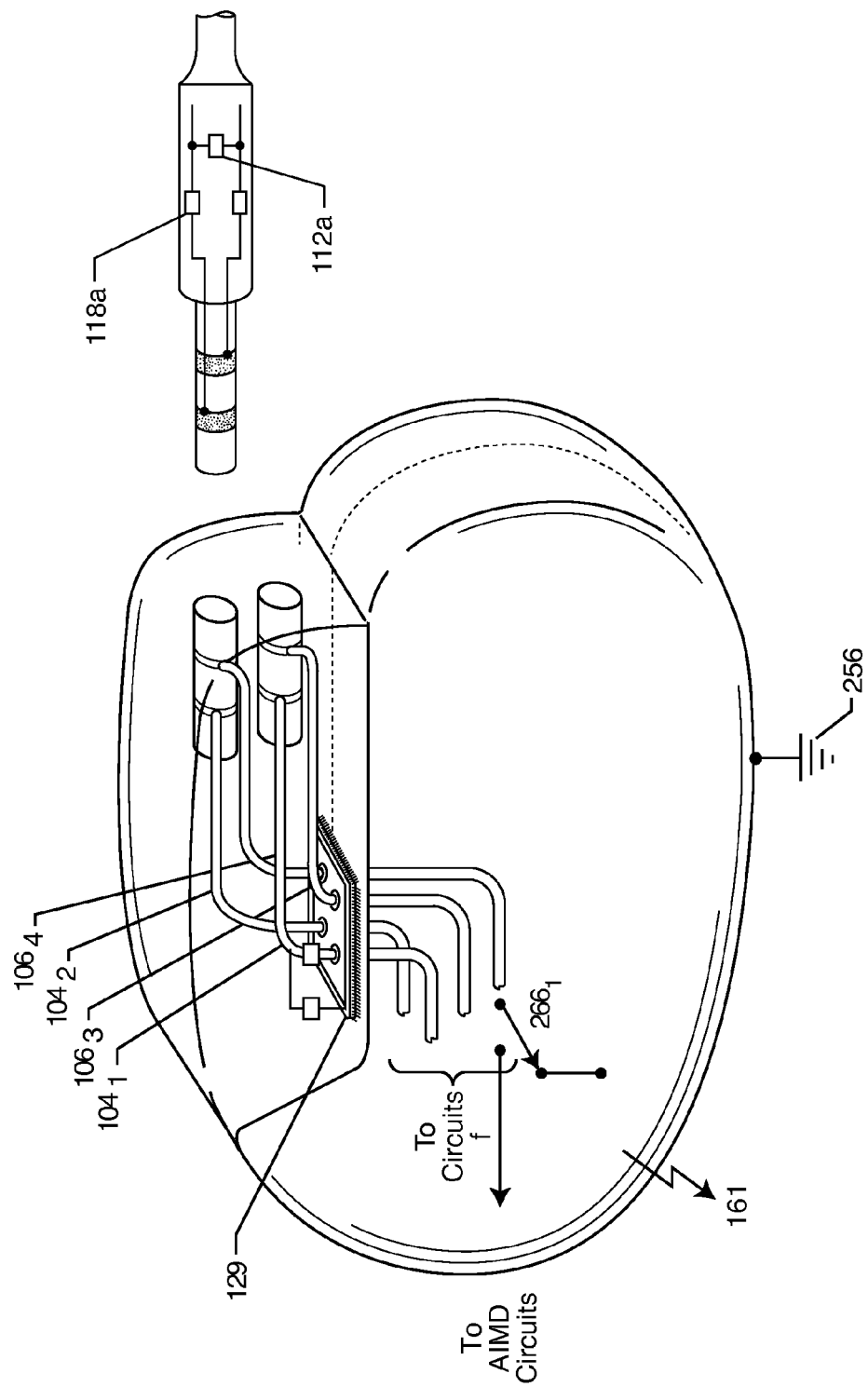
FIG. 115 is similar to FIG. 81, except that it shows optional locations for the frequency selective diverter elements and the frequency selective impeder elements.

FIG. 115 is very similar to FIG. 81 except that it shows optional locations for the frequency selective diverter elements 112 and the frequency selective impeder elements 118 of the present invention. As shown in FIG. 115, impeder elements 118a and diverter elements 112a can be located at or near the proximal end of an implanted lead $104_1$. These would be preferably located in an implanted lead proximal male connector shown as diverter element 112a associated with one or more impeder elements 118a. These impeder and diverter elements were previously described in FIGS. 2 through 11. There is an advantage to locating the tuned diverter elements 112 outside of the AIMD housing. This can also be true for the impeder elements, but is not as critical. The reason has to do with the high volumes that certain AIMDs are manufactured in. For example, there are over 650,000 cardiac pacemakers manufactured every year. It would be highly impractical to have a different pacemaker design associated with every different type of lead. Hospitals, in general, inventory a great number of leads of varying lengths. This is because they can be used in pediatric applications, children and full-size adult applications. Accordingly, implanted cardiac leads can vary anywhere from 20 cm to over 60 cm in length in some cases. The characteristic impedance of these implanted leads varies not only with their length, but with their implant geometries and trajectories through body tissues. In accordance with the tuned energy balance principles of the present invention, ideally, the reactive component of the lead, which is usually an inductive reactance, would be canceled by the reactance of the impeder element 112 of the present invention (ref. FIGS. 89-93). As previously mentioned, since cardiac pacemakers are manufactured in high volume automated facilities, it's really not practical to have a custom internal impeder element 112 for each and every external implanted lead possibility. An additional complication occurs because of the tendency to mix and match. That is, it is very common in medical practice to use one manufacturer's pacemaker with another manufacturer's leads. In other words, a St. Jude pacemaker might be implanted with Medtronic leads. Installation of the cardiac pacemaker header block HB is a subsequent manufacturing operation. Therefore, it would be relatively easy and inexpensive to custom tailored diverter elements 112a and impeder elements 118a to a particular lead. In a particularly preferred embodiment, the impeder 112 and diverter 118 elements would be located at or near the proximal end of a lead $104_1$ as shown. In this case, each lead could have its own custom impeder element 112b whose reactance would be tuned and equal and opposite to that of the characteristic reactance (impedance) of the lead. This would achieve optimal energy transfer through the wiring of the AIMD to the energy dissipating surface housing 161 in accordance with the present invention. Referring once again to FIG. 115, one can see that there is a novel switch $266_1$ in accordance with the present invention that is shown inside the housing of the AIMD. This can, of course, be mounted on an AIMD circuit board substrate or the like. In the MRI compatible mode, the switch grounds at least one of the lead wires that are routed to the proximal connector assembly PCA in order to provide a ground connection to diverter element 112a. This provides a circuit path from the one or more diverter elements located at or near the proximal end of lead $104_1$ and/or in a proximal lead connector PCA such that high frequency energy picked up by the lead $LW_1$ can be routed through lead 118 to switch $266_1$ and in turn to the energy dissipating surface 161. In this way, impeder element 112a and diverter elements 118a work in accordance with the present invention.

Figure 116:
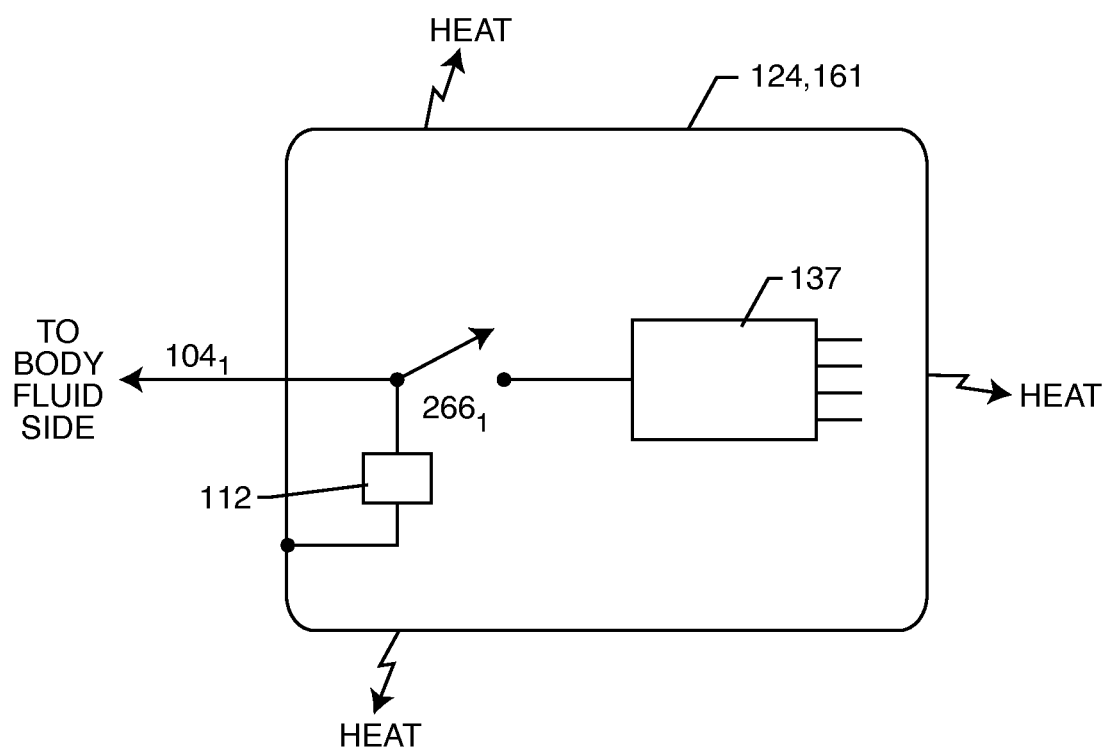
FIG. 116 is similar to FIGS. 98 and 100, illustrating an alternative embodiment.

FIG. 116 illustrates an alternative embodiment wherein the frequency diverter element 112 is any of the previously shown or described diverter elements including short circuits, capacitors, L-C traps or low pass filters and the like. The diverter element(s) would be permanently connected to the AIMD housing 124 as shown. In a preferred embodiment, the diverter element 112 is frequency selective. A switch $266_1$ shown in the open position would be incorporated between the frequency diverter element 112 and any non-linear AIMD electronics, such as those on circuit board 137. In FIG. 116, the switch $266_1$ is shown in the open position which is also the MRI compatible mode for the AIMD. During normal operation in the patient's normal daily environment, switch $266_1$ would normally be closed (not shown). This would connect the AIMD electronics 137 to the implanted lead $104_1$. In this normal operating mode, the frequency selective diverter element 112 could not be a short circuit. In a preferred embodiment, it would be a frequency selective reactance, such as a capacitor or an L-C trap filter. During this normal mode of operation, the AIMD would have EMI protection from diverter element 112. In the MRI compatible mode, switch $266_1$ is opened up as shown. In this case, the AIMD electronics would be completely disconnected from the implanted lead $104_1$. In general, this would work very well for AIMDs that are not life-sustaining. For a spinal cord stimulator patient, urinary incontinence patient, or a cochlear implant patient, it really is no more than a small inconvenience to have the AIMD inoperable during the relatively short time of an MRI scan. Immediately after the MRI scanning was complete, the device would be re-programmed or reset so that the switch $266_1$ would be switched back to its closed position also known as the AIMD normal operating mode. If the AIMD were a cardiac pacemaker and the patient were pacemaker dependent, then it would not be possible to disconnect the AIMD electronics 137 from the implanted lead $104_1$ (lack of pacing pulses would be life threatening). In this case, alternative methods would be required to protect the implanted lead from overheating and also protect AIMD electronics from EMI. In particular, it's very important that the switch $266_1$ be incorporated between the frequency selective diverter element(s) 112 and any non-linear circuit elements, such as over-voltage or transient protection diodes, Transorbs and the like. Non-linear circuit elements can act as detectors for pulse modulation that could be coupled to implanted leads from the high powered MRI RF or gradient fields. As previously illustrated in FIG. 101 and described, it is important that RF rectification pulses not appear on the implanted lead where they could potentially capture (stimulate) or damage body tissues at the electrode interface. In a preferred embodiment, the frequency selective diverter element 112 could be a feedthrough capacitor 114 (FIG. 39) which would be mounted directly on the hermetic terminal 128 of the AIMD. In this case, switch $266_1$ would be disposed between the frequency diverter element 112 and all non-linear or other AIMD internal electronic circuits. This would be a safety measure to make sure that no non-linear circuit elements would be connected. This is very important so that there would be no chance for MRI RF or gradient rectification or tissue stimulation ratification to occur during high intensity MRI scans.

Referring once again to FIG. 116, there are a number of very important advantages of this switched safety protection circuit for an AIMD system during exposure to high power electromagnetic fields such as those produced by MRI scanners. The AIMD system includes an active implantable medical device, such as a cardiac pacemaker, which generally includes internal electronic circuits. The system also includes at least one implanted lead or leadwire associated with the AIMD electronics. Part of the system is an energy dissipating surface 161, which in a preferred embodiment, is the conductive AIMD housing 124. As illustrated, one or more diversion circuits 112 are associated with the energy dissipating surface 161. In general, the diversion circuit is coupled between the implanted lead or leadwire and the AIMD housing 124 which acts as an energy dissipating surface 161. In a particularly preferred embodiment, the diversion circuit is a frequency selective diversion circuit, which includes reactances. As can be seen, at least one switch is disposed between the diversion circuit and the AIMD electronics. The purpose of the switch is to open up or disconnect the AIMD electronics from the implanted lead while at the same time diverting energy in the implanted lead or leadwire to the energy dissipating surface 161. It will be obvious to those skilled in the art that switch $266_1$ can be a single pole-single throw or a multi-pole single throw. It is common for AIMDs to have not just one (unipolar), but a number of implanted leads. In accordance with the present invention, switch $266_1$ as described in FIG. 116 could be disposed in one, several or even all of the implanted lead or leadwire circuits (multi-pole). The switch circuit of FIG. 116 accomplishes three very important objectives: (1) it disconnects AIMD electronics therefore making them highly immune to EMI that may be coupled onto leads in the presence of high power electromagnetic fields. High powered electromagnetic fields include the RF pulsed and gradient fields produced by an MRI scanner; (2) the switch $266_1$ also disconnects any non-linear AIMD circuit elements. This prevents a condition known as RF or gradient field rectification. As previously described, RF or gradient rectification can cause low frequency pulses to appear on implanted leads which could improperly stimulate or damage body tissues. For example, low frequency pulses at 300 Hz may cause the heart to beat too fast and lead to a very dangerous condition known as ventricular fibrillation; (3) the permanently wired diverter 112 of FIG. 116 acts to pull unwanted RF energy from the implanted lead and divert it to the AIMD housing 124 which acts as an energy dissipating surface 161. This is very important to prevent overheating of the implanted lead and/or its distal electrode-to-tissue interface.

Figure 117:
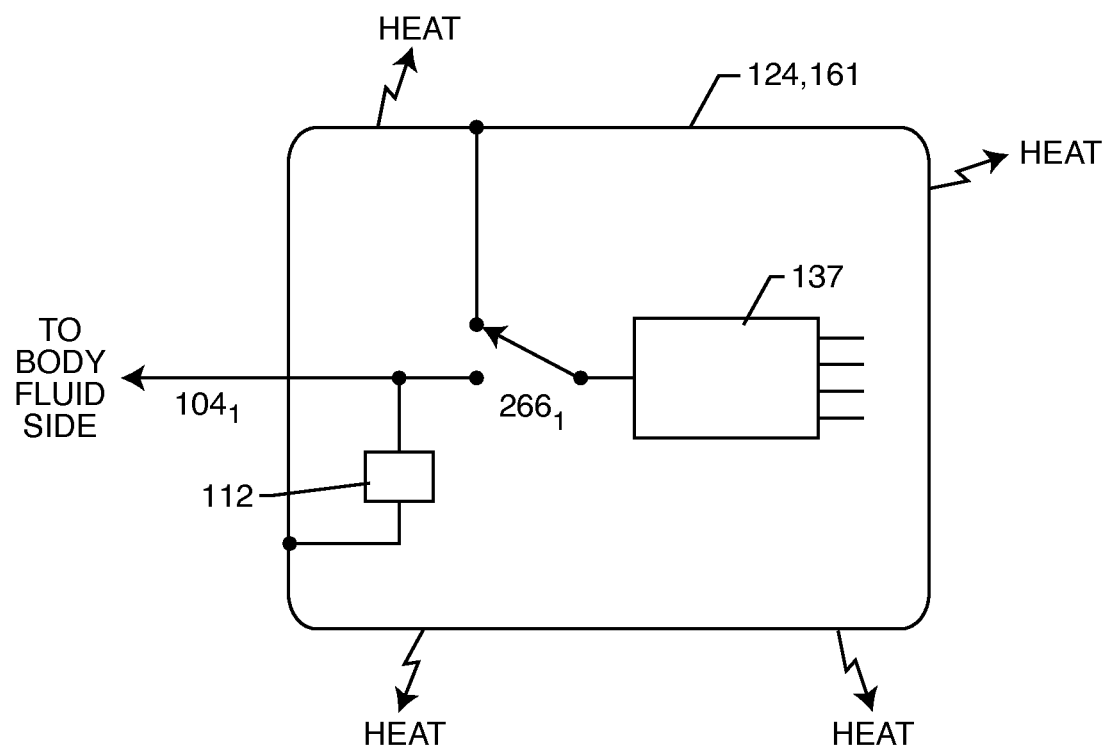
FIG. 117 is similar to FIG. 116 except that the switch is a single-pole double throw switch.

FIG. 117 is very similar to FIG. 116 except that the switch $266_2$ has been reversed and is now a single pole double throw switch. It operates very much as described in FIG. 116, but it also offers another advantage. When the switch is switched open into the MRI compatible position as shown, the wiper is also grounded to the housing 124 of the AIMD. This is an additional safety feature. By grounding the AIMD electronics 137, one provides additional protection against the chance that EMI could cross couple over to sensitive AIMD circuitry. As previously mentioned, switch $266_2$ is shown in the MRI compatibility position. As previously described in FIG. 116, the switch would be switched into the closed position during the normal AIMD operating mode. In other words, during daily life, the patient's AIMD electronics 137 would be directly connected through switch $266_2$ to the implanted lead $104_1$.

In summary, compatibility of probes, catheters, cardiac pacemakers, implantable defibrillators and other types of active implantable medical devices with magnetic resonance imaging and other types of hospital diagnostic equipment has become a major issue. The present invention addresses this by providing an overall energy management system which is capable of controlling the energy induced in implanted leads from RF pulsed fields, such as those generated by MRI scanners. More particularly, a tuned energy balanced system including a switched safety protection circuit minimizes heating of an implanted lead in a high power electromagnetic field environment. The tuned energy balanced system comprises an implanted lead having impedance characteristics at a selected RF frequency or frequency band, and an energy dissipating surface associated with the implanted lead. A diversion circuit conductively couples the implanted lead to the energy dissipating surface. The diversion circuit comprises one or more passive electronic network components whose impedance characteristics are at least partially tuned to the implanted lead's impedance characteristics, to facilitate transfer to the energy dissipating surface of high frequency energy induced on the implanted lead at the selected RF frequency or frequency band.

The switched safety protection circuit includes at least one switch disposed between the diversion circuit and the AIMD electronics for diverting energy in the implanted lead or the leadwire through the diversion circuit to the energy dissipating surface. The switch is disposed so as to electrically open the implanted lead or the leadwire when diverting energy in the implanted lead or the leadwire through the diversion circuit to the energy dissipating surface. Alternatively or in addition, a switch may be disposed between the implanted lead or the leadwire and the diversion circuit. In preferred embodiments, the switches may comprise a single or multi-pole double throw switch, or a single or multi-pole single throw switch.

The tuned energy balanced system utilizing the switched safety protection circuit of the present invention harmlessly shunts RF energy induced on an implanted lead or leadwire into either an EDS surface, the AIMD housing, a bulk thermal mass, or the handle of a probe or catheter.

Impedance circuits may be combined with the diversion or diverter circuits to raise and further control the overall impedance of the system to achieve maximal energy transfer and minimum thermal rise in the implanted lead system.

Although several embodiments have been described in detail for purposes of illustration, various modifications may be made without departing from the scope and spirit of the invention. Accordingly, the invention is not to be limited, except as by the appended claims.

What is claimed is:

1. An active implantable medical device, comprising:
   a) a conductive device housing for the medical device, the housing containing tissue-stimulating or biological-sensing circuits connected to a first electrical switch point;
   b) a second electrical switch point that is electrically connectable to an electrode configured for tissue-stimulating or biological-sensing;
   c) an energy dissipating surface provided by the device housing as a third electrical point;
   d) at least one diversion circuit electrically connected between the second electrical switch point and the third electrical point at the device housing providing the energy dissipating surface; and
   e) at least one switch that is actuatable in response to a magnetic resonance $B_0$ field sensor that, in the absence of a static magnetic field, electrically connects the first electrical point at the tissue-stimulating or biological-sensing circuits to the second electrical switch point and, in the presence of a static magnetic field, electrically disconnects the first electrical point from the second electrical switch point and electrically connects the first electrical switch point to the third electrical point at the device housing in the presence of a static magnetic field,
   f) wherein regardless the position of the switch:
      i) at relatively high frequencies attendant to the medical device being in the presence of an RF pulse field, the diversion circuit acts as a relatively low impedance circuit from the second electrical switch point to the third electrical point at the energy dissipating surface, and
      ii) at relatively low frequencies attendant to the medical device being in the presence of an MRI gradient field, the diversion circuit acts as a relatively high impedance circuit between the second electrical switch point and the third electrical point at the energy dissipating surface.

2. The active implantable medical device of claim 1 wherein the diversion circuit is permanently conductively connected between the second electrical switch point and the third electrical point at the energy dissipating surface.

3. The active implantable medical device of claim 1 wherein the switch is selected from the group consisting of a single throw switch, a multi-pole single throw switch, and a double throw switch.

4. The active implantable medical device of claim 1 wherein the switch is selected from the group consisting of a MEMS switch, a mechanical switch, a reed switch, an electronic switch, a programmable switch, an automatically actuated switch, a Hall Effect switch, and a field effect transistor (FET) switch.

5. The active implantable medical device of claim 1 wherein in response to the magnetic resonance $B_0$ field sensor, the switch electrically disconnects the second electrical switch point from the first electrical switch point and simultaneously conductively couples the tissue-stimulating or biological-sensing circuits connected to the first electrical switch point to the third electrical point at the energy dissipating surface.

6. The active implantable medical device of claim 1 wherein the tissue-stimulating or biological-sensing circuits connected to the first electrical switch point are selected from the group consisting of non-linear circuit elements, over-voltage circuit elements, transient voltage suppression diodes, Transorbs, AIMD sensing circuits, and AIMD therapy delivery circuits.

7. The active implantable medical, device of claim 1 wherein the diversion circuit further comprises a low pass or a high pass filter.

8. The active implantable medical device of claim 7, wherein the low pass filter is selected from the group consisting of a capacitor, an inductor, a Pi filter, a T filter, an LL filter, and an "n" element filter.

9. The active implantable medical device of claim 1 wherein the diversion circuit comprises a unipolar or multipolar feedthrough capacitor.

10. The active implantable medical device of claim 1 wherein the diversion circuit comprises at least one series resonant L-C trap filter.

11. The active implantable medical device of claim 10, wherein the diversion circuit comprises a plurality of L-C trap filters connected in parallel with each other and disposed in series between the second electrical switch point and the third electrical point, the L-C trap filters being resonant, respectively, at different MRI frequencies.

12. The active implantable medical device of claim 1 selected from the group consisting of an implantable hearing device, a neurostimulator, a brain stimulator, a cardiac pacemaker, a left ventricular assist device, an artificial heart, a drug pump, a bone growth stimulator, a urinary incontinence device, a spinal cord stimulator, an anti-tremor stimulator, an implantable cardioverter defibrillator, a congestive heart failure device, a probe, a catheter, and a cardio resynchronization therapy device.

13. The active implantable medical device of claim 1 wherein the diversion circuit is disposed within the housing.

14. The active implantable medical device of claim 1 wherein the diversion circuit is disposed within a header block for the medical device.

15. The active implantable medical device of claim 1 including an EMI shield conductively coupled to the housing and coaxially extending about the lead or the leadwire in non-conductive relation thereto.

16. The active implantable medical device of claim 15, wherein the diversion circuit is conductively coupled between the second electrical switch point and the EMI shield, which is in turn connected to the device housing at the third electrical.

17. The active implantable medical device of claim 1 wherein the diversion circuit comprises a high pass filter.

18. The active implantable medical device of claim 17, wherein the high pass filter substantially prevents low frequency gradient field-induced energy at the second electrical switch point from passing through the diversion circuit to the energy dissipating surface.

19. The active implantable medical device of claim 17, wherein the high pass filter comprises a capacitor.

20. The active implantable medical device of claim 1 wherein the diversion circuit comprises a resistor in series with a capacitor.

21. The active implantable medical device of claim 1 wherein the second electrical switch point is electrically connectable to an implantable lead comprising at least one leadwire having a length extending between and to a proximal end that is electrically connected to the second electrical switch point, which in the absence of a static magnetic field is switchably connectable to the first electrical switch point at the tissue-stimulating or biological-sensing circuits and an electrode configured for tissue-stimulating or biological-sensing at or near a distal end of the leadwire.

22. The active implantable medical device of claim 21 wherein the implantable lead comprises at least a portion of a probe or a catheter.

23. The active implantable medical device of claim 22, wherein the energy dissipating surface comprises at least a portion of a handle for a probe or catheter as the third electrical point.

24. The active implantable medical device of claim 1 wherein the energy dissipating surface comprises a material capable of being visualized during a magnetic resonance scan.

25. The active implantable medical device of claim 1 wherein the energy dissipating surface includes a biomimetic coating.

26. The active implantable medical device of claim 1 wherein in the presence of a static magnetic field and at relatively high frequencies attendant to the AIMD being subjected to an MRI RF pulse field, the diversion circuit acts as a short from the second electrical switch point to the third electrical point at the energy dissipating surface, and at relatively low frequencies attendant to the medical device being subjected to an MRI gradient field, the diversion circuit acts as an open circuit between the second and third electrical points.

27. The active implantable medical device of claim 1 wherein, in the presence of the static magnetic field, the switch electrically connects the first electrical switch point connected to the tissue-stimulating and biological-sensing circuits to a fourth electrical switch point on the device housing and wherein the third electrical point and the fourth electrical switch point are either spaced apart or at the same location on the device housing serving as the energy diversion surface.

28. The active implantable medical device of claim 1 wherein the magnetic $B_0$ field sensor actuates in the presence of a static field of at least 0.5 Tesla.

29. An active implantable medical device (AIMD), comprising:
  a) a conductive device housing for the AIMD, the housing containing tissue-stimulating or biological-sensing circuits;
  b) an implantable lead comprising at least one leadwire having a length extending between and to a proximal end electrically connected to the medical device including the tissue-stimulating or biological-sensing circuits and an electrode configured for tissue-stimulating or biological-sensing at or near a distal end of the leadwire;
  c) an energy dissipating surface provided by the device housing;
  d) at least one diversion circuit electrically connected from the leadwire to the device housing; and
  e) at least one switch that is actuatable in response to a magnetic resonance $B_0$ field sensor to electrically connect the leadwire to the tissue-stimulating or biological-sensing circuits for the medical device in the absence of an MRI static magnetic field and, in the presence of an MRI static magnetic field, to electrically disconnect the leadwire from the tissue-stimulating or biological-sensing circuits and to connect the tissue-stimulating or biological-sensing circuits to the device housing at a position that is either spaced apart or at the same location as where the diversion circuit is connected thereto as the energy dissipating surface,
  f) wherein regardless the position of the switch:
    i) at relatively high frequencies attendant to the medical device being subjected to an RF pulse field, the diversion circuit act as a relatively low impedance circuit between the leadwire and the energy dissipating surface, and
    ii) at relatively low frequencies attendant to the medical device being subjected to an MRI gradient field, the diversion circuit acts as an relatively high impedance circuit between the leadwire and the energy dissipating surface.

30. The active implantable medical device of claim 29 wherein the implantable lead comprises at least a pair of leadwires, each leadwire having a length extending between, and to a proximal end and a tissue stimulating or biological-sensing electrode at each distal end.

31. The active implantable medical device of claim 30, wherein a respective diversion circuit couples each of the leadwires to the third electrical point at the energy dissipating surface.

32. The active implantable medical device of claim 29 wherein the magnetic $B_0$ field sensor actuates in the presence of a static field of at least 0.5 Tesla.

33. The active implantable medical device of claim 29 wherein the implantable lead comprising the at least one leadwire has impedance characteristics at a selected RF frequency or frequency band, and wherein the diversion circuit has impedance characteristics at least partially tuned to the impedance characteristics of the implantable lead or the leadwire.

34. The active implantable medical device of claim 33 wherein the selected RF frequency or frequency band comprises an MRI RF pulsed frequency.

35. The active implantable medical device of claim 34 wherein the MRI RF pulsed frequency comprises a range of MRI frequencies.

36. The active implantable medical device of claim 33 wherein the diversion circuit has a reactance that is vectorially opposite to the characteristic reactance of the implantable lead.

37. The active implantable medical device of claim 36 wherein the diversion circuit has a capacitive reactance that is substantially equal and opposite to the characteristic inductive reactance of the implantable lead.

38. The active implantable medical device of claim 33 wherein the capacitive reactance and the inductive reactance each have a resistor component.

39. The active implantable medical device of claim 29 wherein the diversion circuit comprises a unipolar or multipolar feedthrough capacitor.

40. The active implantable medical device of claim 29 wherein the diversion circuit comprises at least one series resonant L-C trap filter.

41. The active implantable medical device of claim 40 wherein the diversion circuit comprises a plurality of L-C trap filters connected in parallel with each other and in series between the leadwire and the device housing, the L-C trap filters being resonant, respectively, at different MPI frequencies.

42. The active implantable medical device of claim 29 selected from the group consisting of an implantable hearing device, a neurostimulator, a brain stimulator, a cardiac pacemaker, a left ventricular assist device, an artificial heart, a drug pump, a bone growth stimulator, a urinary incontinence device, a spinal cord stimulator, an anti-tremor stimulator, an implantable cardioverter defibrillator, a congestive heart failure device, a probe, a catheter, and a cardio resynchronization therapy device.

43. The active implantable medical device of claim 29 wherein the diversion circuit is disposed within the housing.

44. The active implantable medical device of claim 29 wherein the diversion circuit is disposed within a header block for the medical device.

45. The active implantable medical device of claim 29 including an EMI shield conductively coupled to the housing and coaxially extending about the lead or the leadwire in non-conductive relation thereto.

46. The active implantable medical device of claim 45 wherein the diversion circuit is conductively coupled to the EMI shield, which is in turn connected to the device housing.

47. The active implantable medical device of claim 29 wherein the diversion circuit comprises a high pass filter.

48. The active implantable medical device of claim 47 wherein the high pass filter substantially prevents low frequency gradient field-induced energy at the second electrical switch point from passing through the diversion circuit to the energy dissipating surface.

49. The active implantable medical device of claim 47 wherein the high pass filter comprises a capacitor.

50. The active implantable medical device of claim 29 wherein the implantable lead comprises at least a portion of a probe or a catheter.

51. The active implantable medical device of claim 50 wherein the energy dissipating surface comprises at least a portion of a handle for a probe or catheter as the third electrical point.

52. An implantable medical device, comprising:
   a) a conductive device housing for the medical device, the housing containing tissue-stimulating or biological-sensing circuits;
   b) an implantable lead comprising at least one leadwire having a length extending between and to a proximal end electrically connected to the medical device including the tissue-stimulating or biological-sensing circuits and an electrode configured for tissue-stimulating or biological-sensing at or near a distal end of the leadwire;
   c) an energy dissipating surface provided by the device housing;
   d) at least one diversion circuit electrically connected from the leadwire to the device housing; and
   e) at least one switch that is selectively actuatable in response to programmable telemetry to electrically connect the leadwire to the tissue-stimulating or biological-sensing circuits for the medical device in the absence of an MRI static magnetic field and, in anticipation of being in the presence of an MRI static magnetic field, to electrically disconnect the leadwire from the tissue-stimulating or biological-sensing circuits and to connect the tissue-stimulating or biological-sensing circuits to the device housing at a position that is either spaced apart or at the same location as where the diversion circuit is connected thereto as the energy dissipating surface,
   f) wherein regardless the position of the switch:
      i) at relatively high frequencies attendant to the medical device being subjected to an RF pulse field, the diversion circuit acts as a relatively low impedance circuit from the leadwire to the energy dissipating surface, and
      ii) at relatively low frequencies attendant to the medical device being subjected to an MRI gradient field, the diversion circuit acts as a relatively high impedance circuit between the leadwire and the energy dissipating surface.

53. The active implantable medical device of claim 52 wherein the magnetic $B_0$ field sensor actuates in the presence of a static field of at least 0.5 Tesla.

54. The active implantable medical device of claim 52 wherein the diversion circuit is permanently conductively connected between the leadwire and the device housing serving as the energy dissipating surface.

55. The active implantable medical device of claim 52 wherein the switch is selected from the group consisting of a single throw switch, a multi-pole single throw switch, and a double throw switch.

56. The active implantable medical device of claim 52 wherein the switch is selected from the group consisting of a MEMS switch, a mechanical switch, a reed switch, an electronic switch, a programmable switch, an automatically actuated switch, a Hall Effect switch, and a field effect transistor (FET) switch.

57. The active implantable medical device of claim 52 wherein the tissue-stimulating or biological-sensing circuits are selected from the group consisting of non-linear circuit elements, over-voltage circuit elements, transient voltage suppression diodes, Transorbs, AIMD sensing circuits, and AIMD therapy delivery circuits.

58. The active implantable medical device of claim 52 wherein the implantable lead comprising the at least one leadwire has impedance characteristics at a selected RF frequency or frequency band, and wherein the diversion circuit has impedance characteristics at least partially tuned, to the impedance characteristics of the implantable lead or the leadwire.

59. The active implantable medical device of claim 58 wherein the selected RF frequency or frequency band comprises an MRI RF pulsed frequency.

60. The active implantable medical device of claim 59 wherein the MRI RF pulsed frequency comprises a range of MRI frequencies.

61. The active implantable medical device of claim 58 wherein the diversion circuit has a reactance that is vectorially opposite to a characteristic reactance of the implantable lead.

62. The active implantable medical device of claim 61 wherein the diversion circuit has a capacitive reactance that is substantially equal and opposite to a characteristic inductive reactance of the implantable lead.

63. The active implantable medical device of claim 58 wherein the diversion circuit has a reactance that is vectorially opposite to a characteristic reactance of the implantable lead and a capacitive reactance that is substantially equal and opposite to a characteristic inductive reactance of the implantable lead and wherein the capacitive reactance and the inductive reactance each have a resistor component.

64. The active implantable medical device of claim 58 wherein the implantable lead comprises at least a pair of leadwires, each having a length extending between and to a proximal end and a tissue-stimulating or biological-sensing electrode at each distal, end.

65. The active implantable medical device of claim 64 wherein the diversion circuit couples each of the leadwires to the energy dissipating surface.

66. The active implantable medical device of claim 52 wherein the diversion circuit further comprises a low pass or a high pass filter.

67. The active implantable medical device of claim 66 wherein the low pass filter is selected from the group consisting of a capacitor, an inductor, a Pi filter, a T filter, an LL filter, and an "n" element filter.

68. The active implantable medical device of claim 52 selected from the group consisting of an implantable hearing device, a neurostimulator, a brain stimulator, a cardiac pacemaker, a left ventricular assist device, an artificial heart, a drug pump, a bone growth stimulator, a urinary incontinence device, a spinal cord stimulator, an anti-tremor stimulator, an implantable cardioverter defibrillator, a congestive heart failure device, a probe, a catheter, and a cardio resynchronization therapy device.

69. The active implantable medical device of claim 52 wherein the diversion circuit comprises a resistor in series with a capacitor.

70. The active implantable medical device of claim 52 wherein the diversion circuit comprises at least one LC trap filter.

71. The active implantable medical device of claim 52 wherein the diversion circuit comprises a plurality of L-C trap filters connected in parallel with each other and in series between the leadwire and the device housing, the L-C trap filters being resonant, respectively, at different MRI frequencies.

72. The active implantable medical device of claim 52 wherein the energy dissipating surface comprises a material capable of being visualized during a magnetic resonance scan.

73. The active implantable medical device of claim 52 wherein the energy dissipating surface includes a biomimetic coating.

74. An implantable medical device, comprising:
  a) a conductive device housing containing tissue-stimulating or biological-sensing circuits;
  b) an energy dissipating surface provided by the device housing;
  c) at least one frequency variable impedance diversion circuit electrically connected between a terminal and the device housing; and
  d) at least one switch that is actuatable in response to a magnetic resonance $B_0$ field sensor to electrically connect the terminal for an implantable lead to the tissue-stimulating or biological-sensing circuits for the medical device in the absence of an MRI static magnetic field and, in the presence of an MRI static magnetic field, to electrically disconnect the terminal from the tissue-stimulating or biological-sensing circuits and to connect the tissue-stimulating or biological-sensing circuits to the device housing at a position that is either spaced apart or at the same location as where the diversion circuit is connected thereto as the energy dissipating surface,
  e) wherein regardless the position of the switch:
    i) at relatively high frequencies attendant to the medical device being subjected to an RF pulse field, the diversion circuit acts as a relatively low impedance circuit from the leadwire to the energy dissipating surface, and
    ii) at relatively low frequencies attendant to the medical device being subjected to an MRI gradient field, the diversion circuit acts as a relatively high impedance circuit between the leadwire and the energy dissipating surface.

75. The active implantable medical device of claim 74 wherein at relatively high frequencies attendant to the AIMD being subjected to an MRI RF pulse field, the diversion circuit acts as a short from the leadwire to the energy dissipating surface, and at relatively low frequencies attendant to the medical device being subjected to an MRI gradient field, the diversion circuit acts as an open circuit between the leadwire and the energy dissipating surface.

* * * * *

UNITED STATES PATENT AND TRADEMARK OFFICE
CERTIFICATE OF CORRECTION

| | | |
|---|---|---|
| PATENT NO. | : 8,447,414 B2 | Page 1 of 1 |
| APPLICATION NO. | : 12/731764 | |
| DATED | : May 21, 2013 | |
| INVENTOR(S) | : Robert Shawn Johnson et al. | |

It is certified that error appears in the above-identified patent and that said Letters Patent is hereby corrected as shown below:

On the Title Page

Page 3 Column 2, line 30 (Other Publications) delete "Steriotaxis" and insert --Stereotaxis--

In the Specification

Column 1, line 10 delete "Nos." and insert --No.--

In the Claims

Column 68, line 41 (Claim 6, line 6) delete "Transorhs" and insert --Transorbs--

Column 68, line 43 (Claim 7, line 1) delete "," after the word "medical"

Column 69, line 17 (Claim 16, line 5) after the word "electrical" insert the word --point--

Column 70, line 51 (Claim 30, line 3) delete "," after the word "between"

Column 71, line 29 (Claim 41, line 5) delete "MPI" and insert --MRI--

Column 72, line 65 (Claim 58, line 5) delete "," after the word "tuned"

Column 73, line 26 (Claim 64, line 5) delete "," after the word "distal"

Column 73, line 50 (Claim 70, line 2) delete "LC" and insert --L-C--

Signed and Sealed this
Third Day of June, 2014

Michelle K. Lee
*Deputy Director of the United States Patent and Trademark Office*